US009452976B2

(12) United States Patent
Mahmud et al.

(10) Patent No.: US 9,452,976 B2
(45) Date of Patent: Sep. 27, 2016

(54) PACTAMYCIN ANALOGS AND METHODS OF MAKING THEREOF

(71) Applicant: Oregon State University, Corvallis, OR (US)

(72) Inventors: Taifo Mahmud, Corvallis, OR (US); Takuya Ito, Tokushima (JP); Patricia M. Flatt, Corvallis, OR (US); Niran Roongsawang, Corvallis, OR (US); Norifumi Shirasaka, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 22 days.

(21) Appl. No.: 14/590,677

(22) Filed: Jan. 6, 2015

(65) Prior Publication Data
US 2015/0183730 A1 Jul. 2, 2015

Related U.S. Application Data

(63) Continuation of application No. 12/596,429, filed as application No. PCT/US2008/060876 on Apr. 18, 2008, now Pat. No. 8,957,251.

(60) Provisional application No. 60/912,824, filed on Apr. 19, 2007.

(51) Int. Cl.
| *C07C 275/26* | (2006.01) |
| *C07D 263/52* | (2006.01) |
| *C12N 15/52* | (2006.01) |
| *C12P 13/02* | (2006.01) |

(52) U.S. Cl.
CPC .......... *C07C 275/26* (2013.01); *C07D 263/52* (2013.01); *C12N 15/52* (2013.01); *C12P 13/02* (2013.01)

(58) Field of Classification Search
CPC .. C07C 275/26; C07D 263/52; C12N 15/52; C12P 13/02
See application file for complete search history.

(56) References Cited

U.S. PATENT DOCUMENTS

| 3,272,697 | A | 9/1966 | Lemin et al. |
| 4,629,786 | A | 12/1986 | Debono et al. |
| 2004/0034207 | A1 | 2/2004 | Ramakrishnan et al. |
| 2010/0210837 | A1 | 8/2010 | Mahmud |

FOREIGN PATENT DOCUMENTS

| GB | 980346 | 1/1965 |
| JP | 1-168660 | 4/1989 |
| WO | WO 2008/131258 | 10/2008 |

OTHER PUBLICATIONS

Brodersen et al., "The Structural Basis for the Action of the Antibiotics Tetracycline, Pactamycin and Hygromycin B on the 30S Ribosomal Subunit," Cell, vol. 103, 1143-1154, Dec. 22, 2000, pp. 1143-1154.*
Admiraal et al., "The Loading and Initial Elongation Modules of Rifamycin Synthetase Collaborate to Produce Mixed Aryl Ketide Products," Biochemistry, vol. 41, pp. 5313-5324, 2002.
Admiraal et al., "The Loading Module of Rifamycin Synthetase Is an Adenylation—Thiolation Didomain with Substrate Tolerance for Substituted Benzoates," Biochemistry, vol. 40, pp. 6116-6123, 2001.
Ahlert et al., "Identification of stsC, the gene encoding the $_L$-glutamine: scyllo-inosose aminotransferase from streptomycin-producing Streptomycetes," Arch. Microbiol., vol. 168, pp. 102-113, 1997.
Ahlert et al., "The Calicheamicin Gene Cluster and Its Iterative Type I Enediyne PKS," Science, vol. 297, pp. 1173-1176, 2002.
Ando et al., "Trehazolin, a new trehalase inhibitor," J. Antibiot., vol. 44, pp. 1165-1168, 1991.
Arslanian et al., "A New Cytotoxic Epothilone from Modified Polyketide Synthases Heterologously Expressed in Myxococcus xanthus," J. Nat. Prod., vol. 65, pp. 1061-1064, 2002.
August et al., "Biosynthesis of the ansamycin antibiotic rifamycin: deductions from the molecular analysis of the rif biosynthetic gene cluster of Amycolatopsis mediterranei S699," Chemistry & Biology, vol. 5, No. 2, pp. 69-79, 1998.
Badger et al., "Comparative Genomic Evidence for a Close Relationship between the Dimorphic Prosthecate Bacteria Hyphomonas neptunium and Caulobacter Crescentus," J. Bacter., vol. 188, No. 19, pp. 6841-6850, 2006.
Begg et al., "Aminoglycosides—50 Years," Br. J. Clin. Pharmac., vol. 39, pp. 597-603, 1995.
Bentley et al., "Complete genome sequence of the model actinomycete Streptomyces coelicolor A3(2)", Nature, vol. 417, pp. 141-147, 2002.
Bhuyan, "Pactamycin Production by Streptomyces pactum," Research Laboratories, vol. 10, pp. 302-304, 1962.
Bibb et al., "Cloning, sequencing and deduced functions of a cluster of Streptomyces genes probably encoding biosynthesis of the polyketide antibiotic frenolicin," Gene, vol. 142 No. 1, pp. 31-39, 1994.
Biehl et al., "Anthelmintics for swine," Vet. Clin. North. Am. Food. Anim. Pract., vol. 2, pp. 481-487, 1986.
Binnie et al., "Heterologous biopharmaceutical protein expression in Streptomyces", TIB TECH, vol. 15, pp. 315-320, 1997.
Chen et al., "Identification of genes subject to positive selection in uropathogenic strains of Escherichia coli: A comparative genomics approach," PNAS, vol. 103, No. 15, pp. 5977-5982, 2006.

(Continued)

Primary Examiner — Paul A Zucker
Assistant Examiner — Mark Luderer
(74) Attorney, Agent, or Firm — Klarquist Sparkman, LLP

(57) ABSTRACT

This disclosure describes the molecular cloning of a pactamycin biosynthetic gene cluster from Streptomyces pactum ATCC 27456, characterization of individual genes in the gene cluster and the proteins encoded thereby as well as uses thereof. The pactamycin gene cluster is located within an 86.35 kilobases genetic locus and includes 53 open reading frames, 26 of which are considered to be the core cluster directly involved in the biosynthesis of pactamycin. The present disclosure also relates to the use of the pactamycin biosynthetic genes located within the identified gene cluster for drug design and development purposes, including the development of pactamycin analogs that are more efficacious and less toxic. Also provided are drugs and antibiotics so produced, as well as methods of their use.

18 Claims, 15 Drawing Sheets

(56) References Cited

OTHER PUBLICATIONS

Freitag et al., "Biosynthesis of the unusual 5,5-*gem*-dimethyl-deoxysugar noviose: investigation of the C-methyltransferase gene *cloU*," *Microbiology*, vol. 152, pp. 2433-2442, 2006.
Galm et al., "Cloning and analysis of the simocyclinone biosynthetic gene cluster of Streptomyces antibioticus Tü 6040," *Arch. Microbiol.*, vol. 178, pp. 102-114, 2002.
GenBank Accession No. AL939118. Complete genome sequence of the model actinomycete Streptomyces coelicolor A3(2), 2005 (221 pages).
Hayashi et al., "Studies on Neplanocin A, New Antitumor Antibiotic. II Structure Determination," *J. Antibiot.*, vol. 34, No. 6, pp. 675-680, 1981.
Holden et al., "Complete genomes of two clinical *Staphylococcus aureus* strains: Evidence for the rapid evolution of virulence and drug resistance," *PNAS*, vol. 101, No. 26, pp. 9786-9791, 2004.
Hurley et al., "PD 113,618 and PD 118,309, New Pactamycin Analogs," *J. Antibiot*, 39(8), pp. 1086-1091, Aug. 1986.
Ikeda et al., "Complete genome sequence and comparative analysis of the industrial microorganism *Streptomyces avermitilis,*" *Nature Biotechnology*, vol. 21, pp. 526-531, 2003.
International Preliminary Report on Patentability issued by the International Bureau of WIPO on Feb. 5, 2013, for related PCT Patent Application No. PCT/US2011/046322, 5 pp.
International Search Report and Written Opinion issued by the ISA/KR (Korean Intellectual Property Office) on Mar. 27, 2012, for related PCT Patent Application No. PCT/US2011/046322, 9 pp.
International Search Report and Written Opinion, dated Oct. 2, 2008, for corresponding PCT Patent Application No. PCT/US08/60876, filed Apr. 18, 2008, 10 pp.
Ishikawa et al., "The complete genomic sequence of *Nocardia farcinica* IFM 10152," *PNAS*, vol. 101, No. 41, pp. 14925-14930, 2004.
Ito et al., "Deciphering Pactamycin Biosynthesis and Engineered Production of New Pactamycin Analogues," *ChemBioChem*, vol. 10, pp. 2253-2265, 2009.
Jia et al., "Genetic Characterization of the Chlorothricin Gene Cluster as a Model for Spirotetronate Antibiotic Biosynthesis," *Chemistry & Biology*, vol. 13, pp. 575-585, 2006.
Kawamura et al., "Pyralomicins, Novel Antibiotics from *Microtetraspora spiralis* II. Structure Determination," *J. Antibiot.*, vol. 49, No. 7, pp. 651-656, 1996.
Kudo et al., "Biosynthesis of 2-Deoxystreptamine by Three Crucial Enzymes in *Streptomyces fradiae* NBRC 12773," *J. Antibiot.*, vol. 58, No. 12, pp. 766-774, 2005.
Kudo et al., "Cloning of the Pactamycin Biosynthetic Gene Cluster and Characterization of a Crucial Glycosyltransferase Prior to a Unique Cyclopentane Ring Formation", *J. Antibot.*, vol. 60, No. 8, pp. 492-503, 2007.
Kusaka et al., "*Streptomyces citricolor* Nov. Sp. and A New Antibiotic, Aristeromycin," *J. Antibiot.*, vol. 21, No. 4, pp. 255-263, 1968.
Kuzuyama et al., "Nucleotide Sequence of Fortimicin KL1 Methyltransferase Gene Isolated from *Micromonospora olivasterospora*, and Comparison of Its Deduced Amino Acid Sequence with Those of Methyltransferases Involved in the Biosynthesis of Bialaphos and Fosfomycin," *J. Antibiot.*, vol. 48, No. 10, pp. 1191-1193, 1995.
Mahmud, "The $C_7N$ aminocyclitol family of natural products," *Nat. Prod. Rep.*, vol. 20, pp. 137-166, 2003.
Mao et al., "Genetic Localization and Molecular Characterization of Two Key Genes (*mitAB*) Required for Biosynthesis of the Antitumor Antibiotic Mitomycin C," *J. Bacter.*, vol. 181, No. 7, pp. 2199-2208, 1999.
Mao et al., "Molecular characterization and analysis of the biosynthetic gene cluster for the antitumor antibiotic mitomycin C from *Streptomyces lavendulae* NRRL 2564," *Chemistry & Biology*, vol. 6, pp. 251-263, 1999.

Marsden et al., "Engineering Broader Specificity into an Antibiotic-Producing Polyketide Synthase," *Science*, vol. 279, pp. 199-202, 1998.
McDaniel et al., "Multiple genetic modification fo the erythromycin polyketide synthase to produce a library of novel 'unnatural' natural products," *PNAS*, vol. 96, pp. 1846-1851, 1999.
Molnar et al., "Biocatalytic Conversion of Avermectin to 4"-Oxo-Avermectin: Heterologous Expression of the *emal* Cytochrome P450 Monooxygenase," *Applied and Environmental Microbiology*, vol. 71, No. 11, pp. 6977-6985, 2005.
Moran et al., "Genome sequence of *Silicibacter pomeroyi* reveals adaptations to the marine environment," *Nature*, vol. 432, pp. 910-913, 2004.
Naganawa et al., "Biosynthesis of the Cyclitol Moiety of Pyralomicin 1a in *Nonomuraea spiralis* MI178-34F18," *J. Antibiot.*, vol. 55, No. 6, pp. 578-584, 2002.
Naganawa et al., "Hygromycin A, An Antitreponemal Substance II. Therapeutic Effect for Swine Dysentary," *J. Antibiot.*, vol. 40, No. 11, pp. 1627-1635, 1987.
Nishimura et al., "Structure, Biosynthesis, and Function of Queuosine in Transfer RNA," *Prog. Nucleic Acid Res. Mol. Biol.*, vol. 28, pp. 49-73, 1986.
Nunez et al., "The Biosynthetic Gene Cluster for the β-Lactam Carbapenem Thienamycin in *Streptomyes cattleya,*" *Chemistry & Biology*, vol. 10, pp. 301-311, 2003.
Omura et al., "Adecypenol, A Unique Adenosine Deaminase Inhibitor Containing Homopurine and Cyclopentene Rings; Taxonomy, Production and Enzyme Inhibition," *J. Antibiot.*, vol. 39, No. 9, pp. 1219-1224, 1986.
Omura et al., "Genome sequence of an industrial microorganism *Streptomyces avermitilis*: Deducing the ability of producing secondary metabolites," *PNAS*, vol. 98, No. 21, pp. 12215-12220, 2001.
Rascher et al., "Insights into the Biosynthesis of the Benzoquinone Ansamycins Geldanamycin and Herbimycin, Obtained by Gene Sequencing and Disruption," *Applied and Environmental Microbiology*, vol. 71, No. 8, pp. 4862-4871, 2005.
Rinehart et al., "Recent Biosynthetic Studies on Antibiotics," *J. Nat. Prod.*, vol. 43, No. 1, pp. 1-20, 1980.
Sakuda et al., "Search for Microbial Insect Growth Regulators II. Allosamidin, A Novel Insect Chitinase Inhibitor," *J. Antibiot.*, vol. 15, No. 3, pp. 296-300, 1987.
Schendel et al., "Formylglycinamide Ribonucleotide Synthetase from *Escherichia coli*: Cloning, Sequencing, Overproduction, Isolation, and Characterization", *Biochemistry*, vol. 28, No. 6, pp. 2459-2471, 1989.
Schupp et al., "Cloning and sequence analysis of the putative rifamycin polyketide synthase gene cluster from *Amycolatopsis mediterranei,*" *FEMS Microbiology Letters*, vol. 159, pp. 201-207, 1998.
Schwarz et al., "In vitro activities of spectinomycin and comparator agents against *Pasteurella multocida* and *Mannheimia haemolytica* from respiratory tract infections of cattle," *J. Antimicrobial Chemotherapy*, vol. 53, pp. 379-382, 2004.
Staunton et al., "Polyketide biosynthesis: a millennium review," *Nat. Prod. Rep.*, vol. 18, pp. 380-416, 2001.
Stutzman-Engwall et al., "Engineering the *aveC* gene to enhance the ratio of doramectin to its CHC-B2 analogue produced in *Streptomyces avermitilis,*" *Biotechnol. Bioeng.*, vol. 82, pp. 359-369, 2003.
Thieme et al., "Insights into Genome Plasticity and Pathogenicity of the Plant Pathogenic Bacterium *Xanthomonas campestris* pv. vesicatoria Revealed by the Complete Genome Sequence," *J. Bacter.*, vol. 187, No. 21, pp. 7254-7266, 2005.
Weller et al., "Biosynthesis of the Antitumor Antibiotic Pactamycin. A Methionine-Derived Ethyl Group and a $C_7N$ Unit, " *J. Amer. Chem. Soc.*, vol. 100, No. 21, pp. 6757-6760, 1978.
Wiley et al., "The Structure of Pactamycin," *J. Organic Chem.*, vol. 35, No. 5, pp. 1420-1425, 1969.
Yaginuma et al., "Studies on Neplanocin A, New Antitumor Antibiotic I. Producing Organism, Isolation and Characterization," *J. Antibiot.*, vol. 34, No. 4, pp. 359-366, 1981.

* cited by examiner

```
                          SEQUENCE LISTING

<160> NUMBER OF SEQ ID NOS: 58

<210> SEQ ID NO 1
<211> LENGTH: 483
<212> TYPE: PRT
<213> ORGANISM: Streptomyces pactum

<400> SEQUENCE: 1

Val Phe Arg Glu Asp Leu Val Ala Gly Ile Gln Asp Leu Gly Gly Ala
1               5                   10                  15

Gly Leu Ser Cys Ala Thr Ser Glu Leu Ala Ser Ala Gly Ser Gly Gly
            20                  25                  30

Met Arg Val Asp Leu Asp Ala Val Pro Leu Arg Asp Ala Thr Leu Ser
        35                  40                  45

Pro Glu Glu Ile Leu Met Ser Glu Ser Gln Glu Arg Met Cys Ala Ile
    50                  55                  60

Val Glu Pro Gly Lys Val Glu Arg Phe Leu Glu Ile Cys Glu Lys Trp
65                  70                  75                  80

Asp Val Ile Ala Thr Val Ile Gly Glu Val Thr Asp Gly Asp Arg Leu
                85                  90                  95

Glu Ile Phe Trp His Gly Glu Gln Ile Val Asp Val Pro Pro Arg Ser
            100                 105                 110

Val Ala His Glu Gly Pro Thr Tyr His Arg Pro Tyr Ala Arg Pro Asp
        115                 120                 125

Trp Gln Asp Ala Leu Gln Ala Asp Ala Gly Lys Leu Pro Arg Pro
    130                 135                 140

Arg Thr Ser Glu Glu Leu Arg Asp Gln Val Leu Ala Leu Val Gly Ser
145                 150                 155                 160

Pro Asn Gln Ala Ser Lys Ala Trp Val Thr Asp Gln Tyr Asp Arg Phe
                165                 170                 175

Val Gln Gly Asn Thr Val Leu Ala Gln Pro Glu Asp Ala Gly Val Ile
            180                 185                 190

Arg Ile Asp Glu Glu Ser Asn Leu Gly Val Ala Leu Ala Thr Asp Gly
        195                 200                 205

Asn Gly Arg Tyr Thr Lys Leu Asp Pro Tyr Thr Gly Ala Gln Leu Ala
    210                 215                 220

Leu Ala Glu Ala Tyr Arg Asn Val Ala Ala Thr Gly Ala Arg Pro Leu
225                 230                 235                 240

Ala Val Ser Asp Cys Leu Asn Phe Gly Ser Pro Glu Asp Pro Ala Val
                245                 250                 255

Met Trp Gln Phe Ala Glu Ala Thr Arg Gly Leu Ala Asp Gly Cys Gln
            260                 265                 270

Lys Leu Gly Thr Pro Val Thr Gly Gly Asn Val Ser Leu Tyr Asn Gln
        275                 280                 285

Thr Gly Glu Asn Ala Ile His Pro Thr Pro Val Val Ala Val Leu Gly
    290                 295                 300

Val Ile Asp Asp Val Ser Arg Arg Thr Pro Ile Ala Phe Ala Glu Asp
305                 310                 315                 320

Gly Gln Leu Leu Tyr Leu Leu Gly Asp Thr Arg Glu Glu Phe Gly Gly
```

```
                    325                 330                 335
Ser Ala Trp Ser Gln Val Val His Asp His Leu Gly Leu Pro Pro
                340                 345                 350

Ala Val Asp Leu Asp Arg Glu Lys Leu Leu Ala Glu Ile Leu Ile Ala
                355                 360                 365

Ala Ser Arg Asp Gly Met Ile Asp Ala Ala His Asp Leu Ser Asp Gly
            370                 375                 380

Gly Leu Ile Gln Ala Val Val Glu Ser Cys Leu Arg Gly Gly Lys Gly
385                 390                 395                 400

Ala Arg Leu Ile Val Pro Asp Gly Leu Asp Ala Phe Thr Leu Leu Phe
                405                 410                 415

Ser Glu Ser Ala Gly Arg Ala Val Val Ala Val Pro Arg Ser Glu Glu
                420                 425                 430

Val Arg Phe Asn Asp Met Cys Gly Ala Arg Gly Leu Pro Ala Thr Arg
                435                 440                 445

Ile Gly Val Val Asp Gly Asp Thr Val Glu Val Gln Gly Glu Phe Ser
                450                 455                 460

Ile Pro Leu Ala Glu Leu Lys Gln Val His Glu Ala Thr Ile Pro Ala
465                 470                 475                 480

Leu Leu Ala

<210> SEQ ID NO 2
<211> LENGTH: 295
<212> TYPE: PRT
<213> ORGANISM: Streptomyces pactum

<400> SEQUENCE: 2

Val Pro Gly Val Ile Gly Leu Ser Gly Ala Val Pro Val Val Leu Gly
1               5                   10                  15

Met Leu Ala Gly Met Pro Ala Ala Pro Arg Lys Ser Arg Ala Arg Thr
                20                  25                  30

Tyr Asp Phe Ala Arg Thr His Ala Ala Val Ala Ala Gln Leu Asp His
            35                  40                  45

Val Arg Asp Ala Val Gly Arg Leu Thr Asp Glu Gln Leu Ala Ala Pro
50                  55                  60

Thr Arg Leu Ser Gly Pro Ala Asp Thr Gly Gly Ala Gly Ala Val Trp
65                  70                  75                  80

Thr Val Arg Asp Leu Val Ala His Leu Val Leu Val Glu His Val
                85                  90                  95

Asn Arg Asn Leu Glu Gln Pro Ala Pro Pro Ala Val Glu Val Thr Leu
                100                 105                 110

Thr Asp Trp Val Phe Ala Thr Ala Thr Phe Ala Gly Ala Ile Gly Asp
            115                 120                 125

Asp Ala Arg Ser Ala Ala Gly Ser Ala Asp Leu Ala Glu Ser Leu Asp
        130                 135                 140

Arg Ala Ala Ala Arg Phe Ala Glu Leu Val Pro Pro Ala His Pro Asp
145                 150                 155                 160

Arg Leu Leu Ala Ala Arg Val Gly Ala Ile Arg Leu Asp Asp Phe Leu
                165                 170                 175

Val Thr Arg Cys Val Glu Leu Val Val His Thr Asp Asp Leu Ala Ala
            180                 185                 190

Ala Thr Gly Ala Glu Ile Arg Tyr Asp Arg Gln Ala Leu Ala Ala Ala
        195                 200                 205

Val Arg Val Leu Ala Asp Ala Leu Ala Ala Arg Ala Pro Gly Gly Ser
```

```
                        210                 215                 220
Val Glu Val Arg Val Pro Pro Phe Ala Val Val Gln Cys Val Glu Gly
225                 230                 235                 240

Pro Arg His Thr Arg Gly Thr Pro Pro Asn Val Val Glu Thr Asp Pro
                245                 250                 255

Leu Thr Trp Leu Arg Leu Ala Thr Gly Arg Arg Thr Trp Ala Glu Ala
            260                 265                 270

Val Glu Ala Ala Glu Val Thr Ala Ser Gly Glu Arg Ala Asp Leu Ser
        275                 280                 285

Gly Leu Leu Pro Leu Leu Gly
    290                 295

<210> SEQ ID NO 3
<211> LENGTH: 524
<212> TYPE: PRT
<213> ORGANISM: Streptomyces pactum

<400> SEQUENCE: 3

Val Pro Arg Arg Thr Arg Pro Pro Ala Ala Gly Gly Ser Ala Arg Leu
1               5                   10                  15

Pro Arg Ser Pro Ala Met Ser Ser Asn Asp Arg Pro Ser Pro Ala Asp
            20                  25                  30

Arg Ser Pro Gly Thr Ala Pro Asp His His Asp Ala Gly Thr Ser Gly
        35                  40                  45

Arg Pro Leu Ser Arg Arg Gly Phe Gly Gln Leu Ala Ala Val Ser Ala
    50                  55                  60

Gly Ala Gly Leu Ala Ala Thr Ala Ala Thr Gly Leu Ala Ala Ala Glu
65                  70                  75                  80

Ala Ala Ala Asp Gly Arg Gly Ala Val Arg Glu Arg Pro Phe Arg Ala
                85                  90                  95

Ala Thr His Arg Arg Ser Pro Arg Pro Asn Ile Leu Phe Ile Leu Ala
            100                 105                 110

Asp Asp Leu Gly Trp Ala Asp Leu Ser Ser Tyr Gly Ser Pro His Ile
        115                 120                 125

His Thr Pro His Leu Asp Arg Leu Ala Arg Gln Gly Val Arg Phe Thr
    130                 135                 140

His Ala Tyr Ala Gly Ser Ser Thr Cys Ser Pro Thr Arg Phe Ser Leu
145                 150                 155                 160

Tyr Thr Gly Arg Phe Pro Gly Arg Thr Pro Gly Gly Leu His Glu Pro
                165                 170                 175

Ile Pro Gly Gly Ser Asp Ala Gly Leu Pro Pro Asn His Pro Thr Leu
            180                 185                 190

Ala Ser Leu Leu Arg Gly Ala Gly Tyr Ala Thr Ala Leu Ile Gly Lys
        195                 200                 205

Trp His Cys Gly Tyr Leu Pro Asp His Ser Pro Thr Lys Ser Gly Trp
    210                 215                 220

Glu Thr Phe Phe Gly Asn Phe Gly Gly Ala Leu Glu Tyr Tyr Ser Lys
225                 230                 235                 240

Leu Gly Leu Thr Gly Glu Tyr Asp Leu Tyr Glu Gly Glu Val Ser His
                245                 250                 255

Gln Asp Leu Arg Tyr Tyr Thr Arg Ile Ile Thr Glu Arg Ala Ala Glu
            260                 265                 270

Tyr Ile Gly Arg Asp His Arg Lys Pro Trp Leu Leu Asn Leu Asn Phe
        275                 280                 285
```

```
Thr Thr Pro His Trp Pro Trp Ile Ala Glu Gly Asp Thr Ala Glu Ser
    290                 295                 300

Ala Arg Val Thr Ala Arg Ile Lys Ala Gly Gln Arg Gly Ala Leu Asn
305                 310                 315                 320

His Arg Asp Gly Gly Ser Leu Glu Lys Tyr Arg Glu Leu Val Glu Asp
                325                 330                 335

Leu Asp Arg Ser Val Gly Glu Val Leu Ala Ala Leu Arg Arg Ser Gly
            340                 345                 350

Gln Glu Glu Asn Thr Leu Val Val Phe Ala Ser Asp Asn Gly Gly Glu
        355                 360                 365

Arg Phe Ser Tyr Gln Trp Pro Leu Ser Gly Lys Phe Thr Leu Leu
370                 375                 380

Glu Gly Gly Ile Arg Val Pro Thr Ile Val Arg Trp Pro Ala Arg Ile
385                 390                 395                 400

Asp Gly Gly Ala Gln Val Ser His Glu Pro Val Tyr Thr Pro Asp Trp
                405                 410                 415

Thr Ala Thr Leu Leu Glu Val Gly Gly Ala Arg Pro Asp Arg Ala His
            420                 425                 430

Pro Leu Asp Gly Thr Ser Leu Ala Gly Tyr Leu Leu Arg Gly Glu Glu
        435                 440                 445

Leu Pro Glu Arg Asp Leu Phe Trp Arg Val Arg Gly Glu Arg Ala Leu
450                 455                 460

Arg Arg Gly Ala Trp Lys Tyr His Arg Asp Ala Gln Gly Arg Asp His
465                 470                 475                 480

Leu Phe Asn Ile Pro Asp Asp Pro Arg Glu Gln Ala Asp Arg Ala Ala
                485                 490                 495

Leu Glu Pro Glu Arg Leu Ala Ser Leu Arg Thr Ala Trp Glu Arg Thr
            500                 505                 510

Ala Ala Thr Leu Leu Pro Tyr Pro Ala Ala Gly Gly
        515                 520

<210> SEQ ID NO 4
<211> LENGTH: 527
<212> TYPE: PRT
<213> ORGANISM: Streptomyces pactum

<400> SEQUENCE: 4

Val Ile Tyr Val Arg Tyr Arg Val Leu Arg Ser Glu Ala Pro Arg Asn
1               5                   10                  15

Trp Pro Arg Leu Asp Asp Val Pro Arg Gly Asp Gly Arg Leu Ser His
            20                  25                  30

Asp Leu Leu Pro Gly Glu Lys Gly Pro Gln Asp Ala Cys Gly Val Phe
        35                  40                  45

Gly Val Trp Ala Pro Gly Glu Val Ala Lys Leu Thr Tyr Phe Gly
    50                  55                  60

Leu Tyr Ala Leu Gln His Arg Gly Gln Glu Ser Ala Gly Ile Ala Val
65                  70                  75                  80

Ser Asn Gly Ser Gln Ile Leu Val Phe Lys Asp Met Gly Leu Val Ser
                85                  90                  95

Gln Val Phe Asp Glu Thr Ser Leu Gly Ser Leu Gln Gly His Ile Ala
            100                 105                 110

Val Gly His Ala Arg Tyr Ser Thr Thr Gly Ala Ser Val Trp Glu Asn
        115                 120                 125

Ala Gln Pro Thr Phe Arg Ala Thr His Gly Ser Ile Ala Leu Gly
    130                 135                 140
```

```
His Asn Gly Asn Leu Val Asn Thr Ala Glu Leu Ala Glu Met Val Ala
145                 150                 155                 160

Asp Leu Pro Arg Gln Asp Gly Arg Ala Thr Gln Val Ala Ala Thr Asn
            165                 170                 175

Asp Thr Asp Leu Val Thr Ala Leu Leu Ala Gly Gln Thr Gly Glu Asp
            180                 185                 190

Gly Lys Pro Leu Thr Val Glu Glu Ser Ala Ala Gln Val Leu Pro Lys
            195                 200                 205

Val Lys Gly Ala Phe Ser Leu Val Phe Met Asp Glu Gln Thr Leu Tyr
210                 215                 220

Ala Ala Arg Asp Pro Gln Gly Ile Arg Pro Leu Val Leu Gly Arg Leu
225                 230                 235                 240

Glu Arg Gly Trp Val Val Ala Ser Glu Thr Ala Ala Leu Asp Ile Val
                245                 250                 255

Gly Ala Ser Phe Val Arg Glu Val Glu Pro Gly Glu Leu Ile Ala Ile
                260                 265                 270

Asp Glu Asn Gly Met Arg Ala Ser Arg Phe Ala Asp Ala Arg Pro Lys
            275                 280                 285

Gly Cys Val Phe Glu Tyr Val Tyr Leu Ala Arg Pro Asp Thr Asp Ile
290                 295                 300

Ala Gly Arg Asn Val Tyr Leu Ser Arg Val Glu Met Gly Arg Arg Leu
305                 310                 315                 320

Ala Ala Glu Ala Pro Ala Asp Ala Asp Leu Val Ile Ala Thr Pro Glu
                325                 330                 335

Ser Gly Thr Pro Ala Ala Ile Gly Tyr Ala Glu Ala Ser Gly Ile Pro
            340                 345                 350

Tyr Gly Ser Gly Leu Val Lys Asn Ala Tyr Val Gly Arg Thr Phe Ile
            355                 360                 365

Gln Pro Ser Gln Thr Ile Arg Gln Leu Gly Ile Arg Leu Lys Leu Asn
370                 375                 380

Pro Leu Lys Glu Val Ile Arg Gly Lys Arg Leu Val Val Val Asp Asp
385                 390                 395                 400

Ser Ile Val Arg Gly Asn Thr Gln Arg Ala Leu Val Arg Met Leu Arg
                405                 410                 415

Glu Ala Gly Ala Ala Glu Val His Ile Arg Ile Ser Ser Pro Pro Ile
                420                 425                 430

Lys Trp Pro Cys Phe Phe Gly Ile Asp Phe Ala Thr Arg Ala Glu Leu
            435                 440                 445

Ile Ala Asn Gly Leu Ser Val Glu Glu Ile Gly Thr Ser Leu Gly Ala
            450                 455                 460

Asp Ser Leu Ala Tyr Ile Ser Leu Asp Ala Met Val Glu Ala Thr Thr
465                 470                 475                 480

Ile Ala Lys Pro Asp Leu Cys Arg Ala Cys Phe Asp Gly Glu Tyr Pro
                485                 490                 495

Met Glu Leu Pro Asp Pro Glu Leu Leu Gly Lys His Leu Leu Glu Thr
            500                 505                 510

Glu Leu Ala Gly Gly Thr Asp Ala Ala Asp Ala Leu Arg Arg Pro
            515                 520                 525
```

<210> SEQ ID NO 5
<211> LENGTH: 366
<212> TYPE: PRT
<213> ORGANISM: Streptomyces pactum

<400> SEQUENCE: 5

| Met | Ser | Ala | Glu | Ser | Ser | Glu | Arg | Ala | Pro | Gln | His | Ala | Gly | Ala | Gly |
| 1 | | | | 5 | | | | | 10 | | | | | 15 | |

Ala Ser Tyr Ala Gly Ala Gly Val Asp Ile Glu Ala Gly Asp Arg Ala
                20                  25                  30

Val Glu Leu Met Lys Glu Trp Val Lys Lys Ala Thr Arg Pro Glu Val
            35                  40                  45

Val Gly Gly Leu Gly Gly Phe Ala Gly Leu Phe Asp Ala Ser Ala Leu
        50                  55                  60

Lys Arg Tyr Glu Arg Pro Leu Leu Ala Ser Ala Thr Asp Gly Val Gly
65                  70                  75                  80

Thr Lys Val Asp Ile Ala Arg Arg Met Gly Val Tyr Asp Thr Ile Gly
                85                  90                  95

His Asp Leu Val Gly Met Val Val Asp Leu Val Val Cys Gly Ala
                100                 105                 110

Glu Pro Leu Phe Met Thr Asp Tyr Ile Cys Val Gly Lys Val His Pro
            115                 120                 125

Glu Arg Val Ala Ala Ile Val Lys Gly Ile Ala Glu Gly Cys Val Leu
        130                 135                 140

Ala Gly Cys Ala Leu Val Gly Gly Glu Thr Ala Glu His Pro Gly Leu
145                 150                 155                 160

Leu Gly Val Asp Glu Phe Asp Val Ala Gly Ala Gly Thr Gly Val Val
                165                 170                 175

Glu Ala Asp Arg Leu Leu Gly Ala Asp Arg Ile Arg Ser Gly Asp Ala
            180                 185                 190

Val Ile Ala Met Ala Ser Ser Gly Leu His Ser Asn Gly Tyr Ser Leu
        195                 200                 205

Val Arg His Val Leu Phe Asp Arg Ala Gly Trp Ser Leu Asp Arg Glu
210                 215                 220

Val Ala Glu Leu Gly Arg Thr Leu Gly Glu Glu Leu Leu Glu Pro Thr
225                 230                 235                 240

Arg Ile Tyr Ser Leu Asp Cys Leu Ala Leu Thr Arg Thr Thr Glu Val
                245                 250                 255

His Gly Phe Ser His Val Thr Gly Gly Leu Ala Asn Asn Leu Ala
            260                 265                 270

Arg Val Val Pro Asp His Leu His Ala Thr Val Asp Arg Ser Thr Trp
        275                 280                 285

Thr Pro Gly Ala Ile Phe Asp Leu Val Gly Gln Ala Gly Ala Val Glu
290                 295                 300

Arg Leu Glu Leu Glu Lys Thr Leu Asn Met Gly Val Gly Met Val Ala
305                 310                 315                 320

Val Val Pro Gln Glu Ser Val Asp Val Ala Leu Thr Thr Leu Ala Asp
                325                 330                 335

Arg Gly Leu Asp Ser Trp Val Cys Gly Glu Val Val Asp Arg Asp Ala
            340                 345                 350

Ala His Thr Glu Ala Val Thr Leu Thr Gly Asp Tyr Ala Ala
        355                 360                 365

<210> SEQ ID NO 6
<211> LENGTH: 364
<212> TYPE: PRT
<213> ORGANISM: Streptomyces pactum

<400> SEQUENCE: 6

Val Thr Asp Val Arg Pro Thr Asp Ala Asp Gly Val Leu Asn Thr
1               5                   10                  15

Leu Phe Arg Ser Asp Gln Gly Gly His Glu Gln Val Val Leu Cys Gln
            20                  25                  30

Asp Arg Ala Thr Gly Leu Lys Ala Val Ile Ala Leu His Ser Thr Ala
        35                  40                  45

Leu Gly Pro Ala Leu Gly Gly Thr Arg Phe His Ala Tyr Ala Ser Asp
    50                  55                  60

Glu Glu Ala Val Leu Asp Ala Leu Asn Leu Ser Arg Gly Met Ser Tyr
65                  70                  75                  80

Lys Asn Ala Leu Ala Gly Leu Asp His Gly Gly Gly Lys Ala Val Ile
                85                  90                  95

Ile Gly Asp Pro Glu Gln Leu Lys Thr Glu Glu Leu Leu Leu Ala Tyr
            100                 105                 110

Gly Arg Phe Val Ala Ser Leu Gly Gly Arg Tyr Val Thr Ala Cys Asp
        115                 120                 125

Val Gly Thr Tyr Val Ala Asp Met Asp Val Val Ala Arg Glu Cys Arg
    130                 135                 140

Trp Thr Thr Gly Arg Ser Pro Glu Asn Gly Gly Ala Gly Asp Ser Ser
145                 150                 155                 160

Val Leu Thr Ala Phe Gly Val Phe Gln Gly Met Arg Ala Ser Ala Gln
                165                 170                 175

Ala Ala Trp Gly Ala Pro Thr Leu Arg Gly Arg Val Gly Val Ala
            180                 185                 190

Gly Val Gly Lys Val Gly His His Leu Val Ala His Leu Val Glu Asp
    195                 200                 205

Gly Ala Glu Val Val Val Thr Asp Val Arg Ala Glu Ser Val Asp Arg
    210                 215                 220

Ile Arg Ser Lys Phe Pro Gln Val Thr Ala Val Ala Asp Thr Asp Ser
225                 230                 235                 240

Leu Ile Arg Ala Asp Leu Asp Val Tyr Ala Pro Cys Ala Leu Gly Gly
                245                 250                 255

Ala Leu Asn Asp Asp Thr Val Pro Ala Leu Thr Ala Lys Val Val Cys
            260                 265                 270

Gly Ala Ala Asn Asn Gln Leu Ala His Pro Gly Val Glu Lys Asp Leu
        275                 280                 285

Ala Asp Arg Gly Ile Leu Tyr Ala Pro Asp Tyr Val Val Asn Ala Gly
    290                 295                 300

Gly Val Ile Gln Val Ala Asp Glu Leu His Gly Phe Asp Phe Asp Arg
305                 310                 315                 320

Ala Lys Ala Lys Ala Thr Lys Ile Phe Asp Thr Thr Val Ala Ile Phe
                325                 330                 335

Glu Arg Ala Ala Lys Asp Gly Val Pro Pro Ala Val Ala Ala Asp Arg
            340                 345                 350

Leu Ala Glu Gln Arg Ile Ala Glu Ala Arg Gln Ala
        355                 360

<210> SEQ ID NO 7
<211> LENGTH: 272
<212> TYPE: PRT
<213> ORGANISM: Streptomyces pactum

<400> SEQUENCE: 7

Val Thr Val Pro Tyr Ala Ala Tyr Leu Arg Val Tyr Glu Pro Leu Ala
1               5                   10                  15

Ala Phe Pro Glu Pro Glu Arg Thr His Trp Ala Arg Tyr Ala Arg Arg
            20                  25                  30

Asp Arg Leu Pro Gly Ala Gln Glu Leu Arg Arg Ala Leu Thr Asp
        35                  40                  45

Leu Leu Pro Leu Pro Pro Val Pro Val Pro Val His Glu Ser Pro Asp
50                  55                  60

Ala Phe Val Thr Val Val Asp Gly Ile Val Cys Val Cys Pro Trp Arg
65                  70                  75                  80

Thr Arg Leu Arg Gly Trp Met Ala Leu Glu Glu Ala Ala Glu Arg Tyr
                85                  90                  95

Pro Ala Pro Leu Leu Asp Ala Val Leu Pro Pro Leu Val Arg Arg Gln
            100                 105                 110

Ala Val Ala Asp Phe Glu Arg Trp Leu Glu Arg Asn Pro Asp Ala Arg
        115                 120                 125

Pro Trp Ile Arg Ser Ala Thr Trp His Val Pro Val Arg Trp Phe Val
130                 135                 140

Leu Phe Ala Asp Glu Glu Arg Glu Phe Thr Lys Gly Ser Glu Gly Leu
145                 150                 155                 160

Val Met Arg Tyr Arg Thr Pro Met Val Glu Ala Arg Arg Val Ala
                165                 170                 175

Arg Gly Leu Lys Val Leu Arg Glu Thr Leu Gly Glu Gly Pro Leu Ile
            180                 185                 190

Asp Gly Leu Val Asp Val Gly Arg Trp Leu Glu Glu Phe His Pro Arg
        195                 200                 205

Ser Leu Val Glu Leu Asp Tyr Gly Gly Leu Val Glu Val Val Pro Glu
    210                 215                 220

Glu Arg Leu His Ala Asp Arg Ser Ala Arg Asp Val Ala Glu Gly Leu
225                 230                 235                 240

Ser Ala Leu Arg Asp Gly Asp Gly Glu Arg Ala Gly Gly Ala Tyr Glu
                245                 250                 255

Arg Leu Thr Glu Arg Trp Ala Ala Val Arg Gly Leu Gln His Ala Ser
            260                 265                 270

<210> SEQ ID NO 8
<211> LENGTH: 211
<212> TYPE: PRT
<213> ORGANISM: Streptomyces pactum

<400> SEQUENCE: 8

Met Pro Ala Thr Ala Arg Arg Glu Ile Arg Ala Leu Leu Arg Ala His
1               5                   10                  15

Leu Ser Ala Ala Ala Gly Arg Pro His Ser Thr Arg His Cys Pro Val
            20                  25                  30

Cys His Arg Leu Leu Arg Leu Ala Met Gln Pro Gly Ala Ala Asp Gly
        35                  40                  45

Arg Pro Arg Tyr Glu Arg Ala Ala Pro Ala Ala Pro Ala Ala Ala Thr
    50                  55                  60

Val Pro Ser Pro Ala Pro Val Pro Gly Arg Pro Ser Ser Gly Pro Gln
65                  70                  75                  80

Glu Ala Thr Pro Pro Ala Pro Thr Gly Ala Arg Pro Thr Pro Ala
                85                  90                  95

Thr Pro Ser Ala Pro Pro Ala Arg Pro Ala Arg Ser Ala Ala Ser Ala
            100                 105                 110

Pro Pro Ala Arg Ser Ala Thr Ala Leu Pro Ala Pro Ser Ala Ser Pro

```
                115                 120                 125
Ala Arg Pro Glu Pro Val Ala Arg Pro Ala Ala Gly Pro Ser Gly
    130                 135                 140

Ser Val Pro Gly Thr Thr Gly Thr Glu Asp Arg Gly Thr Thr Arg Pro
145                 150                 155                 160

Leu Ser Thr Pro Ala Ser Glu Ala Ala Gly Ala Thr Ala Thr Ala Gly
                165                 170                 175

Ala Gly Arg Pro Leu Pro Asp Gly Pro Thr Gly Pro Ala Thr Pro Glu
            180                 185                 190

Arg Ala Ala Arg Pro Ala Ala Gly Thr Thr Pro Ser Arg Thr Ser Asp
        195                 200                 205

Arg Thr Arg
    210

<210> SEQ ID NO 9
<211> LENGTH: 1328
<212> TYPE: PRT
<213> ORGANISM: Streptomyces pactum

<400> SEQUENCE: 9

Met Ser Thr Thr Pro Ala Pro Thr Leu Pro Ala Leu Leu Glu Arg Ile
1               5                   10                  15

Pro Glu Leu Met Leu Arg Asp Gln Gln Arg Leu Gly Arg Arg Leu Asp
            20                  25                  30

Gly Ala Arg Arg Ile Arg Lys Pro Glu Ala Arg Asp Ala Val Leu Ala
        35                  40                  45

Glu Ile Ala Ala Asp Ile Asp Arg Ala Glu Ser Arg Val Ala Asp Arg
    50                  55                  60

Arg Ala Ala Val Pro Glu Val Ser Tyr Pro Glu Ser Leu Pro Val Ser
65                  70                  75                  80

Gln Lys Lys Asp Ala Ile Ala Glu Ala Ile Arg Asp His Gln Val Val
                85                  90                  95

Ile Val Ala Gly Glu Thr Gly Ser Gly Lys Thr Thr Gln Ile Pro Lys
            100                 105                 110

Ile Cys Leu Glu Leu Gly Arg Gly Val Arg Gly Leu Ile Gly His Thr
        115                 120                 125

Gln Pro Arg Arg Ile Ala Ala Arg Thr Val Ala Glu Arg Val Ala Glu
    130                 135                 140

Glu Leu Arg Thr Pro Leu Gly Glu Ser Val Gly Trp Lys Val Arg Phe
145                 150                 155                 160

Thr Asp Gln Val Ser Gln Asp Thr His Val Lys Leu Met Thr Asp Gly
                165                 170                 175

Ile Leu Leu Ala Glu Ile Gln Thr Asp Arg Glu Leu Arg Gln Tyr Asp
            180                 185                 190

Thr Ile Ile Ile Asp Glu Ala His Glu Arg Ser Leu Asn Ile Asp Phe
        195                 200                 205

Ile Leu Gly Tyr Leu Ala Gln Leu Leu Pro Arg Arg Pro Asp Leu Lys
    210                 215                 220

Val Val Ile Thr Ser Ala Thr Ile Asp Pro Glu Arg Phe Ser Arg His
225                 230                 235                 240

Phe Gly Asp Ala Pro Ile Ile Glu Val Ser Gly Arg Thr Tyr Pro Val
                245                 250                 255

Glu Val Arg Tyr Arg Pro Leu Leu Glu Glu Gly Gly Glu Asp Gly Asp
            260                 265                 270
```

-continued

```
Arg Asp Gln Ile Thr Ala Ile Cys Glu Ala Val Asp Glu Leu Arg Gly
        275                 280                 285

Glu Gly Pro Gly Asp Ile Leu Val Phe Leu Ser Gly Glu Arg Glu Ile
290                 295                 300

Arg Asp Thr Ala Asp Ala Leu Asn Lys Arg Gln Leu Pro Met Thr Glu
305                 310                 315                 320

Val Leu Pro Leu Tyr Ala Arg Leu Ser His Ala Glu Gln His Arg Val
                325                 330                 335

Phe Gln Arg His Thr Gly Arg Arg Ile Val Leu Ala Thr Asn Val Ala
            340                 345                 350

Glu Thr Ser Leu Thr Val Pro Gly Ile Arg Tyr Val Ile Asp Thr Gly
        355                 360                 365

Met Ala Arg Ile Ser Arg Tyr Ser Tyr Arg Thr Lys Val Gln Arg Leu
370                 375                 380

Pro Ile Glu Pro Ile Ser Gln Ala Ser Ala Asn Gln Arg Lys Gly Arg
385                 390                 395                 400

Cys Gly Arg Thr Ser Asp Gly Ile Cys Ile Arg Leu Tyr Ser Glu Glu
                405                 410                 415

Asp Phe Leu Ser Arg Pro Glu Phe Thr Asp Ala Glu Ile Leu Arg Thr
            420                 425                 430

Asn Leu Ala Ser Val Ile Leu Gln Met Thr Ala Ala Gly Leu Gly Asp
        435                 440                 445

Ile Glu Lys Phe Pro Phe Ile Asp Pro Pro Asp Arg Arg Asn Ile Lys
450                 455                 460

Asp Gly Val Gln Leu Leu Glu Glu Leu Gly Ala Ile Asp Pro Gln Gln
465                 470                 475                 480

Lys Asp Leu Arg Lys Arg Leu Thr Pro Leu Gly Arg Lys Leu Ser Gln
                485                 490                 495

Leu Pro Val Asp Pro Arg Leu Ala Arg Met Val Leu Glu Ala Asp Arg
            500                 505                 510

Thr Gly Cys Ala Arg Glu Val Met Val Ile Ala Ala Ala Leu Ser Ile
        515                 520                 525

Gln Asp Pro Arg Glu Arg Pro Ala Asp Lys Gln Gln Gln Ala Asp Gln
530                 535                 540

Asn His Ala Arg Phe Lys Asp Glu Asn Ser Asp Phe Leu Ala Phe Leu
545                 550                 555                 560

Asn Leu Trp Arg Tyr Val Arg Glu Arg Gln Lys Glu Leu Ser Ser Ser
                565                 570                 575

Ala Phe Arg Arg Met Cys Arg Asn Glu Tyr Leu Asn Tyr Leu Arg Ile
            580                 585                 590

Arg Glu Trp Gln Asp Ile Tyr Ser Gln Leu Arg Thr Val Ala Lys Thr
        595                 600                 605

Met Gly Ile His Leu Asn Glu Gln Asp Ala Ala Pro Asp His Val His
610                 615                 620

Thr Ala Leu Leu Ala Gly Leu Leu Ser His Val Gly Leu Lys Asn Thr
625                 630                 635                 640

Val Ala Glu Gly Gly Lys Glu Thr Gly Lys Gly Asn Glu Tyr Leu Gly
                645                 650                 655

Ala Arg Gly Ala Lys Phe Ala Val Phe Pro Gly Ser Ala Leu Phe Lys
            660                 665                 670

Lys Pro Pro Arg Trp Ile Met Ser Ala Glu Leu Val Glu Thr Ser Arg
        675                 680                 685

Leu Trp Ala Arg Val Asn Ala Arg Ile Glu Pro Glu Trp Ile Glu Pro
```

```
              690                 695                 700
Leu Ala Gln His Leu Val Lys Arg Thr Tyr Ser Glu Pro His Trp Glu
705                 710                 715                 720
Gln Lys Gln Ala Ala Val Met Ala Tyr Glu Arg Val Thr Leu Tyr Gly
                    725                 730                 735
Val Pro Ile Val Ala Gln Arg Lys Val Asn Tyr Gly Arg Ile Asp Pro
                740                 745                 750
Glu Thr Ser Arg Asp Leu Phe Ile Arg Asn Ala Leu Val Glu Gly Asp
            755                 760                 765
Trp Arg Thr His His Gln Phe Phe His Asp Asn Arg Lys Leu Leu Gly
        770                 775                 780
Glu Val Glu Glu Leu Glu His Arg Ala Arg Arg Asp Ile Leu Val
785                 790                 795                 800
Asp Asp Glu Thr Leu Phe Asp Phe Tyr Asp Gln Arg Ile Pro Glu His
                    805                 810                 815
Val Val Ser Gly Ala His Phe Asp Ser Trp Trp Lys His Lys Arg Arg
                820                 825                 830
Glu Glu Pro Glu Leu Leu Asn Phe Glu Lys Ser Met Leu Ile Asn Glu
            835                 840                 845
Arg Ala Glu Gly Val Thr Lys Asp Ala Tyr Pro Asp Thr Trp Arg Gln
        850                 855                 860
Arg Asn Leu Lys Phe Arg Val Thr Tyr Gln Phe Glu Pro Gly Ala Asp
865                 870                 875                 880
Ala Asp Gly Val Thr Val His Ile Pro Leu Gln Val Leu Asn Gln Val
                    885                 890                 895
Ser Pro Glu Gly Phe Asp Trp Gln Ile Pro Gly Leu Arg Glu Asp Leu
                900                 905                 910
Val Thr Glu Leu Ile Arg Ser Leu Pro Lys Pro Ile Arg Arg Asn Cys
            915                 920                 925
Val Pro Ala Pro Asn Tyr Ala Lys Arg Phe Leu Asp Ser Ala Val Pro
        930                 935                 940
Pro Ser Leu Pro Ala Gly Gly Gln Glu Gly Pro Thr Gln Glu Pro Leu
945                 950                 955                 960
Thr Val Ala Leu Gly Arg Glu Leu Gln Arg Met Thr Gly Val Arg Ile
                    965                 970                 975
Glu Pro Asp Trp Asp Pro Ser Lys Val Pro Asp His Leu Lys Ile
                980                 985                 990
Thr Phe Arg Val Val Asp Glu Arg Arg Arg Lys Leu Ala Glu Asp Lys
            995                 1000                1005
Asp Leu Glu Ala Leu Arg Leu Arg Leu Lys Pro Lys Thr Arg Ala
        1010                1015                1020
Ala Ile Thr Lys Ala Phe Ala Thr Ser Lys Glu Gly Gly Gly Ile
        1025                1030                1035
Glu Gln Arg Ser Gly Leu Thr Ser Trp Thr Val Gly Ala Leu Pro
        1040                1045                1050
Arg Thr Phe Glu Thr Arg Arg Ala Gly Gln Pro Val Lys Ala Tyr
        1055                1060                1065
Pro Ala Leu Val Asp Glu Gly Ser Ser Val Ala Val Arg Leu Phe
        1070                1075                1080
Asp Thr Glu Ala Glu Gln Gln Gln Ala Met Trp Arg Gly Thr Arg
        1085                1090                1095
Arg Leu Ile Leu Leu Asn Leu Pro Ala Ser Pro Val Lys Phe Val
        1100                1105                1110
```

```
Gln Gly Lys Leu Gly Asn Ser Ala Lys Leu Ala Leu Ala Ser Ser
    1115                1120                1125

Pro His Gly Ser Val Gln Ala Leu Phe Glu Asp Cys Val Ser Ala
    1130                1135                1140

Ala Val Asp Arg Leu Val Ala Ala Arg Gly Gly Pro Ala Trp Asp
    1145                1150                1155

Glu Glu Gly Phe Arg Lys Leu Phe Asp Ala Val Arg Ala Asp Ile
    1160                1165                1170

Met Asp Ala Thr Leu Asp Thr Val Arg Lys Val Gln Glu Val Leu
    1175                1180                1185

Ala Ala Trp Gln Ala Cys Glu Arg Arg Leu Lys Ala Thr Ser Ser
    1190                1195                1200

Pro Val Leu Leu Pro Ser Leu Thr Asp Ile Arg Glu Gln Leu Asp
    1205                1210                1215

Arg Leu Val Pro Pro Gly Phe Val Thr Ala His Gly Val Arg Arg
    1220                1225                1230

Leu Pro Asp Leu Met Arg Tyr Leu Val Ala Val Asp Arg Arg Leu
    1235                1240                1245

Gln Gln Leu Pro Thr Asn Ala Glu Arg Asp Arg Ala Arg Met Ala
    1250                1255                1260

Lys Val Lys Glu Met Gln Asp Glu Tyr Ala Trp Leu Leu Glu Gln
    1265                1270                1275

Phe Pro Pro Gly Arg Pro Val Pro Ala Gln Ala Leu Glu Ile Arg
    1280                1285                1290

Trp Met Ile Glu Glu Leu Arg Val Ser Tyr Phe Ala His Ala Leu
    1295                1300                1305

Gly Thr Ala Tyr Pro Ile Ser Asp Lys Arg Ile Val Lys Ala Val
    1310                1315                1320

Asp Ala Ala Ala Pro
    1325

<210> SEQ ID NO 10
<211> LENGTH: 328
<212> TYPE: PRT
<213> ORGANISM: Streptomyces pactum

<400> SEQUENCE: 10

Val Leu Cys Leu Ile Leu Ala Gly Ala Ala Gly Phe Phe Ala Gly Ser
1               5                   10                  15

Tyr Thr Tyr Ala Met Ala Asn Pro Thr Pro His Arg Leu Pro Val Ala
            20                  25                  30

Val Val Gly Glu His Arg Ser Pro Ser Gly Gln Ala Phe Leu Ala Gly
        35                  40                  45

Met Glu Lys Ala Leu Asp Thr Ser Leu Arg Ile Arg Pro Tyr Glu Asp
    50                  55                  60

Asp Arg Ala Ala Arg Arg Ala Val Glu Glu Gln Glu Val Phe Ala Val
65                  70                  75                  80

Leu Glu Leu Gly Gly Glu Arg Val Arg Leu Asp Leu Ser Gly Ala Ser
                85                  90                  95

Gly Ala Ser Val Ala Glu Leu Leu Ala Arg Ala Gly Pro Glu Val Gly
                100                 105                 110

Arg Glu Thr Gly Val Pro Val Thr Val Arg Asp Ile Asn Pro Leu Gln
            115                 120                 125

Glu Gly Asp Pro Arg Gly Leu Ala Leu Phe Tyr Ile Ser Leu Ala Ala
```

```
                130               135               140
Val Ile Val Gly Phe Val Gly Ala Ile Gln Leu Ser Val His Ala Arg
145                 150               155                 160

Ala Leu Asn Pro Gly Glu Arg Ile Ala Phe Thr Ala Gly Tyr Ala Leu
                165               170                 175

Leu Cys Gly Phe Ala Ile Ala Ala Val Val Asp Trp Leu Leu Gly Ala
                180               185                 190

Val Asp Leu Pro Phe Val Glu Ser Trp Leu Ile Leu Ala Leu Thr Leu
                195               200                 205

Phe Thr Ser Gly Met Val Phe Ser Met Phe Asn Thr Leu Phe Gly Arg
                210               215                 220

Trp Ala Met Leu Pro Thr Trp Gly Leu Met Val Leu Val Gly Asn Pro
225                 230               235                 240

Ser Ser Gly Gly Ala Val Ser Trp Pro Leu Leu Pro Ser Pro Leu Gly
                245               250                 255

Val Ile Gly Gln Trp Leu Pro Pro Gly Ala Ser Val Asn Ala Gln His
                260               265                 270

Thr Ala Val Tyr Phe Gly Asp His Gln His Ala Phe Pro Phe Leu Val
                275               280                 285

Leu Gly Gly Trp Ala Val Leu Ser Ser Thr Val Phe Trp Val Trp Arg
                290               295               300

His Arg His Pro Gly Gly Arg Asp Val Pro Ala Arg Glu Pro Ala Gly
305                 310               315                 320

Ala Gly Gly Gly Gly Pro Ala Asp
                325

<210> SEQ ID NO 11
<211> LENGTH: 575
<212> TYPE: PRT
<213> ORGANISM: Streptomyces pactum

<400> SEQUENCE: 11

Met Gly Arg Trp Ala Gly Arg His Arg Ser Arg Gly Pro Val Gly Gly
1                   5                 10                  15

Arg Ala Arg Pro Gly Val Arg Thr Arg Leu Leu Arg Pro Asp Ala Phe
                20                25                  30

Arg Arg Thr Pro Thr Arg Ala Ser Leu Glu Ala Val Thr Ala Glu Ser
                35                40                  45

Leu Gly Gly Val Thr Gly Val Arg Pro Gly His Ala Thr Val Gln Asp
            50                55                60

Gly Arg Ala Gly Asp Ala Val Arg Asp Gly His Ala Gly Glu Thr
65                  70                75                  80

Ala Ala Ala Gly Gly Arg Ala Glu Gly Arg Ala Gly Gly Arg Ala Glu
                85                90                  95

Ala Asn Ala Gly Gly Thr Thr Val Arg His Glu Arg Pro Gly Glu Asn
                100               105                 110

Arg Ala Ser Gly Gly Pro Gly Asp Ala Pro Ala Asp Gly Pro Gly Ala
                115               120                 125

Val Thr Ala Asp Ala Pro Val Gly Asp Ala Val Glu Val Thr Ala Asp
                130               135                 140

Leu Pro Gly Thr Gly Ala Ala Gly Gly Ser Gly Gly Leu Pro Ala Asp
145                 150               155                 160

Arg Ser Gly Ala Ala Gly Gly Asn Pro Ala Pro Pro Gly Asp Gly Ala
                165               170                 175
```

```
Ala Val Leu Thr Ala Ala Pro Val Thr Ala Ala Val Ser Ala Ala Val
            180                 185                 190

Ser Ala Thr Val Ser Ala Thr Ala Ser Ala Thr Val Ala Ala Ser Val
        195                 200                 205

Ala Glu Ala Ala Ala Val Pro Ser Val Thr Val Pro Gly Pro Ala Pro
210                 215                 220

Val Pro Ala Ala Glu Arg Leu Pro Val Thr Ala Pro Phe Gly Val Gln
225                 230                 235                 240

Val Phe Gly Leu Ala Tyr Arg Met Leu Gly Thr Ala Thr Glu Ala Glu
                245                 250                 255

Gln Val Val His Glu Ala Arg Leu Leu Arg Gln Arg Ala Gly Val Ala
            260                 265                 270

Gly Ala Gly Pro Arg Arg Leu Val Arg Leu Val Ala Asp Leu Cys Leu
        275                 280                 285

Asp Arg Leu Ala Ala Ala Arg Thr Arg Arg Glu Glu Tyr Val Gly Ser
290                 295                 300

Trp Leu Pro Glu Pro Val Pro Tyr Ala Glu Asn Arg Leu Val Pro Leu
305                 310                 315                 320

Glu Thr Ala Ala Gln Arg Asp Ser Val Ser Pro Ala Val Leu Val Leu
                325                 330                 335

Leu Glu Arg Leu Ser Pro Ala Glu Arg Leu Ala Tyr Leu Leu Arg Glu
            340                 345                 350

Val Tyr Gly His Ser Asp Ala Asp Thr Ala Arg Val Leu Gly Ile Asp
        355                 360                 365

Glu Ala Asp Ala Arg His Leu His His Leu Ala Arg Thr Glu Val Gly
370                 375                 380

Ala Pro Arg Arg Arg Pro Ala Asp Ser Pro Glu Glu Ala Ala Arg Ile
385                 390                 395                 400

Val Gly His Phe Arg Ser Ala Leu Ile Asp Gly Asp Ala Ala Gly Leu
                405                 410                 415

Glu Glu Leu Leu Ala Asp Asp Ala Met Ala Trp Phe Asp Gly Gly Gly
            420                 425                 430

Lys Val Gly Thr Ala Arg Arg Pro Val Ile Gly Gly Thr Lys Val Ala
        435                 440                 445

Arg His Leu Ala Gly Trp Ala Gly Asp Phe Gly Met Ala Asp Ala Arg
450                 455                 460

Thr Arg Ile Val Pro Val Asn Gly Glu Pro Ala Val Leu Val His Arg
465                 470                 475                 480

Ala Gly Ala Leu Val Cys Val Ile Ala Pro Glu Leu Ala Glu Gly Arg
                485                 490                 495

Ile Ile Gly Val Arg Thr Val Ala Asn Pro Asp Lys Leu Ala Phe Ala
            500                 505                 510

Ala Ala Arg Thr Gly Ala Asp Gly Thr Ala Asp Ala Thr Ala Ala
        515                 520                 525

Pro Arg Thr Gly Gly Ala Gly Thr Glu Ala Arg Asp Val Pro Asp Leu
530                 535                 540

Pro Asp Ala Thr Ala Ala Thr Ala Gly Pro Ala Gly Ser Gly Asp
545                 550                 555                 560

Ala Gly Asp Glu Ala Arg Gly Ala Thr Val Pro Val Cys Gly Arg
                565                 570                 575

<210> SEQ ID NO 12
<211> LENGTH: 385
<212> TYPE: PRT
```

<213> ORGANISM: Streptomyces pactum

<400> SEQUENCE: 12

```
Met Gly Leu His Ile Val Val Leu Gly Ala Gly Tyr Ala Gly Leu Ala
1               5                   10                  15

Ala Ala Lys Leu Ala Ala Arg Trp Thr Asp Ala Arg Val Thr Leu Val
            20                  25                  30

Asn Ala Glu Asp Arg Phe Val Gln Arg Val Arg Leu His Gln Leu Ala
        35                  40                  45

Ala Gly Glu Pro Leu Pro Asp Leu Pro Leu Ala Arg Leu Leu Arg Gly
    50                  55                  60

Thr Gly Val Arg Leu Val Val Asp Arg Val Thr Gly Ile Asp Ala Ala
65                  70                  75                  80

Ser Lys Thr Val Asp Leu Ala Gly Ala Ala Gly Gly Pro Leu Arg Tyr
                85                  90                  95

Asp Leu Leu Ile Tyr Ala Leu Gly Ser Gln Asp Ala Pro Ser Pro Val
            100                 105                 110

Leu Gly Val Ala Glu His Ala Tyr Arg Val Gly Thr Leu Glu Gln Ala
        115                 120                 125

Ala Arg Leu Arg Glu Arg Leu Ala Val Ser Arg Thr Val Ala Val Val
    130                 135                 140

Gly Gly Gly Leu Thr Gly Ile Glu Thr Ala Ala Glu Leu Ala Glu Ser
145                 150                 155                 160

Phe Ala Ala Asp Ala Arg Arg Lys Gly Ala Ala Gly Ala Gly Pro Ala
                165                 170                 175

Gly Arg Thr Val Arg Leu Val Thr Gly Gly Ala Leu Gly Ala Ala Leu
            180                 185                 190

Ser Arg Pro Gly Ala Asp His Leu Arg Arg Thr Phe Asp Arg Leu Gly
        195                 200                 205

Val Glu Val Arg Ala Asp Ala Arg Val Ala Ala Val Asp Ala Asp Gly
    210                 215                 220

Leu Leu Leu Glu Asp Gly Gly Arg Val Ala Ala Asp Thr Val Val Trp
225                 230                 235                 240

Thr Thr Gly Phe Arg Val Pro Asp Leu Ala Arg Gln Ala Gly Phe Ala
                245                 250                 255

Val Asp Glu Asp Gly Arg Val Leu Val Asp Pro Thr Leu Arg Ser Val
            260                 265                 270

Ser His Pro Glu Val Tyr Ala Ile Gly Asp Ala Ala Ala Pro Arg Thr
        275                 280                 285

Pro Asp Gly Gln Val Leu Arg Met Ala Cys Ala Thr Ser Ile Pro Ala
    290                 295                 300

Ala Gln Gln Ala Ala Arg Ala Leu Ala Ala Arg Leu Ser Gly Arg Glu
305                 310                 315                 320

Pro Arg Pro Leu Arg Phe Arg Tyr Ala Leu Gln Cys Ile Ser Leu Gly
                325                 330                 335

Arg Arg Asp Gly Leu Ile Gln Phe Val Asn Gly Asp Asp Ser Pro Arg
            340                 345                 350

Glu Arg Val Leu Thr Gly Arg Lys Ala Ala Phe Val Lys Glu Ala Val
        355                 360                 365

Val Arg Gly Thr Val Leu Phe Gln Arg His Pro Thr Ile Pro Ala Thr
    370                 375                 380

Arg
385
```

<210> SEQ ID NO 13
<211> LENGTH: 156
<212> TYPE: PRT
<213> ORGANISM: Streptomyces pactum

<400> SEQUENCE: 13

```
Met Gly Trp Arg Gly Gly Ser Pro Lys Arg Leu Ser Glu Gly Phe Ala
1               5                   10                  15

Gly Val Ala Pro Gly Arg Pro Ala Arg Val Arg His Cys Pro Leu Pro
            20                  25                  30

Gly Pro Leu Ala Asp Asn Gly Gly Val Leu Glu Met Thr Arg Glu Glu
        35                  40                  45

Phe Glu Glu Leu Val Ala Glu Ala Leu Asp Arg Ile Pro Thr Glu Leu
    50                  55                  60

Thr Arg Leu Met Asp Asn Val Ala Val Phe Val Glu Asp Glu Pro Pro
65                  70                  75                  80

Ala Asp Asp Pro Glu Leu Leu Gly Leu Tyr Glu Gly Thr Pro Leu Thr
                85                  90                  95

Asp Arg Gly Glu Trp Tyr Ala Gly Val Leu Pro Asp Arg Ile Thr Ile
            100                 105                 110

Tyr Arg Gly Pro Thr Leu Arg Met Cys Glu Thr Arg Glu Asp Val Val
        115                 120                 125

Ala Glu Thr Glu Ile Thr Val Val His Glu Ile Ala His His Phe Gly
    130                 135                 140

Ile Asp Asp Glu Arg Leu His Ala Leu Gly Tyr Gly
145                 150                 155
```

<210> SEQ ID NO 14
<211> LENGTH: 255
<212> TYPE: PRT
<213> ORGANISM: Streptomyces pactum

<400> SEQUENCE: 14

```
Val Arg Cys Gly Val Pro Asp Leu Leu Arg Pro Gly Gln Gly Arg Gly
1               5                   10                  15

Ala Gly Arg Ala Gly Val Arg Thr Ser Gly Asn Ala Gly Arg Ala Leu
            20                  25                  30

Arg Ala Val Pro Gly Arg Glu Ala Gly Val Ser Trp Ala Val Arg
        35                  40                  45

Arg Gln Leu Gly Arg Gly Pro Val Pro Cys Pro Gly Gly Ala Pro Thr
    50                  55                  60

Met Pro Ala Ile Pro Asp Arg Pro Ala Arg Pro Ser Ser Arg Thr Ala
65                  70                  75                  80

Thr Arg Val Ala Val Ala Trp Val Ala Ala Ala Leu Ala Gly Cys
                85                  90                  95

Met Ser Val Ser His Asp Gly Glu Arg Ser Gly Asn Arg Gly Ala
            100                 105                 110

Glu Arg Gly Arg Ala Ala Glu Gln Asp Gly Gly Ala Thr Val Ala
        115                 120                 125

Gly Ala Pro Val Gly Pro Glu Ala Gly Val Arg Arg Gly Gly Lys
    130                 135                 140

Gly Arg Gly Lys Thr Lys Lys Lys Asp Asp Asp Gly Asp Arg Lys Gly
145                 150                 155                 160

Arg Ala Ser Ala Ser Ala Ser Pro Ser Gly Lys Glu Glu Ala Ala Arg
                165                 170                 175
```

```
Thr Ser Gly Pro Gly Gly Arg Pro Thr Ala Ala Pro Pro Asp Pro
            180                 185                 190

Gly Gly Gly Pro Ser Asp Thr Ala Pro Ala Pro Arg Pro Pro Glu
            195                 200                 205

Pro Ser Ser Ala Pro Pro Glu Thr Ala Gly Pro Gly Pro Ser Glu Pro
            210                 215                 220

Gly Pro Thr Glu Pro Pro Ser Gly Glu Pro Gly Gly Gly Asp Gln
225             230                 235                 240

Gly Gly Gly Ala Gly Gly Gly Ser Gly Gly Pro Ala Asn Pro Ala
            245                 250                 255
```

<210> SEQ ID NO 15
<211> LENGTH: 150
<212> TYPE: PRT
<213> ORGANISM: Streptomyce pactum

<400> SEQUENCE: 15

```
Val Gly Arg Val Arg Pro Arg Ser Gly Ser Pro Pro Ala Gly Pro Ala
1               5                   10                  15

Ala Trp Thr Arg Pro Gly Gln Ala Gly Pro Asp Val Arg Gly Gly Arg
                20                  25                  30

Thr Pro Ala Gly Ser Gly Glu Cys Ala Ala Pro Val Ala Gly Leu Pro
            35                  40                  45

Thr Arg Arg Pro Asp Ala Gly Gly Ala Ala Pro Gly Arg Ser Gly
        50                  55                  60

Asp Arg Ala Asp Gly Arg Pro Pro Ala Ala Arg Gly Arg Gly Arg Ser
65              70                  75                  80

Ser Pro Gly Ala Gly Cys Gly Gly Arg Pro Ala Gly Ser Arg Pro
                85                  90                  95

Pro Val Arg Arg Ser Arg Trp Gly Asp Ala Gly Gly Glu Leu Arg
                100                 105                 110

Ala Ala Pro Ala Thr Gly Pro Ala Thr Pro Pro Ser Ala Arg Leu His
                115                 120                 125

Gly Pro Val Pro Asp Cys Leu Arg Val Gly Glu Phe Ala Phe Pro Gly
            130                 135                 140

Glu Glu Cys Val Trp Trp
145             150
```

<210> SEQ ID NO 16
<211> LENGTH: 788
<212> TYPE: PRT
<213> ORGANISM: Streptomyce pactum

<400> SEQUENCE: 16

```
Met Thr Arg Ser Trp Ala Arg Ala Glu Thr Pro Glu Gly Phe Ala Phe
1               5                   10                  15

Arg Met Ser Ile Ser Thr Asp His Ser Ala Met Pro Ala Ala Asp Glu
                20                  25                  30

Thr Val Gln Thr Ser Asp Ala Ala Glu Ala Thr Val Ala Pro Glu
            35                  40                  45

Val Thr Gly Thr Pro Glu Val Thr Ala Pro Gly Thr Ala Asp Ala Asp
        50                  55                  60

Ala Glu Gln Ala Ala Asp Ala Ala Thr Gly Pro Ala Asp Asp Ala Asp
65              70                  75                  80

Ala Glu Gln Ala Pro Thr Leu Thr Phe Ala Asp Leu Gly Leu Pro Glu
                85                  90                  95
```

-continued

```
Gln Ile Val Arg Lys Leu Ala Gln Asn Gly Val Thr Thr Pro Phe Pro
            100                 105                 110
Ile Gln Ala Ala Thr Ile Pro Asp Ala Met Ala Gly Arg Asp Ile Leu
        115                 120                 125
Gly Arg Gly Arg Thr Gly Ser Gly Lys Thr Leu Ser Phe Gly Leu Pro
    130                 135                 140
Leu Leu Thr Thr Leu Ser Gly Gly His Thr Glu Lys Lys Arg Pro Arg
145                 150                 155                 160
Gly Leu Ile Leu Thr Pro Thr Arg Glu Leu Ala Met Gln Val Ser Asp
                165                 170                 175
Ala Leu Gln Pro Tyr Gly Asp Val Leu Gly Leu Lys Leu Lys Val Val
            180                 185                 190
Cys Gly Gly Thr Ser Met Gly Asn Gln Ile Tyr Ala Leu Glu Arg Gly
        195                 200                 205
Val Asp Ile Leu Val Ala Thr Pro Gly Arg Leu Arg Asp Ile Ile Asp
    210                 215                 220
Arg Gly Ala Ala Ser Leu Asp Arg Val Gln Val Ala Val Leu Asp Glu
225                 230                 235                 240
Ala Asp Gln Met Ala Asp Met Gly Phe Leu Pro Glu Val Thr Glu Ile
                245                 250                 255
Leu Asp Leu Val Pro Gln Gly Gly Gln Arg Leu Leu Phe Ser Ala Thr
            260                 265                 270
Leu Glu Asn Glu Ile Asp Thr Leu Val Lys Arg Tyr Leu Val Asp Pro
        275                 280                 285
Val Thr His Glu Val Asp Pro Ser Ala Gly Ala Val Ser Thr Met Thr
    290                 295                 300
His His Val Leu Val Val Lys Pro Lys Asp Lys Ala Pro Val Thr Ala
305                 310                 315                 320
Ala Ile Ala Ala Arg Lys Gly Arg Thr Ile Ile Phe Val Arg Thr Gln
                325                 330                 335
Leu Gly Ala Asp Arg Val Ala Glu Gln Leu Arg Asp Ser Gly Val Arg
            340                 345                 350
Ala Asp Ala Leu His Gly Gly Met Thr Gln Gly Ala Arg Thr Arg Thr
        355                 360                 365
Leu Ala Asp Phe Lys Asp Gly Tyr Val Asn Val Leu Val Ala Thr Asp
    370                 375                 380
Val Ala Ala Arg Gly Ile His Val Asp Gly Ile Asp Leu Val Leu Asn
385                 390                 395                 400
Val Asp Pro Ala Gly Asp His Lys Asp Tyr Leu His Arg Ser Gly Arg
                405                 410                 415
Thr Ala Arg Ala Gly Gln Ser Gly Thr Val Val Ser Leu Ala Leu Pro
            420                 425                 430
His Gln Arg Arg Gln Ile Phe Arg Leu Met Glu Asp Ala Gly Val Asp
        435                 440                 445
Ala Ser Arg His Ile Val Gly Gly Ala Gly Ala Phe Asp Glu Asp Val
    450                 455                 460
Ala Arg Ile Thr Gly Ala Arg Ser Leu Thr Glu Val Gln Ala Glu Ser
465                 470                 475                 480
Ala Ala Asn Ser Ala Lys Gln Ala Glu Arg Glu Val Glu Gln Leu Thr
                485                 490                 495
Arg Glu Leu Glu Arg Val Gln Arg Arg Ala Thr Glu Leu Arg Glu Glu
            500                 505                 510
Ala Asp Arg Leu Ala Ala Arg Ala Ala Arg Glu Arg Gly Glu Asp Pro
```

```
            515                 520                 525
Gln Ala Val Ala Pro Ala Glu Pro Ala Ala Asp Gly Ala Glu Ala
    530                 535                 540

Pro Ala Ala Ala Pro Ser Val Pro Glu Gln Thr Ala Ala Pro Val Val
545                 550                 555                 560

Glu Asn Thr Val Ala Asp Glu Ala Pro Arg Thr Gly Pro Glu Arg
                565                 570                 575

Arg Asp Glu Arg Gly Ser Tyr Glu Arg Arg Asp Arg Gly Gly Asp Asp
            580                 585                 590

Arg Gly Gly Phe Gly Arg Asp Arg Asp Arg Asp Asp Arg Pro Phe
            595                 600                 605

Asn Arg Asp Arg Arg Asp Asp Arg Gly Gly Phe Gly Arg Glu Arg Arg
    610                 615                 620

Asp Gly Asp Arg Asp Arg Gly Phe Gly Asp Arg Asp Arg Arg Glu Arg
625                 630                 635                 640

Pro Ser Phe Arg Asp Arg Arg Asp Gly Asp Asp Arg Arg Asp Gly
                645                 650                 655

Glu Arg Gly Gly Ser Gly Gly Arg Ser Tyr Glu Arg Arg Asp Arg Asp
            660                 665                 670

Asp Arg Gly Phe Gly Arg Asp Arg Asp Asp Arg Gly Gly Phe Asn Arg
    675                 680                 685

Asp Arg Asp Arg Arg Asp Asp Arg Pro Phe Asn Arg Asp Arg Arg Asp
690                 695                 700

Asp Arg Gly Gly Phe Gly Arg Glu Arg Arg Glu Asp Arg Pro Gly Arg
705                 710                 715                 720

Pro Phe Glu Arg Arg Asp His Ala Pro Arg Asp His His Arg Gly Gly
                725                 730                 735

Asp Arg Pro Phe Asn Arg Asp Arg Arg Asp Asp Arg Pro Phe Gly Arg
            740                 745                 750

Asp Arg Arg Asp Asp Arg Pro Ala Arg Arg Asp Asp His Arg Gly Gly
    755                 760                 765

Thr Thr Gly Ser Arg Ser Phe Asp Arg Arg Ala Asp Lys Pro Arg Trp
770                 775                 780

Lys Arg Asn Gly
785

<210> SEQ ID NO 17
<211> LENGTH: 397
<212> TYPE: PRT
<213> ORGANISM: Streptomyces pactum

<400> SEQUENCE: 17

Met His Thr Pro Thr Leu Asp Asp Leu Ala Arg Pro Gly Thr Gly Leu
1               5                   10                  15

Ser Asp Asn Pro Tyr Pro Val Leu Ala Arg Leu Arg Ala Arg Gly Pro
                20                  25                  30

Val His Arg Leu Arg Thr Gly Asp Thr Gln Glu Val Trp Val Ile Val
            35                  40                  45

Gly His Asp Glu Ala Arg Ala Ala Leu Ala Asp Pro Arg Leu Arg Asn
        50                  55                  60

Asp Ala Arg His Ala Asp Gly Ala Asp Ala Gly His Ala Val Gly
65                  70                  75                  80

Arg Asn Met Leu Gln Val Asp Pro Pro His Thr Arg Leu Arg Arg
                85                  90                  95
```

Leu Val Ala Ala Gln Phe Ala Ala Arg Arg Ile Glu Ala Leu Arg Pro
            100                 105                 110

Arg Val Arg Ala Ile Thr Asp Asp Leu Leu Glu Lys Met Val Pro Leu
        115                 120                 125

Gly Arg Ala Asp Leu Val Glu Arg Phe Ala Gln Pro Leu Pro Leu Ala
    130                 135                 140

Val Ile Cys Glu Leu Leu Gly Val Pro Ala Ala Asp Arg Lys Ala Phe
145                 150                 155                 160

Gly Glu Trp Ser Ala Asp Ile Val Thr Pro Gly Ser Pro Ala Ala Ala
                165                 170                 175

Asp Ser Ala Ala Thr Met Thr Gly Tyr Leu Thr Gly Leu Val Glu Asp
            180                 185                 190

Lys Arg Arg Asp Gly Gly Asp Asp Leu Leu Ser Ala Leu Val Ala Ala
        195                 200                 205

Arg Asp Gly Gly Asp Arg Leu Thr Pro Glu Glu Thr Ile Gly Met Ala
    210                 215                 220

Phe Leu Leu Leu Val Ala Gly Tyr Glu Thr Thr Val Asn Leu Ile Ser
225                 230                 235                 240

Ser Gly Val Cys Ala Leu Leu Leu Arg Pro Glu Gln Leu Ala Ala Leu
                245                 250                 255

Arg Asp Asp Pro Ser Leu Leu Asp Gly Ala Val Glu Glu Met Leu Arg
            260                 265                 270

His Glu Ser Pro Leu Gly Thr Ser Ala Tyr Arg Tyr Thr Thr Glu Pro
        275                 280                 285

Val Glu Ile Ala Gly Thr Arg Ile Pro Ala Gly Gln Arg Val Leu Val
    290                 295                 300

Val Leu Asn Ala Ala Asp Arg Asp Pro Asp Arg Phe Pro Asp Pro Asp
305                 310                 315                 320

Arg Phe Asp Ile Arg Arg Asp Ala Arg Gly His Leu Ala Phe Gly His
                325                 330                 335

Gly Leu His His Cys Leu Gly Ala Pro Leu Ala Arg Leu Glu Ala Thr
            340                 345                 350

Val Ala Leu Arg Gly Leu Leu Glu Arg Ala Pro Gly Leu Arg Leu Ala
        355                 360                 365

Ala Asp Pro Ala Thr Leu Thr Trp Arg Ser Gly Leu Met Arg Gly Leu
    370                 375                 380

His Arg Leu Pro Val Thr Phe Gly Pro Val Pro Glu Pro
385                 390                 395

<210> SEQ ID NO 18
<211> LENGTH: 162
<212> TYPE: PRT
<213> ORGANISM: Streptomyces pactum

<400> SEQUENCE: 18

Met Ser Leu Tyr Asp Ile Pro Val Arg Thr Leu Ala Gly Glu Pro His
1               5                   10                  15

Asp Leu Ser Arg Tyr Arg Gly Lys Ala Leu Leu Val Val Asn Val Ala
            20                  25                  30

Ser Gln Cys Gly Arg Thr Arg Gln Tyr Ala Ala Leu Glu Glu Leu His
        35                  40                  45

Arg Arg Tyr Gly Pro Arg Gly Phe Ser Val Leu Gly Phe Pro Cys Asn
    50                  55                  60

Gln Phe Gly Glu Gln Glu Pro Gly Gly Pro Glu Ile Glu Arg Phe
65                  70                  75                  80

```
Cys Thr Thr Thr Tyr Gly Val Thr Phe Pro Leu Phe Glu Lys Val Glu
                85                  90                  95

Val Asn Gly Pro Gly Arg His Pro Leu Tyr Ala Leu Leu Thr Ala Ala
            100                 105                 110

Pro Asp Asp Arg Gly Val Ala Gly Asp Ile Glu Trp Asn Phe Glu Lys
        115                 120                 125

Phe Leu Ile Ser Pro Glu Gly Arg Val Ala His Arg Ile Ala Ser Arg
    130                 135                 140

Thr Arg Pro Asp Asp Pro Asp Val Val Ala Arg Ile Glu Ala Leu Leu
145                 150                 155                 160

Pro Ala

<210> SEQ ID NO 19
<211> LENGTH: 391
<212> TYPE: PRT
<213> ORGANISM: Streptomyces pactum

<400> SEQUENCE: 19

Met Arg Tyr Glu Pro Trp Arg Ala Leu Ala Leu Trp Gly Glu Glu Glu
1               5                   10                  15

Ala Ala Ala Ala Leu Glu Val Val Arg Ser Arg Ser Leu Phe Arg Tyr
                20                  25                  30

Tyr Gly Pro Asp Leu Gly His Arg Thr Asp Ala Phe Glu Arg Ala Phe
            35                  40                  45

Ala Glu Leu Ala Gly Val Pro His Thr Val Ala Val Ser Ser Gly Thr
        50                  55                  60

Ala Ala Leu Thr Ala Ala Met Val Gly Leu Gly Ile Pro Glu Gly Ala
65                  70                  75                  80

Glu Val Ile Val Pro Ala Val Thr Phe Val Ala Ser Val Gly Ala Val
                85                  90                  95

Val Ala Ala Arg Gly Val Pro Val Phe Ala Glu Val Asp Asp Thr Leu
                100                 105                 110

Thr Leu Asp Pro Ala Lys Leu Glu Glu Leu Val Thr Glu Arg Thr Trp
            115                 120                 125

Gly Val Met Pro Val His Leu Ala Asn Val Ala Ala Asp Met Asp Pro
        130                 135                 140

Ile Leu Glu Val Ala Arg Arg His Gly Leu Arg Val Ile Glu Asp Ala
145                 150                 155                 160

Ala Gln Ala Ala Gly Val Ser Tyr Arg Gly Arg Pro Val Gly Gly Ile
                165                 170                 175

Gly Asp Ala Gly Ala Phe Ser Phe Gln Leu Asp Lys Asn Ile Thr Ala
            180                 185                 190

Gly Glu Gly Gly Ala Val Thr Val Thr Asp Ala Asp Val Tyr Asp Arg
        195                 200                 205

Val Ala Arg Tyr Gln Asp Gln Gly Gly Gln Phe Thr Thr Ser Lys Gly
    210                 215                 220

Ala Thr Arg Gly Thr Ala Asp His Pro Pro Phe Ile Gly Ala Asn Leu
225                 230                 235                 240

Arg Met Thr Glu Leu Thr Ala Ala Ile Leu Ser Val Gln Leu Pro Arg
                245                 250                 255

Leu Val Pro Leu Cys Lys Arg Leu Arg Asp Val Ala Arg Gln Val Arg
            260                 265                 270

Ala Glu Thr Ala Gly Leu Pro Leu Gln Trp Arg Arg Leu Pro Asp Glu
        275                 280                 285
```

```
Glu Gly Ser Gly Gly Asp Leu Thr Phe Phe Thr Glu Ser Arg Leu Glu
    290                 295                 300

Ala Arg Arg Val Val Gly Ala Leu Thr Ala Ala Gly Ile Pro Ala His
305                 310                 315                 320

Thr Met Tyr Gln Gly Gln Thr Val Thr Ser Asn Arg Ala Val Arg Glu
                325                 330                 335

Gly Arg Thr Pro Trp Gly Val Ala Trp Glu Arg Pro Pro Arg Phe Arg
                340                 345                 350

Ala Ser Glu Gly Tyr Leu Gly Arg Ser Val Thr Val Gly Leu Gly Ala
                355                 360                 365

Ala Met Thr Asp Glu Asp Val Asp Thr Ile Val Ala Thr Leu Arg Ser
370                 375                 380

Ala Trp Ala Asp Ala Ala Gly
385                 390

<210> SEQ ID NO 20
<211> LENGTH: 570
<212> TYPE: PRT
<213> ORGANISM: Streptomyces pactum

<400> SEQUENCE: 20

Met Leu Ala Leu Gly Leu Gly Gly Ser Asn His Asp Phe Ser Ala Cys
1               5                   10                  15

Leu Val Glu Asn Gly Glu Ile Ala Val Gly Ile Glu Glu Arg Leu
            20                  25                  30

Ala Arg Arg Lys Tyr Ala Val Asn Val Asn Ser Leu Ala Asn Gln Gly
            35                  40                  45

Trp Arg Tyr Cys Leu Glu Thr Arg Gly Val Arg Leu Ala Asp Val Glu
50                  55                  60

Ala Ile Val Ala Asp Asp Thr Leu Leu Pro Ser Cys Tyr Phe Pro Phe
65                  70                  75                  80

Arg Ser Arg Thr Thr Leu Ile Arg His His Met Ala His Ala Ala Ser
                85                  90                  95

Ala Phe Tyr Pro Ser Pro Tyr Asp Glu Ala Ala Val Leu Val Val Asp
            100                 105                 110

Gly Ala Gly Ser Leu Phe Glu Gly Arg Gly Ile Glu Thr Met Thr Leu
        115                 120                 125

Ser Val Gly His Gly Val Glu Ile Asp Glu Ile Ser Lys Val Tyr Gly
    130                 135                 140

Thr Asn Trp Ser Thr Asp Gly Leu Arg Ser Asp Arg Val Tyr Gln Ala
145                 150                 155                 160

Gly Asp Ser Asp His Ser Leu Gly Phe Met Tyr Lys Ala Val Ser Arg
                165                 170                 175

Ala Val Gly Phe Thr Leu Tyr Glu Glu Gly Ser Trp Tyr Leu Thr Glu
            180                 185                 190

Asp Gly Lys Thr Met Gly Leu Ala Pro Tyr Gly Thr Asp Arg Tyr Arg
        195                 200                 205

Glu Glu Phe Arg Arg His Leu Glu Leu Leu Pro Glu Gly Arg Phe Ala
    210                 215                 220

Leu His Leu Lys Asp Gly Gly Leu Leu Ala Phe Val Glu His Ala Leu
225                 230                 235                 240

Asp Gly Leu Glu Gly Glu Glu Arg Phe Ala Arg Gly Ala Asp Leu Ala
                245                 250                 255

Trp Ala Ala Gln Asp Leu Leu Glu Thr Ala Val Leu His Ala Ala Arg
```

```
                260                 265                 270
Trp Leu His Ala Glu Thr Gly Leu Ser Arg Leu Cys Leu Ala Gly Gly
                275                 280                 285

Val Val Leu Asn Ser Val Ala Asn Gly Lys Ile Leu Arg Glu Thr Pro
        290                 295                 300

Phe Thr Glu Val Phe Ala Gln Pro Ala Ala Gly Asp Asn Gly Cys Ala
305                 310                 315                 320

Val Gly Cys Ala Tyr Tyr Gly Tyr His Val Leu Gly Glu Arg Pro Arg
                325                 330                 335

Thr Arg Gly Pro Ala Ala Ser Gly Pro Gly Ser Arg Pro Gln Ile His
                340                 345                 350

Thr Tyr Leu Gly Arg Ser Tyr Pro Thr Glu Arg Ile Gln Ala Ala Leu
                355                 360                 365

Asp Ala Ser Gly Leu Pro Tyr Arg Arg Val Glu Asn Pro Ala Arg Leu
        370                 375                 380

Ala Ala Glu Leu Leu Pro Lys Gly Lys Leu Ile Gly Trp Tyr Thr Gly
385                 390                 395                 400

Gly Ser Glu Phe Gly Pro Arg Ala Leu Gly His Arg Ser Ile Leu Ala
                405                 410                 415

Asp Pro Arg Arg Ala Glu Met Lys Asp Ile Leu Asn Ser Lys Val Lys
                420                 425                 430

His Arg Glu Trp Phe Arg Pro Phe Ala Pro Ala Val Pro Ala His Arg
                435                 440                 445

Ala Ala Glu Tyr Phe Asp Leu Asp Thr Glu Ser Pro Phe Met Leu Ile
        450                 455                 460

Val Ala Pro Val Arg Glu Asp Lys Arg Glu Glu Val Pro Ala Ile Thr
465                 470                 475                 480

His Val Asp Gly Thr Ala Arg Val Gln Thr Leu Thr Pro Glu Ala Asn
                485                 490                 495

Gly Pro Phe Tyr Glu Leu Val Glu Arg Phe Gly Glu Leu Thr Gly Val
                500                 505                 510

Pro Val Val Leu Asn Thr Ser Phe Asn Asp Arg Gly Glu Pro Ile Val
                515                 520                 525

Glu Thr Ala Glu Gln Ala Leu Ala Phe Phe Gly Pro Ser Gln Leu Asp
        530                 535                 540

Tyr Leu Phe Leu Glu Asp Phe Leu Val Gly His Ser Val Thr Asp Leu
545                 550                 555                 560

Asp Thr Ala Thr Glu Thr Glu Thr Glu
                565                 570

<210> SEQ ID NO 21
<211> LENGTH: 367
<212> TYPE: PRT
<213> ORGANISM: Streptomyces pactum

<400> SEQUENCE: 21

Met Phe Ala His Arg Asp Gly Gln Asn Arg Leu Lys Leu Leu Met Asn
1               5                   10                  15

Asp Met Val Ile Glu Glu Gln Leu Cys Gln Met Arg Cys Ser Tyr Cys
                20                  25                  30

Leu Thr Glu Asp Phe Asn Leu Leu Met Asn Val Pro Asp Ala Arg Leu
        35                  40                  45

Arg Leu Thr Thr Asp Arg Arg Ala Asp Trp His Glu Ile Leu Asp Ala
50                  55                  60
```

```
Tyr His Arg Thr Val Asp Ser Pro Ile Met Arg Leu Ser Gly Gly Glu
 65                  70                  75                  80

Phe Phe Trp Leu Lys Gly Ser Thr Glu Phe Val Glu Glu Cys Ser Ala
             85                  90                  95

Lys Tyr Glu Val Val Gln Val Ile Thr Asn Gly Val Phe Leu Thr Pro
           100                 105                 110

Pro Arg Leu Glu Ala Leu Ala Ala Leu Gly Asn Val Gln Leu Cys Leu
       115                 120                 125

Ser Leu Asp Gly His Thr Leu Glu Met Asn Gly His Arg Phe Pro Pro
130                 135                 140

Lys Gln His Arg Leu Phe Asp Val Ile Met Gly His Leu Asp His Ala
145                 150                 155                 160

Val Glu Leu Gly Ile Pro Ile Glu Ile Gln Ser Val Leu Ser Asp Leu
                165                 170                 175

Asn Val Thr Arg Gln Ala Asp Phe Ala Glu Phe Leu Leu Glu Arg Tyr
            180                 185                 190

Gly Ser Gly Val Met Leu Tyr Phe Phe Pro Val Arg Gly Glu Thr Arg
        195                 200                 205

Thr Thr His Ala Pro Ala Leu Gly Asp His Phe Ala Glu Leu Leu Glu
210                 215                 220

Arg Tyr Asp Glu Leu Ser Ala Val Leu Pro Pro Arg Ala Phe Val Ala
225                 230                 235                 240

His Ile Ala Asn Gln Leu Ser Thr Gly Val Arg Thr Leu Arg Cys Tyr
                245                 250                 255

Ala Thr Ala Thr Met Val Gln Leu Phe Gly Gln Gly Asp Val Ser Cys
            260                 265                 270

Cys Pro Tyr Ala Trp Leu Lys Pro Met Gly Asn Ile Lys Asn Glu Pro
        275                 280                 285

Glu Leu Ile His Glu Gln Phe Gly Lys His Gln His Tyr Glu Met Phe
    290                 295                 300

Met Gln Pro Arg Pro Arg Phe Pro Tyr Cys Lys Ser Cys Thr Gly Pro
305                 310                 315                 320

Ile Asp Val Val Asn Leu Tyr Leu Phe Gly Gly Ile Thr Glu Glu Glu
                325                 330                 335

Ile Ala Arg Cys Ala Pro Tyr Ala Gly Pro Arg Ala Leu Glu Arg Leu
            340                 345                 350

Arg Glu Leu Lys Ser Ala Phe Asp Pro Met Phe Gln Ala Ala Glu
        355                 360                 365

<210> SEQ ID NO 22
<211> LENGTH: 358
<212> TYPE: PRT
<213> ORGANISM: Streptomyces pactum

<400> SEQUENCE: 22

Met Ile Ser Val Asp Gly Ile Ser Ala Asp Asp Phe Ala Gly Ala Gly
  1               5                  10                  15

Leu Ser Arg Leu Leu Arg Leu Pro Gln His Asp Leu Leu Thr Leu Ala
             20                  25                  30

Gly Asp Trp Leu Gly Glu Leu Ala Pro Trp Arg Asn Thr Glu Thr Leu
         35                  40                  45

Ala Ala Ile Ser Thr Thr Leu Ser Ala Glu Ala Gln Leu Ala Ala Leu
     50                  55                  60

Phe Ile Phe Gly Glu Pro Val Ala Glu Ala Ala Arg Asp Arg Leu
 65                  70                  75                  80
```

Pro Gly Pro Leu Leu Asp Leu Leu Arg Thr Gly Ala Leu Ala Ala
            85                  90                  95

Asp Ser Gly Lys Leu Ser Ala Arg Tyr Cys Leu Val Arg Gly Asp Gly
            100                 105                 110

Met Ser Leu Leu Ala Ala Trp Arg Ala Ala Gly Arg Asp Val Gly Gly
            115                 120                 125

Tyr Ala Pro Trp Val Gly Thr Asp Ser Met Thr Leu Ser Arg Leu Val
            130                 135                 140

Ala Ala Arg Arg Asp Val Arg Thr Ala Leu Asp Leu Gly Cys Gly Thr
145                 150                 155                 160

Gly Ile Leu Gly Leu Ser Ala Ala Arg Asn Gly Ala Asp Val Val Ser
                165                 170                 175

Val Asp Val Asn Pro Glu Cys Thr Ala Ala Thr Val Asn Ala His
            180                 185                 190

Ile Asn Gly Leu Gly Glu Arg Leu Thr Ala Val Glu Gly Asp Ile Met
            195                 200                 205

Ser Leu Asp Leu Asp Arg Arg Phe Asp Leu Val Ile Ser Asn Pro Pro
            210                 215                 220

Cys Leu Pro Leu Arg Arg Gly Ser Leu Gly Trp Leu Ala Gly Glu Ala
225                 230                 235                 240

Gly Leu Asp Gly Leu Glu Phe Phe Trp Glu Leu Leu Arg Arg Val Pro
            245                 250                 255

Gly Leu Leu Thr Gly Glu Gly Glu Ala Leu Leu Gln Ala Ala Ala Tyr
            260                 265                 270

Gly Asp Glu Arg Gly Pro Phe Phe Val Glu Glu Leu Ala Glu Leu
            275                 280                 285

Arg Arg Leu Lys Val Ser Gly Arg Leu Leu Arg Pro Ser Thr Pro
            290                 295                 300

Pro Arg Trp Pro Ala Phe Ala Pro Arg Asp Glu Glu Gly Gln Leu Thr
305                 310                 315                 320

Gly Pro Leu Gly Asp Glu Val Arg Glu Tyr Val Asn Arg Ile Gly Ala
            325                 330                 335

Thr His Tyr Tyr Gly Phe Val Leu Ser Val Arg Ala Gly Glu Gly Leu
            340                 345                 350

Asp Val Gly Arg Phe Ser
            355

<210> SEQ ID NO 23
<211> LENGTH: 178
<212> TYPE: PRT
<213> ORGANISM: Streptomyces pactum

<400> SEQUENCE: 23

Met Arg Val Val Ile Thr Gly Ala Pro Gly Val Gly Lys Thr Arg
1               5                   10                  15

Leu Gly His Gln Leu Val Ala Arg Tyr Gly Val Pro Ala Ala Val
            20                  25                  30

Asp Cys Asp Pro Val Val Tyr Pro Trp Asp Gly Asn Glu Ser Leu Tyr
            35                  40                  45

Ala Leu Met Ala Ala Thr Val Arg Ala Ser Leu Pro Val Tyr Arg Asp
            50                  55                  60

Trp Gly Ala Arg Val Val Leu Ser Gly Val Leu Ala Gly Arg
65                  70                  75                  80

Ala Tyr Glu Pro Leu His Arg Val Phe Ala Asp Leu Gly Ala Asp Pro

```
                    85                  90                  95
Val Tyr Tyr Gly Leu Arg Ala Ala Pro Glu Ala Leu Ala Ala Arg Ile
                100                 105                 110

Ser Gly Asp Pro Gly Gly Glu His Phe Val Glu Gly Arg Leu Ala Glu
            115                 120                 125

Arg His Leu Asp Glu Glu Val Pro Gly Val Pro Gly Ile Arg Leu Ile
        130                 135                 140

Asp Thr Thr Glu Leu Thr Leu Ala Ala Thr Asp Ala Val Ala Ala
145                 150                 155                 160

Ala Glu Phe Ala Asp Leu Gly Pro Gly Trp Leu Pro Asp Pro Arg Val
                165                 170                 175

Ile Ser

<210> SEQ ID NO 24
<211> LENGTH: 216
<212> TYPE: PRT
<213> ORGANISM: Streptomyces pactum

<400> SEQUENCE: 24

Val Lys Gly Phe Pro Val Tyr Val Leu Ala Gln Ser Leu Thr Pro Glu
1               5                   10                  15

Asp Leu Ala Ile Leu Ala Asp Ala Cys Ala Glu Val Gly Leu Thr Leu
            20                  25                  30

His His Ser Glu Pro Gly Ser Ala Pro Pro Asp Pro Ser Asp Ala Leu
        35                  40                  45

Leu Val Ser Phe His Arg Val Gly Ala Asp Pro Ala Gly Gly Pro Thr
    50                  55                  60

Ala Gln Glu Leu Lys Glu Ile Gly Gly Tyr Ala Val Ala Val Leu Asp
65                  70                  75                  80

Gly Ile Ala Ala Gly Ala Val Leu Ala Ala Val Thr Asn Gly Tyr Ser
                85                  90                  95

Phe Thr Leu Ala Ser Pro Leu Arg Arg Pro Arg Leu Val Glu Thr Leu
            100                 105                 110

Thr Tyr Leu Lys His Ile Thr Pro Pro Glu Asn Thr Gln Val Leu Thr
        115                 120                 125

Leu Asp Gly Ala Gly Ser Leu His Ser Pro Ser Lys Ser Thr Pro Val
    130                 135                 140

Thr Asp Ala Glu Ala Gly Leu Leu Arg Met Leu Ala Ala Arg Pro Gly
145                 150                 155                 160

Gln Ile Val Ser Arg Glu Asp Leu Thr Glu Ala Thr Gly Gly Glu Asp
                165                 170                 175

Val Ser Arg Val Thr Ser Val Leu Lys Gln Lys Leu Leu Asp Ile Asp
            180                 185                 190

Ser Gly Ala Lys Leu Lys Leu Lys Ile Pro His Leu Gly Phe Arg Leu Val
        195                 200                 205

Gly Thr Val Arg Gln Asp Ala Arg
    210                 215

<210> SEQ ID NO 25
<211> LENGTH: 378
<212> TYPE: PRT
<213> ORGANISM: Streptomyces pactum

<400> SEQUENCE: 25

Met Thr Glu Ile Pro Asp Thr Trp Cys Pro Ile Ala Leu Pro His Val
1               5                   10                  15
```

Glu Thr Ala Asp Gly Glu Ile Leu Phe Met Gly Arg Ile Thr Gly
        20                  25                  30

Ser Gly Arg Thr Ala Gly Glu Asp Ala Gly Leu Leu Ala Arg Cys Asp
    35                  40                  45

Gly Ala Arg Pro Leu Thr Ala Phe Pro Ala Ala Asp Arg Ala Val Leu
50                  55                  60

Asp Gly Trp Leu Arg Asp Gly Val Val Val Met Ala Pro Ala Pro Ala
65                  70                  75                  80

Arg Ala Ala Pro Gly Thr Ala Ala Pro Glu Ala Pro Glu Pro Pro
                85                  90                  95

Arg Pro Ala Gly Thr Pro Glu Thr Pro Glu Ala Ser Gly Gly Pro Gly
            100                 105                 110

Ala Thr Ala Ala Pro Gly Thr Pro Asp Pro Ser Gly Gly Pro Ala Ile
            115                 120                 125

Pro Gly Thr Pro Val Ile Val Ser Pro His Pro Asp Asp Ala Ala Leu
    130                 135                 140

Ala Val Gly Gly Thr Val Ala Arg Glu Gly Gly Arg Phe Leu Asp Val
145                 150                 155                 160

Phe Ser Glu Glu Thr Trp Thr Lys Asp Pro Tyr Tyr Ala Glu Arg Pro
                165                 170                 175

Ala Gln Thr Arg Arg Leu Leu Leu Ala Glu Glu Thr Val Ala Ala Arg
            180                 185                 190

Val Leu Gly Ala Glu Val Glu Leu Leu Gly Phe Thr Asp Ala Ala Asp
        195                 200                 205

Arg Glu Leu Arg Arg Asp Arg Phe Phe Ala Asp Lys Pro Trp Ser Asp
    210                 215                 220

Gly Phe Ala Arg Glu Glu Pro Glu Leu Phe Glu Ala Val Thr Glu Arg
225                 230                 235                 240

Leu Ala Pro Leu Leu Ala Gly Thr Ala Pro Val Tyr Ala Pro Leu Gly
                245                 250                 255

Val Gly Gly His Val Asp His Leu Ala Cys Arg Asp Ala Val Val Ala
            260                 265                 270

Leu Ala Arg Thr Gly Arg Ile Asp Pro Gly Arg Leu Arg Phe Tyr Glu
        275                 280                 285

Asp Gln Pro Tyr Ser Leu Phe Ser Ser Ala Glu Glu Thr Ala Arg Arg
    290                 295                 300

Leu Gly Pro Trp Leu Glu Leu Ala Gly Leu Gly Pro Leu Asp Pro Glu
305                 310                 315                 320

Leu Arg Pro Val Asp Gly Thr Ala Leu Ala Lys Arg Glu Ala Leu
                325                 330                 335

Lys Ala Tyr Arg Ile Gln Val Arg Arg Gly Ile Ile His Arg Ile Gly
            340                 345                 350

Arg His Asp Met His Leu Ala Ser Gln Ser Ser Gln Ser Gly Ser Pro
        355                 360                 365

Ala Ala Glu Arg Leu Trp Arg Leu Arg Gly
    370                 375

<210> SEQ ID NO 26
<211> LENGTH: 661
<212> TYPE: PRT
<213> ORGANISM: Streptomyces pactum

<400> SEQUENCE: 26

Val Ala Pro Leu Arg Gly Arg Ser Ser Pro Val Ala Ser Glu Gly Asp

-continued

```
1               5                   10                  15
Leu Ala Cys Arg Leu Glu Ser Gly Gly Glu Ala Gly Met Lys Thr Arg
                20                  25                  30
Val Leu Leu Val Gln Gln Gly Val Trp Gly Asn Ser Val Ala Ser Met
                35                  40                  45
Pro Leu Ala Ile Gly Tyr Leu Lys Ala Tyr Ala Asp Ala Asp Glu Arg
50                  55                  60
Ile Arg Arg Arg Met Asp Ile Ser Ile Arg Asn Tyr Pro Gly Asp Ala
65                  70                  75                  80
Gly Leu Asn Ala Met Gly Arg Asp Leu Ile Arg Asp Gly Val Pro Asp
                85                  90                  95
Val Leu Cys Phe Ser Val Leu Gly Trp Asn Phe Arg Ala Phe Gly Thr
                100                 105                 110
Leu Ala Glu Thr Phe Lys Gln Val Asn Pro Asp Gly Trp Val Ile Phe
                115                 120                 125
Gly Gly Asn His Val Ala His Gln Ala Glu Arg Val Phe Arg Met Phe
                130                 135                 140
Pro Gln Val Asp Val Val Asn Gly Glu Gly Glu Leu Val Phe Arg
145                 150                 155                 160
Asp Leu Met Asn Gly Tyr Leu Asp Gly Ala Arg Pro Thr Ala Leu His
                165                 170                 175
Glu Ile Ser Gly Val Ser Phe Arg Glu Ala Asp Gly Asn Leu Val Thr
                180                 185                 190
Thr Pro Glu Arg Glu Arg Ile Gln Asp Leu Glu Ile Leu Pro Ser Pro
                195                 200                 205
Ile Leu Thr Gly Ala Ile Pro Leu Ala Asp Ser Gln Gly Arg Phe Leu
210                 215                 220
Tyr Asp Tyr Ala Ile Met Glu Thr Asn Arg Gly Cys Pro Tyr Lys Cys
225                 230                 235                 240
Ala Phe Cys Tyr Trp Gly Gly Ala Thr Gly Gln Lys Met Arg Ala Phe
                245                 250                 255
Ser Arg Glu Arg Leu Arg Glu Glu Leu Asp Val Leu Gly Arg His Gly
                260                 265                 270
Ala Glu Ile Leu Met Leu Ala Asp Ser Asn Phe Gly Leu Leu Arg Gln
                275                 280                 285
Asp Glu Glu Phe Leu Glu Asp Leu Leu Arg Val Arg Ala Lys Tyr Gly
                290                 295                 300
Tyr Pro Asn Arg Leu Glu Thr Ser Trp Ala Lys Asn Lys Ser Ala Gly
305                 310                 315                 320
Phe Tyr Arg Ile Met Glu Lys Met Lys Glu Ser Gly Met His Ser Ala
                325                 330                 335
Phe Ile Leu Ala Leu Gln Thr Met Asp Glu Ser Val Leu Asp Leu Met
                340                 345                 350
Arg Arg Arg Asn Met Lys Leu Asn Asp Trp Glu Ser Leu Val Gly Trp
                355                 360                 365
Leu Thr Asp His Gly Ile Thr Pro Tyr Leu Glu Leu Ile Trp Gly Ala
                370                 375                 380
Pro Gly Glu Thr Val Glu Ser Phe Leu Asp Gly Tyr Asp Arg Ala Ala
385                 390                 395                 400
Arg His Thr Pro Phe Ile Ala Val His Pro Leu Met Leu Leu Pro Asn
                405                 410                 415
Thr Glu Tyr His Asp Lys Arg Gln Val His Gly Leu Val Thr Val Arg
                420                 425                 430
```

Gly Glu Gln Asp Asp Phe Asp Tyr Val Leu Ala His Arg Thr Met Thr
            435                 440                 445

Leu Asp Asp Asn Glu Arg Met Leu Arg Phe Ile Cys Trp Asn Arg Val
450                 455                 460

Leu Ala Arg Ser Leu Trp Leu His Asn Ile Trp Val Ala Leu Arg Glu
465                 470                 475                 480

Leu Ala Asp Val Pro Gln Ser Arg Val Ile Leu Ser Phe Ser Asp Trp
            485                 490                 495

Val Glu Ser Ser Asp Asp Pro Asp Ala Arg Glu Leu His Ala Leu Ala
            500                 505                 510

Arg Pro Thr Ser Ser Ala Ser Glu Gln Val Asp Pro His Val Trp Arg
            515                 520                 525

Leu Leu Thr Lys Arg Leu Leu Arg Lys Trp Trp Asp Glu Ala Met Arg
            530                 535                 540

Pro Asp Leu Pro Glu Ala Leu Leu Pro Leu Leu Asp Glu Val Phe Arg
545                 550                 555                 560

Tyr Asp Leu Met Cys Gln Pro Val Arg Met Leu Pro Asp Gly Ser Gly
                565                 570                 575

Pro Glu Glu Asp Leu Pro Val Val Glu Lys Tyr Gly Ser Glu Trp Tyr
            580                 585                 590

Met Arg Asp Lys Val Thr Phe Thr His Pro Val Pro Glu Leu Ile Ala
            595                 600                 605

Ala Leu Arg Arg Gly Glu Thr Val Ser Thr Glu Pro Arg Cys His Ala
            610                 615                 620

Val Thr Phe Tyr Tyr Arg Thr Gln Phe Gly Gly Asp Leu Gln His Tyr
625                 630                 635                 640

Phe Arg Met Asp Arg Phe Arg Gly Leu Thr Ala Glu Gln Leu Asp His
                645                 650                 655

Gln Phe Thr Arg Val
            660

<210> SEQ ID NO 27
<211> LENGTH: 94
<212> TYPE: PRT
<213> ORGANISM: Streptomyces pactum

<400> SEQUENCE: 27

Met Asp Arg Ala Gly Leu Ile Arg Glu Leu His Glu Ile Ala Ala Gly
1               5                   10                  15

Met Thr Lys Ser Asp Gln His Arg Gln Val Pro Ala Glu Gly Ala Gly
            20                  25                  30

Asp Ala Ser Leu Val Asp Gln Tyr Gly Phe Ser Ser Leu Asp Ala Leu
        35                  40                  45

Glu Tyr Leu Leu Ile Leu Glu Glu Lys Phe Asp Val Val Phe Glu Asp
    50                  55                  60

Glu Asp Leu Thr Glu Glu Thr Leu Phe Ser Ile Glu Gly Leu Ala Thr
65                  70                  75                  80

Tyr Ile Leu Asp Gln Lys Val Gly Glu Thr Thr Ser Ser Ser
                85                  90

<210> SEQ ID NO 28
<211> LENGTH: 318
<212> TYPE: PRT
<213> ORGANISM: Streptomyces pactum

<400> SEQUENCE: 28

```
Met Glu Ala Thr Pro Ala Arg Pro Gly Gly Pro Gly Asp Ile Ser
1               5                   10                  15

Val Ser Val Val Pro Thr Arg Asp Arg Thr Arg Leu Leu Leu
            20                  25                  30

Thr Leu Ala Ala Leu Ala His Gln Thr Leu Asp Arg Asp Arg Phe Glu
        35                  40                  45

Val Ile Leu Val Asp Asp Ala Pro Glu Arg Gly Ala Val Asp Arg Val
50                  55                  60

Leu Ala Ala Ala Pro Gly Thr Pro Pro Leu Arg His Ala Arg Thr Gly
65                  70                  75                  80

Gly Arg Gly Pro Ala Arg Ala Arg Asn Ala Gly Ala Glu Leu Ala Arg
                85                  90                  95

Gly Glu Leu Leu Leu Phe Leu Asp Asp Asp Thr Val Ala Thr Pro Glu
                100                 105                 110

Leu Leu Thr Ala His Leu Ala Ala His Arg Asp Ala Pro Gly Thr Val
                115                 120                 125

Val His Gly Thr Ile Thr Asp Leu Ser Ala Phe Ala Leu Thr Pro Asp
        130                 135                 140

Pro Pro Ala Pro Arg Pro Ala Leu Thr Gly Ala Arg Gly Arg Ser Ile
145                 150                 155                 160

Asp Ala Arg Arg Val Ala Arg Leu Arg Glu Asp Ala Gln Leu Leu Gly
                165                 170                 175

Pro Arg Arg Ser Phe Ile Glu Arg Thr Ala Ala Lys Val Ile Arg Asp
                180                 185                 190

Pro Ala Leu Ala Gly Leu Arg Trp Leu Ala Cys Ile Gly Thr Ser Thr
                195                 200                 205

Ser Val Arg Arg Ala Asp Phe Glu Arg Ala Gly Phe Asp Glu Gly
    210                 215                 220

Phe Gly Glu Leu Trp Gly Gly Glu Asp Leu Glu Leu Gly Leu Arg Leu
225                 230                 235                 240

His Ala Ala Gly Ala Arg Phe Ala Leu Leu Asp Thr Val Ala Tyr His
                245                 250                 255

Leu Pro Thr Ala Arg Arg Asp Thr Gly Glu Leu Leu Pro Arg Phe Trp
                260                 265                 270

Arg Leu Ala Ala Glu Arg His Gly Asp Pro Arg Leu Ala Asp Val Gly
                275                 280                 285

Thr Phe Leu Ala Gly Arg Leu Ser Pro Glu Leu Ala Ala Arg Leu
        290                 295                 300

Gly Thr Arg Thr Ala Ala Leu Ser Pro Gly Arg Ala Ala Pro
305                 310                 315

<210> SEQ ID NO 29
<211> LENGTH: 562
<212> TYPE: PRT
<213> ORGANISM: Streptomyces pactum

<400> SEQUENCE: 29

Met Thr Ala Pro Arg Ala Gly Thr Val Val Gly Gly Thr Ala Ala
1               5                   10                  15

Glu Arg Leu Ala Glu Leu Arg Ser Arg Pro Asp Leu Ala Val Thr Ala
            20                  25                  30

Pro Ala Gln Ser Leu Ala Thr Ala Phe Thr Gly Val Leu Thr Ala Ala
        35                  40                  45

Leu Ala Gly Leu Pro Ala Gly His Arg Arg Gln Ala Pro Val Val Met
```

-continued

```
            50                  55                  60
Ala Ala Thr Asp Tyr Ala Val Ala Ala Thr Ser Gly Tyr Val Ala Arg
 65                  70                  75                  80

Cys Ala Glu Ala Glu Ala Gly Gly Arg Arg Leu Arg Pro Ser Glu Ala
                 85                  90                  95

Met Thr Pro Glu Pro Ala Gln Leu Leu Gln Glu Leu Ala Glu Arg Thr
                100                 105                 110

Asp Trp Gln Gly Pro Gly His Val Leu Ile Ser Pro Arg Ser Ala Thr
                115                 120                 125

Trp Gln Ala Val Arg Trp Ala Phe Gly Ala Val Ser Ala Gly Leu His
                130                 135                 140

Pro Ala Met Val Val Cys Glu Val Ala Arg Asp Pro Ala Gly Gly
145                 150                 155                 160

Tyr Arg Val Ala Ala Val Pro Val Thr Ala Pro Gly Pro His Ala Asp
                165                 170                 175

Pro Pro Thr Gly Pro Val Val Ile Ser Gly Thr Gly Leu Val Thr Ala
                180                 185                 190

Phe Gly Asp Gly Ala Asp Thr Phe Trp Arg Asn Leu Leu Ala Gly Arg
                195                 200                 205

Arg Gly Thr Gly Glu Leu Thr Arg Phe Asp Ala Gly Arg Phe Arg Ser
                210                 215                 220

Arg Thr Val Cys Gln Thr Thr Val Ala Ala Pro Gly Arg Pro Val
225                 230                 235                 240

Arg Arg Ala Leu Val Asp Arg Ala Arg Ala Glu Ala Leu Ala Glu Ala
                245                 250                 255

Gly Leu Gly Arg Leu Pro Glu Arg Thr Leu Leu Val Tyr Ala Gly Val
                260                 265                 270

Val Pro His Leu Pro Ala Val Ala Gly Ala Pro Gly Val Gly Glu Ile
                275                 280                 285

Ala Leu Glu Pro Glu Trp Asp Gly Asp Gly Phe Gly Ala Ala Pro Gly
                290                 295                 300

Asp Arg Val Leu Met Ala His Ala Cys Ala Ser Gly Ala Phe Gly Leu
305                 310                 315                 320

Ala Met Ala Arg Glu Trp Leu Leu Cys Gly Leu Ala Asp Thr Ala Val
                325                 330                 335

Ile Val Gly Val Ser Ala Leu Asn Thr Tyr Asp Tyr Ala Cys Leu Asp
                340                 345                 350

Val Leu Arg Ala Thr Thr Thr Gly Ile Ala Arg Pro Phe Asp Glu Asp
                355                 360                 365

Arg Ser Gly Val Thr Val Gly Glu Gly Ala Gly Val Ile Val Leu Glu
                370                 375                 380

Thr Ala Ala Arg Ala Ala Arg Gly His Arg Pro Pro Ala Val Leu
385                 390                 395                 400

Ala Gly Ile Ser Cys Arg Val Ala Gly Gln Gly Val Ser Ala Leu Ser
                405                 410                 415

Thr Arg Val Gly Ala Val Cys Met Arg Glu Ala Leu Ala Met Ala Gly
                420                 425                 430

Leu Arg Thr Val Asp Tyr Val His Gly His Ala Pro Gly Thr Arg Gln
                435                 440                 445

Gly Asp Glu Ala Glu Leu Arg Ala Leu Asp Gln Val Gly Ala Glu Leu
                450                 455                 460

Gly Trp Arg Asp Val Pro Val Ser Ser Cys Lys Gly Ala Ser Gly His
465                 470                 475                 480
```

```
Leu Leu His Ala Ser Val Phe Pro Ala Val Thr Ala Val Arg Ala
                485                 490                 495

Leu Arg Asp Gly Val Leu Pro Gly Thr Pro Gly Leu Arg Thr Pro Leu
            500                 505                 510

Gly Ala Arg His Val Arg Val Leu Arg Asp Ala Glu Ser Arg Glu Gly
            515                 520                 525

Leu Ser Ser Val Leu Val Asp Asn Phe Gly Phe Gly Gly Asn Asn Ala
            530                 535                 540

Ala Phe Leu Leu Thr Gly Asp Ala Ala Gly His Leu Glu Trp Ser Ala
545                 550                 555                 560

His Gly

<210> SEQ ID NO 30
<211> LENGTH: 575
<212> TYPE: PRT
<213> ORGANISM: Streptomyces pactum

<400> SEQUENCE: 30

Met Ala Asp Ala Val Leu Leu Thr Pro Arg Glu Ile Leu Thr Gly Phe
1               5                   10                  15

Ser Ser Val Asn Asn Gln Asn Val Leu Ile Asn Asp Glu Glu Tyr Leu
            20                  25                  30

Arg Leu Asp Pro Ala Met Arg Leu Phe Tyr Glu Lys Val Arg Glu Asn
            35                  40                  45

Leu Gly Val Ala Cys Ile Ala Gly His Leu Arg Ala Cys Gly Tyr Ser
        50                  55                  60

Val Arg Ala Leu Asn Leu His Gly Arg Asn Pro Ser Asp Glu Ala Ile
65              70                  75                  80

Thr Asp Leu Ile Arg Arg Glu Arg Pro Lys Phe Val Gly Ile Ser Ile
                85                  90                  95

Met Tyr Asp Leu His Ile Val Asp Ala Val Arg Leu Leu Arg Cys Val
            100                 105                 110

Arg Lys Ala Asp Pro Ser Val Phe Val Ala Ile Gly Gly Ala Phe Cys
            115                 120                 125

Thr Tyr Asn Ala Lys Leu Ile Ala Glu Arg Ile Pro Glu Ala Asp Cys
        130                 135                 140

Val Ala Phe Gly Glu Gly Glu Leu Thr Val Glu Gly Leu Met Glu Cys
145                 150                 155                 160

Leu Ala Ala Gly Arg Asp Trp Arg Ser Val Pro Gly Val Trp Phe Trp
                165                 170                 175

Gln Glu Gly Arg Val Arg Ser Ser Gly Pro Pro Lys Leu Pro Asp Leu
            180                 185                 190

His Lys Gln Ala Trp Pro Ala Arg Asp Leu Leu Val His His Arg Gly
            195                 200                 205

Ala Gly Ile Pro Thr Pro Val Ala Ser Thr Tyr Thr Ser Arg Gly Cys
        210                 215                 220

His Ala Lys Cys Thr Phe Cys Tyr Val Pro Arg Ala Pro Gly Val Thr
225                 230                 235                 240

Ala Gly Asn Ala Trp Arg Val Ser Pro Val Asp Val Asp Glu
                245                 250                 255

Ile Glu Phe Leu Gln Arg Glu Phe Gly Thr Arg Phe Leu Trp Phe Asn
            260                 265                 270

Asp Asp Asn Phe Gly Gly Ala Phe Gln Asp Gly Tyr Asn His Ala Val
        275                 280                 285
```

```
Gly Phe Ala Glu Glu Ile Leu Arg Arg Asp Leu Lys Ile Ser Phe His
    290                 295                 300

Cys Glu Phe Arg Val Asp Thr Gly Leu Ile Asp Arg Glu Ala Leu Arg
305                 310                 315                 320

Thr Leu Arg Arg Ala Gly Met Ala Ser Ala Leu Leu Gly Met Glu Thr
                325                 330                 335

Gly Ser Pro Ala Met Ala Lys Arg Phe Arg Lys Gly Thr Leu Val Glu
            340                 345                 350

Tyr Asn Phe Asp Ala Ala Arg Met Phe Arg Gln Glu Asn Ile Glu Leu
        355                 360                 365

Glu Pro Gly Trp Ile Met Val Glu Pro Gly Thr Thr Val Asp Asp Leu
370                 375                 380

Trp Glu Asn Leu Lys Phe Ile Val Ala Ala Asp Ile Ala Val Ser Glu
385                 390                 395                 400

Asn Pro Phe Ser Phe Ile Ser Arg Ala Ile Ala Leu Arg Gly Thr Glu
                405                 410                 415

Met Tyr Asp Lys Ile Thr Asp Pro Ala Pro Pro Asp Leu Ala Glu Val
            420                 425                 430

Glu Gly Pro Ala Arg Glu Val Leu Ser Glu Ala Arg Arg Glu Tyr Arg
        435                 440                 445

Ile Ala Asp Gly Arg Val Glu Asp Val Trp Asp Ala Trp Ala Arg Val
450                 455                 460

Ser Ala Glu Val Ser Asp Arg Lys Glu Glu Leu Pro Phe Val Ala Gln
465                 470                 475                 480

Ile Ile Val Asp Ala Thr Arg Ala Arg Ser Gln Gly Glu Gln Gly
                485                 490                 495

Leu Arg Pro Arg Leu Ser Arg Leu Arg Arg Trp Val Gly Asp Leu Pro
            500                 505                 510

His Leu Leu Ile Ala Phe Leu Asn Val Gly Leu Leu Ala Asp Glu
        515                 520                 525

Asn Pro Pro Gly Leu Ala Gly Arg Leu Glu Thr Glu Leu Arg Ala Leu
530                 535                 540

Val Asp Ala Tyr Asp Arg Glu His Leu Gly Leu Thr Tyr Pro Asp Phe
545                 550                 555                 560

Val Ala Glu Thr Glu Arg Leu Cys Gly Ala Arg Ala Leu Ala Gly
                565                 570                 575

<210> SEQ ID NO 31
<211> LENGTH: 578
<212> TYPE: PRT
<213> ORGANISM: Streptomyces pactum

<400> SEQUENCE: 31

Met Ser Asp Val Val Leu Leu Thr Pro Arg Glu Ile Pro Thr Gly Ala
1               5                   10                  15

Ala Ser Leu Asn Asn Gln Asn Val Leu Ile Asn Asp Glu Glu Tyr Leu
                20                  25                  30

Ser Leu Asp Pro Ala Met Arg Leu Phe Tyr Lys Arg Val Arg Glu Asn
            35                  40                  45

Leu Gly Val Ala Cys Ile Ala Gly His Leu Arg Gly Cys Gly Tyr Ser
        50                  55                  60

Val Arg Ala Leu Asn Leu His Gly Arg Asn Pro Ser Asp Glu Val Ile
65                  70                  75                  80

Thr Asp Leu Ile Arg His Glu Arg Pro Lys Phe Val Gly Ile Ser Ile
```

```
                    85                  90                  95
Met Tyr Asp Leu His Ile Val Asp Ala Val Arg Leu Leu Arg Cys Val
            100                 105                 110

Arg Ala Ala Asp Pro Ser Val Phe Val Ala Ile Gly Gly Ala Phe Cys
            115                 120                 125

Thr Tyr Asn Gly Lys Leu Ile Ala Glu Arg Ile Pro Glu Ala Asp Cys
            130                 135                 140

Val Ala Phe Gly Glu Gly Glu Leu Thr Val Glu Gly Leu Met Glu Cys
145                 150                 155                 160

Leu Ala Ala Gly Arg Asp Trp Arg Ser Val Pro Gly Leu Trp Phe Trp
                165                 170                 175

Gln Asp Gly Arg Val Arg Ser Ser Gly Pro Pro Lys Leu Pro Asp Leu
                180                 185                 190

Ser Lys Gln Ala Trp Pro Ala Arg Asp Val Leu Ile His His Arg Glu
                195                 200                 205

Ala Gly Ile Pro Thr Pro Arg Ala Ser Thr Tyr Thr Ser Arg Gly Cys
                210                 215                 220

His Ala Lys Cys Thr Phe Cys Tyr Ala Pro Arg Gln Pro Gly Val Glu
225                 230                 235                 240

Asn Gly Pro Trp Arg Val Arg Pro Ile Gly Asp Ala Val Asp Glu Ile
                245                 250                 255

Glu Tyr Leu Gln Arg Glu Phe Gly Thr Arg Phe Leu Trp Phe Asn Asp
                260                 265                 270

Asp Asn Phe Gly Gly Ala Phe Gln Asp Gly Tyr His His Ala Val Gly
                275                 280                 285

Phe Ala Glu Glu Ile Leu Arg Arg Gly Leu Lys Ile Asn Phe His Cys
290                 295                 300

Glu Phe Arg Val Asp Thr Gly Leu Ile Asp Arg Glu Ala Leu Arg Thr
305                 310                 315                 320

Leu Arg Arg Ala Gly Met Asp Leu Ala Leu Leu Gly Met Glu Thr Gly
                325                 330                 335

Ser Pro Gly Met Met Lys Arg Phe Arg Lys Gly Thr Thr Val Ala Tyr
                340                 345                 350

Asn Phe Asp Ala Ala Arg Leu Phe Lys Glu Glu Gly Ile Glu Leu Glu
                355                 360                 365

Pro Gly Trp Ile Met Ile Glu Pro Gly Thr Thr Leu Asp Glu Leu Trp
                370                 375                 380

Glu Asn Leu Lys Phe Ile Val Thr Ala Arg Val His Glu Ser Glu Asn
385                 390                 395                 400

Pro Phe Phe Leu Ile Asn Arg Ala Ile Ala Leu Arg Gly Thr Glu Ile
                405                 410                 415

Tyr Asp Lys Ala Thr Arg Tyr Glu Glu Pro Asp Ile Pro Gly Val Glu
                420                 425                 430

Gly Pro Ala Trp Glu Val Leu Arg His Ala Arg Arg Asp Tyr Arg Val
                435                 440                 445

Glu Asp Asp Arg Val Glu His Leu Trp Thr Ala Trp Ser Arg Val Ser
                450                 455                 460

Ser Glu Ile Asn Asp Arg Lys Glu Asn Glu Val Pro Phe Leu Ala Gln
465                 470                 475                 480

Ser Ile Ala Asp Ala Val Arg Ala Arg Gly Thr Gly Ala Glu Ser
                485                 490                 495

Leu Arg Pro Leu Leu Gly Arg Leu Arg Ser Trp Asp Gln Gly Leu Asp
                500                 505                 510
```

```
Ala Leu Leu Ile Ala Phe Leu Asn Val Gly Leu Leu Ala Asp Glu
            515                 520                 525

Asn Pro Pro Glu Leu Ala Asp Arg Leu Glu Ala Gln Leu Arg Asp Met
530                 535                 540

Ile Asn Ala Tyr Asp Arg Glu His Leu Gly His Thr Phe Pro Asp Phe
545                 550                 555                 560

Val Ala Glu Thr Ala Arg Ala Cys Gly Glu His Ala Met Ala Gln Val
            565                 570                 575

Arg Gly

<210> SEQ ID NO 32
<211> LENGTH: 351
<212> TYPE: PRT
<213> ORGANISM: Streptomyces pactum

<400> SEQUENCE: 32

Met Thr Arg Glu Lys Pro Ile Arg Phe Ala Ala Val Gly Ala Gly Arg
1               5                   10                  15

Val Phe Gln Arg Tyr His Leu Pro Cys Val Asp Ala Arg Asp Asp Val
                20                  25                  30

Glu Leu Val Gly Leu Val Asp Ala Asp Ala Asp Arg Ala Ala Ser Val
            35                  40                  45

Ala Ala Gly Arg Pro Gly Val Trp Thr Gly Thr Asp Val Ala Arg Leu
        50                  55                  60

Ile Arg Glu Ala Arg Pro Asp Ala Leu Ser Val Cys Thr Pro Asn Asp
65                  70                  75                  80

Ala His Ala Ala Pro Val Leu Ala Ala Leu Asp Ala Gly Ile Pro Val
                85                  90                  95

Leu Cys Glu Lys Pro Leu Ala Ala Thr Val Asp Glu Ala Arg Arg Met
                100                 105                 110

Ala Glu His Pro Ala Ala Ala Glu Leu Leu Ala Val Asn Met Pro Phe
            115                 120                 125

Arg Cys His Ser Leu Thr Ala Pro Phe Ala Glu Ala Ala Gly Lys Gly
        130                 135                 140

Ala Gln Arg Val Glu Val Ser Phe Val Thr Pro Gly Asn Arg Val Trp
145                 150                 155                 160

Arg Ala Cys Thr Pro Trp Tyr Gly Asp Ala Arg Arg Ala Gly Gly Gly
                165                 170                 175

Ala Leu Leu Asp Leu Gly Pro His Ala Ile Asp Leu Leu Met Thr Val
            180                 185                 190

Phe Gly His Pro Asp Val Glu Ala Cys Thr Val Asn Ala Glu Gly Val
        195                 200                 205

Glu Glu Gln Ala Glu Leu Gln Leu Ser Phe Gln Gly Leu Pro Ala Thr
210                 215                 220

Ile Arg Ile Asp Arg Ala Ala Arg Arg Met Glu Thr Ala Val Thr Val
225                 230                 235                 240

Thr Thr Ala Asp Gly Ala His Val Leu Asp Leu Arg Arg Asn Glu Leu
                245                 250                 255

Arg Leu Ala Asp Gly Thr Val Arg Gln Gly Ala Asp Arg Pro Glu Leu
            260                 265                 270

Ala Ala Ile Ser Ala Phe Phe Asp Ala Val Thr Gly Ala Ala Thr Gly
        275                 280                 285

Ala Ala Gly Ala Ala Gly Asp Gly Pro Ala Ala Gly Gly Ala Ala Gly
            290                 295                 300
```

```
Thr Ser Gly Ala Asp Ala Ala Gly Ala Gly Ala Thr Gly Val Thr Gly
305                 310                 315                 320

Ala Gly Ala Val Gly Ala Arg Glu Ala Leu Ala Val Gln Leu Val Val
            325                 330                 335

Asp Glu Ala Tyr Arg Arg Ala Arg Gly Ala Ala Pro Ala Val Thr
        340                 345                 350
```

<210> SEQ ID NO 33
<211> LENGTH: 257
<212> TYPE: PRT
<213> ORGANISM: Streptomyces pactum

<400> SEQUENCE: 33

```
Val Leu Arg Asp Arg Asp Gln Ser Asn Arg Trp Ser Gly Pro Ala Glu
1               5                   10                  15

Gly Pro Pro Leu Pro Leu Ser Cys Arg Val Thr Gly Glu Pro Asp Gly
            20                  25                  30

Lys Pro Val Val Leu Leu His Ala Leu Gly Asn Thr Gly Arg Asp Trp
        35                  40                  45

Ala Pro Leu Ile Thr Ala Leu Ala Pro Leu Gly Arg Arg Leu Tyr Val
    50                  55                  60

Pro Asp Leu Arg Gly His Gly Ala Ser Pro Arg Ser Glu Arg Tyr Thr
65                  70                  75                  80

Phe Glu Leu Met Tyr Arg Asp Val Val Ala Leu Leu Asp Arg Tyr Arg
                85                  90                  95

Leu Asp Thr Val Asp Leu Val Gly His Ser Met Gly Gly His Ile Gly
            100                 105                 110

Trp Leu Ile Ala Gln Arg Gln Pro Ala Arg Val Arg Arg Leu Val Ile
        115                 120                 125

Glu Asp Thr Pro Pro Pro Arg Asp Ala Ala Ala Glu Glu Glu Met
130                 135                 140

Arg Leu Arg Ser Ala Arg Glu Asp Asp Arg Ala Pro Val Ile Ser Leu
145                 150                 155                 160

Tyr Gln Glu Phe Arg Asp Leu Arg Arg Ser Gly Gly Leu Asp Ser Ala
                165                 170                 175

Ala Val Arg Pro Ile Ile Asp Glu Leu Arg Arg Ala Asp Pro Gly Trp
            180                 185                 190

Trp Arg Arg Leu Ala Glu Val Thr Ala Glu Thr Leu Val Ile Ser Gly
        195                 200                 205

Gly Leu Ser Ser Pro Val Pro Arg Ser Leu Leu Ala Glu Val Ala Gly
    210                 215                 220

Arg Val Pro His Gly Arg Leu Leu Ala Ile Asp Ala Gly His Tyr Val
225                 230                 235                 240

His Arg Thr Glu Pro Glu Arg Phe Cys Ala Glu Val Val Arg Phe Leu
                245                 250                 255

Ser
```

<210> SEQ ID NO 34
<211> LENGTH: 211
<212> TYPE: PRT
<213> ORGANISM: Streptomyces pactum

<400> SEQUENCE: 34

```
Val Ile Leu Phe Ala Thr Ala Val Ala Ala Pro Tyr Gly Pro Arg
1               5                   10                  15
```

```
Glu Gln His Leu Ala Gly Arg Ala Ala Ala Asp Ala Leu Arg Arg
             20                  25                  30

Ala Gly Ser Thr Arg Leu Thr Val Gly Arg Arg Gly Asp Gly Ala Pro
         35                  40                  45

Cys Phe Pro Pro Gly Phe Thr Gly Ser Ile Thr His Thr Arg Arg Leu
 50                  55                  60

Ala Val Ala Val Val Cys Arg Ala Gly Glu Val Arg Gly Ile Gly Val
 65                  70                  75                  80

Asp Leu Glu Thr Asp Pro Val Pro Gly Arg Leu His Arg Ile Leu Leu
                 85                  90                  95

Gly Glu Glu Arg Ala Ala Leu Trp Thr Pro Ala Asp Glu Thr Thr
            100                 105                 110

Leu Arg Gly Leu Phe Val Ala Lys Glu Ala Ala Phe Lys Ala Phe Ser
        115                 120                 125

Ala Gly Gly Glu Arg Ala Thr Arg Met Phe Trp Arg Ile Arg Leu Glu
    130                 135                 140

Arg Pro Asp Pro Gly Pro Glu Pro Pro Gly Ala Val Cys Gly Thr Ser
145                 150                 155                 160

Asp Pro Ala Ser Gly Ala Ser Pro Ser Arg Gly Ala Ser Thr Gly Ser
                165                 170                 175

Gly Thr Trp Leu Val Ala Arg Ala Gly Arg Glu Arg Ala Arg Val Arg
            180                 185                 190

Val Arg Thr Gly Arg Glu Leu Ala Trp Ala Val Ala Val Leu Pro Ala
        195                 200                 205

Pro Ala Pro
    210

<210> SEQ ID NO 35
<211> LENGTH: 1844
<212> TYPE: PRT
<213> ORGANISM: Streptomyces pactum

<400> SEQUENCE: 35

Val Pro Glu Gly Thr Ala Gly Ala Gly Gln Val Thr Tyr Gly Thr Asp
1               5                  10                  15

Gly Thr Asp Arg Ala Ala Gly Thr Arg Gln Val Thr His Gly Thr Asp
             20                  25                  30

Gly Ala Ala Gly Thr Arg Pro Ala Ala His Gly Ala Asp Glu Pro Val
         35                  40                  45

Ala Ile Ile Gly Met Ser Cys Arg Phe Pro Gly Gly Ala Asp Ser Pro
 50                  55                  60

Asp Ala Phe Trp Glu Leu Leu Ala Gln Gly Arg Asp Gly Ile Arg Asp
 65                  70                  75                  80

Gly Ser Ala Arg Trp Ala Ala Tyr Ala Ala Ala Gly His Glu His Ala
                 85                  90                  95

Ala Val Val Arg Arg Thr Thr Gly Phe Gly Gly Phe Leu Asp Asp Ile
            100                 105                 110

Ala Gly Phe Asp Ala Glu Phe Phe Gly Ile Ser Pro Arg Glu Ala Glu
        115                 120                 125

Leu Met Asp Pro Gln Gln Arg Leu Leu Leu Glu Leu Ala Trp Glu Ala
    130                 135                 140

Leu Glu His Ala Gly Leu Pro Pro Leu Glu Leu Ala Gly Gly Asp Cys
145                 150                 155                 160

Gly Val Phe Val Gly Val Gly Ser Asp Asp Tyr Gly Arg Arg Leu Leu
                165                 170                 175
```

-continued

Glu Asp Leu Pro Arg Ile Glu Pro Trp Thr Gly Ile Gly Ala Ser Met
            180                 185                 190
Cys Ala Thr Ala Asn Arg Val Ser His Ser Leu Asp Leu Arg Gly Pro
            195                 200                 205
Ser Leu Ala Val Asp Thr Ala Cys Ser Ala Ser Leu Val Ala Val His
210                 215                 220
Leu Ala Cys Arg Ser Leu Leu Ala Gly Glu Ser Glu Val Ala Leu Ala
225                 230                 235                 240
Ala Gly Val Asn Leu Met Val Ala Pro Gly Leu Ser Val Thr Leu Asp
            245                 250                 255
Arg Ala Gly Ala Thr Ser Pro Asp Gly Arg Ser Lys Pro Phe Asp Ala
            260                 265                 270
Ala Ala Asp Gly Tyr Gly Arg Gly Glu Gly Ala Gly Val Val Val Leu
            275                 280                 285
Lys Arg Leu Ala Asp Ala Glu Arg Ala Gly Asp Pro Val Leu Ala Val
            290                 295                 300
Ile Arg Gly Thr Gly Val Ser Gln Asp Gly Arg Thr Asp Gly Ile Met
305                 310                 315                 320
Ala Pro Ser Gly Glu Ala Gln Ala Asp Leu Leu Arg Arg Thr Tyr Arg
            325                 330                 335
Arg Cys Gly Ile Ala Pro Gly Thr Val Asp Tyr Val Glu Ala His Gly
            340                 345                 350
Thr Gly Thr Val Ala Gly Asp Pro Leu Glu Ala Gly Ala Leu Gly Ala
            355                 360                 365
Val Phe Gly Ala Gly Arg Pro Ala Asp Arg Pro Cys Leu Ile Gly Ser
            370                 375                 380
Val Lys Gly Asn Ile Gly His Leu Glu Ala Gly Ser Gly Ile Ala Gly
385                 390                 395                 400
Val Ile Lys Thr Val Leu Ala Leu Gly Arg Glu Glu Ile Pro Pro Ser
            405                 410                 415
Val His Phe Ser Ala Pro Asn Pro Arg Ile Pro Trp Glu Thr Ala Arg
            420                 425                 430
Leu Arg Val Ala Thr Gly Arg Thr Pro Trp Pro Arg Gly Asp Gly Pro
            435                 440                 445
Arg Arg Ala Gly Val Ser Ser Phe Gly Tyr Gly Gly Thr Ile Ala His
            450                 455                 460
Val Val Leu Glu Glu Ala Pro Ala Pro Ala Pro Gly Arg Ala Pro Ala
465                 470                 475                 480
Pro Glu Pro Ala Val Gly Ala Glu Gly Ala Val Gly Thr Glu Arg Ala
            485                 490                 495
Val Val Thr Glu Pro Ala Pro Ala Ala Gly Pro Ala Pro Ala Ala Gly
            500                 505                 510
Pro Ala Ala Ala Ser Gly Pro Ala Ala Ala Pro Glu Ala Ala Gly Ala
            515                 520                 525
Glu Ala Gly Pro Pro Ser Leu Leu Phe Pro Leu Ser Ala Arg Ser Arg
            530                 535                 540
Glu Ala Val Arg Ala Asp Ala Ala Arg Leu Ala Asp Trp Leu Asp Gly
545                 550                 555                 560
Pro Gly Ala Gly Ala Ala Pro Ala Ser Leu Ala His Thr Leu Gly Val
            565                 570                 575
Arg Arg Ser His Leu Glu His Arg Val Ala Val Val Ala Arg Asp Arg
            580                 585                 590

```
Ala Glu Leu Ala Ala Arg Leu Arg His Val Ala Ala Gly Glu Ala Ala
            595                 600                 605
Pro Gly Val Thr Glu Gly Thr Val Glu Gly Ala Gly Thr Gly Val
610                 615                 620
Val Trp Val Phe Ser Gly Thr Gly Ala Gln Trp Pro Gly Met Gly Arg
625                 630                 635                 640
Glu Leu Leu Ala Thr Glu Pro Ala Phe Ala Ala Val Ile Asp Arg Ile
                645                 650                 655
Asp Pro Val Tyr Ala Ala Glu Ile Gly Thr Thr Ala Arg Arg Met Ile
                660                 665                 670
Gln Glu Gly Asp Val Ser Arg Val Asp Val Ala Gln Ala Met Ile Phe
            675                 680                 685
Ala Val Gln Ala Gly Leu Thr Ala Val Trp Thr Ser Leu Gly Val Arg
            690                 695                 700
Pro Ala Ala Val Val Gly His Ser Leu Gly Glu Ile Ala Ala Ala Val
705                 710                 715                 720
Ala Ala Gly Val Leu Ser Val Glu Asp Gly Ala Arg Leu Val Cys Arg
                725                 730                 735
Arg Ser Val Leu Leu Arg Arg Val Ala Gly Ala Gly Gly Met Leu Leu
            740                 745                 750
Val Gly Leu Ser Ala Glu Glu Ala Thr Asp Arg Leu Gly Thr Ala Asp
            755                 760                 765
Asp Val Val Pro Ala Val Leu Ala Ser Pro Thr Ser Thr Val Leu Ser
            770                 775                 780
Gly Pro Val Ala Arg Ile Asp Ala Leu Ala Arg Glu Trp Ser Ala Asp
785                 790                 795                 800
Pro Glu Leu Leu Val Arg Arg Val Asp Ser Glu Val Ala Phe His Ser
                805                 810                 815
Pro Gln Met Asp Pro Leu Leu Asp Glu Leu Ala Arg Ala Ala Ala Pro
                820                 825                 830
Leu Thr Val His Pro Pro Ala Val Pro Ile Tyr Gly Thr Ala Leu Ala
            835                 840                 845
Asp Pro Arg Asp Pro Ala Pro Arg Gly Gly Ala Tyr Trp Ala Ala Asn
850                 855                 860
Leu Arg Asn Pro Val Arg Leu Ala Gly Ala Val Ala Ala Ala Ala Glu
865                 870                 875                 880
Asp Gly Phe Arg Ala Phe Leu Glu Ile Ser Ala His Pro Val Val Gly
                885                 890                 895
His Ser Val Gln Glu Thr Leu Asp Ala Ala Gly Ala Ala Gly His Cys
            900                 905                 910
Val Ala Gly Ser Leu Arg Arg Asp Ala Gly Gly Arg Asp Gln Leu Leu
            915                 920                 925
Leu Asn Ala Gly Leu Leu Tyr Cys His Gly Ala Ala Pro Asp Arg Ala
930                 935                 940
Ala Phe Pro Asp Gly Glu Leu Leu Ala Leu Pro Pro Thr Trp Arg
945                 950                 955                 960
Arg Arg Thr Tyr Trp Arg Asp Leu Pro Ala Arg Arg Glu Asp Arg Gly
                965                 970                 975
Arg His Asp Pro Ala Gly Arg Thr Leu Leu Gly Pro Arg Thr Val Leu
            980                 985                 990
Ala Gly Ala Thr Pro Leu His Leu Trp Arg Thr Arg Val Asp Met Glu
            995                1000                1005
Thr Arg Pro Tyr Pro Gly His His Thr Ile Gln Gly Thr Glu Ile
```

-continued

```
                1010                1015                1020
Val Pro Ala Ala Val Val Leu Gln Thr Phe Leu Asp Ala Thr Gly
            1025                1030                1035
Thr Gly Pro Gly Pro Arg Gly Leu Thr Gly Val Asp Phe Ala Leu
            1040                1045                1050
Pro Leu Thr Leu Glu Pro Ala Arg Asp Ile Asp Val Thr Ala Gln
            1055                1060                1065
Asp Gly Val Val Arg Leu Leu Ser Arg Pro Ala Ala Thr Gly Thr
            1070                1075                1080
Asp Ser Asp Thr Gly Arg Gly Pro Glu Gly Gly Gly Ser Asp Ala
            1085                1090                1095
Gly Pro Asp Gly Gly Glu Arg Glu Trp Leu Thr His Ala Ser Ala
            1100                1105                1110
Ser Ala Ala Glu Asp Leu Thr Pro Pro Asp Ala Ala Pro Pro Ala
            1115                1120                1125
Gly Gly Pro Gly Thr Val Leu Pro Pro Asp Arg Ala His Ala Asp
            1130                1135                1140
Leu Ala Ala Val Gly Val Pro Thr Met Ala Phe Pro Trp Glu Val
            1145                1150                1155
Thr Arg Leu Glu Arg Leu Pro Asp Gly Leu Arg Ala Glu Val Thr
            1160                1165                1170
Ala Ala Asp Gly Pro Glu Gly Thr Pro Asp Gly Trp Ala Pro Leu
            1175                1180                1185
Leu Asp Ala Ala Leu Ser Val Ala Ala Val Ala Phe Pro Gly Thr
            1190                1195                1200
Pro Ala Leu Arg Val Val Ala Gly Val Ser Arg Val Trp Thr Ala
            1205                1210                1215
Gly Gly Ala Pro Asp Arg Ala Arg Ile Glu Ala Arg Val Thr Gly
            1220                1225                1230
Pro Val Thr Glu Ala Ala Gly Thr Val Asp Val Thr Leu Val Ala
            1235                1240                1245
Ala Asp Gly Arg Thr Val Ala Val Leu Ala Gly Val Arg Tyr Ala
            1250                1255                1260
Gly Ala Ala Ala Asp Gln Pro Arg Ala Ala Glu Pro Glu Glu Leu
            1265                1270                1275
Leu Tyr Ala Thr Glu Trp His Pro Leu Thr Val Asp Pro Ala Asp
            1280                1285                1290
Leu Pro Leu Pro Pro Arg Pro Leu Val Leu Val Gly Pro Ala Glu
            1295                1300                1305
Gly Pro Gly Pro Ala Leu Arg Ala Arg Cys Thr Glu Thr Gly Arg
            1310                1315                1320
Arg Val Ala Leu Leu Ala Asp Pro Asp Gly Leu Asp Pro Leu Leu
            1325                1330                1335
Asp Arg Ala Gly Gly Pro Val Asp Val Leu Val Leu Pro Val Ala
            1340                1345                1350
Ala Glu Pro Ala Glu Pro Ala Ala Asp Arg Ala Val Arg Glu Ala
            1355                1360                1365
Trp Leu Leu Ala Arg Thr Ala Arg Arg Leu Ala Ala Arg Pro Pro
            1370                1375                1380
Gly Gln Ala Arg Leu Trp Ser Leu Thr Val Gly Val Arg Glu Ala
            1385                1390                1395
Ala Gly Ala Asp Ser Val Ala Gln Ala Ala Arg Trp Gly Leu Gly
            1400                1405                1410
```

Arg Ile Ile Gly Gly Glu His Pro Asp Leu Trp Gly Gly Thr Leu
1415                1420                1425

Asp Leu Ala Pro Asp His Thr Ala Ala Asp Leu Ala Thr Ala Leu
1430                1435                1440

Asp Val Ser Ala Ala Gly Pro Gly Glu Asp Val Val Ala Val Arg
1445                1450                1455

Gly Gly Arg Ala Glu Ala Asn Arg Leu Val Arg Cys Ala Ala Pro
1460                1465                1470

Pro Ala Arg Pro Pro Leu Arg Cys Arg Ala Asp Gly Ser Tyr Leu
1475                1480                1485

Ile Thr Gly Gly Leu Gly Gly Leu Gly Gly Glu Ile Ala Arg Arg
1490                1495                1500

Leu Val Glu Leu Gly Ala Arg Arg Leu Val Leu Ala Gly Arg Ser
1505                1510                1515

Ala Leu Pro Pro Arg Ser Ala Trp Asp Thr Val Thr Asp Pro Glu
1520                1525                1530

Gln Ala Arg Arg Ile Ala Thr Val Arg Arg Leu Glu Ala Leu Gly
1535                1540                1545

Ala Thr Val Arg Val Val Ala Leu Asp Ile Ala Asp Ala Gly Ala
1550                1555                1560

Ala Ala Ala Ala Leu Asp Pro Asp Ala Leu Asp Leu Pro Pro Ile
1565                1570                1575

Arg Gly Val Val His Ala Ala Gly Val Thr Asp Asp Arg Leu Val
1580                1585                1590

Glu Gln Leu Asp Arg Asp Ala Leu Ala Ala Val Ile Arg Pro Lys
1595                1600                1605

Ala Ala Gly Ala Phe Thr Leu His Arg Leu Phe Pro Pro Gly Ser
1610                1615                1620

Leu Asp Phe Val Val His Phe Ser Ser Cys Gly Gln Leu Leu Gly
1625                1630                1635

Leu Thr Gly Gln Gly Ala Tyr Ala Ala Ala Asn Ala Phe Leu Asp
1640                1645                1650

Ala Val Ala Gly Tyr Glu Arg Ala Ala Gly Ser Ala Gly Ser Met
1655                1660                1665

Ser Leu Ala Trp Thr Ser Trp Arg Gly Ile Gly Leu Ala Asp Asn
1670                1675                1680

Ala Ala Val Asp Ala Glu Leu Ala Ala His Gly Val Gly Asp Val
1685                1690                1695

Thr Val Pro Glu Ala Leu Ala Ala Trp Asp His Ala Ala Arg Leu
1700                1705                1710

Gly Leu Pro Ser Leu Ala Val Leu Arg Thr Val Pro Leu Pro Glu
1715                1720                1725

Gly Thr Arg Arg Thr Gly Leu Leu Arg Asp Val Thr Asp Pro Glu
1730                1735                1740

Pro Ala Thr Pro Ala Pro Gly Gly Ala Ala Ala Gly Ala Gly Ile
1745                1750                1755

Asp Gly Leu Ser Gly Glu Glu Leu Arg Ala Ala Leu Arg Glu Arg
1760                1765                1770

Thr Ala Ala Leu Ile Val Gly Glu Met Arg Trp Asp Pro Ala Gly
1775                1780                1785

Leu Asp Pro Asp Arg Ser Leu Leu Lys Met Gly Met Asp Ser Val
1790                1795                1800

```
Met Ala Ile Val Ile Arg Arg Lys Leu Glu Gln Leu Leu Gly Arg
    1805                1810                1815

Lys Leu Pro Ala Asn Leu Val Trp His Gln Gln Thr Val Ser Asn
    1820                1825                1830

Ile Val Asp Tyr Leu Val Thr Thr Ser Arg Pro
    1835                1840
```

<210> SEQ ID NO 36
<211> LENGTH: 357
<212> TYPE: PRT
<213> ORGANISM: Streptomyces pactum

<400> SEQUENCE: 36

```
Val Arg Thr Pro Gly Ile Phe Leu Ala Ala Thr Gly Ala Tyr Leu Pro
  1               5                  10                  15

Glu Arg Thr Ser Val Glu Asp Ala Val Arg Arg Gly Trp Tyr Glu Arg
             20                  25                  30

Glu Arg Met Glu Ser Cys Gly Trp Arg Asn Val Ala Val Ala Asp Gly
         35                  40                  45

Ile Ser Ala Pro Asp Met Ala Val Ala Val Arg Gln Ala Val Ala
     50                  55                  60

Arg Ser Gly Leu Ser Arg Asp Asp Ile Asp Leu Val His Ser Cys
 65                  70                  75                  80

Ala Tyr His Gln Gly Pro Asp Gly Trp Ser Ala Pro His Tyr Ile Leu
                 85                  90                  95

Arg Ala Thr Leu Gly Thr Pro Val Pro Ala Leu Thr Val Glu Gln Gly
            100                 105                 110

Cys Asn Ala Phe Leu Ala Ala Leu Glu Met Ala Thr Gln Tyr Leu Leu
        115                 120                 125

Cys Ala Pro Thr Arg Ser Gly Ala Val Val Ser Ala Ala Asp Asn Phe
    130                 135                 140

Gly Ala Pro Ser Val Asp Arg Trp His Ala His Arg Asp Ser Val Leu
145                 150                 155                 160

Ala Asp Ala Gly Ala Ala Val Val Leu Ser Lys Arg Ser Gly Trp Ala
                165                 170                 175

Glu Leu Arg Ala Val Glu Ser Val Ser Leu Pro Gln Phe Glu Ile Leu
            180                 185                 190

Asn Arg Gly His Ala Pro Ile Phe Pro Pro Ala Leu Thr Leu Gly Lys
        195                 200                 205

Lys Leu Asp Met Asn Glu His Leu Glu Ala Met Val Ala Glu Leu Gly
    210                 215                 220

Pro Arg Ala Ser Glu Ile Val Glu Tyr Gly Ala Ser Gly Thr Lys
225                 230                 235                 240

Leu Val Glu Gln Val Ala Ser Glu Ala Gly Ile Thr Val Pro Asp Leu
                245                 250                 255

Ser His Val Leu His Leu Gly Ala Ala Thr Thr Asp Phe Leu Asp Ser
            260                 265                 270

His Leu Arg Pro Met Gly Leu Asp Ala Ser Leu Gly Ser Val Glu Phe
        275                 280                 285

Phe Arg Asp Val Gly His Ala Gly Ala Ala Asp Val Gly Ile His Leu
    290                 295                 300

Asp His Leu Ala Cys Ser Gly Arg Leu Ala Ala Gly Asp His Leu Leu
305                 310                 315                 320

Met Leu Ser Ala Gly Pro Gly Leu Met Ile Thr Ala Ala Val Val Thr
                325                 330                 335
```

```
Val Leu Glu Thr Pro Ala Ser His Thr Ala Ala Pro Ala Asp Asp Glu
            340                 345                 350

Gly Ser Gly Ala Trp
        355

<210> SEQ ID NO 37
<211> LENGTH: 505
<212> TYPE: PRT
<213> ORGANISM: Streptomyces pactum

<400> SEQUENCE: 37

Met Thr Ser Ala Arg Ala Glu Leu Leu Ala Arg Leu Arg Asp Arg Ala
1               5                   10                  15

Ala Arg Leu Gly Asp Ala Pro Leu Val Val Ala Gly Asp Thr Val Thr
            20                  25                  30

Gly Ala Arg Glu Leu Leu Ala Arg Thr Glu Ala Lys Val Arg Ala Leu
        35                  40                  45

Gly Glu Leu Gly Val Gly Pro Gly Ala Leu Val Gly Thr Val Ala Gly
    50                  55                  60

Pro Pro Ala Glu Phe Ile Ser Asp Val Phe Ala Ile Ile Glu Ala Gly
65                  70                  75                  80

Gly Val Ala Val Pro Leu Ser Arg Lys Leu Thr Arg Trp Glu Leu Asp
                85                  90                  95

Arg Leu Gln Glu Gly Cys Pro Leu Asp Phe Leu Ala Ala Pro Pro Glu
            100                 105                 110

Ser Pro Leu Thr Leu Ala Gly Pro Val Thr Gly Cys Gly Asp Arg Ala
        115                 120                 125

Leu Ser Arg Gly Pro Gly Arg Ile Arg Pro Ala Phe Ala Glu Ala Ala
    130                 135                 140

Thr Ala Gln Leu Thr Ser Gly Thr Thr Gly Arg Pro Arg Val Ala Leu
145                 150                 155                 160

Arg Pro Ala Ala Ala Leu Leu Ala Glu Ala Asp His Tyr Arg Asp Ala
                165                 170                 175

Leu Arg Leu Thr Pro Arg Thr Thr Leu Leu Cys Pro Val Pro Leu Gln
            180                 185                 190

His Ala Tyr Gly Phe Gly Leu Cys Ala Leu Ala Ala Pro Leu Ala Gly
        195                 200                 205

Ala Pro Val Arg Gln Leu Pro Pro Asp Arg Pro Arg Met Leu Leu Arg
    210                 215                 220

Glu Leu Ala Ala Gly Asp Val Ala Leu Phe Val Gly Val Pro Pro Met
225                 230                 235                 240

Leu Arg Leu Leu Ala Lys Ser Ala Arg Gly Pro Val Pro Ala Gly Arg
                245                 250                 255

Pro Val Gly Phe Leu Ser Ala Gly Met Ala Leu Asp Ala His Thr Ala
            260                 265                 270

Glu Gln Val Ala Val Arg Leu Gly Gly Asn Val Gly Glu Val Tyr Gly
        275                 280                 285

Thr Thr Glu Thr Gly Pro Ile Cys Val Arg Ala Pro Arg Pro Trp Arg
    290                 295                 300

Pro Gly Leu Arg Arg Pro Gly Val Pro Leu Pro Gly Val Lys Val Thr
305                 310                 315                 320

Leu Ala Pro Val Pro Gly Asp Ala Pro Glu Ala Gly Ala Gly Thr Gly
                325                 330                 335

Ser Gly Asp Ala Thr Arg Ala Asp Ala Thr Gly Pro Arg Asp Ala Thr
```

```
                340             345             350
Gly Pro Gly Ala Gly Pro Gly Ala Gly Thr Gly Leu Val Thr Val Glu
            355             360             365
Ser Pro Ser Met Met Leu Gly Tyr Ala Asp Gly Asp Ala Val Asp Thr
        370             375             380
Gly Pro Ser Arg Gly Gly Phe Thr Thr Gly Asp Leu Ala Arg Trp Glu
385             390             395             400
Gly Asp Asp Leu Val Leu Ala Gly Arg Leu Ser Thr Cys Ile Asn Val
                405             410             415
Ala Gly Ala Lys Val Ser Pro Glu Glu Val Glu Ala Val Leu Leu Ala
            420             425             430
Trp Pro Glu Val Ala Ser Cys Leu Val Thr Gly Val Pro Asp Pro Val
        435             440             445
Leu Gly Gln Arg Val Ser Ala Thr Val Thr Pro Glu Thr Val Asp Leu
    450             455             460
Ala Ala Leu Asp Arg Phe Cys Arg Glu Arg Leu Ser Asp Ser Arg Thr
465             470             475             480
Pro His Thr Phe Ala Ala Val Ala Glu Leu Pro Thr Thr Glu Thr Gly
                485             490             495
Lys Val Ile Arg Pro Arg Asn Asp Gln
            500             505

<210> SEQ ID NO 38
<211> LENGTH: 444
<212> TYPE: PRT
<213> ORGANISM: Streptomyces pactum

<400> SEQUENCE: 38

Val Gly Ala Asn Asp Ala Asp Arg Pro Thr Asn Ala Glu Ser Leu Asp
1               5               10              15
Gly Ile Lys Ser Val Ile Ala Gly Val Ser Ser Ser Met Arg Ala
            20              25              30
Ala Ala Val Pro Leu Pro Leu Val Val Arg Ser Ala Gly Gly Cys Leu
        35              40              45
Leu Arg Asp Val Glu Asp Gly Glu Ile Ile Asp Leu Asn Met Gly Tyr
    50              55              60
Gly Pro His Leu Phe Gly Tyr Ala Asp Arg Glu Val Leu Asp Ala Val
65              70              75              80
Ala Asp Gln Phe Ala Lys Gly His Met Thr Gly Leu Pro His Glu Leu
            85              90              95
Asp Ala Arg Ala Gly Ala Leu Ile Ala Glu Leu Val Pro Gly Val Glu
        100             105             110
Gln Val Arg Phe Ala Asn Ser Gly Thr Glu Ala Val Ala Ser Ala Leu
    115             120             125
Arg Leu Ala Arg Ala Thr Thr Gly Arg Thr Leu Val Val Thr Phe Glu
130             135             140
Gly His Tyr His Gly Trp Ser Glu Thr Val Leu Arg Ala Gly Lys Thr
145             150             155             160
Ala Leu His Met Glu Gly Thr Arg Pro Thr Asp Val Val Pro Gly Ala
            165             170             175
Leu Gly Met Ile Pro Glu Ala Leu Ala His Thr Val Gln Leu Gly Trp
        180             185             190
Asn Asp Pro Asp Ala Leu Arg Glu Leu Phe Ala Arg Asp Gly Asp Arg
    195             200             205
```

```
Ile Ala Ala Val Ile Val Glu Pro Val Leu Ala Asn Ala Gly Val Ile
        210                 215                 220

Pro Pro Ala Pro Gly Phe Leu Gln Leu Leu Arg Glu Leu Thr Gly Arg
225                 230                 235                 240

Ser Gly Ala Met Leu Val Phe Asp Glu Val Ile Thr Gly Phe Arg Val
                245                 250                 255

Ala Arg Gly Gly Ala Gln Glu Arg Tyr Gly Val Glu Pro Asp Leu Thr
            260                 265                 270

Val Leu Ser Lys Val Met Gly Gly Phe Pro Val Ala Ala Phe Gly
        275                 280                 285

Gly Arg Arg His Ala Met Arg Met Leu Ala Ser Asn Glu Ala His His
290                 295                 300

Ala Gly Val Tyr Ala Gly Asn His Ala Ala Leu Arg Ala Val Val Ala
305                 310                 315                 320

Met Leu Gly Lys Ile Arg Ser Leu Pro Asp Leu Tyr Glu Arg Leu Glu
                325                 330                 335

Asp Thr Gly Gln Tyr Met Glu Asp Thr Val Arg Glu Val Phe Ala Thr
            340                 345                 350

Glu Lys Arg Pro Val His Ile Asn Arg Val Gly Thr Leu Met Ser Val
        355                 360                 365

Ala Leu Leu Lys Gly Ser Ala Glu Pro Ser Ala Glu Pro Arg Asp Leu
370                 375                 380

Arg Gln Leu Ala Ala Leu Val Asp Phe Pro Arg His Arg Arg Leu Gln
385                 390                 395                 400

Thr Leu Ala Gln Lys Glu Gly Val Tyr Phe His Pro Asn Ala Leu Glu
                405                 410                 415

Pro Trp Phe Leu Ser Thr Ala His Thr Arg Asp Val Ile Asp Lys Val
            420                 425                 430

Ala Gly Ala Leu Gln Arg Ser Leu Val Gly Leu Gly
        435                 440

<210> SEQ ID NO 39
<211> LENGTH: 279
<212> TYPE: PRT
<213> ORGANISM: Streptomyces pactum

<400> SEQUENCE: 39

Met Pro Arg Ser Ala Thr Glu Lys Asp Ser Ala Thr Ala Lys Val His
1               5                   10                  15

Ile Ala Asp Gly Gly Val Pro Pro Arg Gly Asp Val Met Ser Ser Arg
            20                  25                  30

Arg Ala Val Ala Val Val Thr Gly Ala Gly Ser Gly Leu Gly Ala Ala
        35                  40                  45

Val Ala Leu Arg Leu Ala Thr His Asp Leu Val Leu Thr His Leu
    50                  55                  60

Thr Glu Asp Asp Ala Leu Ala Glu Thr Ala Gly Arg Ala Ala Ala Ala
65                  70                  75                  80

Gly Ala Arg Val Leu Ala Thr Val Pro Gly Asp Leu Thr Asp Arg Arg
                85                  90                  95

Thr Val Asp Arg Leu Glu Ala Arg Met Ala Glu His Ala Glu His Leu
            100                 105                 110

Asp Val Leu Val Cys Asn Ala Gly Ala Tyr Arg Tyr Val Pro Trp Pro
        115                 120                 125

Glu Thr Ser Trp Glu Asp Ile Arg Ala Ala Val Glu Val Asn Leu Leu
130                 135                 140
```

```
Ala His Ile Ala Cys Ile His Ala Ala Thr Pro His Leu Val Ala Arg
145                 150                 155                 160

Gly Met Gly Arg Ile Val Ala Ile Ser Thr Val Leu Thr Gln Leu Gly
                165                 170                 175

Arg Val Glu Leu Ala Pro Tyr Ile Ala Lys Gly Gly Leu Glu Ser
            180                 185                 190

Leu Val Arg Ala Leu Ala Arg Glu Leu Gly Pro His Gly Ile Thr Val
            195                 200                 205

Asn Ala Val Arg Pro Gly Ser Ile Glu Leu Ser Val Glu Gln Arg Arg
210                 215                 220

His Pro Asp Tyr Pro Thr Trp Arg Gln Arg Glu Phe Ala Arg Gln Cys
225                 230                 235                 240

Ile Lys Arg His Gly Arg Pro Glu Asp Val Ala Ala Val Ala Phe
            245                 250                 255

Leu Val Ser Pro Glu Ala Gly Phe Ile Thr Gly Gln Ser Leu Thr Val
            260                 265                 270

Asp Gly Gly Trp Asp Leu Asn
            275

<210> SEQ ID NO 40
<211> LENGTH: 226
<212> TYPE: PRT
<213> ORGANISM: Streptomyces pactum

<400> SEQUENCE: 40

Met Thr Leu Met Ala Tyr Gly Glu Gln Pro Leu Thr Arg Val Leu Leu
1               5                   10                  15

Val Arg His Ala Gln Ser His Ala Ser Val Arg Lys Val Val Ala Gly
                20                  25                  30

Ala Ala Thr Cys Glu Gly Leu Thr Glu His Gly Arg Glu Gln Ala Gly
            35                  40                  45

Arg Leu Ala Ala Arg Leu Ala Ala Glu Arg Leu Arg Pro Asp Ala Leu
    50                  55                  60

Leu Thr Ser Pro Val Arg Arg Ala Arg Glu Thr Ala Thr Val Leu Ala
65                  70                  75                  80

Ala Gly Leu Gly Leu Pro Glu Pro Val Val Glu Pro Val Arg Glu
                85                  90                  95

Leu Asp Phe Gly Ala Ala Asp Gly Leu Ser Ile Asp Glu Tyr Gly Arg
            100                 105                 110

Arg His Gly Thr Phe Asp Met Thr Ala Glu Pro Asp Arg Pro Phe Ala
            115                 120                 125

Pro Gly Gly Glu Ser Trp Ser Gly Phe Arg Gly Arg Ala Gly Arg Val
130                 135                 140

Met Gly Glu Leu Ala Asp Arg Tyr Pro Gly Gly Thr Val Leu Val Val
145                 150                 155                 160

Cys His Ala Gly Leu Ile Val Ala Thr Ser Gly Leu Leu Asp Val
            165                 170                 175

Ala Pro Pro Val Leu Phe Thr Asp Ala Ser Pro Ala Ala Thr Ser Val
            180                 185                 190

Asn Glu Phe Val Arg Ser Asp Thr Gly Trp Ser Leu Leu Arg Phe Asp
            195                 200                 205

Asp Ala Ala His Leu Glu Gly Ala Ala Gly Pro Leu Pro Gly Glu Pro
210                 215                 220

Val Arg
```

-continued

225

<210> SEQ ID NO 41
<211> LENGTH: 271
<212> TYPE: PRT
<213> ORGANISM: Streptomyces pactum

<400> SEQUENCE: 41

Val Ser Leu Arg Gly Arg Gly Glu Ser Ile Gly Arg Glu Arg Asp
1               5                   10                  15

Met Val His Glu Gln Ser Gly Gly Thr Pro Ala Glu His Leu Asp Gly
        20                  25                  30

Leu Leu Ala Arg Ala Gln Asn Gly Phe Glu Ile Asp Asp Thr Val Ile
        35                  40                  45

Ile Arg Leu Arg Asp Ala Leu Met His Gln Thr Glu Leu Arg Ser Cys
        50                  55                  60

Arg Gln Cys Asn Glu Pro Pro Ala Pro Arg Gly Tyr Thr Thr Phe Arg
65                  70                  75                  80

His Ile Phe Leu Leu Pro Asp Gly Ser Ser Val Val Leu Trp Glu Leu
                85                  90                  95

Gln His Ser Ala Gly Pro Gly Asp Gly Leu Gln His Glu Leu Tyr Ala
            100                 105                 110

Asp Glu Glu Ala Leu Leu Arg Ala Glu Arg Arg Ala His Leu Arg Thr
        115                 120                 125

Gly Gly Thr Ser Trp Ala Glu Val Thr Leu Glu Gly Leu Arg Pro Glu
    130                 135                 140

Glu Val Leu Arg Thr Pro Leu Pro Val Glu Thr Val Arg Ala Tyr Val
145                 150                 155                 160

Ala Asp Asn Ser Ala Asp His Ala Arg Arg Val Leu Arg Arg Ala Glu
                165                 170                 175

Asn Glu Asp Arg Pro Gly Lys Asp Val Glu Arg Leu Leu Glu Thr Ala
            180                 185                 190

Phe Ala His Asp Ile Ala Leu Ala Pro Lys Pro Arg Arg Arg Ser Gly
        195                 200                 205

Gly Glu Asp Thr Thr Trp Cys Arg Phe Tyr Glu His Ala Phe Leu Leu
    210                 215                 220

Ala Gly Gly Asp Glu Ile Thr Leu Trp Glu Leu Glu His Asn Leu Thr
225                 230                 235                 240

Ser Asp Gly Arg Leu Val Cys Glu Val Tyr Leu Asp Glu Gly Ala Ala
                245                 250                 255

Glu Met Ala Ala Asp Arg Arg Ala Arg Ala Arg Gly Val Glu Leu
            260                 265                 270

<210> SEQ ID NO 42
<211> LENGTH: 431
<212> TYPE: PRT
<213> ORGANISM: Streptomyces pactum

<400> SEQUENCE: 42

Val Arg Thr Pro Asp Gly Gly Gly Gly Gly Gly Gly Gly Asp Arg
1               5                   10                  15

Pro Arg Gly Arg Gly Ala Arg Arg Gly Gly Gly Ala Asn Gly Arg Glu
        20                  25                  30

Ala Asp Arg Glu Arg Arg Arg Asn Arg Arg Phe Ala Gly Trp Leu Ser
        35                  40                  45

Ala Ala Leu Ile Ala Gly Gly Val Val Phe Asp Leu Leu Thr Pro Arg

```
                50                  55                  60
Asn Val Ser Ala Ala Pro Phe Ala Ala Pro Leu Ile Ala Ala
 65                  70                  75                  80

Pro Phe Ala Thr Phe Ala Val Thr Ala Phe Thr Ala Ala Ser Val
                 85                  90                  95

Gly Thr Ala Leu Val Leu Met Leu Cys His Gly Phe Asp Gly Pro His
                100                 105                 110

Asp Arg Thr Glu Ser Leu Phe Glu Phe Val Thr Val Leu Thr Val Ala
                115                 120                 125

Leu Leu Ala Leu Ala Thr Asn Arg Val Val Arg Gly Gly Arg Lys
                130                 135                 140

Leu Ala Ser Ala Arg Gly Ile Ala Ala Val Gln Arg Ala Val Leu
145                 150                 155                 160

Pro Val Pro Pro Ala Val Val Gly Gly Leu Gly Val Ala Ala Arg Tyr
                165                 170                 175

Glu Ala Ala Gln Ala Asp Ala Gly Ile Gly Gly Asp Leu Tyr Ala Val
                180                 185                 190

Gln Glu Thr Pro His Gly Val Arg Ala Val Gly Asp Val Arg Gly
                195                 200                 205

Lys Gly Leu Gly Ala Val Glu Ala Val Thr Val Val Leu Gly Ala Phe
210                 215                 220

Arg Glu Ala Ala Glu Glu Pro Asp Leu Glu Gly Leu Ala Gly Arg
225                 230                 235                 240

Leu Glu Arg Ala Leu Asp Arg Glu Gly Arg Arg Ala Asn Leu Asp
                245                 250                 255

Gln Val Glu Gly Phe Thr Thr Ala Val Leu Ala Glu Ile Pro Pro Gly
                260                 265                 270

Ala Ser Thr Val Arg Leu Leu Asn Arg Gly His Pro Pro Leu Leu
                275                 280                 285

Phe Leu Pro Gly Gly Val Arg Thr Thr Glu Pro Ala Val Pro Ala
                290                 295                 300

Met Pro Leu Gly Met Arg Glu Leu Gly Glu Trp Pro Asp Arg Ala Asp
305                 310                 315                 320

Glu Leu Ala Phe Pro Pro Gly Ala Thr Leu Leu Phe Thr Asp Gly
                325                 330                 335

Val Thr Glu Ala Arg Asp Ala His Gly Val Phe Tyr Asp Pro Ala Gly
                340                 345                 350

Arg Leu Gly Asp Arg Thr Trp Pro Asp Pro Asp Thr Leu Leu Asp Ala
                355                 360                 365

Leu Val Thr Asp Val Val Arg His Thr Gly Gly Ala Ala Asp Asp
370                 375                 380

Met Ala Leu Leu Ala Val His Arg Pro Gly Glu Ser Gly Glu Pro Ala
385                 390                 395                 400

Ala Glu Pro Gly Pro Val Glu Arg Asn Arg Thr Gly Pro Gly Asn Gly
                405                 410                 415

Pro Gly Asn Gly Pro Ala Pro Ser Arg Asp Gly Ser Gly Pro Ala
                420                 425                 430
```

<210> SEQ ID NO 43
<211> LENGTH: 448
<212> TYPE: PRT
<213> ORGANISM: Streptomyces pactum

<400> SEQUENCE: 43

```
Val Ala Pro Cys Ala Val Ala Glu Ser Arg Thr His His Gly Arg Arg
1               5                   10                  15

Gln Ala Val Thr Ser Ser Thr Arg Glu Pro Gly Asn His His Pro Trp
            20                  25                  30

Gly Glu Ser Gly Arg Ser Arg Pro Val Gly Asp Leu Pro Ala Pro Asn
        35                  40                  45

Pro Ser Ala Asn Pro Val Gly Glu Arg Glu Gly Lys Glu Cys Ala Ser
    50                  55                  60

Val Ala Ser Asn Arg Ser Ala Leu Asp Glu Ala Pro Tyr Gly Ser Leu
65                  70                  75                  80

Thr Gly Pro Ala Asp Gly Ala Asp Pro Ala Thr Ala Thr Leu Thr Ala
                85                  90                  95

Gly Glu Pro Ala Gly Gly Glu Trp Asn Pro Thr Ala Glu Ser Leu Ala
                100                 105                 110

Pro Val Arg Arg Arg His Arg Val Lys Gln Arg Gly Thr Met Ala
                115                 120                 125

Arg Ser Gly Ala Val Leu Gly Val Gly Val Ile Ala Ala Val Gly Ala
            130                 135                 140

Gly Gly Met Ala Thr Ala Lys Asp Arg Pro Asn Pro Pro Ile Ser Met
145                 150                 155                 160

Pro Asp Leu Ala His Leu Ala Asp Asp Val Thr Asp Ala Leu Pro Ala
                165                 170                 175

Val Gln Asp Leu Pro Gly Ile Gly Pro Leu Leu Ala Gly Glu Ser Gly
            180                 185                 190

Glu Glu Thr Ala Gly Ala Val Pro Ala His Gly Ser Pro Gln Pro Phe
            195                 200                 205

Ser Gln Val Gly Leu Thr Ala Gln Asp Arg Ala Asn Gly Thr Thr Asp
            210                 215                 220

Ala Gly Glu Ala Leu Arg Ala Arg Ile Met Arg Gln Ala Glu Gln Gln
225                 230                 235                 240

Gln Thr Ala Ala Asp Glu Ala Glu Arg Glu Ala Ala Val Arg Ala Ala
                245                 250                 255

Thr Glu Ala Ala Ser Glu Ala Ala Ala Glu Gln Lys Ala Gln Glu Glu
                260                 265                 270

Ala Glu Arg Glu Ala Ala Ala Lys Glu Ala Glu Arg Lys Ala Ala Ala
                275                 280                 285

Glu Ala Glu Arg Lys Ala Ala Glu Ala Lys Arg Lys Ala Ala Glu Ala
            290                 295                 300

Glu Arg Lys Ala Glu Ala Asp Arg Leu Ala Glu Leu Ala Gly Ser Tyr
305                 310                 315                 320

Ala Leu Pro Leu Ser Ser Tyr Thr Leu Thr Ser Thr Phe Gly Glu Ala
                325                 330                 335

Gly Asp Met Trp Ser Ala Asn His Thr Gly Gln Asp Phe Ala Ala Pro
                340                 345                 350

Thr Gly Thr Pro Val Lys Ala Val His Gly Gly Thr Ile Thr Glu Ala
                355                 360                 365

Gly Trp Ala Gly Ala Tyr Gly Tyr Arg Ile Val Leu Thr Leu Asp Asp
            370                 375                 380

Gly Thr Glu Val Trp Tyr Cys His Leu Ser Ser Met Val Arg Thr Ser
385                 390                 395                 400

Gly Ser Val Ser Thr Gly Glu Val Ile Gly Arg Val Gly Ala Thr Gly
                405                 410                 415

Asn Val Thr Gly Pro His Leu His Leu Glu Val Arg Pro Gly Gly Gly
```

```
                420             425             430
Ala Pro Ile Asn Pro Leu Ser Trp Leu Arg Gln Phe Gly Leu Asn Pro
            435             440             445

<210> SEQ ID NO 44
<211> LENGTH: 193
<212> TYPE: PRT
<213> ORGANISM: Streptomyces pactum

<400> SEQUENCE: 44

Val Pro Ala Pro Arg Leu Thr Tyr Arg Pro Thr Pro Asp Asp Glu
1               5                   10                  15

Glu Gln Leu Ala Ala Leu Asp Thr Ser Phe Thr Thr Asp Thr Val His
            20                  25                  30

Arg Val Thr Ala Gly Pro Thr Gly Phe Thr Ile Arg Pro Glu Pro Val
        35                  40                  45

His Pro Pro Leu Thr Lys His Phe Pro Ala Asp Asp Glu Asp Glu
    50                  55                  60

Asp Asp Asp Asp Ala Pro Lys His Thr Val Val Ala Leu Asp Gly Asp
65                  70                  75                  80

Arg Val Cys Gly Phe Val Ala Val Asp His Glu Pro Trp Asn Ala Arg
                85                  90                  95

Leu Thr Ile Arg Asp Ile Ala Val Ala Pro Thr His Arg Gly His Gly
            100                 105                 110

Ile Ala Gly Glu Leu Met Thr Arg Ala Tyr Ala Tyr Gly Arg Gln Arg
        115                 120                 125

Gly Ala Arg His Val Trp Leu Glu Val Thr His Leu Asn Ala Pro Ala
    130                 135                 140

Ile Arg Ala Tyr Gln Arg Met Gly Phe Thr Phe Cys Gly Leu Asp Thr
145                 150                 155                 160

Thr Leu Tyr Thr Gly Thr Pro Ser Glu Gly Glu Ile Ala Leu Phe Met
                165                 170                 175

Ser Arg Ser Leu Pro Thr Ala Pro Asp Ala Pro Gly Pro Thr Ser Arg
            180                 185                 190

Pro

<210> SEQ ID NO 45
<211> LENGTH: 1043
<212> TYPE: PRT
<213> ORGANISM: Streptomyces pactum

<400> SEQUENCE: 45

Met Glu Phe Thr Ala Arg Pro Gly Leu Tyr Glu Arg Leu Ile Thr His
1               5                   10                  15

Arg Leu Glu Gly Arg Leu Gln Gln Leu Asp Ala Gly Thr Trp Arg Ala
            20                  25                  30

Ile Glu Gln His Val Gly Ala Gly Ser Thr Pro Gln Val Leu Ala Arg
        35                  40                  45

His Ile Ala Glu Thr Val His Arg Val Leu Thr Gln Leu Pro Ala Glu
    50                  55                  60

Gln Gln Val Gly Ala Ala Asn Gln Ile Leu Glu Ser Ile Gly Thr Leu
65                  70                  75                  80

Asp Gly Ala His Gln Trp Ile Asp Leu Val Ala Asp Gly Pro Arg Gln
                85                  90                  95

Leu Thr Ala Val Ala Glu Glu Glu Ala Pro Gly Val Tyr Ser Ile Arg
            100                 105                 110
```

```
Pro Ala Thr Pro Leu Ser Glu Ala Ala Leu Ile Thr Asn Ala Pro Glu
        115                 120                 125

Asp Pro Asn Leu Gly Ser Glu Leu Arg Ala Glu Leu Ala Thr Ala Asp
        130                 135                 140

Gln Val Asp Leu Leu Cys Ala Phe Val Lys Trp His Gly Leu Arg Val
145                 150                 155                 160

Leu Glu Glu Ala Leu Arg Ser Ala Arg Glu Arg Asn Val Pro Leu Arg
                    165                 170                 175

Leu Ile Thr Thr Thr Tyr Leu Gly Ala Thr Glu Gln Arg Ala Leu Asp
                180                 185                 190

Arg Leu Val Thr Glu Phe Gly Ala Gln Val Lys Val Asn Tyr Glu Leu
            195                 200                 205

Arg Ser Thr Arg Leu His Ala Lys Ala Trp Leu Phe Arg Arg Asn Ser
        210                 215                 220

Gly Tyr Asp Thr Ala Tyr Ile Gly Ser Ser Asn Leu Ser Lys Ala Ala
225                 230                 235                 240

Leu Leu Asp Gly Leu Glu Trp Asn Val Arg Leu Ser Ser Val Ala Thr
                    245                 250                 255

Pro Ala Val Leu Glu Lys Phe Glu Ala Thr Phe Asp Thr Tyr Trp Ser
                260                 265                 270

Asp Ala Ala Phe Glu Pro Tyr Asp Pro Asp Lys Asp Gly Ala Arg Leu
            275                 280                 285

Ala Glu Ala Leu Ala His Ala Ser Ser Gln Gly Leu Pro Gly Pro Ala
        290                 295                 300

Ala Leu Thr Leu Ser Arg Glu Val Arg Pro Tyr Pro His Gln Glu
305                 310                 315                 320

Asp Met Leu Glu Arg Leu Arg Ile Glu Arg Glu Ile His Lys Ile His
                    325                 330                 335

Arg Asn Leu Leu Val Ala Ala Thr Gly Thr Gly Lys Thr Val Met Ala
                340                 345                 350

Ala Leu Asp Tyr Arg Thr Leu Arg Glu Gln His Arg Gly Lys Pro Leu
            355                 360                 365

Arg Leu Leu Phe Val Ala His Arg Gln Glu Ile Leu Ala Gln Ser Leu
        370                 375                 380

Arg Thr Tyr Arg Asn Val Leu Gly Asp Pro Thr Phe Gly Glu Leu Leu
385                 390                 395                 400

Val Gly Gly Asp Val Pro Lys His Trp Arg His Val Phe Ala Ser Val
                    405                 410                 415

Gln Ser Leu Asn Ala Arg Ser Leu Glu Gln Leu Ala Pro Asp His Phe
                420                 425                 430

Asp Val Val Ile Asp Glu Phe His His Gly Val Ala Pro Thr Tyr
            435                 440                 445

Arg Arg Val Ile Asp His Phe Arg Pro Ile Glu Leu Leu Gly Leu Thr
450                 455                 460

Ala Thr Pro Glu Arg Met Asp Gly Arg Asn Val Gln Asp Glu Phe Phe
465                 470                 475                 480

Asn Gly Arg Ile Ala Ala Glu Met Arg Leu Trp Glu Ala Leu Glu Asn
                    485                 490                 495

Asp Leu Leu Ser Pro Phe His Tyr Phe Gly Ile Ala Asp Glu Thr Asp
                500                 505                 510

Leu Gln Gly Val Ala Trp Arg Asn Gly Ser Tyr Asp Thr Gly Glu Leu
            515                 520                 525
```

```
Gly Lys Val Tyr Ala Gly Asp Gln Glu Arg Ala Gln Leu Ile Val Arg
    530                 535                 540
Gln Val Arg Asp Lys Val Ser Asp Pro Ala Thr Met Arg Ala Leu Gly
545                 550                 555                 560
Phe Cys Val Thr Val Ala His Ala Thr Phe Met Ala Asp Val Phe Cys
                565                 570                 575
Gln Glu Gly Ile Asn Ala Lys Ala Leu Asp Gly Thr Thr Pro Arg Ala
                580                 585                 590
Glu Arg Ala Gln Ala Leu Asp Asp Leu Arg Asp Gly Lys Val Gln Ile
            595                 600                 605
Leu Phe Ser Val Asp Leu Phe Asn Glu Gly Leu Asp Val Pro Asp Val
610                 615                 620
Asp Thr Leu Leu Leu Arg Pro Thr Ser Ala Thr Val Phe Leu
625                 630                 635                 640
Gln Gln Leu Gly Arg Gly Leu Arg Arg Thr Pro His Lys Ala Val Leu
                645                 650                 655
Thr Val Leu Asp Phe Ile Gly Gln His Arg Lys Glu Phe Arg Phe Glu
                660                 665                 670
Glu Gln Phe Arg Ala Leu Thr Asn Phe Ser Arg Gln Arg Leu Ala Asp
            675                 680                 685
His Ile Glu Arg Asp Phe Pro Gln Leu Pro Ser Gly Cys His Ile Ile
        690                 695                 700
Leu Asp Pro Val Ser Lys Gln Arg Ile Leu Glu Asn Ile Gln Ser Gln
705                 710                 715                 720
Leu Arg Val Asn Val Gln Gln Leu Ala Lys Glu Val Ala Gln Tyr Gly
                725                 730                 735
Glu Thr Gln Leu Gly Ala Tyr Leu Arg Glu Ser Arg Arg Glu Leu Lys
            740                 745                 750
Gln Ile Tyr Arg Gly Asn Gly Ser Trp Thr Asp Leu Leu Arg Arg Ala
        755                 760                 765
Arg Leu Leu Pro Gly Thr Ala Pro Ala Gly Glu Glu Lys Leu Leu Lys
    770                 775                 780
Arg Val Ser Ser Phe Leu His Val Ser Asp Pro Gln Arg Val Ala Ala
785                 790                 795                 800
Tyr Arg Leu Leu Val Ser Asp Asp Ala Pro Ala Tyr Glu Ser Leu Ser
                805                 810                 815
Thr Gln Gln Gln Ala Tyr Ala Arg Met Leu Phe Ser Leu Trp Pro
            820                 825                 830
Leu Gly Gly Phe Thr Ser Tyr Thr Ala Gly Phe Glu Tyr Leu Arg
        835                 840                 845
Gln His Pro Ala Phe Arg Arg Glu Leu Arg Asp Leu Leu Ala Tyr Asn
    850                 855                 860
Leu Asp His Ala Asp His Tyr Pro Ile Pro Leu Asp Gly Thr His Glu
865                 870                 875                 880
Asp Tyr Ala Asp Ser Pro Leu Gln Ile His Ala Ser Tyr Ser Arg Glu
                885                 890                 895
Glu Ile Leu Pro Ala Leu Gly Glu Ala Asn Leu Thr Gly Phe Leu Pro
            900                 905                 910
Gly His Phe Arg Glu Gly Val Lys Trp Cys Pro Gly Val Lys Thr Asp
        915                 920                 925
Ala Leu Phe Ile Thr Leu Glu Lys Asp Glu Lys Asp Phe Ser Pro Gln
    930                 935                 940
Thr Arg Tyr Lys Asp His Ala Ile Thr Ser Asp Ser Phe His Trp Glu
```

```
                945                 950                 955                 960
Ser Gln Asn Gln Thr Ser Glu Ala Ser Pro Thr Gly Gln Arg Tyr Gln
                    965                 970                 975

Asn His Lys Lys Leu Gly Ser His Val Leu Leu Phe Val Arg Arg Tyr
            980                 985                 990

Lys Lys Ser Asp Ile Gly Gly Ala  Gln Pro Trp Met Leu  Leu Gly Pro
        995                 1000                1005

Ala Glu  Tyr Asp Thr His Ser  Gly Ser Lys Pro Met  Gly Ile Val
    1010                1015                1020

Trp Lys  Leu Arg Tyr Glu Leu  Pro Ala Asp Val Tyr  Thr Tyr Ser
    1025                1030                1035

Val Lys  Ala Ala Arg
    1040

<210> SEQ ID NO 46
<211> LENGTH: 360
<212> TYPE: PRT
<213> ORGANISM: Streptomyces pactum

<400> SEQUENCE: 46

Met Gly Ile Arg Asn Leu Leu Leu Asp Val Ala Asn Thr Tyr Asp Lys
1               5                   10                  15

Ser Met Gly Val Lys Arg Gly Val Phe Ala Gln Asp Arg Leu Arg Gln
            20                  25                  30

Val Ala Glu Glu Trp Ala Pro Ala Leu Pro Phe Gly Cys Glu Ala Glu
        35                  40                  45

Gly Tyr Gly Gly Lys Gly Glu Gly Ser Ala Thr Pro Trp Ile Gly Val
    50                  55                  60

Tyr Asp Pro Asp Val Thr Arg Asp Pro Lys Glu Gly Leu Tyr Leu Ala
65                  70                  75                  80

Tyr Ile Tyr Ala Ala Asp Leu Ser Thr Val Thr Leu Thr Leu Gln Gln
                85                  90                  95

Gly Val Thr Ser Leu Glu Pro Thr Leu Gly Thr Gly Lys Arg Arg Gln
            100                 105                 110

Ala Tyr Leu Trp Gly Arg Ala Arg Ala Ile Ala Ala Gly Leu Pro Pro
        115                 120                 125

Ala Ala Leu Asn Asp Trp Ala Asp Val Pro Asp Phe Lys Cys Asp Leu
    130                 135                 140

Pro Arg Pro Leu Ser Tyr Glu Ala Gly Ser Val Ala Ala Arg Cys Tyr
145                 150                 155                 160

Gln Thr Ala Ser Leu Pro Asp Glu Asp Gln Leu Arg Ser Asp Leu Arg
                165                 170                 175

Ala Met Val Glu Leu Leu Gln Arg Ala Ala Leu Val Ala Glu Arg Leu
            180                 185                 190

Lys Pro Gly Glu Asp Gly Asp Gly Trp Asp Val Pro Ala Asp Val Arg
        195                 200                 205

Glu Tyr Arg Gly Leu Asp Gly Phe Arg Pro Lys Asn Asp Ser Asp Tyr
    210                 215                 220

Ile Thr His Phe Pro Ala Arg Thr Val Arg Lys Lys Arg Ile His Glu
225                 230                 235                 240

Arg Leu Ile Ser Glu Phe Ala Pro Phe Val Glu Lys Arg Gly Phe Val
                245                 250                 255

Pro Ile Thr Arg Asp Val His Pro Lys Asp Leu Val Ile Arg Lys Gly
            260                 265                 270
```

```
Gly Val Glu Trp Leu Val Glu Ala Lys Val Val Lys Arg Ala Asn Pro
                275                 280                 285

Thr Leu Ala Val Arg Gln Ala Val Gly Gln Leu Leu Glu Tyr Gln His
            290                 295                 300

Phe Leu Tyr Arg Arg Ala Glu Arg Gly Thr Pro His Leu Leu Gly Leu
305                 310                 315                 320

Phe Thr Glu Asp Ile Gly Arg Tyr Ala Asp Tyr Leu Glu Glu Leu Gly
                325                 330                 335

Met Gly Ser Val Trp Arg Ile Pro Glu Gly Trp Ala Gly Ser Pro Ser
                340                 345                 350

Ala Val Ala Trp Gly Leu Val Gln
            355                 360

<210> SEQ ID NO 47
<211> LENGTH: 549
<212> TYPE: PRT
<213> ORGANISM: Streptomyces pactum

<400> SEQUENCE: 47

Val Ala Asp Gln Pro Ala Gly Pro Pro Val Pro Ala Tyr Ser Pro Gln
1               5                   10                  15

Pro Arg Phe Asp Ala Val Pro Glu Pro Ala Gly Trp Arg Tyr Arg Pro
            20                  25                  30

Arg Arg Ala Val Trp Glu Ser Arg Ala Leu Arg Ala Thr Ala Leu Val
        35                  40                  45

Leu Val Leu Ser Leu Cys Gly Leu Ile Ile Leu Ala Leu Val Arg Lys
    50                  55                  60

Gln Thr Gly Thr Glu Gly Phe Leu Val Gly Leu Gly Leu Ser Val Leu
65                  70                  75                  80

Pro Val Pro Leu Leu Val Ala Ala Phe Arg Trp Leu Asp Arg Val Glu
                85                  90                  95

Pro Lys Pro Trp Arg Asn Leu Val Phe Ala Phe Ala Trp Gly Ala Cys
            100                 105                 110

Ala Ala Thr Leu Val Ala Leu Ile Ala Asn Gly Phe Ala Thr Glu Trp
        115                 120                 125

Leu Val Thr Asn Ile Ala Glu Ser Ser Ala Ala Glu Glu Ser Ala Asp
    130                 135                 140

Ala Asp Ala Trp Gly Ala Thr Leu Val Ala Pro Val Val Glu Glu Ser
145                 150                 155                 160

Ala Lys Ala Gly Ala Leu Leu Phe Leu Phe Leu Phe Arg Arg Arg Asp
                165                 170                 175

Phe Asn Gly Ile Leu Asp Gly Leu Val Ile Ala Gly Ile Ala Ala Thr
            180                 185                 190

Gly Phe Ala Phe Thr Glu Asn Ile Leu Tyr Leu Gly Ser Ala Phe Val
        195                 200                 205

Ser Asp Gln Glu Phe Gly His Ser Gly Leu Arg Ser Thr Thr Ala Ala
    210                 215                 220

Thr Phe Phe Val Arg Val Ile Met Ser Pro Phe Ala His Pro Leu Phe
225                 230                 235                 240

Thr Ala Met Thr Gly Ile Gly Phe Gly Leu Ala Ala Ala Thr His
                245                 250                 255

Arg Gln Arg Val Arg Arg Val Leu Leu Pro Ile Ala Gly Leu Leu Ala
            260                 265                 270

Ala Met Val Leu His Gly Leu Trp Asn Gly Ser Ala Ile Leu Gly Ser
        275                 280                 285
```

```
Gly Ala Gly Phe Met Ala Val Tyr Leu Leu Phe Met Val Pro Ala Phe
        290                 295                 300

Gly Leu Leu Val Trp Leu Ala Val Trp Ser Arg Asn His Glu Leu Arg
305                 310                 315                 320

Thr Ile Arg Ala Tyr Leu Pro Val Tyr Gln Ala Ala Gly Trp Leu Thr
                325                 330                 335

Ala Pro Glu Pro Val Ala Leu Ser Ser Phe Arg Ala Arg Gly Ile Ala
            340                 345                 350

Arg Asp Val Ala Arg Arg Val His Gly Pro Ala Ala Ala Arg Thr Val
        355                 360                 365

Ala Glu Tyr Thr Ala Phe Ala Thr Ser Leu Ala Phe Leu Arg Ser Arg
370                 375                 380

Ala Tyr Arg Asp Thr Pro Gly Pro Asp Phe Thr Ala Arg Glu Gln Glu
385                 390                 395                 400

Leu Leu His His Leu Trp Gln Arg Lys Asp Val Ala Arg Pro Ile Leu
                405                 410                 415

Ala His Ala Ala Leu Leu Pro Pro Ala Pro Arg Arg Pro Tyr Pro
            420                 425                 430

Val Arg Pro Pro Tyr Pro Gly Ala Trp Pro Tyr Gly Pro Tyr Ala His
        435                 440                 445

Pro Gly Pro Tyr Ala Ala His Pro His Ala His Ala Gly Pro Tyr Pro
450                 455                 460

His Ala Gln Pro Gly Pro Tyr Ala His Ala His Pro Gly Leu Tyr Ala
465                 470                 475                 480

Ala His Pro Gly Thr Pro Pro Thr Leu Thr His Pro Tyr Pro Ala Gly
                485                 490                 495

Ala Tyr Gly Pro Ala Pro Tyr Pro Pro Gly Thr Tyr Gly Pro Ala Pro
            500                 505                 510

His Pro Ala Pro Gly Pro Leu Thr Pro Pro Gly Thr Pro Gly Pro Asp
        515                 520                 525

Pro Val Ala Pro Pro Asp Thr Gly Thr Pro Thr Ala Pro Gly Thr
530                 535                 540

Ser Ala Pro Pro Pro
545

<210> SEQ ID NO 48
<211> LENGTH: 134
<212> TYPE: PRT
<213> ORGANISM: Streptomyces pactum

<400> SEQUENCE: 48

Val Ser Arg Pro Val Pro Arg Ser Gly Ala Gly Pro Gly Thr Gly Trp
1               5                   10                  15

Gly Val Val Ala Val Pro Gly Pro Val Ala Ala Pro Glu Ala Arg Thr
                20                  25                  30

Gly Glu Ser Ala Val Pro Gly Ala Pro Cys Pro Ala Ser Ala Gly Arg
            35                  40                  45

Ala Ser Gly Thr Gly Ala Ala Val Asp Gly Met Ser Ala Gly Arg Ala
        50                  55                  60

Ser Gly Val Pro Val Pro Ala Gly Gly Ala Ala Ala Gly Pro Ala Ser
65                  70                  75                  80

Val Gly Arg Ala Ser Ala Ala Trp Ala Ser Val Ala Arg Gly Ser Ala
                85                  90                  95

Val Arg Ala Ser Ala Val Arg Gly Ala Ser Gly Pro Asp Arg Pro Val
```

```
            100                 105                 110
Val Ala Trp Pro Gly Arg Ser Gly Pro Gly Ser Cys Gly Asp Glu Asp
            115                 120                 125

Trp Cys Thr Arg Arg Pro
            130

<210> SEQ ID NO 49
<211> LENGTH: 430
<212> TYPE: PRT
<213> ORGANISM: Streptomyces pactum

<400> SEQUENCE: 49

Val Pro Gly Ala Ser Ala Ser Asp Gly Cys Arg Gly Ala Pro Pro Gly
1               5                   10                  15

Pro Glu Ala Tyr Gly Pro Gly Arg Ser Arg Lys Asp Thr Val Gly Val
            20                  25                  30

Arg Ser Gly Ala Gly Cys Thr Glu Arg Gly Pro Gly Ser Pro Arg Val
        35                  40                  45

Thr Pro Glu Gly Thr Arg Pro Pro Ala Gly Arg Thr Val Arg Thr Asp
    50                  55                  60

Thr Arg Ser Arg Thr Gly Ala Val Arg Pro Ala His Ser Arg Gly Asp
65                  70                  75                  80

Leu Pro His Arg Arg Gln Ala Ala Glu Glu Trp Pro Ser Pro Gly
                85                  90                  95

Arg Ala His Pro His Asp Thr Arg His Arg Arg Gly Pro Ala Gly Arg
                100                 105                 110

His Ala Ser Pro Arg Arg Pro Gly Arg Lys Gly Ala Arg His Arg Glu
            115                 120                 125

Arg Gly Arg Pro Gly Pro Gly Ala Arg Thr Gly Ala Gln Pro Pro Arg
        130                 135                 140

Pro Ala Arg His Arg Gly Gly Ala Ala Gly Arg Ala Ser Ala Pro
145                 150                 155                 160

Pro Thr Val Glu Ser Thr Tyr Met Ser Glu Asn Ser Thr Ala Pro Arg
                165                 170                 175

Ser Ala Glu Ala His Asp His Arg Asp Arg Gly Ala Arg Leu Phe Pro
            180                 185                 190

Gly Gly Pro Ser Ala Asp Pro Ala Gly Ser His His Glu Arg Arg Ile
        195                 200                 205

Arg Ser Phe Arg Pro Arg Arg Gly Arg Val Thr Pro Gly Gln Glu Gln
    210                 215                 220

Ala Leu Arg Arg Leu Trp Pro Gln Trp Gly Leu Asp Ile Asp Gly Leu
225                 230                 235                 240

His Arg Ile Asp Leu Gly Arg Leu Phe Gly Asp Pro Glu Met Pro Val
                245                 250                 255

Val Leu Glu Ile Gly Phe Gly Met Gly Glu Ala Thr Ala Gln Met Ala
            260                 265                 270

Ala Ala Asp Pro Gly Thr Gly Ile Leu Ala Ala Asp Val His Thr Pro
        275                 280                 285

Gly Gln Gly Asn Leu Leu Ala Leu Ala Glu Arg Asn Gly Leu Thr Asn
    290                 295                 300

Ile Arg Val Ala Asn Gly Asp Ala Ile Ile Leu Arg Glu Met Leu
305                 310                 315                 320

Ala Pro Ser Ser Leu Ala Gly Leu Arg Val Tyr Phe Pro Asp Pro Trp
                325                 330                 335
```

```
Pro Lys Lys Arg His His Lys Arg Arg Leu Ile Gln Pro Glu Phe Val
            340                 345                 350

Ala Leu Ala Ala Thr Arg Leu Arg Pro Gly Ala Leu Leu His Cys Ala
        355                 360                 365

Thr Asp Trp Glu Pro Tyr Ala Glu Gln Met Leu Glu Val Leu Ser Ala
370                 375                 380

Ser Pro Asp Phe Glu Asn Thr Gln Pro Asp Gly Gly Tyr Ala Pro Arg
385                 390                 395                 400

Pro Asp Phe Arg Pro Leu Thr Lys Phe Glu Gly Gln Gly Leu Asp Lys
            405                 410                 415

Gly His Val Val His Asp Leu Leu Phe Arg Arg Arg Thr Asp
            420                 425                 430

<210> SEQ ID NO 50
<211> LENGTH: 394
<212> TYPE: PRT
<213> ORGANISM: Streptomyces pactum

<400> SEQUENCE: 50

Val Ile Gly Gly Gly Ile Val Gly Leu Ser Thr Ala Tyr Ala Ile Thr
1               5                   10                  15

Arg Ala Ala Pro Gly Thr Arg Val Ile Val Leu Glu Lys Glu Ala Gly
            20                  25                  30

Pro Ala Arg His Gln Thr Gly Arg Asn Ser Gly Val Ile His Ser Gly
        35                  40                  45

Ile Tyr Tyr Pro Pro Gly Ser Leu Lys Ala Arg Phe Ala Val Glu Gly
    50                  55                  60

Ala Ala Glu Leu Val Lys Phe Cys Ala Glu Tyr Asp Ile Pro His Glu
65                  70                  75                  80

Thr Thr Gly Lys Leu Ile Val Ala Thr Asp Arg Ala Glu Leu Pro Arg
                85                  90                  95

Leu His Ala Leu Val Gln Arg Gly Arg Glu Asn Gly Ile Pro Val Arg
            100                 105                 110

Glu Leu Gly Pro Ala Gln Ile Met Glu Tyr Glu Pro His Val Arg Gly
        115                 120                 125

Leu Ala Ala Ile His Val Gly Thr Thr Gly Thr Cys Asp Tyr Gly Ala
    130                 135                 140

Val Ala Asn Arg Leu Ala Gly Leu Ala Thr Asp Ala Gly Thr Ser Val
145                 150                 155                 160

Arg Tyr Gly Glu Glu Val Arg Ala Ile Gly Arg Arg Ala Ser Ala Val
                165                 170                 175

Ala Val Arg Thr Ala Ser Gly Ser Val Val Arg Ala Gly Ala Leu Val
            180                 185                 190

Asn Cys Ala Gly Leu His Cys Asp Arg Ile Ala Gln Leu Ala Gly Asp
        195                 200                 205

Asp Pro Gly Met Arg Ile Val Pro Phe Arg Gly Glu Tyr Tyr Glu Leu
    210                 215                 220

Val Pro Ser Arg Ala Pro Leu Val Arg Gly Leu Val Tyr Pro Val Pro
225                 230                 235                 240

Asp Pro Ala Phe Pro Phe Leu Gly Val His Leu Thr Arg Gly Ile Asp
                245                 250                 255

Gly Arg Val His Ile Gly Pro Asn Ala Val Pro Ala Leu Ala Arg Glu
            260                 265                 270

Gly Tyr Thr Trp His Thr Val Arg Pro Asp Glu Phe Ala Ala Thr Leu
        275                 280                 285
```

```
Ala Tyr Pro Gly Ala Trp Arg Ile Ala Arg Arg His Trp Arg Tyr Gly
        290                 295                 300

Ala Gly Glu Leu Arg Arg Ser Ala Ser Lys Arg Ala Phe Thr Asp Ala
305                 310                 315                 320

Val Arg Arg Leu Leu Pro Val Val Arg Thr Asp Asp Leu Val Arg Ala
                325                 330                 335

Pro Ala Gly Val Arg Ala Gln Ala Val Leu Pro Asp Gly Thr Leu Val
            340                 345                 350

Asp Asp Phe Leu Phe Ala Glu Ser Ala Arg Ala Val His Val Leu Asn
        355                 360                 365

Ala Pro Ser Pro Ala Ala Thr Ala Ser Leu Pro Ile Gly Arg Glu Val
    370                 375                 380

Ala Arg Arg Ala Leu Ala Ala Leu Asp Gly
385                 390
```

<210> SEQ ID NO 51
<211> LENGTH: 492
<212> TYPE: PRT
<213> ORGANISM: Streptomyces pactum

<400> SEQUENCE: 51

```
Met Pro Arg Ala Tyr Ala Gly Ala Ala Val Gly Val Val Arg Gly Val
1               5                   10                  15

Arg Met Ser Arg Glu Pro Arg Gly Pro Asn Glu Lys Leu Gly Ala Val
            20                  25                  30

Leu Ala Leu Ala Gly Ile Ser Asn Ala Gly Leu Ala Arg Arg Val Asn
        35                  40                  45

Asp Leu Gly Ala Gln Arg Gly Leu Thr Leu Arg Tyr Asp Lys Thr Ser
    50                  55                  60

Val Ala Arg Trp Val Ser Lys Gly Met Val Pro Gln Gly Ala Ala Pro
65                  70                  75                  80

His Leu Ile Ala Ala Ile Gly Ser Lys Leu Gly Arg Pro Val Pro
                85                  90                  95

Leu His Glu Ile Gly Leu Ala Asp Ala Asp Pro Ala Pro Glu Val Gly
            100                 105                 110

Leu Ala Phe Pro Arg Asp Ile Gly Gln Ala Val Arg Ser Ala Thr Glu
        115                 120                 125

Leu Tyr Arg Leu Asp Leu Ala Gly Arg Gly Gly Ser Gly Ile Trp
    130                 135                 140

Gln Ser Leu Ala Gly Ser Phe Ala Val Ser Ala Tyr Ala Thr Pro Ala
145                 150                 155                 160

Ser Arg Trp Leu Ile Ser Pro Ala Asp Ser Ser Val Ala Arg Glu Pro
                165                 170                 175

Lys Thr Asp Gly Pro Gly Thr Asp Gly Leu Pro Gln Arg Val Gly His
            180                 185                 190

Ser Asp Val Asn Lys Leu Arg Glu Ala Glu Asp Ala Arg Arg Trp
        195                 200                 205

Asp Ser Lys Tyr Gly Gly Gly Asp Trp Arg Ser Ser Met Val Pro Glu
    210                 215                 220

Cys Leu Arg Val Asp Ala Pro Leu Leu Leu Gly Ser Tyr Ser Asp
225                 230                 235                 240

Glu Val Gly Arg Ala Leu Phe Gly Ala Thr Ala Glu Leu Thr Arg Leu
                245                 250                 255

Ala Gly Trp Met Ala Phe Asp Thr Gly Gln Gln Glu Ala Ala Gln Arg
```

```
                      260                 265                 270
Tyr Tyr Ile Gln Ala Leu Arg Leu Ala Arg Ala Ala Asp Val Pro
            275                 280                 285

Leu Gly Gly Tyr Val Leu Ala Ser Met Ser Leu Gln Ala Thr Tyr Arg
        290                 295                 300

Gly Phe Ala Asp Glu Gly Val Asp Leu Ala Gln Ala Ala Leu Glu Arg
305                 310                 315                 320

Asn Arg Gly Leu Ala Thr Ala Arg Thr Met Ser Phe Phe Arg Leu Val
                325                 330                 335

Glu Ala Arg Ala Gln Ala Lys Ala Gly Asp Gly Pro Ala Cys Gly Ala
            340                 345                 350

Ala Leu Lys Ala Ala Glu Gly Trp Leu Glu Arg Ser Arg Ala Gly Asp
        355                 360                 365

Pro Asp Pro Ser Trp Leu Asp Phe Tyr Thr His Glu Arg Phe Ala Ala
    370                 375                 380

Asp Ala Ala Glu Cys Tyr Arg Asp Leu Arg Leu Pro Arg Gln Val Arg
385                 390                 395                 400

Arg Phe Thr Glu Gln Ala Leu Ala Arg Pro Thr Glu Glu Phe Val Arg
                405                 410                 415

Ser His Gly Leu Arg Leu Val Val Ser Ala Val Ala Glu Leu Glu Ser
            420                 425                 430

Gly Asn Leu Asp Ala Ala Cys Ala Gln Gly Ala Arg Ala Val Glu Val
        435                 440                 445

Ala Gly Arg Ile Ser Ser Ala Arg Thr Thr Glu Tyr Val Arg Asp Leu
    450                 455                 460

Leu His Arg Leu Glu Pro Tyr Gly Asn Glu Pro Arg Val Ala Glu Leu
465                 470                 475                 480

Arg Glu Arg Ala Arg Pro Leu Leu Val Ala Pro Val
                485                 490

<210> SEQ ID NO 52
<211> LENGTH: 720
<212> TYPE: PRT
<213> ORGANISM: Streptomyces pactum

<400> SEQUENCE: 52

Val Ala Pro Gly Thr Gly Asp Gln Pro Cys Met Met Ala Arg Ala Tyr
1               5                   10                  15

Trp Trp Pro Arg Ser Val Glu Ala Ala Met Arg Trp Leu Val Gly Trp
            20                  25                  30

Ser Arg Ala Thr Ala Gly Pro Ala Thr Ala Gly Ala Asp Ala Leu Gln
        35                  40                  45

Pro Val Gly Ala Gln Leu Leu Trp Asp Gly Pro Asp Pro Leu Trp Ala
    50                  55                  60

Val Gly Asp Trp Arg Pro Asp Glu Val Arg Val Gln Thr Asp Pro
65                  70                  75                  80

Leu Thr Arg Leu Ala Val Ile Gly Cys Cys Gly Ala Ser Asp Glu Glu
                85                  90                  95

Leu Arg Leu Gly Leu Phe Ala Ala Arg Gly Gly Ala Leu Arg His Leu
            100                 105                 110

Thr Ala Trp Pro Gly Ser Tyr Thr Ala Val Ala Arg Ala Gly Arg Arg
        115                 120                 125

Ile Thr Val Val Gly Asp Leu Ala Gly Ala Arg Pro Val Phe His Thr
    130                 135                 140
```

```
Arg Trp Ala Gly Gly Thr Ala Tyr Ala Thr Ala Leu Pro Leu Ala
145                 150                 155                 160

Asp Leu Val Glu Ala Gln Leu Asp Val Ser His Leu Ala Ala Leu Leu
                165                 170                 175

Ala Cys Pro Asp Thr Pro Glu Ala Val Gly Asp Gly Thr Pro Tyr Ala
            180                 185                 190

Gly Val Arg Arg Thr Ala Pro Gly His Ala Leu Val Leu Arg Glu Gly
        195                 200                 205

Ala Pro Asp Leu Val Gly Tyr Glu Pro Thr Ala Ser Leu Ala Ser Ala
    210                 215                 220

Ala Pro Pro Met Asp Pro Glu Ala Ala Val Ala Gly Val Arg Asp Ala
225                 230                 235                 240

Leu Leu Asp Ala Val Arg Ala Arg Leu Ala Ala Pro Arg His Ala Pro
                245                 250                 255

Gly Thr Gly Gly Arg Leu Asp Pro Gly Pro Val Pro Gly Met Gly Pro
            260                 265                 270

Ala Asp Arg Arg Ala Ala Arg Gly Ala Pro Ala Pro Gly Leu Gly Ala
        275                 280                 285

Asp Leu Ser Gly Gly Ser Ala Ser Gly Thr Leu Ala Leu Leu Ala Ala
    290                 295                 300

Gly Leu Pro Gly Ile Pro Gly Thr Pro Ala Gly His Gly Ala Glu Ala
305                 310                 315                 320

Gly Glu Arg Leu Gln Ala Val Thr Phe Asn Asp Leu Ala Val Gly Arg
                325                 330                 335

Gly Arg Ala Arg Glu Ala Glu Leu Glu Arg Ala Arg Ala Met Ala Glu
            340                 345                 350

Asn Pro Arg Leu His His Val Val Ala Gly Gly Thr Glu Ala Leu
        355                 360                 365

Pro Tyr Ala Ala Leu Asp Gly Pro Leu Thr Asp Glu Pro Ala Ser
    370                 375                 380

Cys Leu Val Leu Ala Glu Arg His Arg Arg Leu Val Ala Gly Ser
385                 390                 395                 400

Ala Asp His Phe Val Gly His Gly Ala Arg Gln Val Leu Asp Ala His
                405                 410                 415

Pro Ala Arg Leu Ala Asp Leu Leu Asp Arg Arg Arg His Leu
            420                 425                 430

Leu Arg Pro Ala Thr Ala Leu Ala Arg Ala Asp Gly Pro Ser Ala His
        435                 440                 445

Ser Phe Phe Val Pro Phe Thr Val Tyr Arg Ala Arg Arg Leu Ala
    450                 455                 460

Arg Thr Pro Tyr Arg Asp Gly Leu Glu Gln Val Ala His His Leu Leu
465                 470                 475                 480

Glu Gly Arg Phe Thr Pro Glu Pro Gly Pro Gly Arg Pro Gly Ala Val
                485                 490                 495

Ser Ala Ser Leu Ala Ala Leu Thr Trp Cys Arg Pro Gly Pro Ala Ala
            500                 505                 510

Arg Trp Leu Thr Gly Glu Ala Leu Ala Glu Val Ser Val Arg Leu Glu
        515                 520                 525

Ala Ala Ala Ala Arg Pro Ala Leu Leu Arg Arg Pro Gly Glu Arg Arg
    530                 535                 540

Ala Asp Ala Ala Leu Asn Arg Phe Ala Ala Asp His Arg Ile Phe Glu
545                 550                 555                 560

Gln Ala Val Glu Val Arg Gly Gln Arg Leu His Ala Pro Tyr Leu Asp
```

```
                    565                 570                 575
Asn Gln Val Val Arg Ala Cys Arg Ala Leu Pro Glu Ala Leu Arg Val
                580                 585                 590

Gln Pro Gly Ala Arg Ala Ala Val Leu Arg Ala Val Leu Ala Gly Ala
            595                 600                 605

Gly Val Arg Asp Leu Pro Pro Gly Trp Gly Ala Thr Ser Gln Gly Ala
        610                 615                 620

His Val Thr Ala Val Arg Ala Gly Leu Arg Thr His Ala Gly Glu Leu
625                 630                 635                 640

Ile Asp Leu Phe His Ala Pro Leu Leu Ala Asp Ala Gly Leu Val Glu
                645                 650                 655

Ala Arg Val Val Arg Lys Ala Leu Arg Ala Ala Gly Gly Glu Arg
                660                 665                 670

Leu Pro Leu Asp Gly Leu Ala Glu Leu Ala Thr Glu Val Trp Leu
            675                 680                 685

Arg Arg Leu Leu Ala Arg Gly Thr Cys Trp Thr Gly Thr Glu Gly
        690                 695                 700

Pro Arg Arg Ala Val Ala Gly Val Val Pro Arg Gln Gly Val
705                 710                 715                 720

<210> SEQ ID NO 53
<211> LENGTH: 398
<212> TYPE: PRT
<213> ORGANISM: Streptomyces pactum

<400> SEQUENCE: 53

Val Val Gly Ser Gly Pro Gly Arg Val Arg Ala Gly Val Val Arg Ser
1               5                   10                  15

Gly Phe Arg Pro Ser Val Arg Pro Arg Ala Arg Pro Arg Arg Arg
            20                  25                  30

Ser Ser Ala Ala Ala Pro Pro Ile Ser Glu Asp Asn Glu Ser Val Arg
        35                  40                  45

Tyr Leu Ile Leu Gly Ala Thr Glu Ala Arg Asp Ser His Gly Gln Pro
    50                  55                  60

Leu Pro Leu Gly Ala Gly Ala Arg Leu Arg Ala Leu Leu Thr Ala Leu
65                  70                  75                  80

Ala Leu Arg Ala Ala Arg Ala Leu Pro Val Pro Val Asp Val Leu Ile
                85                  90                  95

Gly Glu Val Trp Ala Asp Asp Pro Pro Gln Asp Pro Pro Ala Ala Leu
            100                 105                 110

Gln Ala Leu Val Gly Arg Leu Arg Arg Val Gly Arg Ala Ala Val
        115                 120                 125

Asp Ser Gly Pro Gly Gly Tyr Arg Leu Val Thr Pro Ala Asp Glu Val
    130                 135                 140

Asp Leu Phe Arg Phe Glu Arg Leu Val Gly Glu Gly Ser Arg Ala Leu
145                 150                 155                 160

Asp Ser Gly Asp Ala Glu Thr Ala Gly Thr Leu Arg Ala Ala Leu
                165                 170                 175

Ala Leu Trp Arg Gly Pro Ala Phe Ala Asp Leu Pro Asp Arg Glu Ser
            180                 185                 190

Ala Ala Ala Arg Pro Glu Ala Leu Arg Thr Thr Ala Leu Tyr Arg Arg
        195                 200                 205

Ile Glu Ala Asp Leu Ala Leu Gly Arg Ala Val Glu Val Val Pro Glu
    210                 215                 220
```

```
Leu Arg Glu Leu Val Ala Gly Asp Pro Leu His Glu Pro Phe Gln Ala
225                 230                 235                 240

Gln Leu Ile Arg Ala Leu Ser Ala Ala Gly Arg Pro Ala Asp Ala Leu
            245                 250                 255

Thr Ala Tyr Glu Asp Ala Arg Arg Ala Ile Ala Asp Arg Leu Gly Ser
        260                 265                 270

Arg Pro Gly Thr Glu Leu Ala Gly Leu His Ala Arg Leu Leu Arg Gly
    275                 280                 285

Asp Arg Pro Ala Asp Ala Arg Gly Ala Ala Asp Gly Arg Asn Gly
290                 295                 300

Thr Gly Thr Pro Tyr Gly Pro Pro Trp Gly Ala Leu Asp Val Pro Pro
305                 310                 315                 320

Ala Pro Gly Pro Ala Pro Gly Pro Ala Ser Gly Val Thr Ala Asp Gly
            325                 330                 335

Gly Ser Pro Thr Arg Glu Leu Arg Ala Pro Gly Ile Pro Ala Val Gly
        340                 345                 350

Asp Arg Pro Pro His Asp Ala Pro Asn Ala Gly Ser Ala Pro Val Ser
    355                 360                 365

Ala Pro Ala Pro Gly Ala Gly Thr Pro Ala Pro Asp Gly Arg Pro Arg
370                 375                 380

Ser Ala Pro Ala Asp Gly Gly Pro Asp His Gly Ala Gly Ser
385                 390                 395
```

<210> SEQ ID NO 54
<211> LENGTH: 86350
<212> TYPE: DNA
<213> ORGANISM: Streptomyces pactum

<400> SEQUENCE: 54

```
cttccaggag aagctgctca tcgagtgcac cctggaggtg ttccgggagg acctggtcgc    60
cggcatccag gacctgggcg cgccggtct gtcctgcgcc accagcgagc tggccagcgc   120
cggttccggc ggcatgcggg tggacctgga cgcggtgccg ctgcgcgacg cgacgctctc   180
gccggaggag atcctcatga gcgagtcgca ggagcgcatg tgcgcgatcg tggagcccgg   240
caaggtcgag cgcttcctgg agatctgcga gaagtgggac gtgatcgcca ccgtcatcgg   300
tgaggtcacc gacggcgacc ggctggagat cttctggcac ggcgagcaga tcgtggacgt   360
gccgccgcgg tccgtcgcgc acgaggggcc cacctaccac cgcccctacg cccgccccga   420
ctggcaggac gcgctccagg cggacgacgc cggcaagctg ccgcgcccgc gcacctccga   480
ggagctgcgc gaccaggtgc tggcgctggt cggctcgccg aaccaggcgt cgaaggcctg   540
ggtcaccgac cagtacgacc gcttcgtgca gggcaacacg gtgctcgcgc agcccgagga   600
cgccggcgtc atccggatcg acgaggagtc gaacctgggc gtggccctgg cgacggacgg   660
caacggccgc tacaccaagc tcgacccgta taccggtgcc cagctggcgc tggccgaggc   720
gtaccggaac gtggcggcga ccggggcccg gccgctggcc gtctccgact gcctgaactt   780
cggttcgccg gaggacccgg ccgtgatgtg gcagttcgcc gaggccaccc gcggcctggc   840
ggacggctgc cagaagctgg gcacgccggt caccggcggc aacgtctcgc tgtacaacca   900
gaccggtgag aacgccatcc acccgacccc ggtggtcgcg gtgctcggcg tcatcgacga   960
cgtcagccgg cgcacccccga tcgccttcgc cgaggacggc cagctgctgt acctgctggg  1020
cgacacccgc gaggagttcg gcggttcggc gtggtcccag gtcgtccacg accacctcgg  1080
cggcctgccg ccgccgtgg acctggaccg ggagaagctg ctcgccgaga tcctcatcgc  1140
```

```
ggcctcccgc gacggcatga tcgacgcggc gcacgacctc tccgacggcg gtctgatcca    1200
ggccgtggtg gagtcctgcc tgcgcggcgg caagggcgca cggctgatcg tcccggacgg    1260
tctggacgcg ttcaccctgc tgttctccga gtcggcggga cgggccgtgg tggccgtgcc    1320
gcgcagcgag gaggtccgct tcaacgacat gtgcggtgcg cggggcctgc cggccacccg    1380
gatcggcgtc gtcgacggcg acacggtgga ggtgcagggc gagttcagca tcccgctggc    1440
cgagctgaag caggtgcacg aggccaccat cccggcgctg ctggcctgac gcgcccggcc    1500
gggcgcggcg acctcacggg gccccggcgg accgagcgtc cgccggggcc ccggtgtgtc    1560
cgggacgcgg tcggggccct ggcgggcggg tacgggcct gccggccgg tgccgcggcc      1620 gttcggggtg gggtcggacg ggttcgggtg tgcccccgc cgttcggggc gggcgcccgg     1680
ccgtgccgtt gccgggaacg ccggccggcg cgggcgatc cggtgcgccg ggcgtgatcg     1740
ggcggtgccg ggccggtgcc gggggtgatc gggctgtccg gggcggtgcc ggtggtgctg    1800
ggtatgctcg ccggtatgcc cgccgcgccc cgcaagtccc gtgcccggac gtacgacttc    1860
gccaggaccc acgccgcggt cgcggcccag ctggaccacg tgcgcgacgc ggtgggccgg    1920
ctcaccgacg agcagctggc cgcgcccacc cggctgtccg ggccggcgga caccggcggt    1980
gccggggcgg tgtggacggt acgggacctg gtcgcccacc tcgtcctggt ggtggagcac    2040
gtgaaccgga acctggagca gcccgcgcca ccggccgtgg aggtcaccct caccgactgg    2100
gtgttcgcca ccgccacgtt cgccggggcg atcggcgacg acgcccggtc cgccgccggg    2160
agcgccgacc tcgccgagtc gctggaccgg gcggccgccc gtttcgccga actggtgccg    2220
ccggcccacc cggaccggct gctggcggcc cgggtgggtg ccatccggtt ggacgacttc    2280
ctggtcaccc gctgtgtcga actggtggtg cacaccgacg acctggccgc cgccaccggt    2340
gcggagatcc gttacgaccg gcaggcgctg ccgccgcgg tccgggtgct cgccgacgcg     2400
ctggcggcca gggcgcccgg cggttcggtg gaggtccggg tgccgccgtt cgccgtcgtg    2460
cagtgcgtcg agggcccccg gcacacccgc ggcacgccgc caacgtggt ggagacggac     2520 ccgctgacct ggctccggct ggccaccggg cggcggacct gggcggaggc ggtcgaggcg    2580
gcggaggtca ccgcgagtgg cgagcgggcc gatctgtcgg ggctgctccc gctgctcggc    2640 tgaccccgg gacgggcccg cccgaccgtc ggccggcccc gccccgtcg gccggccccg      2700 cccccgacgg cccgcccgac ggccggcccg gctcccggtc gccgacgtgc ccggccctcc    2760
gcgagccggt ccgccccgcc ccgcggccgg gcgcgccgcc ggtcagcccc cggccgcggg    2820
atagggcagc agggtggcgg cggtgcgctc ccacgcggtc cggagcgagg cgagccgctc    2880
cggctccagc gccgcgcggt cggcctgctc ccgcgggtcg tccgggatgt tgaacaggtg    2940
gtcccggccc tgcgcgtccc ggtggtactt ccaggcgccg cggcgcagcg cccgctcccc    3000
gcgcacccgc cagaacaggt cccgctcggg cagctcctcg ccgcgcagca ggtatccggc    3060
gaggctggtg ccgtccagcg ggtgggcccg gtccggtcgg gcgccgccca cctccagcag    3120
ggtcgcggtc cagtcggggg tgtagaccgg ctcgtgggag acctgcgcgc cgccgtcgat    3180
gcgggccggc cagcgcacga tggtgggcac ccggatgccg ccctccagca gcgtgaactt    3240
ctcgccggac agcggccact ggtacgagaa ccgctcaccg ccgttgtcgc tggcgaagac    3300
gaccagggtg ttctcctcct ggccggagcg gcggagcgcg gccagcacct cgccgacgga    3360
gcggtcgagg tcctcgacca gctcgcggta cttctccagc gagccgccgt cgcggtggtt    3420
gagcgcgccc cgctgccccg ccttgatgcg cgcggtcacc cgtgcgctct ccgcggtgtc    3480
gccctcggct atccacggcc agtgcggggt ggtgaagttc aggttgagca gccacggctt    3540
```

```
tcggtggtcg cggccgatgt actcggcggc ccgctcggtg atgatcctcg tgtagtagcg    3600
caggtcctgg tggctgacct cgccctcgta gaggtcgtac tcgccggtca ggccgagctt    3660
ggagtagtac tccagggccc cgccgaagtt gccgaagaac gtctcccagc cggacttggt    3720
ggggctgtgg tcgggcaggt agccgcagtg ccacttgccg atcagcgcgg tcgcgtaccc    3780
ggcgccgcgc agcagcgagg ccagggtggg gtggttcggc ggcagcccgg cgtcggaccc    3840
gccggggatc ggctcgtgga ggccgccggg ggtgcggccg gggaagcgcc cggtgtagag    3900
gctgaaccgg gtgggggagc aggtcgagga gcccgcgtag gcgtgggtga agcgcacccc    3960
ctggcgggcg agccggtcca ggtgggggt gtggatgtgc ggggagccgt acgaggacag    4020
gtcggcccag ccgaggtcgt cggcgaggat gaagaggatg ttgggccggg gcgaacggcg    4080
gtgggtggcc gcccggaacg gccgctcgcg gacggccccg cggccgtcgg cggcggcttc    4140
ggcggcggcg agcccggtgg ccgcggtggc ggccaggccg gcaccggcgg agaccgcggc    4200
cagctggccg aagccgcgcc gggacagcgg tcgcccgctc gtgcccgcgt cgtggtggtc    4260 ggggcggtg ccgggagagc ggtcggccgg cgagggacgg tcgttcgagg acatggcggg    4320
actcctgggg agacgggcgc tcccgccggc ggccggtggc cggtacggc gtggcacggg    4380 ccgggagcgg gacgggctcc ggcaccgccg tcacgcggac gcggccgggg aacgggacgg    4440
gcccgtgccg gcggtgcggc ggaagcggga ggggcagggg agggcgggac agggcagggc    4500
agggcagggg ccggacggcc ggaaccgggg aacggcgccg accgcccggg gccgggacgg    4560
aacaggccgg ggtacggaag gacgagcggc agggaagaca ccgggcgcgg acgagagaac    4620
cgggacgacg aagcaccgga ccccggcaca accccggcac ggacccgggc acggaccgga    4680
ggcacggcca cctggcccgg atccggaacg gaggacccga ggcacgacca ccgggccgg    4740 atccggaacg gaggaccgca ggacgggccg ccgaacccgc atccggaacg gaaccgcagg    4800 accaccctc ggaccgcaca tccgcggat ccccccag gagcccgccc cggccccgca    4860
cccggagcgc gaactgcggg tgcggacctg gggacagccc cggtgcgggc tccccgcgg    4920 gccgagagtg cgggccgacg ggcccgggcc ggagcacggg caggcggtcc ggatccggac    4980 gcggggaac aggggagca gcggtcggag aggggatcag cgggcggtgg ccaccgggtg    5040
ggccgagggc cgtgcgccgc cggaggcggt gcacaccacg ccggtcaccc cgggcgctcc    5100
tgggtgcgcc ggcccgggtg ccaggccgc gcagacccg ttgccgggcc cgcgccgtcc    5160
cgggtgttca ccctcggtga ggggcaccgg acgcggccgg gcccggcgct ccgggacgga    5220
tctccgggcg gggcggcacc gcggtcgccg ggccggcggt ggtcggcgtg ccggcgcgct    5280
cgcggtcagc gacagatcgc gctggccatc cggccgaaat cgacgtggcg gcgctcgacg    5340
agggtgccgt gcacaccgta tggctgctgc atgaatgtga tcctcgccgc agcgcggggc    5400
ccgcgtcaat gccccgccgc tggccggagg cggtagcagg gtgtgatcta cgtccggtat    5460
cgcgtcctcc gttcggaggc accccggaac tggcctagac tcgatgacgt gccacgtggt    5520
gacggacgac tcagccacga cctgctcccc ggtgagaagg gcccccagga cgcctgcggc    5580
gtcttcggtg tctgggcccc gggggaagag gtcgccaaac tcacctattt cgggctgtac    5640
gcactgcagc accgtggaca ggagtccgcg ggcatcgcgg tgagcaacgg ctcacagatc    5700
ctcgttttca aggacatggg actggtctcc caggtcttcg acgaaacctc cctcggctcc    5760
ctccagggcc acatcgcggt cggccatgcc cgctactcca ccaccggtgc ctcggtgtgg    5820
gagaacgcgc agccgacctt ccgggccacc gcgcacggtt cgatcgccct cggccacaac    5880
```

-continued

```
ggcaacctgg tcaacaccgc cgagctggcg gagatggtgg ccgacctgcc gcgccaggac    5940
ggccgcgcca cccaggtggc tgcgaccaac gacaccgacc tggtcaccgc gctgctggcg    6000
ggccagaccg gtgaggacgg caagccgctc accgtcgagg agtcggcagc tcaggtgctg    6060
ccgaaggtca agggtgcttt cagcctcgtt ttcatggacg agcagaccct gtacgccgcc    6120
cgtgacccgc agggcatccg cccgctggtg ctgggccggc tggagcgcgg ctgggtggtc    6180
gcctccgaga ccgcggcgct ggacatcgtc ggcgcgagct tcgtccgcga ggtggagccg    6240
ggcgagctga tcgccatcga cgagaacggc atgcgcgcct cccggttcgc cgacgcccgc    6300
cccaagggct gtgtcttcga gtacgtctac ctggcccgcc ccgacaccga catcgccggg    6360
cggaacgtct acctctcgcg ggtggagatg gccgccggc tggccgccga ggccccggcc    6420
gacgccgacc tggtgatagc cacgccggag tccggcaccc cggccgcgat cggctacgcc    6480
gaggccagcg ggattccgta cggctccggc ctggtgaaga acgcgtacgt gggccggacc    6540
ttcatccagc cctcgcagac catccgccag ctgggcatcc ggctgaagct gaacccgctg    6600
aaggaagtca tccgcggcaa gcggctggtg gtcgtggacg actccatcgt ccgcggcaac    6660
acccagcggg cgctggtgcg gatgctccgc gaggccggcg cggccgaggt gcacatccgg    6720
atctcgtcgc cgccgatcaa gtggccgtgc ttcttcggca tcgacttcgc cacccgcgcc    6780
gaactgatcg ccaacgggct gtcggtcgag gagatcggca cctcgctggg cgccgactcc    6840
ctggcgtaca tctcgctcga cgcgatggtc gaggcgacca cgatcgccaa gcccgacctg    6900
tgccgcgcct gcttcgacgg cgagtacccg atggagctgc cggacccgga gttgctgggc    6960
aagcacctcc tggagaccga gctcgcgggc gggacggacg ccgcggacgc cctgcgccgc    7020
ccgtgacgtc cctgccccac gacacgaaag ttcccagcca tgtctgctga gtcctccgag    7080
cgtgcgccgc agcacgcggg cgccggcgcc agttacgccg gcgcgggcgt cgatatcgag    7140
gcgggcgacc gcgccgtcga gctgatgaag gagtgggtga agaaggccac ccgacccgag    7200
gtcgtcggcg gcctcggcgg cttcgccggg ctcttcgacg cctccgccct gaagcgctac    7260
gagcgtccgc tgctcgcctc cgccaccgac ggcgtgggca ccaaggtgga catcgcccgc    7320
cggatgggcg tgtacgacac catcggccac gacctggtcg gcatggtcgt ggacgacctg    7380
gtggtgtgcg gtgccgagcc gctgttcatg accgactaca tctgcgtcgg caaggtccac    7440
ccggagcggg tggcggcgat cgtcaagggc atcgccgagg gctgtgtgct ggccggctgt    7500
gcgctggtcg gcggcgagac cgccgagcac cccggcctgc tgggcgtgga cgagttcgac    7560
gtggccggcg cgggcaccgg ggtggtcgag gcggaccggc tgctgggcgc ggaccgtatc    7620
cgttcgggcg acgcggtgat cgcgatggcg tcctccggtc ttcactccaa cgggtactcg    7680
ctcgtccgcc atgtgctgtt cgaccgggcc ggctggtcgc tggaccggga ggtcgcggag    7740
ctgggccgga ccctgggcga ggagctgctg gagcccaccc ggatctactc gctggactgc    7800
ctggcgctca cccgtacgac ggaggtccac gggttctcgc acgtcaccgg cggcgggctg    7860
gccaacaacc tggcccgggt cgtccccgac cacctgcacg ccacggtgga ccggtccacc    7920
tggaccccgg gcgcgatctt cgacctggtc gggcaggccg gcgcggtgga gcggctggag    7980
ctggagaaga ccctcaacat gggcgtcggc atggtcgccg tggtgccgca ggagtccgtg    8040
gacgtcgccc tgaccaccct cgccgaccgc ggcctggact cctgggtgtg cggcgaggtc    8100
gtggaccggg acgccgccca caccgaggcc gtgaccctga ccggtgacta cgcggcctga    8160
cgtgagaggt accgccggac ccgtcggcg taccgcgcac ggtcgcggtc gcccggcacc    8220
cggcgccatc gccccgcggc ggtggcggga gccggggtct cccgcggcgt gtccggggac    8280
```

```
cgcccggtcc gcgccgatgt gccggggtac cgcccggcac cacccgccgc gtcagcgggc    8340
cggtcggtcc cggtcggcac gccgggcgcc cggacagcac ggaaggcagc acgaaaaccg    8400
gcccggggcg ggaaccccga accggctcag gtgctgctgc cgcgatgcgc cggaagcccg    8460
gtgaccgagc gtggtcaggc gcgccgacgg tacgggacg gtgccgacgg atggtcgtcg     8520
tcctcgtcct cgtcgtcgtt gtaccgctgc gcgtactgtg cgtacgggtc gtcttccagc    8580
tcatcgtcgt cctcgaacgg gtcgccgttc ggctcccggt tcgatgttgg cgatgcgccc    8640
agctcctcgg ccaggcgtga gaggtccgtc ccgccgctct ggtacttcag ctggcgggcg    8700
accttcgtct gcttggcctt ggcccggccg cgccccatgg ctcgaccccc tcaacgacgg    8760
ggctcgacgg ccccagagtc ttgacacgcg ttcacgttca tgaagtggag cggactctta    8820
ccaagagacc gtccgtaggg cttcaacggt acctgcttct gtggccatac ggtacgtcgc    8880
ccgcatgacg tgccacgtca cagtggccac gaggcgcccc gtcccgctg gtcagctgcg     8940 agtttaaccg gtccggggcg gcaacccgcc gagcggccgt gagggatctc tccctcacgg    9000
cctgtcggcg taccgacaat cgggctcacc gcccgataaa aatggccgaa atcgaccgt     9060 tcggcctacg cctggcgagc ctccgcgatc cgctgctcgg cgaggcggtc cgccgcgacg    9120
gccggcggga caccgtcctt ggcggcccgt tcgaatatgg ccaccgtggt gtcgaagatc    9180
ttcgtcgcct tggccttggc ccggtcgaag tcgaatccgt gcagctcgtc ggcgacctgg    9240
atgacgccgc cggcgttcac cacgtagtcc ggcgcgtaga ggatgccgcg gtccgcgagg    9300
tccttctcca cgcccgggtg ggcgagctgg ttgttggccg cgccgcacac caccttggcg    9360
gtcagggccg ggacggtgtc gtcgttgagg gcgccgccga gcgcgcacgg agcgtacacg    9420
tcgaggtcgg cgcggatcag ggagtcggtg tccgccaccg ccgtgacctg cgggaacttc    9480
gaccggatgc ggtccaccga ctcggcgcgc acgtccgtga cgaccacctc ggcgccgtcc    9540
tcgaccaggt gcgcgacgag gtggtggccc accttcccga cgcccgcgac gccgacccgg    9600
cggccgcgca gcgtgggcgc tccccaggcg gcctgggcgg aggcgcgcat gccctggaag    9660
acaccgaagg cggtgagcac cgaggagtcg ccggcaccgc cgttctccgg ggagcggccg    9720
gtggtccagc ggcactcgcg ggccaccacg tccatgtcgg cgacgtaggt gccgacgtca    9780
caggccgtga cgtagcggcc gccgagggag gcgacgaagc gcccgtaggc gagcagcagc    9840
tcctcggtct tgagctgctc ggggtcgccg atgatgacgc ccttgccgcc accgtggtcg    9900
aggccggcca gcgcgttctt gtacgacatg ccgcgcgaga ggttcagcgc gtcgaggacc    9960
gcctcctcgt ccgaggcgta cgcgtggaag cgggtgccgc cgagggcggg gcccagcgcg   10020
gtggagtgga gggcgatcac ggccttgagg ccggtcgcgc ggtcctggca gaggacgacc   10080
tgctcgtggc cgccctgatc cgatcggaag agtgtgttca gcacgccgtc agcatcgtcg   10140
gtgggacgta cgtcggtcac ggtggtgact cccataagtc gcggaattgg acgccctccg   10200
ggggtgggga gggccggtgg gtcagagcgt aagccctgga gggcctcggg tgggcccgg    10260 tctcacgagg cgatttccgc aggtggtgcc gaggacggcg ggcgccggtc cggccggcgc   10320
ccgccgtcgc ggtccgccgg tgcaccgcgc accgccgggc ccgcgccgcc acggggcccg   10380
tccatgggac gattcgagca tccggggtag gcaactaccg gcactcgaat cgggcttgag   10440
gagcgtgcgt gaccgtggca gtgaccgtcc cgtacgcggc gtacctgcgg gtctacgagc   10500
cgctggccgc gttccccgag ccggagcgga cccactgggc gcgctacgcc cggcgggacc   10560
ggctccccgg ggcccaggag gagctgcggc gggcgctgac cgacctgctg ccgctgccgc   10620
```

```
cggtgccggt cccggtgcac gagagcccgg acgccttcgt caccgtggtg gacggcatcg   10680
tctgcgtctg cccgtggcgg acccggctgc gcggctggat ggcgctggag gaggccgcgg   10740
agcggtatcc ggccccgctg ctggacgcgg tgctgccgcc gctggtccgc cggcaggcgg   10800
tggccgactt cgagcggtgg ctggagcgga atccggacgc ccggccgtgg atccggtccg   10860
cgacctggca cgtgccggtg cgctggttcg tgctcttcgc ggacgaggag cgcgagttca   10920
ccaagggctc cgagggcctg gtgatgcggt accggacccc gatggtggag gcccgccggc   10980
gggtggcgcg ggggctgaag gtgctccggg agacgctggg cgagggcccg ctcatcgacg   11040
gcctggtaga tgttggccgg tggctggagg aattccaccc gcggtccctg gtcgagctcg   11100
actacggggg gctggtggag gtggtgcccg aggagcggct gcacgccgac cgctcggccc   11160
gcgacgtggc cgaggggctg tcggcgctgc gggacgggga cggcgagcgg gccggcggcg   11220
cgtacgagcg gctgacggag cgctgggccg cggtccgggg gttgcagcac gcgagttgag   11280
cggcgggctg caggcgccgt cgcgcggagg ttttccggcc atggcggcgg gagcggttcc   11340
atgagagggt cggacaggac gtaggtcccg atacggactt ttaacggcaa ccgtgacgta   11400
acccacttac tgcgggtctt gcggctatcc ccagtcctcg tgtcaaaata ggacaaggag   11460
tccaaggggg cctccttccg tccaactaag ggcggattcc tctgtattgc acgccttggt   11520
tgggtctggt ggctcctgat cccgttgtga ctgatcgtca cggcagggtg actgtccgct   11580
atgacatggt ccatcggctt ccgccgaggt tgaacacctg agagggcaat tccatcggtt   11640
tggccgatgg ggctggacag atggtgtagt tgtagtgccg aggacaagcc gttcgtccta   11700
taaccgactc ggcccgcgtc cgccatatcg ggcaacgcgg gtcaaggcgc agaatttaga   11760
ggaaagaacc gtgatggttc ggttctcccg aggaggccgc tcatgaccgc tcgcacccct   11820
gatgctgagc cgctgctgac cccggctgag gttgccacga tgttccgcgt ggacccgaag   11880
acggtcacgc gttgggccaa ggcaggcaag ctcacgtcca tccgcacgct cggaggccac   11940
cggcgctacc gcgaagcgga ggtccgggca ctgctcgcgg gcatcccgca gcagcgcagc   12000
gaagcctgaa acaccgtttg accgggcatt tcccgggccg taggcccggt ggacgcccac   12060
cttaagcacc acacgactgg tgcctgcccc aacaggcccc gccgcccgca gcgtcatggg   12120
tgagtcgttg atcgcgctgg actccgccgg gtccagcgcg attttttgtg cccgcgccgg   12180 cccccggggcg cccggccggg tccgccggct gccccgtcgg gggcccgtcg ccaccgtgcg   12240
cagtggcgcc gtggcgcgcc gcgagcgggt ccggcgccgc gggccgaagg tttcagcaag   12300
cgctttctgc gagcggcccg tcgcgccccg ttcccggctc gaaacggccc cttcggatgg   12360
gtgcaattgc acatattaaa ttgacctgct gtcgaagagg ggtaagtcac cccacttggg   12420
aaagctgttc ggtgactccc gtcacatcgc atgcggcttg tcatcaagcg catacctacg   12480
gtaaagggct cggggccgc taacgggtgc ggtcggaggt ccgtgacggg gtggtgccgg   12540
ccgcgggtcg cgcggcgcgt tccggcgtgg cggcccggt gggaccgtcg ggcagcggcc   12600
ggccggcccc ggcggtcgcg gtggcgccgg cggcctcgga ggcgggtg gacagcggcc   12660 gggtcgtgcc gcggtcctcg gtccggtgg tgcccggtac ggagccggac ggtcccgccg   12720
ccgggcgggc cgcgaccggt tccggcgcg cggggatgc cgacgcgcc gggagtgccg   12780 ttgccgatcg tgccggggt gcggaggcgg ccgatcgcgc cgggcgtgcc ggaggcgccg   12840
acggagtcgc cggcgtcggc gggcgggccc cggtgggcgc cggaggggtg gcctcctgcg   12900
gcccggagga cggacggccg gggacgggcg cgggggacgg cacggtggcg gccggggcgg   12960
cggcgggtgc ggcccgctcg taccggggac gcccgtcggc ggcgccgggc tgcatcgcca   13020
```

```
ggcgcagcag ccggtggcag accgggcagt gccgggtgga gtgcggacgg cccgccgccg    13080
ccgacagatg ggcgcgcagc agcgcccgga tttcacgcct cgcggtcgcc ggcatacgcc    13140
gcacctcccg tgccccgcgc gtcggtctct gcttgggtac cgccggtatg tgccgcagtc    13200
aagacggccg aaggcccgga tccctgcggg gatccgggcc ttcgatgatg cggtcctgac    13260
gggatttgaa cccgcggcct ccaccttgac agggtggcga gcactccaaa ctgctccaca    13320
ggaccttgct tttcgcttcg cgctgcgtgc gctggcgaag cagactctac agcagctcag    13380
ggggtgcggt cgaactcgcg cccggcgggc cggcgacggc cccggcgagt ggtgccgcg     13440
ggccgcgtcc ggggtgggcg gagcccggtg cgggggccca ccccgggccg gggtcgtgcg    13500
gtccgtcggg tggtgcgggt ccgtcgggtg gtgcggggcc ggcgcgtccg ggccgcggtc    13560
gtgcggcccg cgccgggaac gccccacgga ccgtacggcg gggctgccgg cggtacgggg    13620
gcgggatggg tcccggccgg gccggagtcg cccacggggg caggagcgcg ctcccaccgg    13680
cgtacggcgc cggggcggtc cacacggtcg cacggcgccg aggggcgcgg tcccacgggc    13740
gtacggaggt tggacgggcc gtcggggcgg gagagcggcc cggaccggcc cggggccgcg    13800
ggggaccggc tggggcggcg tgcggctgtc ggcgaccggc tgctgggggc ttggggttgt    13860
cggcgaacgg ttggggccgc ccgaggctgt cggcgaccgg ctggggcggc cgggagcgtg    13920
agcgggctgc tgcccggtgg atcgccccgg gtcgccccag ccgttgggtc gccccgggcg    13980
gcgggccgcc cggggcgccg gagaggcgca cgcaacggcc gagcgagggg gagacgcccg    14040
cgtacgcccc gtgggccgcc acacgcgtcg tacgcgccac acgcgccgtc ggccgcccgc    14100
cggtccccgg cgagccggaa ccgccgtccg gccgccgccc ggccgccgtg cgggcccggg    14160
cgggcaggac gacggccggg cggcggctcc tcgcggcgtc acggcgccgc cgcgtccacc    14220
gccttcacga tgcgcttgtc ggagatcggg taggcggtgc ccagcgcgtg cgcgaagtag    14280
ctgacccgca gctcctcgat catccagcgg atctccagcg cctgcgcggg caccgggcgt    14340
ccgggcggga actgctccag cagccaggcg tactcgtcct gcatctcctt gaccttggcc    14400
atccgggccc ggtcccgctc ggcgttggtc ggcagctgct gcagccggcg gtccaccgcc    14460
accagatagc gcatcagatc cggcagccgc cggacgccgt cgcgcggtgac gaacccgggc    14520
ggcaccaggc ggtccagctg ctcccggatg tccgtcaggg agggcagcag caccgggctg    14580
ctggtggcct tcagccggcg ctcgcacgcc tgccaggcgg ccagcacctc ctgcaccttg    14640
cggacggtgt ccagcgtggc gtccatgatg tcggcacgca ccgcgtcgaa gagcttgcgg    14700
aagccctcct cgtcccacgc cggaccgccc cgggcggcga ccagccggtc gacggcggcc    14760
gagacgcagt cctcgaagag cgcctggacg ctgccgtgcg ggctgctcgc gagcgccagc    14820
ttcgcgctgt tgcccagctt gccctggacg aacttcaccg gctggcgggg gaggttgagc    14880
aggatcagcc gccgggtgcc gcgccacatc gcctgctgct gctcggcctc ggtgtcgaac    14940
agccgtaccg cgaccgacga gccctcgtcc accagcgccg ggtacgcctt caccggctgt    15000
ccggcgcgcc gggtctcgaa ggtgcgggc  agcgcgccga cggtccagga ggtgagcccg    15060
gaccgctgct cgatgccacc gccctccttg gaggtggcga acgccttggt gatggccgcc    15120
cgcgtcttcg gcttgagccg cagccgcagc gcctccaggt ccttgtcctc ggcgagcttg    15180
cggcgccgct cgtcgacgac ccgaaaggtg atcttcaggt ggtcggggac cttggacggg    15240
tcccagtcct ccggctcgat ccgcacccccc gtcatccgtt gcagctcccg gccgagggcg    15300
acggtcagcg gctcctgggt gggcccctcc tgcccgccgg cgggcaagga gggaggcacc    15360
```

-continued

```
gcgctgtcca gaaagcgctt ggcgtagttg ggcgcaggga cgcagttgcg ccggatcggc    15420
ttgggcagcg aacggatcag ctcggtgacc aggtcctccc gcagcccggg gatctgccag    15480
tcgaagccct ccggggagac ctggttgagc acctggagcg ggatgtgcac cgtcacgccg    15540
tcggcgtcgg cgcccggctc gaactggtag gtcacccgga acttcaggtt ccgctggcgc    15600
caggtgtccg gataggcgtc cttggtgacg ccctccgccc gctcgttgat gagcatggac    15660
ttctcgaagt tgagaagctc cggctcctcc cggcgcttgt gcttccacca ggagtcgaag    15720
tgcgccccgg agaccacgtg ctcggggatc cgctggtcgt agaagtcgaa cagggtctcg    15780
tcgtcgacca ggatgtcccg gcggcgggcc cggtgctcca gctcctccac ctcgccgagg    15840
agcttgcggt tgtcgtggaa gaactggtgg tgggtgcgcc agtcgccctc caccagcgcg    15900
ttgcggatga acaggtcacg gctggtctcc gggtcgatcc gcccgtagtt caccttccgc    15960
tgggcgacga tcggcacgcc gtagagggtg acccgctcgt acgccatcac cgcggcctgc    16020
ttctgctccc agtgcggctc gctgtaggtc cgcttgacca ggtgctgcgc cagcggctcg    16080
atccactccg gctcgatccg cgcgttgacc cgcgcccaca gccgggaggt ctccaccagc    16140
tcggcggaca tgatccaccg tggtggcttc ttgaacagcg ccgaaccggg gaagacggcg    16200
aacttggcgc cgcgcgcgcc caggtactcg ttgcccttgc cggtctcctt gccgccctcg    16260
gccaccgtgt tcttcaggcc cacgtgggac agcagcccgg ccagcagcgc ggtgtgcacg    16320
tggtcggggg ccgcgtcctg ctcgttgaga tggatgccca tcgtcttcgc gaccgtacgc    16380
agctggctgt agatgtcctg ccactcgcgt atccgcaggt agttgaggta ctcgttgcgg    16440
cacatccggg ggaaggccga ggaggacagc tccttctgcc gctcgcggac gtagcgccac    16500
aggttgagga aggcgaggaa gtcggagttc tcgtccttga accgggcgtg gttctggtcg    16560
gcctgctgct gcttgtcggc gggccgctcg cgcgggtcct ggatggacag cgccgccgcg    16620
atcaccatca cctcgcgcgc acagccggtg cggtcggcct ccagcaccat ccgggccagc    16680
cgcgggtcca ccggcagctg ggagagcttc cggccgagcg gggtgagccg cttgcggagg    16740
tccttctgct gcgggtcgat cgcccccagc tcctccagca gctgcacgcc gtccttgatg    16800
ttgcggcggt ccggcgggtc gatgaacggg aacttctcga tgtccccgag cccggcggcg    16860
gtcatctgga ggatcaccga ggccaggttg gtgcggagga tctccgcgtc ggtgaactcc    16920
gggcgggaga ggaagtcctc ctccgagtac agccggatgc agatgccgtc gctggtccgg    16980
ccgcaccggc ccttgcgctg gttcgcgctg gcctggctga tcggctcgat cggcagccgc    17040
tgcaccttgg tgcggtagct gtaccgggag atgcgcgcca tgccggtgtc gatgacgtag    17100
cggatgcccg gcacggtgag cgaggtttcg gccacgttgg tcgccagcac gatccgccgg    17160
ccggtgtggc gctggaagac ccggtgctgc tcggcgtgcg acagccgcgc gtacagcggc    17220
agcacctcgg tcatcggcag ctgccgcttg ttgagcgcgt cggcggtgtc gcggatctcc    17280
cgttcgccgg agaggaagac gaggatgtcg cccgggccct cgccgcgcag ctcgtccacc    17340
gcctcgcaga tcgcggtgat ctggtcccgg tcgccgtcct cgccgccctc ctccagcagc    17400
ggccggtacc gcacctccac cgggtaggtg cgcccgctga cctcgatgat cggcgcgtcg    17460
ccgaagtgcc gggagaagcg ctccgggtcg atggtcgccg aggtgatgac gaccttcaga    17520
tccggccggc gcggcaggag ctgcgccagg tagccgagga tgaagtcgat gttgaggctg    17580
cgttcgtgcg cctcgtcgat gatgatcgtg tcgtactggc gcagctcgcg gtcggtctgg    17640
atctccgcga gcaggatgcc gtcggtcatc agcttgacgt gggtgtcctg gctcacctgg    17700
tcggtgaacc ggaccttcca gccgacggac tcgcccagcg gggtgcgcag ctcctcggcc    17760
```

```
acccgctcgg cgacggtgcg ggcggcgatc cggcgcggct gggtgtgccc gatcaggccg   17820
cgcacgcccc gccccagctc caggcagatc ttcgggatct gggtggtctt gccggagccg   17880
gtctcgcccg cgacgatcac cacctggtgg tcccggatcg cctcggcgat ggcgtccttc   17940
ttctggctga ccggcagtga ctctgggtaa ctgacctcgg gcacggcggc ccggcggtcg   18000
gccacccgcg actcggcccg gtcgatgtcg gccgcgatct cggcgagcac ggcgtcccgg   18060
gcctcgggct tacggatccg gcgggcgccg tcgagccggc gccccagccg ctgctgatca   18120
cgcagcatca gctcggggat ccgttccagc agggccggga gggtggggc aggcgtggtg    18180 gacatacggg atccaggatc tcacttcgcc gaaacggctg cgaaccatt tctgtccgga    18240 ctagtccggg aagtatgtcg gagatgggtg ccttagcgtg cattcatggg cggatatggc   18300
ggggccgagg gcgacgtgg cggtccggc gaccggtgcg gcggggcccg cgccggttgc     18360
ggtgaccggt gcggcgggtc ccttggcggc tgcggcgggt ccggcgaccg gtaccgcggg   18420
tccggcggga cccgcggcgg gccgggcgca gccgccggtg gacatggccg gaccgagggc   18480
gggtacggcg ggtcccatgg atgaacggcc gaagcggtgg cggcccgggc acggcacggg   18540
gcccggtgac ggggttcccgg acgggaacgg agcaggtgac gggcgtggtg acgggcgcgc   18600
ggccgatgcc gggcgcggtg aggtgggcgc ggccggtgcc gggcgcggtg acgggcgggc   18660
ggccgggggc ggaaccgccg gcggcgggtc gtcggccgcc gggtccgacg gcggggcccc   18720
cggcggctcc ggcggcggac accgtgcgg gcggcccggc gggtgggccg ggcgttggtc     18780
ggcgttcacc gcgtcgccgt tcttcccggc cgtggtgctc tgcctcatcc tcgccggcgc   18840
cgccgggttc ttcgccggct cctacacgta cgccatggcg aacccgacgc cgcaccggct   18900
gccggtcgcc gtggtgggcg agcaccgatc gccgagcggg caggcgttcc ttgccggcat   18960
ggagaaggcc ctcgacacct cgctgcggat ccgcccgtac gaggacgacc gggcggcgcg   19020
ccgggcggtg gaggagcagg aggtcttcgc cgtgctggag ctgggcgggg agcgggtccg   19080
gctcgacctc tccggcgcgt ccggcgcctc ggtcgccgag ctgctcgccc gcgccggccc   19140
cgaggtgggg cgggagaccg gggtgccggt gacggtccgg gacatcaacc cgctgcagga   19200
gggcgacccg cgcggcctgg cactgttcta catctcgctc gcggcggtga tcgtcggctt   19260
cgtgggcgcc atccagctga gcgtgcacgc ccgcgcgctc aaccccgggg agcggatcgc   19320
cttcaccgcc ggttacgcgc tgctgtgcgg tttcgccatc gcggcggtcg tggactggct   19380
gctgggcgcg gtggacctgc ccttcgtgga gtcctggctg atcctggccc tcaccctgtt   19440
cacctccggc atggtcttct cgatgttcaa cacgcttttc gggcgctggg cgatgctgcc   19500
cacctggggg ctgatggtgc tggtgggcaa cccctcctcc ggcggcgcgg tctcctggcc   19560
gctgctcccc tccccgctgg gcgtcatcgg gcagtggctg ccgcccggcg cctcggtgaa   19620
cgcccagcac accgccgtct acttcggtga ccaccagcac gccttcccgt tcctggtgct   19680
gggcggctgg gccgtgctgt ccagcacggt cttctgggtc tggcggcacc ggcacccgg    19740 cggccgggac gtaccggcga gggaaccggc cggtgccggg ggcggcggcc cggcggactg   19800
accggcggac ccgccggccg ggcacgcggg ccgaccggcg gcgggccgaa cggcgacggg   19860 cctgcggcg acgcgcgacg gtcctgcgat gggccggtgg gcggggcggc accggagccg    19920
tgggccggtg ggtggacgag cccgaccccgg tgtccgtaca cgtctgttgc gtccggatgc   19980
gttccgccgg acccccaccc gtgccagtct ggaggccgtg accgcagaga gcttgggggg   20040
cgtgaccggc gtacggccgg gccacgcgac ggtgcaggac ggacgcgcgg gggacgccgc   20100
```

| | |
|---|---:|
| cgtgcgcgac gggcacgcgg gggagaccgc cgcggccggg ggacgtgccg agggacgcgc | 20160 |
| cgggggggcgt gccgaggcga atgccggggg gacgacggtg cgccacgaac ggccggggga | 20220 |
| gaaccgggca tccggcgggc ccggtgacgc gccggcggac ggacccggcg cggtgaccgc | 20280 |
| ggacgctcct gtgggcgatg ccgtggaggt gaccgcggac ctgcccggca ccggggccgc | 20340 |
| cggcggatcc ggcggtctgc ccgcggacag gtccggcgcc gccggcggga accccgcgcc | 20400 |
| gcccggcgac ggcgccgccg tcctcacggc cgccccgtg accgccgccg tctccgccgc | 20460 |
| cgtctccgcg accgtctccg cgaccgcctc cgcaaccgtc gccgcgtccg tggccgaggc | 20520 |
| ggctgccgta ccgtccgtca ccgtcccggg gccggccccc gttccggcgg cggagcggct | 20580 |
| gccggtcacc gcgcccttcg gcgtccaggt cttcggcctg gcgtaccgga tgctggggac | 20640 |
| ggcgaccgag gccgagcagg tggtgcacga ggcccggctg ctccggcagc gggccggggt | 20700 |
| ggcgggcgcc gggccgcgcc ggctggtccg gctggtcgcg gacctgtgcc tggaccggct | 20760 |
| ggccgcggcc cggaccccgcc gggaggagta cgtcggctcc tggctgcccg agccggtccc | 20820 |
| gtacgcggag aaccggctgg tcccgctgga gacggccgcc cagcgcgact cggtgtcacc | 20880 |
| ggcggtgctg gtgctgctgg agcggctcag cccggccgaa cggctggcct atctgctccg | 20940 |
| cgaggtctac ggccacagcg acgcggacac cgcacgggtg ctgggcatcg acgaggccga | 21000 |
| cgcccgccac ctccaccacc tggcccggac cgaggtgggc gcgccccgcc ggcggccggc | 21060 |
| cgactcgccg gaggaggcgg cgcggatcgt cggccacttc cggtccgccc tgatcgacgg | 21120 |
| cgacgcggcc ggcctggagg aactgctcgc ggacgacgcg atggcctggt tcgacggcgg | 21180 |
| tggcaaggtc ggcaccgccc gccgcccggt catcggcggc accaaggtcg cccgccacct | 21240 |
| ggccggctgg gccggtgact tcggcatggc ggacgcccgg acgcggatcg tcccggtgaa | 21300 |
| cggcgagccg gccgtgctgg tccaccgcgc cggggccctg gtctgcgtca tcgctccgga | 21360 |
| gctggcggag ggccggatca tcggcgtgcg caccgtggcc aacccggaca agctggcctt | 21420 |
| cgccgccgcc cgcaccggcg cggacggaac cgccgacgac gccaccgccg ccccgcgaac | 21480 |
| cgggggcgcc gggaccgagg cgcgcgacgt ccccgacctc ccggacgcca ccgccgccac | 21540 |
| cgccggcccg gacgcgggga gcgggacgc cggggacgag gcgcgcggcg ccacggtgcc | 21600 |
| ggtctgcggc aggtgagccg gggcgccggc ggtgacccgg aacacaccac cgcggcgtca | 21660 |
| cagtccccgg ccccgtcccg tcccctggt gacggcagac gccgggcggc ggcccgcgga | 21720 |
| accgggggccg ccggggagaa gggacggacg gtatgggact ccacatcgtg gtgctgggcg | 21780 |
| ccgggtacgc ggggctggcc gcggcgaagc tcgcggcacg ctggaccgac gcgcgggtga | 21840 |
| cgctggtcaa cgcggaagac cggttcgtgc agcgggtgcg gctccaccag ctggcggccg | 21900 |
| gtgagccgct gcccgacctg ccgctggcgc ggctgctccg gggcaccggg gtgcggctcg | 21960 |
| tcgtggaccg ggtgaccggc atcgacgccg cctcgaagac cgtggacctg gccggcgccg | 22020 |
| cgggcggtcc gctccggtac gacctgctga tctacgccct gggcagccag gacgcgccgt | 22080 |
| ccccggtgct gggggtggcg gagcacgcgt accgcgtcgg caccctggag caggccgcgc | 22140 |
| ggctgcggga gcgtctcgcg gtgagccgga ccgtcgccgt ggtcggcggg ggcctcaccg | 22200 |
| gcatcgagac cgccgccgaa ctcgccgaga gcttcgccgc ggacgcccgc cggaagggcg | 22260 |
| ccgccggagc cggcccggcc gggcgcacgg tgcggctggt caccggtggc gcgctcggcg | 22320 |
| cggcgctgtc ccgccccggc gcggaccacc tgcggcgcac cttcgaccgc ctcggcgtgg | 22380 |
| aggtccgtgc cgacgccagg gtggcggccg tcgacgcgga cggactgctg ctggaggacg | 22440 |
| gcgggcgggt ggccgcggac accgtggtgt ggacgaccgg cttccgcgta ccggacctgg | 22500 |

```
cgcggcaggc gggggttcgcc gtggacgagg acggccgggt gctggtggac cccaccctgc    22560
gctcggtctc ccaccggag  gtctacgcga tcggtgacgc cgccgcgccc cgcaccccg     22620
acggccaggt ccttcggatg gcgtgcgcga ccagcatccc ggccgcccag caggccgccc    22680
gtgccctcgc cgcccggctg tccggccgcg agccccgccc gctgcgcttc cgctacgcac    22740
tccagtgcat cagcctcggc cggcgcgacg gcctgatcca gttcgtcaac ggggacgaca    22800
gcccgcggga gcgggtgctc accggacgga aggccgcgtt cgtcaaggag gccgtggtgc    22860
gcggcacggt cctcttccag cgccacccca ccatcccggc cacccgctga ccgccggcgc    22920
cccgcggccc cgaccggccc cgccccggac tcctcgcgga gcgggaccgg acgcggcgga    22980
ccgcccccgg aggacgtggc gcgccccgcc ggccggcacc ggaccgggcc gggccggacc    23040
gacagggaac cacctgggtc ggcccgggg  cggtcgtgac gggacgaggt ggggcgcgac    23100
gaggtggggc ggggcggacc gggccgggga tggcggcgag gtcacgccgg agcgggccgg    23160
aaaaccagat gcccgcctcc gagaaccctc ggggcgggca tcttccctgt tcagggactg    23220
tggctggggc cggggtcgaa ccggcgacct tccgcttttc aggcggacgc tcgtaccaac    23280
tgagctaccc agccatgggc acccctggct ccgagagccc ggggaagcaa cctcgcggtt    23340
gcagcggtcc tgacgggatt tgaacccgcg gcctccacct tgacagggtg gcgagcactc    23400
caaactgctc cacaggacca agctcgtgcg agcaccagtc tcgcacaggg tgttgcgtgc    23460
ccccaacggg attcgaaccc gtgctaccgc cttgaaaggg cggcgtcctg ggccactaga    23520
cgatgagggc tgatggccca cctgttcgc  cttccggcgc cgtcgggac  gtgagaagca    23580
tatgggatgg cgagggggtt cgccaaaacg gttgtccgag gggttcgcgg gtgtcgcccc    23640
gggccggccc gcccgggtac ggcactgccc ccttccgggc cccctggcag acaatggcgg    23700
cgtgctggag atgacgcgcg aggagttcga ggaactggtc gccgaggcgc tggaccggat    23760
ccccacggaa ctgacgcggc tgatggacaa cgtggcggtg ttcgtcgagg acgagccgcc    23820
cgccgacgac ccggagctgc tgggcctcta cgaggggacg ccgctcaccg accgggggga    23880
gtggtacgcc ggggtgctgc cggaccggat cacgatctac cgcggtccga ccctgcggat    23940
gtgcgagacc cgggaggacg tggtcgccga gaccgagatc accgtggtgc acgagatcgc    24000
ccaccacttc ggcatcgacg acgaacggct ccacgcgctc ggctacggct gagcggcgcc    24060
gcgcccggc  accgcgcgct gcgggcgtag gccccggtac cggggccggg cgcgcccggc    24120
ccgggctccc tccggcccgg tccgacccgg ccggaaccgt cccggtgcgc tgcggcgtac    24180
ccgacctgct ccgccgggg  cagggcggg  gtgcgggccg ggccggtgta cggacatccg    24240
ggaacgccgg ccgggccttg agggcggtgc cgggccggcg ggaggccggc gtgtcctggg    24300
cggtgcggcg ccagttgggc aggggcccg  ttccctgccc tggaggtgct ccgaccatgc    24360
ccgcgatccc cgaccggccc gcccgtccct cgtcccgcac cgcgaccggg tcgcggtgg    24420
cgtgggtcgc cgccgcggcg ctcgcgggct gcatgagcgt gtcccacgac ggcgaacggt    24480
ccggcaaccg cggcggtgcc gagcggcgcg gccgggccgc cgagcaggac ggcggggcga    24540
cggtggccgg tgcccggtg  gggcggagg  cgggcgtgga gcggcgggc  gggaagggcc    24600
gcggcaagac gaagaagaag gacgacgacg gggaccggaa ggggcgcgcg tcggcgtcgg    24660
cgtccccgtc cggaaggaa  gaggcggcgc gcacttccgg ccccggcggg cggccgccca    24720
cggcggcacc cccggacccc ggcggcgggc cccgtcgga  caccgcgccc gcgcccggc    24780
ccccggagcc gtcctccgcg ccgccggaaa ccgccggccc gggaccgtcc gagcccggcc    24840
```

```
ccaccgaacc gccgccctcg ggcgagcccg ggggcgggga ccaaggggc ggcgcgggcg    24900 gcggcagcgg cggcccggcg aacccggcct gacccggagc cgcgcccgcg ccccggccgg    24960 ccggggggtgt gcgtccgcgc ccgcccgaca gccgacaggt gacgcccgac ctgccggtgg    25020 cgccccggccg gtaggtggcg cccggtccgg tggggcgggt ccggcccgg tccgggagcc    25080 ctccggccgg gccggcggca tggacccggc ccggtcaggc gggccccgac gtccggggcg    25140 gtcggaccccc ggccgggagc ggggagtgcg ccgccccgt ggccggcctg ccgacccgac    25200
ggccggacgc cggcggagcg gcgccgccgg gccggagcgg cgaccgggcg gacggccgac    25260
cgcccgccgc ccgggggcga ggccgttcat ccccgggagc cgggtgcggt ggccgtccac    25320
ccgccggcag tcgtccgccg gtgcgccggt cccggtgggg tgacgcgggt ggtggggaac    25380
tccgggcggc cccggcgacg gggcccgcca ctcccccgtc cgcccgcctg cacgggccgg    25440
ttccggactg cctccgagtg ggtgaatttg ctttcccggg ggaggagtgc gtatggtggt    25500
agatcgtttg atcccatttg cccggcgcca aacccgaagc gcgccgtgtg gcgcgttcct    25560
taccttgccg tggctgaccg cattgaggcg gtcgtttgcg aatgacacgg agctgggcgc    25620
gtgccgagac tccggaaggt ttcgcatttc gcatgtccat ttccactgac cactccgcca    25680
tgcccgccgc cgacgagacc gtgcagacct ccgacgcggc cgcggaggcg accgtggccc    25740
ccgaggtgac cgggacgccc gaggtgacgg cccccgggac ggccgacgcc gacgccgagc    25800
aggccgccga cgccgcgacc ggaccggcgg acgacgccga cgccgagcag gcgcccaccc    25860
tcaccttcgc cgacctcggt ctgcccgagc agatcgtccg caagctggcg cagaacgggg    25920
tgaccacgcc gttcccgatc caggccgcga ccatcccgga cgccatggcc ggccgggaca    25980
tcctgggccg cggacgcacc ggctccggca agaccctctc cttcggtctc ccgctgctga    26040
ccacgctgtc cggcggccac accgagaaga agcgccccg tggcctgatc ctcacgccca    26100
cccgtgagct ggccatgcag gtgagcgacg cgctccagcc gtacggcgac gtcctgggcc    26160
tgaagctcaa ggtcgtctgc ggcggcacct cgatgggcaa ccagatctac gccctggagc    26220
gcggggtgga catcctcgtc gcgaccccgg gccggctgcg cgacatcatc gaccgcggcg    26280
ccgcgtcgct ggaccgcgtg caggtcgcgg tgctggacga ggcggaccag atggccgaca    26340
tgggcttcct gcccgaggtc accgagatcc tcgacctggt gccgcagggc ggccagcggc    26400
tgctgttctc cgccgacgctg gagaacgaga tcgacacccct ggtcaagcgc tacctggtcg    26460
acccggtgac gcacgaggtg gacccgtccg ccggcgcggt ctccacgatg acccaccacg    26520
tgctggtggt gaagccgaag gacaaggccc ggtcaccgc cgccatcgcc gcccgcaagg    26580
gccgcaccat catcttcgtc cgcacccagc tgggcgcgga ccgggtggcc gagcagctgc    26640
gggactccgg ggtgcgggcc gacgccctgc acgcggcat gacccagggc gcccggaccc    26700
ggaccctcgc cgacttcaag gacggttacg tcaacgtcct ggtcgccacc gacgtcgccg    26760
cgcgcggtat ccacgtggac ggcatcgacc tggtgctcaa cgtggacccg gccggcgacc    26820
acaaggacta cctgcaccgc agtgggcgaa ccgcccgcgc cggcagagc ggcaccgtgg    26880 tctcgctcgc cctgccgcac cagcggcggc agatcttccg gctgatggag gacgcgggcg    26940
tggacgcctc gcgccacatc gtcggcgggg ccggcgcgtt cgacgaggac gtggcccgga    27000
tcaccggcgc ccggtcgctc accgaggtgc aggccgagtc ggcggcgaac tccgccaagc    27060
aggccgagcg cgaggtggag cagctcaccc gcgaactgga gcggtgcag cgccgcgcca    27120 ccgagctgcg cgaggaggcc gaccggctgg ccgcccgggg cgcgcgcgag cgtggcgagg    27180
acccgcaggc cgccgtcgcc ccggccgagc cggccgccga cggggccgag gcccggccg    27240
```

-continued

```
ccgcgccgtc ggtgcccgag cagaccgccg cccccgtggt ggagaacacc gtcgcggacg    27300
aggcgccgcg ccgtacgggc ccggagcgcc gggacgagcg gggctcctac gagcgccgtg    27360
accggggcgg ggacgaccgg ggcggcttcg gccgggaccg ggaccgccgg gacgaccgtc    27420
cgttcaaccg tgaccgccgg gacgaccggg gcggcttcgg ccgggagcgc agggacggcg    27480
accgggaccg tggcttcggc cgtgaccgcg accgcgagcg tccgtcgttc cgcgaccgcc    27540
gggacggcga ccgtgaccgc cgggacgcg agcgcggtgg ttccggtggc cgttcgtacg    27600
agcgccgcga ccgcgacgac cgcggcttcg gccgggaccg cgacgaccgg ggcggcttca    27660
accgcgaccg ggaccgccgg gacgaccgtc cgttcaaccg tgaccgccgg gacgaccgcg    27720
gcggcttcgg ccgggagcgc cgggaggacc gcccgggccg tccgttcgag cgccgtgacc    27780
acgccccccg ggaccaccac cggggcgggg accgtccgtt caaccgtgac cgccgcgacg    27840 accgccgtt cggccgggac cgccgggacg accgtccggc ccgtcgtgac gaccaccggg    27900
gcggcaccac cggcagccgg tccttcgacc gccgcgccga caagcccgc tggaagcgca    27960 acggctgatc gcgcccgcag ctgaccgaac ggcccgtacg ccgccggaca tgtccggtgt    28020
cgtacgggcc ttcggctgtc gaggacaagt ccggtggccg gccgccgtgt tgggcggtcc    28080
ggcaccgctc cgggagactt gggaggctca ccgggggtat gggctcgggc ctcggccgcc    28140
gtccgggcta tgctgcgggg tacgggtcat tagctcaatt ggcagagcag tggactttta    28200
atccattggt tcagggttcg agccctgat gacccactcg gcgagaaccg tgaagcccct    28260
ggtcggacac ccccgaccgg gggcttcggc gttcgccac cggcgccctt ccggccggaa    28320
ggggtcagct ccggccgacg cgacgagcgg ccagggcgct tctgcgccgg gtcggatccc    28380
gcggccacgg gtgcgtggag gggcgttggc gcgggcaggg tgccggcgcg cgaagggtga    28440
gggcgagtgc cccgcgccgg gacaggccgt cacgtcgtcg ctgccgcccg tacgcactcc    28500
cgacacgtcg cccggccggg tgggtgacgc ctggtcgtcg cgaccgtgg atcttggccg    28560 ggatgtgacg gtcctcacag taggcgtggc tatgctgcgg ccctctggga ctgctcagct    28620
cgtcgggggg cctcatgtcc agcaacgcgc cgccgccacc gccgtctcgg ccgccggaac    28680
cgcagcgacc acctcgcggg acacccccgg ccacctcacg gcgaccggcc tccgctcccg    28740
gcgcgggcgg tccggacgcg gccgcagcg cctcgcccac cgtgccggtt ccaccagtgc    28800
cggtcacgcc gcccacggtg cccacccggg aacagccgca ggacggcaag gaccgctggg    28860
caaggcccct gggcgtgatc accgcggtga tcacggtcat cggtgcgatc ctcgcggggc    28920
tcgcctacta cgacagtcac cgtacgaccg agatcgccgt ggggacaaa gcggaggagg    28980 acaagcagga ggccgggctt cctctcctcc tctctcccgg agcgtcctgg tacggcccca    29040
cctggtacgc cagcgccgag gtgcacgagg acatcgacgt tgagcggttc ccgctcaacg    29100
gtggtgagtt gtgggactgg ttccggtcga acaccaccga tctggggacc accggaaccg    29160
ccgtcaccgt ggaaagccgg cacaagacga ccgtgctcgt ccaggcgcc caggtgaccg    29220 acctgaagtg cgaggaaccc ctgcgcggga cggcggtcgc accgcccgcc atcggcgacg    29280
gcggcgaaga agcggtgccg gtgttcatgg ggttcgacct cgacgcaccg aggccggtgg    29340
cccagggttt cgacgcgtcg ggaaagctct ccggcccctt caaggagcag atcgcgctcg    29400 acaagggga cgcgcgagag ctctccgtca ccttcatgag tgcccggaag tcgtgcacgt    29460
tccgcgctgg tctcaccgtg agctcgcagg gcaggaagtg gtccatcccc ctcccggccg    29520
gctgggagga cggcaagccc gccgggtacg tgttcaaggt caccggaccg gccgagcggt    29580
```

```
actccaaggg ctacctcacc gattccggta ccgactggcg gttccgggag gtggatcccg    29640
cgctgctcgt cgccaagggg acgaccctcg actacacggg cccccgatag gcggggggcgt   29700
acgccggacc gtcaggggca ccgaggcggg ggcgcccgtg acggtccgga gtgccggcgc    29760
ccgcaggggc taagcccgca ccggcgcccg gcccgccccc gggccgcgga gccccgcccg    29820
cccgcaccgg agaacggggc ccgcgatcac cgccactccg ccgcccccgc ggcgtccgcc    29880
ccgcccggcg ggtcagggct cgggcaccgg gccgaaggtg accgggaggc ggtgcaggcc    29940
gcgcatcagg ccggagcgcc aggtgagggt ggcggggtcc gcggcgaggc ggaggccggg    30000
agcgcgttcc agcaggccgc gcagcgccac cgtggcctcc agcccgggcga gcggcgcgcc   30060
caggcagtgg tggaggccgt ggccgaacgc caggtggccg cgggcgtcgc gccggatgtc    30120
gaagcggtcc gggtccggga agcggtccgg gtcgcggtcg gcggcgttca gcaccaccag    30180
cacccgctgc ccgccgggga tgcgggtgcc ccgcgatctc accggttcgg tggtgtagcg    30240
gtaggcggag gtgcccagcg ggctctcgtg ccggagcatc tcctccaccg cgccgtccag    30300
cagggacggg tcgtcccgca gcgcggccag ctgctccggc cgcagcagca gcgcgcacac    30360
gccgctggag atcaggttga cggtggtctc gtacccggcg acgagcagca ggaacgccat    30420
gccgatcgtc tcctccgggg tgagccggtc accgccgtca cgggccgcga ccagggcgct    30480
gagcaggtcg tccccgccgt cgcggcgctt gtcctcgacc agcccggtga ggtagccggt    30540
catcgtcgcg gcggagtcgg cggcggccgg gctgccgggg gtgacgatgt ccgccgacca    30600
ttcgccgaac gccttccggt cggccgccgg gacgccgagc agctcgcaga tgacggccag    30660
cggcagcggc tgggcgaaac gttccaccag atcggcccgg cccagcggca ccatcttctc    30720
cagcaggtcg tcggtgatcg cccgcacccg gggccgcagc gcctcgatgc gccgggcggc    30780
gaactgtgcg gcgaccagcc gccgcagccg ggtgtggtgg ggcgggtcca cctggagcat    30840
gttccggccg accgcgtggc cggcgtcgtc cgcgccgtcg gcgtgacggg cgtcgttgcg    30900
cagccggggg tcggcgagcg cggccctggc ctcgtcgtgt ccgacgatca cccagaccctc   30960
ctgggtgtcg ccggtgcgca ggcggtggac cggtccccgg gcgcgcagcc gcgcgaggac    31020
cggataggg ttgtcggaca gcccggtgcc ggggcgcgcc agatcgtcga gggtgggggt    31080
gtgcatggtg atgtgctccg tcgcggagaa gaggggcggc cggggagggc gggtgccggt    31140
caggccggca gcagcgcctc gatcctggcg acgacgtccg ggtcgtcggg cctggtgcgg    31200
gaggcgatgc ggtgggccac ccggcccctcg ggggagatga ggaacttctc gaagttccac   31260
tcgatgtccc cggccacccc ccggtcgtcc ggggcggcgg tcagcagcgc gtagagcggg    31320
tgccggccgg ggccattgac ctccaccttc tcgaacagcg ggaaggtgac gccgtaggtg    31380
gtggtgcaga accgttcgat ctcctccggg ccgcccggct cctgctcccc gaactggttg    31440
caggggaagc ccaggaccga aagccgcgc gggccgtacc ggcggtgcag ctcctccagg    31500
gcggcgtact ggcgggtccg gccgcactgc gaggcgacgt tgaccacgag cagcgccttc    31560
ccccggtagc gggagaggtc gtgggggctcg ccggcgagcg tgcggacggg aatgtcgtac   31620
agggacatgc tggtgttccg ctcctgtcgg gtcggtggcg ggcggccgg aagccccgga    31680
cggcgcgcg gaacgccgt ccggggacgg ctgccggaag gtgacgaggg ctggtggtgg     31740
aggggcggga gagcgggacg gggccggccg cggggacgcg cgaggcggcc gtacggcggc    31800
tcgggggagc gccgtacggc cgcgcccggc ggggcgtccg cggctcagcc ggcggcgtcc    31860
gcccaggcca gcggagggt ggcgacgatg gtgtccacgt cctcgtcggt catcgcggcg     31920
cccagcccga cggtgaccga gcggcccagg tagccctcgc tggcccggaa ccgcggcggg    31980
```

```
cgctcccagg ccacgcccca gggggtgcgt ccctcccgca ccgcgcggtt ggaggtgacg    32040
gtctgcccct ggtacatggt gtgcgccggg atgccggcgg cggtgagggc gccgaccacg    32100
cggcgggcct ccagccggga ctcggtgaag aaggtgaggt cgccgccgga gccctcctcg    32160
tcgggcagcc gccgccactg gaggggcagc ccggcggtct cggcgcgcac ctggcgggcc    32220
acgtcgcgca ccgcttgca cagcggcacc agccggggca gctgcaccga gaggatggcc    32280
gcggtcagtt cggtcatccg caggttggcg ccgatgaacg gcgggtggtc ggcggtgccc    32340
cgggtggcgc ccttggaggt ggtgaactgg ccgccctggt cctggtagcg ggccacccgg    32400
tcgtagacgt cggcgtcggt gacggtgacc gcgccgccct cgccggcggt gatgttcttg    32460
tcgagctgga agctgaacgc cccggcgtcg ccgatgccgc ccaccggccg gccgcggtag    32520
gacaccccgg cggcctgggc ggcgtcctcg atcacccgca ggccgtgccg gcgcgccacc    32580
tccaggatcg ggtccatgtc ggcggccacg ttggccaggt ggaccggcat cacgccccag    32640
gtgcgctcgg tgaccagctc ctccagcttc gccgggtcca gggtgagggt gtcgtccacc    32700
tcggcgaaga ccggcacgcc gcgggcggcg acgaccgcgc cgacgctggc cacgaaggtc    32760
accgcgggca cgatgacctc ggccccctcg gggatgccca ggccaccat ggcggcggtg    32820 agcgcggccg tcccggagga ccgcgacg tgtgcggga ccccggccag ctcggcgaag    32880
gcgcgctcga aggcgtcggt gcggtggccc aggtccggcc cgtagtaccg gaacagcgag    32940
cgggacctga cgacctccag cgccgcggcg gcctcctcct cccccacag tgccagggcc    33000 cgccagggct cgtaccgcat cccgggctcg gtggtcactc ggtctcctcc gtctccgtcg    33060
ccgtgtcgag atcggtcacg ctgtggccca ccaggaagtc ctccaggaag aggtagtcga    33120
gctggctcgg cccgaagaag gcgagcgcct gctcggcggt ctccacgatc ggctcgcccc    33180
ggtcgttgaa ggaggtgttg agcaccacgg gtacgccggt gagctcgccg aaccgttcca    33240
ccagttcgta gaagggcccg ttcgcctccg gggtgagcgt ctgcacccgc gcggtgccgt    33300
cgacgtgggt gatcgccggg acctcctcgc gcttgtcctc ccggaccggc gcgacgatca    33360
gcatgaacgg cgactcggtg tcgaggtcga agtactcggc ggcccggtgg gccggcaccg    33420
ccggggcgaa cggccggaac cactcgcggt gcttgacctt gctgttgagg atgtccttca    33480
tctccgcgcg gcgcgggtcg gccaggatgc tgcggtgccc cagcgcccgg ggcccgaact    33540
ccgagccgcc ggtgtaccag ccgatgagct tgcccttggg cagcagttcg gcggcgagcc    33600
gggcggggtt ctccacccgc cggtagggca gcccggaggc gtccagcgcg gcctggatcc    33660
gctcggtggg gtagctgcgg ccgaggtagg tgtggatctg cggccgggag ccggggccgg    33720
acgccgccgg gccgcgggtc cggggccgct cgccgagcac gtggtagccg tagtacgcgc    33780
agccgaccgc gcagccgttg tcgcccgccg cgggctgggc gaagacctcg gtgaacgggg    33840
tctcacggag gatcttgccg ttggcgaccg agttgagcac caccccgccg gccaggcaga    33900
gccgggacag cccggtctcc gcgtgcagcc agcgggcggc gtgcagcacc gcggtctcca    33960
gcaggtcctg gcggcccag gccaggtcgg cgccgcgggc gaagcgctcc tcgcccctcca   34020 gcccgtccag cgcgtgctcc acgaaggcga gcagcccgcc gtccttgagg tgcagcgcga    34080
accggccctc cggcagcagc tccaggtgcc gccggaactc ctcccggtag cggtcggtgc    34140
cgtagggcgc caggcccatc gtcttgccgt cctcggtcag gtaccagctg ccctcctcgt    34200
agagggtgaa gccgacggcg cggctgaccg ccttgtacat gaagcccagc gagtggtcgc    34260
tgtcgccggc ctggtagacc cggtccgacc gcaggccgtc ggtgctccag ttggtcccgt    34320
```

```
acaccttgga gatctcgtcg atctccacgc cgtggcccac cgacagggtc atcgtctcga   34380
tgccccggcc ctcgaagagg ctgccggcgc cgtccaccac gagcaccgcg gcctcgtcgt   34440
acggcgaggg gtagaaggcg ctcgccgcgt gggccatgtg gtgcctgatc agcgtggtgc   34500
ggctgcggaa cggaagtag caactgggca gcagggtgtc gtccgcgacg atcgcttcca   34560
cgtcggcgag ccgtaccccg cgcgtttcca ggcagtaccg ccagccctga ttggccagcg   34620
agttcacatt gactgcgtac ttgcggcgag ccaggcgctc ttcctcgata ccgacagcga   34680
tttcgccgtt ttcgacaaga caggccgaaa agtcatggtt cgaaccgccg agacccagag   34740
ccagcataca gccgtcctaa ctaccggttc agacatgcct attcgatgac tacgtcttgt   34800
cacgctacag cgtcccgacc gatcggccta caggcgaata cgcgccatcc tccactcaga   34860
tcgagacgcc ttgtacggac cacgatcac ctcttgtgag aggcattgac ctcttatcca   34920
gggaaaactt agactcgttc gccaacggca gagtcatgcg caaaaacaac ctgaatgcgg   34980
tgatcgggcg tggcgctgaa gagccaattt cgagaggcga tgttcgcaca tcgcgacgga   35040
cagaaccgcc tcaaactcct gatgaacgac atggtcatcg aggagcagtt gtgccagatg   35100
cgctgctcct actgcctcac cgaggacttc aacctcctca tgaacgtccc ggacgcccgg   35160
ctgcggctga ccaccgaccg gcgggcggac tggcacgaga tactcgacgc ctaccaccgc   35220
accgtggaca gccccatcat gcggctgagc ggcggtgagt tcttctggct gaagggctcc   35280
accgagttcg tcgaggagtg cagtgccaag tacgaggtgg tgcaggtcat caccaacggg   35340
gtcttcctga ccccgccgcg gctggaggcg ctggccgcgc tcggcaacgt ccagctctgc   35400
ctgtcgctgg acgccacac gctggagatg aacgggcacc ggttcccgcc caagcagcac   35460
cggctgttcg acgtcatcat gggccacctg gaccacgcgg tggagctggg catcccgatc   35520
gagatccagt cggtgctcag tgacctgaac gtcacccggc aggcggactt cgccgagttc   35580
ctgctggaac ggtacggcag cggcgtgatg ctgtacttct tcccggtccg cggcgagacc   35640
cgcaccaccc acgcgccggc gctcggcgat cacttcgccg agctgctgga acgctacgac   35700
gagctgtcgg ccgtgctgcc gccgcgcgcc ttcgtggcgc acatcgcgaa ccagctgagc   35760
accggggtcc gtacgctgcg ctgctacgcg acggccacca tggtgcagct tttcggccag   35820
ggcgacgtct cctgctgccc ctatgcctgg ctcaagccca tggggaatat caagaacgag   35880
cccgagctga ttcacgagca gttcggcaag caccagcact acgaaatgtt catgcagccg   35940
cggccccgct tcccgtactg caagagctgc accgggccga tcgacgtggt gaatctctac   36000
ctgttcggcg gcatcaccga ggaagaaatc gcgcgctgtg cgccgtacgc cgggccccgg   36060
gcgctggagc gtctgcggga gctgaagtcg gcattcgacc cgatgttcca ggcggccgaa   36120
tgatctctgc ccggcccgcg gcggcggcat gtcagaagca gtgcatccga ggcgtcgagg   36180
agacgtgaat gatatccgtg gacgggattt cggccgacga tttcgcgggt gccggactga   36240
gcaggctgct caggctgccg cagcacgacc tgctcaccct cgccggtgac tggctcggcg   36300
aactggcgcc ctggcggaac accgagaccc tggcggcgat ctccaccacg ctgtccgccg   36360
aggcccagtt ggccgccctg ttcatcttcg gcgagccggt cgccgaggcc gaggcccgcg   36420
accggctccc cggcccgctg ctcgacctgc tgctgcgcac cggggcgctg gccgcggact   36480
ccgggaagct gtcggcccgg tactgcctgg tccgaggcga cgggatgtcg ctgctcgccg   36540
cgtggcgggc ggcggccgc gacgtgggcg gctacgcgcc gtgggtcggc accgactcca   36600
tgacgctctc ccggctggtc gccgcccgcc gggacgtgcg caccgcgctg gacctggggt   36660
gcggcaccgg catcctgggc ctgtcggcgg cccgcaacgg ggccgacgtg gtgtcggtgg   36720
```

```
acgtcaaccc cgagtgcacc gccgccgcca cggtcaacgc ccacatcaac ggactgggcg    36780
agcggctcac cgcggtcgag ggcgacatca tgtccctgga cctggaccgc cggttcgacc    36840
tggtgatctc caacccgccc tgcctgccgc tgcgccgcgg gtcgctgggc tggctggccg    36900
gcgaggcggg gctggacggg ctggagttct tctgggagct gctgcgccgg gtgcccgggc    36960
tgctgaccgg cgagggtgag gcgctgctgc aggccgccgc ctacggtgac gagcgcggcc    37020
cgttcttcgt cgaggagctg gaggcggagc tgcggcggct gaaggtgtcc gggcggctgc    37080
tgctgcgccc ctccacgccg ccgcgctggc cggccttcgc gccccgcgac gaggaggggc    37140
agctgaccgg tccgctcggc gacgaggtcc gcgagtacgt caaccggatc ggtgccacgg    37200
actactacgg gttcgtgctc tccgtgcggg ccggtgaggg cctggacgtc ggccggttca    37260
gctgatcacc cgggggtccg gcagccagcc gggcccaga tcggcgaact cggcggcggc    37320
gaccgcgtcg gtcgccgccg ccagcgtcag ctcggtggtg tcgatgagcc ggatgccggg    37380
cacgccgggc acctcctcgt cgaggtggcg ctcggcgagc cggccctcga cgaagtgctc    37440
gccgccggga tcgccgctga tccgggcggc gagcgcctcc ggggcggcgc gcaggccgta    37500
gtagaccggg tcgcgccca ggtcggcgaa gacccgtgg aggggctcgt aggcgcggcc    37560
ggccaggacc actccgctga gcaccaccac ccgggcgccc cagtcccggt agaccgggag    37620
ggacgcccgg accgtcgcgg ccatcagggc gtacaggctc tcgttgccgt cccacgggta    37680
gacgaccggg tcgcagtcca ccgcggcggc cggcacgccg taccgggcca ccagctggtg    37740
ccccaggcgg gtcttgccca cgcccgggc accggtgatc accaccacgc gcatcagcgg    37800
gcgtcctgtc gcaccgtgcc gaccagccgg aagcccaggt gcgggatctt cagcagcttc    37860
gcgccggagt cgatgtccag cagcttctgc ttgagcaccg acgtgacccg gctgacgtcc    37920
tcgccgccgg tcgcctcggt gaggtcctcg cgggagacga tctggcccgg gcgggcggcc    37980
agcatccgca gcaagcccgc ctcggcgtcg gtgaccggcg tggacttcga cggcgagtgc    38040
agcgatccgg ccccgtccag ggtgagcacc tgggtgttct ccggcggggt gatgtgcttg    38100
aggtaggtga gggtctccac cagcctcggc cggcgcagcg ggctggccag ggtgaagctg    38160
tagccgttcg tgaccgccgc gagcacgcg ccggcggcta tgccgtccag caccgcgacg    38220
gcgtagccgc cgatctcctt cagctcctgg gccgtcggac cgccggccgg gtcggccccg    38280
acccggtgga aggagaccag cagggcgtcg gacgggtccg ggggagcgga cccgggctcc    38340
gagtggtgca gggtcagccc cacttcggcg caggcgtcgg ccaggattgc gaggtcctcg    38400
ggggtcaggg actgggccag tacgtacacg gggaaccccct tcacacaggc ggcggggccg    38460
cgggtgggtg tcgtcggtcg ggcgggtcgg ccggccgccc cggtggggcc gcccgccggg    38520
ccggggtcgg ccggccggtt cctggtcggc cgaccggtgc gacgggccgg ccgtggttc    38580 ggcggggtc gggtggtcc ggcgggttcg gcggggcggt cagccgcgga ccgccagag    38640 gcgttcggcg gccggcgagc cggactgcga ggactgcgac gccaggtgca tgtcatgccg    38700
gccgatgcgg tggatgatgc cccggcggac ctggatgcgg taggccttca gcgcctcgcg    38760
cttggcgagc gccgcggtgc cgtccaccgg ccgcagttcc gggtcgagcg ggccgagtcc    38820
ggccagctcc agccagggtc cgagccggcg cgcggtctcc tcggcggagg agaacagcga    38880
gtacggctgg tcctcgtaga agcgcagccg gcccgggtcg atccggccgg tccgggccag    38940
cgccaccacc gcgtcccggc aggccaggtg tccacgtgg ccgcccacgc ccagcggggc    39000
gtagaccggg gcggtgcccg ccagcagcgg ggcgagccgt tcggtgaccg cctcgaacag    39060
```

```
ctccggctcc tcccgggcga acccgtccga ccagggcttg tcggcgaaga agcggtcccg    39120
tctcagctcc cggtcggcgg cgtcggtgaa gcccagcagc tccacctcgg cgcccagcac    39180
ccgggcggcg acggtctcct cggccagcag caggcgccgg gtctgcgccg gccgctcggc    39240
gtagtagggg tccttggtcc aggtctcctc gctgaacacg tcgaggaacc ggccgccttc    39300
gcgggccacc gtgccgccca cggccagcgc ccgcgtcgtc ggtgcgggg agacgatcac     39360 gggcgtgccg gggatcgcgg gtccgccgga cggatccggg gtcccggggg ccgcggtggc    39420
acccggtccc ccggacgcct ccggggtctc cggcgttccc gccggccggg gcggctccgg    39480
ggcctccggc gcggccgccg tcccgggcgc gcgcggggcg ggcgcgggcg ccatcaccac    39540
caccccgtcc cgcagccagc cgtcgaggac cgcgcggtcc gccgcgggga aggccgtgag    39600
cgggcgggcg ccgtcgcagc gggccagcag cccggcgtcc tcgccggccg tccgcccgga    39660
gccggtgatc cggcgcccca tgaagaggat ctccccgtcg gccgtttcca cgtgcggcag    39720
cgcgatcggg caccaggtgt caggaatttc cgtcatgtaa ctccgagccc gagcgatgag    39780
gaataacaga cgtaatacgg ccgcactgta ccgattgccg gagcgttgcc acaggggccg    39840
atccagagcc gatccagaaa ggcagaaacc gtgggacggg tggccgaaaa cctgtcggtg    39900
cgccctgcac gggagtcggt cgactgatca ttcggaccga ggggttccgg ccaaacatgg    39960
tggccggtcg ggcttgccc agatcgtttc cggaggccac cgccacccgt cccgacgccc      40020
gctgcgcccc gtgaacacg cacttcagaa gcggtccggc ggaacctgcg caagatcgtt     40080
tcaccggccg tccggccacc ccccgcggcc ggtaatgcgc atggccgaac atatgcggaa    40140
gaagtaaacc ggccatgcct tcacggctgt ttcggtggcc ccattgcgtg ggagatcttc    40200
tcctgtagcc tcagaaggcg acctggcctg tcggctcgaa tcaggggcg aagcaggaat     40260 gaagacccgc gtactactag tacagcaagg cgtctgggga aattccgtag cttcgatgcc    40320
gctggcgatc ggataccctca aagcctatgc cgacgccgat gaacgcatcc ggcgacgcat    40380
ggacatctcg atccgcaact accccggcga cgccggcctc aacgccatgg gccgggacct    40440
catccgggac ggggtgcccg acgtcctgtg cttctccgtg ctgggctgga acttccgcgc    40500
cttcggcacc ctcgccgaga cgttcaagca ggtcaacccg gacggctggg tcatcttcgg    40560
cggcaaccac gtggcccacc aggcggagcg cgtcttccgg atgttcccgc aggtggacgt    40620
ggtggtgaac ggcgagggcg agctggtctt ccgggacctg atgaacggct acctggacgt    40680
cgcccgcccc accgcgctgc acgagatcag cggcgtgtcc ttccgcgagg cggacggcaa    40740
cctggtcacc acgcccgaac gcgagcgcat tcaggacctg gagatcctgc cgtcgcccat    40800
tctcaccggc gcgatcccgc tcgccgacag ccaggggcgt ttcctctacg actacgccat    40860
catggagacc aaccgcggct gccccctacaa gtgcgccttc tgttattggg gcggcgccac    40920
cgggcagaag atgcgcgcct tctccaggga acggctccgc gaggaactcg acgttctcgg    40980
ccggcacggt gcggaaatcc tcatgctcgc cgactccaac ttcggactcc tgcgccagga    41040
cgaggaattc ctcgaagacc tcctccgggt gcgtgccaag tacggctacc cgaaccggct    41100
cgaaacctcc tgggccaaga acaaatcggc cggcttctac cgcatcatgg agaagatgaa    41160
ggagtccggg atgcacagcg ccttcattct ggcgctgcag accatggacg aatccgtact    41220
ggacctgatg cgccggcgga acatgaagct gaacgactgg gagagcctgg tcggctggct    41280
gaccgatcac gggatcaccc cttatctgga actcatctgg ggcgccccg gggagaccgt    41340 ggagtccttc ctgacggtt atgacccggg cgcgcggcac acccgttca tcgccgtcca     41400 cccgctgatg ctgctgccca acaccgagta ccacgacaag cggcaggtgc acggcctggt    41460
```

```
gaccgtgcgc ggcgaacagg acgacttcga ctacgtcctc gcgcaccgga ccatgacgct    41520
cgacgacaac gagcgcatgc tccggttcat ctgctggaac cgggtgctcg cccggagcct    41580
gtggctgcac aacatctggg tcgcgctgcg cgagctcgcc gacgtgccgc agtcccgggt    41640
catcctcagc ttctccgact gggtggagag cagcgacgat cccgacgcca gggagctgca    41700
cgcgctcgcc cggcccacca gctccgccag cgagcaggtc gacccgcacg tctggcggct    41760
gctcaccaaa cggctgctgc gcaagtggtg ggacgaggcg atgcgcccgg acctgcccga    41820
ggcgctgctg ccgctgctgg acgaggtgtt ccgctacgac ctgatgtgcc agccggtgcg    41880
gatgctgccc gacggctccg gtcccgagga ggacctgccg gtcgtcgaga agtacgcag    41940 cgagtggtac atgcgggaca aggtcacctt cacccacccc gtccccgagc tgatcgccgc    42000
cctgcggcgc ggggagacgg tgagcaccga accgcggtgc cacgcggtca ccttctacta    42060
ccgcacgcag ttcggcggcg acctccagca ctacttccgg atggaccgct tccgggggct    42120
gaccgccgag cagctcgacc accagttcac gcgcgtttga cgacatcctt cacaccggga    42180
gagacgacac gatggaccgc gccgggctca tacgagaact gcacgagatc gcagccggga    42240
tgaccaagtc ggaccagcac cggcaggtgc ccgcggaagg ggcgggcgac gccagcctgg    42300
tggaccagta cgggttcagc tccctggacg cgctggagta cctgctgatc ctggaggaga    42360
agttcgacgt cgtcttcgag gacgaggacc tcaccgagga gacgcgtgttc tccatcgagg    42420 gcctcgccac gtacatcctc gatcagaagg tcggcgaaac cacctcctct tcgtgacgaa    42480
gatggaagcg acgcccgccc ggccgggggg aggtcccggc gacatctcgg tgagcgtggt    42540
cgtaccgacc cgggaccgga ccacgcgtct gctgctcacc ctggcggcgc tggcccacca    42600
gaccctggac cgcgaccggt tcgaggtcat cctggtcgac gacgcgcccg aacgcggggc    42660
ggtggaccgg gtgctggccg cggcccccgg gacaccgccg ctgcggcacg cccgcaccgg    42720
cggccggggg cccgcccgcg cccggaacgc cggcgcggag ctggcccgcg ggagctgct    42780 gctcttcctc gacgacgaca ccgtggccac ccccgaactg ctcaccgcgc acctggcggc    42840
gcaccgcgac gccccgggca ccgtggtgca cggcaccatc accgatctgt cggcgttcgc    42900 gctgacccc gatccgccgg ccccgcgcc ggcgctgacc ggtgcccgcg ccgcagcat    42960 cgacgcccgc cgggtggccc ggctgcgcga ggacgcccag ctgctcgggc gcgccggtc    43020 gttcatcgag cggaccgccg ccaaggtcat ccgcgacccg gcgctggccg gcctgcgctg    43080
gctggcgtgc atcggcacca gcaccagtgt gcggcgggcc gacttcgagc gggccggcgg    43140
cttcgacgag ggcttcgggg agctgtgggg cggcgaggac ctggagctgg ggctgcggct    43200
gcacgccgcc ggggcccgct tcgcgctgct ggacacggtc gcgtaccacc tgcccaccgc    43260
ccgccgggac accggcgaac tgctgccccg gttctggcgc ctggcggccg aacggcacg    43320 cgatccgcgg ctggccgacg tcggcacctt cctcgccggc cggctctccc cggaggaact    43380 ggccgccgg ctcggcaccc gcaccgcggc cctctccccg ggagggccg caccatgacc    43440 gcaccccggg ccggcacggt ggtggtgggc ggcaccgccg ccgagcggct ggccgaactg    43500
cgctcccgcc cggacctggc cgtcaccgcc cccgcccagt cgctcgccac cgccttcacc    43560
ggggtgctca ccgcggcgct cgccgggctg cccgccggtc accggcggca ggcgccggtg    43620
gtcatggccg ccaccgacta cgcggtggcg gccacctccg gttacgtcgc ccgctgcgcc    43680
gaggccgagg cggcggccg ccggctcgcg ccgtcggagg cgatgacccc ggagccggcc    43740
cagctcctcc aggagctggc cgaacgcacc gactggcagg gccccggcca tgtgctcatc    43800
```

```
tcccccggt cggcgacctg gcaggcggtc cgctgggcgt tcggcgcggt ctcggccggc   43860
ctgcacccgg cgatggtggt ctgcgaggtg ccccgcgacc cggcgggcgg cggctaccgg   43920
gtggcggccg tgccggtcac cgcaccgggc ccgcacgccg acccgcccac cggaccggtg   43980
gtgatctccg gcaccggcct ggtcaccgcg ttcggcgacg gcgccgacac cttctggcgg   44040
aacctgctcg ccggccgccg gggcacgggc gagctgaccc gcttcgacgc cggccgcttc   44100
cgcagccgca ccgtgtgcca gaccacggtg gctgccgcgc ccggccggcc ggtgcggcgc   44160
gccctggtgg accgcgcccg cgccgaggcg ctcgccgagg ccgggctggg ccggctgccg   44220
gagcgcaccc tgctggtgta cgccggggtg gtgccgcacc tgccggcggt cgccggcgcg   44280
cccggggtcg gggagatcgc cctggaaccg gagtgggacg gcgacggctt cggggccgcc   44340
cccggggacc gggtgctgat ggcgcacgcc tgcgcctcgg gtgccttcgg gctcgccatg   44400
gcccgcgaat ggctgctgtg cggcctcgcc gacaccgcgg tgatcgtggg cgtgtcggcc   44460
ctcaacacct acgactacgc ctgcctggac gtgctccgcg ccaccaccac cggcatcgcc   44520
cgccccttcg acgaggaccg ctccggcgtg accgtcgggg agggcgcggg ggtgatcgtg   44580
ctggagaccg ccgcccgcgc ggcggcccgc ggccaccgcc cgccggccgt gctcgccggc   44640
atctcctgcc gggtggccgg ccagggcgtc agcgcgctga gcaccgggt cggggcggtg   44700
tgcatgcgcg aggcgctggc gatggcgggc ctgcggaccg tggactacgt gcacggtcac   44760
gcccccggca cccgccaggg cgacgaggcc gagctgcggg cgctggacca ggtcggcgcc   44820
gagctgggct ggcgggacgt gccggtcagc tcctgcaagg gggcctccgg ccacctgctg   44880
cacgcctcgg tgttccccgc cgtggtcacg gcggtccggg cgctgcggga cggggtgctc   44940
ccgggcaccc ccggtctgcg gacgcccctg ggtgcgcggc acgtccgcgt actgcgcgac   45000
gcggagtccc gcgaggggct gagctccgtg ctggtggaca acttcggttt cggcggcaac   45060
aacgccgcgt tcctgctcac cggggacgcg gccgggcacc tggagtggag tgcacatggc   45120
tgacgcggtg ctgctgacgc cacgggagat cctcaccggg ttctccagcg tcaacaacca   45180
gaacgttctc atcaacgacg aggaatacct ccggctggat cccgcgatgc gcctgttcta   45240
cgagaaggtg cgggagaacc tgggggtggc gtgcatcgcc ggtcatctgc gggcgtgcgg   45300
gtactcggta cgggcgttga atctgcacgg gcgcaacccc agcgacgagg cgatcacgga   45360
tctgatccgc cgcgagcggc cgaagttcgt gggcatcagc atcatgtacg acctgcacat   45420
cgtggacgcg gtgcggctgc tgcgctgcgt gcgcaaggcc gacccgtcgg tgttcgtggc   45480
gatcggcggg gcgttctgca cgtacaacgc caaactgatc gccgagcgca tcccggaggc   45540
ggactgcgtg gccttcggcg agggcgagct gaccgtcgag gggctgatgg agtgcctggc   45600
cgccggccgc gactggcggt cggtgccggg cgtgtggttc tggcaggaag acgggtgcg   45660
cagcagcggc ccgccgaagc tgccggacct gcacaagcag gcctggcccg cccgcgacct   45720
gctcgtccac caccgcgggg ccggcatccc cacccggtg gcgtccacgt acaccagccg   45780
cggctgccac gccaagtgca ccttctgcta cgtgccgcgg gccccggcg tcaccgccgg   45840
caacgcctgg cgggtgcggt cgcccgtcga cgtggtggac gagatcgagt tcctccagcg   45900
ggagttcggc acccggttcc tgtggttcaa cgacgacaac ttcggcggcg ccttccagga   45960
cggctacaac cacgccgtgg gcttcgccga ggagatcctg cgccgtgatc tgaagatctc   46020
cttccactgc gagttccggg tggacaccgg gctgatcgac cgggaggcgc tgcgcaccct   46080
gcgccggggc ggcatggcct cggcgctgct gggcatggag accggctccc cggcgatggc   46140
caaacggttc cgcaagggca ccctggtcga gtacaacttc gacgccgcgc ggatgttccg   46200
```

```
ccaggagaac atcgagctgg aacccggctg gatcatggtc gagcccggca ccaccgtgga   46260
cgacctgtgg gagaacctga agttcatcgt ggcggccgac atcgccgtca gcgagaaccc   46320
gttctccttc atcagccggg ccatcgcgct gcgcggcacc gagatgtacg acaagatcac   46380
cgatccggcg ccgccggacc tggcggaggt cgagggcccc gcgcgggagg tgctgagcga   46440
ggcgcgccgg gagtaccgga tcgccgacgg ccgggtcgag gacgtgtggg acgcctgggc   46500
cagggtgagc gccgaggtca gcgaccgcaa ggaggagctg cccttcgtcg cccagatcat   46560
cgtggacgcc acccgggccc gccgctccca gggcgagcag ggcctgcgtc cgcgtctgag   46620
ccggctgcgg cgctgggtcg aggacctgcc gcacctgctg atcgccttcc tcaacgtcgg   46680
actgctgctc gcggacgaga acccgccggg tctcgccggc cggctggaga ccgaactgcg   46740
cgcgctggtc gatgcctacg accgcgagca cctgggctc acctaccgg acttcgtggc   46800 ggagaccgag cgtttgtgcg gagcacgggc cctggccgga tgaggccgcc ggcgcccccg   46860
gcgcgcatgt gacgaggaga gaggagaccg gccatgtcgg acgtggtcct gctgacaccc   46920
cgggaaatac ccaccggcgc cgcgagcctg aacaaccaga acgtgctcat caacgacgag   46980
gagtacctgt cgctggaccc ggcgatgcgc ctgttctaca gcgcgtccg ggagaacctg   47040 ggggtggcct gcatcgccgg ccacctgcgc gggtgcgggt actcggtgcg ggcgctcaac   47100
ctgcacgggc gcaaccccag cgacgaggtc atcaccgacc tgatccgcca cgagcggccg   47160
aagttcgtgg gcatcagcat catgtacgac ctgcacatcg tggacgcggt gcggctgctg   47220
cgctgtgtcc gggccgccga tccgtcggtg ttcgtggcga tcggcggggc gttctgcacc   47280
tacaacggca agctgatcgc cgagcgcatc ccggaggcgg actgcgtggc cttcggcgag   47340
ggcgagctga ccgtcgaggg gctgatggag tgcctggccg ccggccgcga ctggcggtcg   47400
gtgccggggc tgtggttctg gcaggacgga cgggtgcgca gcggccc gccgaagctg   47460 ccggacctgt ccaagcaggc ctggcccgcc cgtgacgtcc tgatccacca ccgcgaggcg   47520
ggcatcccca ccccgcgcgc ctcgacgtac accagccgcg gctgccacgc gaagtgcacc   47580
ttctgctacg cgccgcgcca gcccggggtg gagaacgggc cctggcgggt gcggcccatc   47640
ggggacgcgg tggacgagat cgagtacctg cagcgggagt tcggcacccg gttcctgtgg   47700
ttcaacgacg acaacttcgg cggcgccttc caggacggct accaccacgc cgtcgggttc   47760
gccgaggaga tcctgcgccg cggcctgaag atcaacttcc actgcgagtt ccgggtggac   47820
accgggctga tcgaccggga ggcgctgcgc accctgcgcc gggccggcat ggacctggcg   47880
ctgctgggca tggagaccgg ctccccgggg atgatgaagc gcttccgcaa gggcaccacg   47940
gtcgcctaca acttcgacgc cgcccggctg ttcaaggagg agggcatcga gctggagccc   48000
ggctggatca tgatcgagcc cggcaccacc ctcgacgagc tgtgggagaa cctgaagttc   48060
atcgtcaccg cccgggtgca cgagagcgag aacccgttct tcctgatcaa ccgggccatc   48120
gcactgcggg gcacggagat ctacgacaag gccaccgt acgaggagcc ggacatcccc   48180
ggcgtcgagg gccccgcctg ggaggtgctg cggcacgccc gccgcgacta ccgggtcgag   48240
gacgaccggg tggagcacct gtggacggcg tggagccggg tctcctcgga gatcaacgac   48300
cgcaaggaga acgaggtccc gttcctcgcc cagagcatcg cggacgcggt gcgcgcccgc   48360 ccggcaccg gcgccgagtc gctgcgcccg ctgctgggcc ggctgcgcag ctgggaccag   48420
ggcctggacg cgctgctgat cgccttcctc aacgtcgggc tgctgctggc ggacgagaac   48480
ccgccggagc tggccgaccg gctggaggcc cagctgcgcg acatgatcaa cgcctacgac   48540
```

```
cgggagcacc tgggccacac cttcccggac ttcgtggccg agaccgcgcg ggcgtgcggt    48600
gagcacgcca tggcacaggt gaggggctga tccatgaccc gcgagaagcc gatccggttc    48660
gccgcggtgg gggccgggcg ggtgttccag cgctaccacc tgccctgcgt cgacgcccgg    48720
gacgacgtgg aactggtggg gctggtggac gccgacgcgg accggcggc gtccgtcgcg    48780 gccggccggc cgggggtgtg gaccggcacc gacgtcgcgc ggctgatccg cgaggcccgg    48840
ccggacgcgc tcagcgtctg cacccccaac gacgcccacg ccgcgccggt gctggccgcg    48900
ctggacgccg gtatcccggt gctctgcgag aaaccctgg ccgccacggt ggacgaggcg    48960
cggcggatgg ccgagcaccc ggccgcgcg gagctgctgg cggtgaacat gccgttccgc    49020
tgccactcgc tgaccgcgcc gttcgccgag gcggccggca agggcgcgca gcgggtggag    49080
gtctccttcg tcaccccgg caaccgggtg tggcgggcct gcaccccctg gtacggcgac    49140
gcccggcggg ccggcggcgg cgccctgctg gacctcggtc cgcacgccat cgacctgctg    49200
atgaccgtct tcggccatcc ggacgtcgag gcgtgcacgg tgaacgccga ggggtggag    49260 gaacaggccg agctccaact gtccttccag ggcctgccgg ccacgatccg gatcgaccgg    49320
gccgcccgcc ggatggagac cgcggtgacc gtcaccacgg ccgacggcgc gcacgtgctg    49380
gacctgcggc gcaacgagct gcggctcgcc gacggcaccg tccggcaggg cgccgaccgc    49440
ccggaactcg ccgcgatctc cgcgttcttc gacgcggtga ccggcgcggc gaccggcgcg    49500
gcgggggccg ctggggacgg cccggcggct ggcggtgcgg ccggcacgtc cggagcggat    49560
gcggccggtg cgggcgcgac cggtgtgacc ggggcgggg cggtgggcgc ccgggaggcg    49620
ctcgcggtcc agctcgtcgt ggacgaggcc taccgccgcg ccccggggcgc ggccccggcc    49680 gtgacctgac gcggcgggcg gcgcggcggt ccggcgtcgc cgggccgcag gccgggtggc    49740
gtgggcgctc gccacccccc cggggcggc gcctgacgcc gggtgtcccg ctcggcgtcg    49800
caggcgctac gccctggccc gcggagccag caattcgggg tggacctgct cgtgccgtgg    49860
ccggcgccgg cccggcgggc gatttcgggg agcggaaggc cgtctcaccc catcccggcc    49920
caggcgcacc cggaggtcaa cgggtcggcg cacgccgggg cttccgcggt accgggggcc    49980
ggccgcacgg gccggacggt cagctcagga accgtacgac ctcggcgcag aaccgttccg    50040
gctcggtacg gtgcacatag tgcccggcgt cgatggccag cagccggccg tgcgggaccc    50100
ggccggcgac ctcggccagc agcgaccggg gcaccgggct ggagaggccg ccgctgatca    50160
ccagcgtctc ggcggtgacc tccgccagcc gccgccacca gccggggtcg gcccgccgca    50220
gctcgtcgat gatcggccgt accgcggcgc tgtccagccc gccggaccgg cgcaggtcgc    50280
ggaactcctg gtagagcgag atgaccgggg cccggtcgtc ctcccgcgcc gaccgcaggc    50340
gcatctcctc ctcggccgcc gcgtcccggg cggcggggg cgtgtcctcg atcaccagcc    50400
ggcgcacccg ggcgggctgc cgctgggcga tcagccagcc gatgtgcccg cccatcgagt    50460
gccccaccag gtccacggtg tccagccggt accggtcgag cagggcgacg acgtcccggt    50520
acatcagctc gaaggtgtag cgctcggacc ggggctggc gccgtgtccg cgcagatccg    50580
gtacgtagag ccgacggccc agcggggcca gcgcggtgat cagcggggcc cagtcccggc    50640
cggtgttgcc gagggcgtgc agcagcacca ccggcttccc gtccggctcg ccggtgaccc    50700
ggcaactcag cggcagcggc ggcccttccg ccggaccgct ccatctgttc gactggtccc    50760
ggtcgcgcag cacgccgcga tggtatccgc ccaccacccc tctcagacat accgcgtccg    50820 gccccctcggg tccccgggc cgcgcggtcg ggaggccccg tgaccgtgag ccggaggtcg    50880
ccgtgatcct cttcgccacc gcggccgtcg ccgcgccgta cgggccccgg gagcagcacc    50940
```

```
tggccggccg tgcggcggcg gccgacgcgc tgcgccgggc cggcagcacc cggctgacgg    51000
tgggccggcc gggtgacggg gcgccgtgct tcccgcccgg tttcaccggc tccatcaccc    51060
acacccggcg gctggccgtg gcggtggtgt gccgggccgg ggaggtgcgg gggatcgggg    51120
tggacctgga gaccgacccg gtgcccggcc gcctgcaccg catcctgctc ggcgaggagg    51180
agcgcgcggc gctgtggacg cccgccgacg agaccaccct gcgcggcctc ttcgtcgcca    51240
aggaggcggc gttcaaggcg ttctcggcgg gcggggagcg ggcgacgcgg atgttctggc    51300
ggatccggct ggagcggccg gacccggggc cggagcctcc cggcgccgtg tgcggtacgt    51360 cggaccggc gtccggcgcg tcgccgtccc gcggggcgtc caccggttcc gggacgtggc    51420
tggtggcccg cgccggccgg gagcgggccc gggtccgggt ccggaccggc gcgaactgg    51480 cctgggcggt ggccgtcctg ccggcccgg ctccatgact tgccggcccc cgggccgccg    51540
tccgccaccg acgcccccgg cggcggttcg gccgagcctt tcggtgactc cgccggacct    51600
cccggtgact ccgccggacc ggcccggtga cccggccggc cggcgtggt gacccgggcgg    51660 tgcgtgtcac cggcccgggg tgagggccg tccaccgctc cctcggtacc ccgggtggcg    51720
gagacgactg gggacggcgg tccgggcccg atcgccgat gacgcctccg gccgtgccgt    51780
cggggcaacc cgcgaccctg cagtggtggg ttccgcgggg ccggcgcggg aagcgggtcg    51840
cccaagcggg ccgacggaac gtgcgggccg ccgcatgcgt gccgctgggg cgggccggcg    51900
gaacgcgcgg ggccgccgaa cgcgcgggcc acgcgggctg gttgacgccg gcagccggac    51960
gggccgcgcc ggaccggtca ccccgggccc cggcccggg caggccgctc cggcccggcc    52020
ccggcccctg accgggaacg ccctgccccc ggccggacag gggcgggtgc ccggcccggg    52080 caggtgggc ccggtccggc ggtgcgaggt ccgggcccgg cctgcctccg tcgagcgggt    52140
ccggacgggg ttgggcgggc cggagcggg acattcgggg ccgggtgggg caagcgcggc    52200
cgagcggagc cggtcgcccc gggccggggc ctcggcaggc gagggcctg gctccggtgg    52260 ggcagggccc ggcacaccgc ggtcccgtcc gctaccggtc cggccgccgt tgacgggtgg    52320
ccggcccggc ggcgcgagat ccgggcccgg cgggccctca tcgaacgggg cccggccca    52380 gcaagggatt ccgcccggcg gggcgaggtg cggctccaat ccggccccg tgggtcgggg    52440 gccggaccgg agaccgggcg ggtcgggacc gggtcagggg cgggacgtgg tgaccaggta    52500
gtccacgatg ttggacaccg tctgctggtg ccagacgagg ttggccggga gtttgcggcc    52560
cagcagttgc tccagcttcc gccggatgac gatcgccatg accgagtcca tgcccatctt    52620
cagcagcgac cggtccgggt ccagtccggc cgggtcccac cgcatctccc cgacgatcag    52680
ggcggcggtc cgctcccgca gcgctgcccg gagctcctcc ccggacagcc cgtcgatccc    52740
cgcgcccgcc gccgccccgc cgggtgccgg ggtggccgg tcggggtcgg tgacgtcccg    52800
cagcaggccg gtgcggcggg tgccctccgg cagcggcacg gtccgcagga ccgccagcga    52860
gggcaggccg agccgggcgg cgtggtccca ggcggccagc gcctccggca ccgtgacgtc    52920
cccgaccccg tgggcggcga gttcggcgtc caccgccgcg ttgtcggcga ggccgatccc    52980
gcgccacgag gtccacgcca ggctcatgct gccggccgac ccggcggccc gctcgtatcc    53040
ggccaccgcg tccaggaacg cgttggccgc gcgctaggcg ccctgccggg tgagtccgag    53100
cagctggccg caggacgaga agtgcaccac gaagtcgagg ctgccgggcg ggaagagccg    53160
gtgcagggtg aacgccccgg cggccttggg gcggatcacc gcggcgaggg cgtcccggtc    53220
gagctgctcc accagccggt cgtcggtcac gccggccgcg tgcaccacgc cgcggatcgg    53280
```

-continued

```
cggcaggtcc agggcgtccg ggtccagggc ggcggccgcc gccccggcgt cggcgatgtc    53340
cagggcgacc acccgcaccg tggcgccgag cgcctccagc cggcggacgg tcgcgatccg    53400
gcgggcctgt tccggatcgg tgaccgtgtc ccacgccgag cgcggcggca gcgcggagcg    53460
cccggcgagc accagccggc gggcgcccag ctccaccagc cggcgggcga tctcgccgcc    53520
cagtccgccc agtccaccgg tgatcaggta gctgccgtcg gcccggcacc gcagcggcgg    53580
gcgggccggc ggcgcggcgc agcgcaccag ccggttggcc tcggcccggc cgccgcggac    53640
cgccaccacg tcctcgccgg ggcccgcggc cgacacgtcc agcgcggtgg ccaggtccgc    53700
ggcggtgtgg tcgggggcca ggtcgagggt gccgcccac aggtcggggt gctccccgcc     53760
gatgatccgg cccagccccc agcgggccgc ctgggccacc gagtcggcgc cggccgcctc    53820
ccggacgccc acggtcagcg accacagccg ggcctgtccg ggcggccggg cggcgagccg    53880
ccgcgcggtg cgggccagca gccacgcctc ccgtaccgcg cggtccgcgg ccggttccgc    53940
cggttccgcc gcgacgggca gcaccagcac gtccaccggg ccgccggccc ggtcgagcag    54000
cgggtccagc ccgtccgggt cggccagtag cgccacccgc cggccggtct ccgtgcaccg    54060
cgcccgcagc gccgggcccg gcccctcggc ggggccgacc agcaccagcg gccggggcgg    54120
cagcggcagg tcggcggggt ccacggtgag cgggtgccac tcggtcgcgt acagcagctc    54180
ctccggctcg gcgcccggg gctggtctgc cgccgccccc gcgtaccgga ccccggccag     54240
caccgcgacg gtccgcccgt ccgcggccac cagggtcacg tccaccgtgc cggcggcctc    54300
ggtgaccggg ccggtcaccc gcgcctcgat ccgggcgcgg tccggcgcac cgcccgccgt    54360
ccacacccgg gacaccccgg ccacgacccg cagcgccggg gtgccgggga aggcgaccgc    54420
ggcgacggag agcgcggcgt ccagcagcgg ggcccagccg tccggtgtcc cctccggccc    54480
gtcggcggcg gtcaccctcg gcgcgcagcc gtccggcagc cgctccagcc gggtcacctc    54540
ccaggggaag gccatggtcg gtacgccgac cgcggccagg tcggcgtgcg cccggtcggg    54600
cggcagaacc gtgccggcc cgccggccgg ggcgccgcg tccggcggtg tcaggtcctc      54660
ggccgccgac gccgaggcgt gcgtcagcca ctcccgctcc ccgccgtccg ggccggcgtc    54720
cgacccgccg ccctccggtc cgcggccggt gtcgctgtcg gtgccggtcg cggccggccg    54780
ggacagcagc cgcaccaccc cgtcctgcgc ggtgacgtcg atgtcccggg ccggctccag    54840
ggtcagcgga agggcgaagt ccaccccggt caggccccgc gggcccgggc cggttccggt    54900
ggcgtccagg aacgtctgga gcaccaccgc cgccggcacg atctcggtgc cctggatggt    54960
gtggtgcccg gggtagggcc gggtctccat gtccaccgg gtccgccaca ggtgcagcgg     55020
ggtcgccccg gccaggacgg tgcgcggccc cagcagggtc cggccggccg gtcgtgccg     55080 cccccggtcc tcccgccggg ccggcaggtc gcgccagtac gtgcggcgcc gccaggtccg    55140
gggcggcagc gccagcagct ccccgtccgg gaacgcggcc cggtccggcg cggcgccgtg    55200
gcagtacagc agaccggcgt tgagcagcag ctggtcccgg cccccggcgt ccggcggag    55260 gctgccggcg acacagtggc cggcggcgcc ggccgcgtcg agcgtctcct gcaccgagtg    55320
gcccaccacc gggtgggccg agatctccag gaaggcgcgg aagccgtcct cggccgccgc    55380
ggcgaccgcg ccgccagcc ggaccgggtt gcgcaggttc gccgcccagt aggcgccgcc     55440
ccgcggggcc gggtcgcgcg ggtcggccag cgccgtgccg tagatcggca cggccggcgg    55500
gtggacggtc agcggggccg ccgcccgggc cagttcgtcg agcagcgggt ccatctgcgg    55560
gctgtggaac gccacctcgc tgtccaccg ccgcaccagc agctccgggt ccgccgacca     55620
ctcgcgggcc agggcgtcga tccgggccac cgggccggag agcaccgtgc tggtgggtga    55680
```

```
ggcgaggacg gccggcacca cgtcgtccgc cgtgccgaga cggtcggtgg cctcctcggc    55740
ggagagcccc accagcagca tgccgcccgc gccggccacc cgacgcagca gcacgctgcg    55800
gcggcagacc agccgcgccc cgtcctccac ggagagcacc ccggcggcca ccgcggcggc    55860
gatctcgccc agcgagtggc ccaccacggc cgccggccgg acgccgagcg acgtccagac    55920
ggcggtcagc cccgcctgca ccgcgaagat catggcctgg ccacgtcca cccgggagac     55980 gtcccctcc tggatcatcc ggcgcgcggt ggtgccgatc tccgcggcgt agaccgggtc     56040
gatccggtcg atcacggcgg cgaacgcggg ctcggtggcg agcagttcgc ggcccatgcc    56100
gggccactgg gcaccggtgc cggagaacac ccacaccacg ccggtccccg cgccctccac    56160
caccgtgccc tcggtgaccc cgggcgcggc ctcgccggcg gcgacgtggc gcagccgggc    56220
ggcgagttcc gcgcggtccc gggcgaccac cgcgacccgg tgctccagat ggctgcgccg    56280
gaccccgagg gtgtgcgcga gcgaggccgg cgcggcgccg gcgccgggcc cgtccagcca    56340
gtcggcgagc cgggcggcgt ccgcccgcac cgcctcccgc gaccgggcgg agagcgggaa    56400
gagcagggac ggtggcccgg cctcggcgcc cgcggcctcc ggggcggcgg ccggtccgga    56460
ggccgcggcc ggtcccgcgg cgggagccgg tcccgcggcg ggagccggtt ccgtgacgac    56520
ggcccgttcc gtgccgacgg ccccttccgc gccgacggcc ggctccgggg cggggcgcg    56580 tcccggggcg gggccgggg cctcctccag gacgacatgg gcgatggtgc cgccgtaacc    56640
gaagctggac acgcccgccc ggcggggccc gtcgccgcgc ggccaggggg tgcgtccggt    56700
ggccacccgc agccgcgcgg tctcccacgg gatacggggg ttggggggcgg agaagtggac   56760 gctgggcggg atctcctccc ggcccagggc gagcaccgtc ttgatcaccc cggcgatccc    56820
ggaacccgcc tccaggtgac cgatgttgcc cttcaccgag ccgatcagac agggccggtc    56880
cgcgggccgg cccgcgccga acaccgcgcc gagcgccccc gcctcagcg gtcgccggc      56940 caccgtgccg gtcccgtgcg cctccacgta gtcgaccgtg ccgggcgcga tgccgcaccg    57000
ccggtacgtc cgccgcagca ggtccgcctg ggcctcgccg ctgggcgcca tgatcccgtc    57060 ggtacgccg tcctggctca ccccggtgcc gcggatgacg gccagcaccg ggtcacccgc    57120
ccgctccgcg tccgccagcc gcttcagcac caccacgccc gcgccctcac cgcggccgta    57180
gccgtcggcc gccgcgtcga acggcttgct gcggccgtcc ggggaggtgg cgcccgcccg    57240
gtccagggtc accgacagcc cggggcccac catgagggtg cccccgcgg ccagcgccac     57300 ctccgactcc ccggccagca ggctccggca cgccaggtgc acggcgacca gcgacgccga    57360
gcaggcggtg tccaccgcca ggctgggacc gcgcaggtcc aggctgtgcg agacgcggtt    57420
cgcggtggcg cacatcgagg cgccgatgcc ggtccacggc tcgatccggg gcaggtcctc    57480
cagcagccgc gcccgtagt cgtccgaccc gacgcccacg aagacccgc agtcgccgcc      57540 ggccagctcc agcggcggca gcccgcgtg ctccagcgcc tcccaggcca gctccagcag     57600
cagccgctgc tgcgggtcca tcagctccgc ctcgcgcggc gagatgccga agaactcggc    57660
gtcgaacccg gcgatgtcgt cgaggaagcc gccgaacccg gtggtccggc gcaccaccgc    57720
ggcgtgctct gtgtcccgccg ccgcgtacgc cgcccaccgc gcggaaccgt cccggatgcc   57780
gtcccggccc tgcgccagca gctcccagaa ggcgtcgggg gagtccgcgc cgccggggaa    57840
ccggcagctc atcccgatga tcgcgacggg ctcgtcggcg ccgtgcgctg ccggccgggt    57900 gccgccgcg ccgtccgtgc cgtgcgtgac ctgccgggtg ccggccgccc tgtccgtacc     57960
gtccgtgccg tacgtgacct gccggcgcc ggccgtaccc tccggcacct gccggctgcc     58020
```

```
gtccgcctcc gaccggtgcc cgtccttggc cgcgctcacc acgcgccgct ccccctcgtcg    58080 tccgccggtg ccgccgtgtg ggacgcgggc gtctccagca ccgtcaccac cgcggcggtg    58140
atcatcagtc ccgggccggc gctgagcatc agcaggtggt cgcccgcggc cagccgcccg    58200
gagcaggcca ggtggtcgag gtggatgccg acgtcggcgg cgcccgcgtg gcccacgtcg    58260
cggaagaact ccaccgaccc gagcgaggcg tccaggccca tcggccgcag gtggctgtcg    58320
aggaagtcgg tggtggccgc ccccaggtgg agcacgtggg acaggtccgg cacggtgatc    58380
ccggcctcgc tcgccacctg ctccaccagc ttggtgccgc tcgcgccgta ctcctcgacg    58440
atctccgacg cccgggggcc cagttccgcg accatcgcct ccaggtgctc gttcatgtcg    58500
agcttcttcc cgagggtgag cgccggcggg aagatcgggg cgtgcccgcg gttgaggatc    58560
tcgaactgcg gcagcgagac cgactccacc gcccgcagct ccgcccagcc ggaccgcttg    58620
gagagcacca ccgcggcgcc cgcgtcggcg agcaccgagt cccggtgcgc gtgccagcgg    58680
tccaccgacg ggcccccgaa gttgtcggcg gcgctcacca cggcaccgct gcgcgtcggc    58740
gcgcacagca ggtactgggt ggccatctcc agcgcgccaa ggaacgcgtt gcaccccctgt   58800 tccacggtga gcgccgggac cggggtgccc agggtggcgc ggaggatgta gtgcggggcc    58860
gaccagccgt ccgcccctg gtggtaggcg cacgagtgca ccagcaggtc gatgtcgtcc     58920
cggctcaggc cggagcgtgc caccgcctgc cgcaccgcgg ccacggccat gtccggtgcc    58980
gatatcccgt cggccacggc gacgttccgc cagccgcagg actccatccg ttcccgctcg    59040
taccagccgc gccgcaccgc gtcctccacg ctggtccgct cggggaggta cgccccggtc    59100
gctgccagga aaatgcccgg tgttctcact cttccgatgt cctcactgat cgttccgcgg    59160
cctgatgacc ttcccggtct cggtcgtcgg cagttccgcc acggcggcga aggtgtgggg    59220
ggtccgggag tccgacagac gctcccggca gaagcggtcc agcgcggcga ggtccaccgt    59280
ctccggggtc accgtggcgc tgacgcgctg ccccaggacc ggatccggta cgccggtcac    59340
caggcaggag gcgacctccg gccaggcgag caggaccgcc tccacctcct ccggactgac    59400
cttcgcgccg gcgacgttga tgcaggtgga cagccgcccg gccaggacca ggtcgtcccc    59460
ctcccaccgg gccaggtcac cggtggtgaa cccgccgcgc gacgggccgg tgtcgaccgc    59520
gtccccgtcc gcgtaaccga gcatcatcga cggcgactcc acggtcacca gccccgtccc    59580
ggccccgggc ccggctccgg gcccgtcgc gtcccggggc ccgtcgcat cggccctcgt      59640 cgcgtccccg gaccccgttc cggccccggc ctccggcgcg tcccccggaa ccggcgccag    59700
ggtgaccttc accccgggca gcggtacgcc gggccgccgc aggcccggcc gccacggccg    59760
gggggcccgg acacagatcg gcccggtctc ggtggtcccg tacacctcgc cgacgttccc    59820
gccgagccgc accgcgacct gttcggcggt gtgcgcgtcc agcgccatcc cggcggagag    59880
gaacccgacc gggcgcccgg cgggcaccgg gccgcgggcc gacttcgcca gcagccgcag    59940
catcggcggc accccgacga agagcgccac gtccccggcg ccagctcccc gcagcagcat    60000
ccgcggccgg tccggcggca gctggcggac cggcgcgccg gccagcgggg cggccagcgc    60060
gcacagcccg aacccgtagg cgtgctggag cggcaccggg cacagcagcg tggtcctggg    60120
ggtcagccgc agcgcgtcac ggtagtggtc cgcctccgcg agcagggcgg cggccgggcg    60180
cagcgccacc cgcggccggc cggtggtgcc cgaggtgagc tgcgcggtgg cggcctcggc    60240
gaacgccggc cggatacgcc ccggcccccg gctcagcgcc cggtcccgc acccggtgac     60300 cgggccggca agggtgagcg gcgattcggg cggcgcggcc aggaagtcga gcgggcagcc    60360
ctcctggagc cggtccagct cccaccgggt gagcttgcgg gagagcggga cggccacccc    60420
```

```
gccggcctcg atgatcgcga acacatcgct gatgaactcg gccggcggtc cggccacggt   60480
gcccaccagg gcgcccggcc ccacgcccag ctcgccgagg gcccggacct tggcctcggt   60540
ccgggccagc agctcccggg cgccggtgac ggtgtcgccc gccaccacca gcggggcgtc   60600
accgagccgg gcgcccggt  cccggagccg ggcgagcagc tccgcgcggg cggaggtcat   60660
ccgagtccga ccagggaccg ctgcagcgcc ccggcgacct tgtcgatgac gtcgcgggtg   60720
tgcgcggtgc tcaggaacca cggctccagc gcgttgggt  ggaagtacac gccctccttc   60780
tgcgccagcg tctggaggcg gcggtgccgg gggaagtcga cgagcgcggc gagctgccgc   60840
aggtcacggg gttcggcgga gggctcggcc gacccctcca ggagggccac cgacatcagg   60900
gtgccgaccc ggttgatgtg caccggccgc ttctcggtgg cgaacacctc gcgcacggtg   60960
tcctccatgt actgcccggt gtcctccagc cgttcgtaca gatcgggcag ggaacgtatc   61020
ttgccgagca tggcgaccac cgcccgcagc gcggcgtggt tgcccgcgta gacgcccgcg   61080
tggtgcgcct cgttgctggc cagcatccgc atggcgtgcc ggcgcccgcc gaacgcggcc   61140
accgggaaac cgccgcccat caccttggag agcacggtca ggtcgggctc gacgccgtac   61200
cgttcctgtg ccccgccgcg ggccaccccgg aagccggtga tcacctcgtc gaagacgagc   61260
atcgcgccgc tgcgcccggt cagctcccgc agcagctgga ggaagccggg cgccggcggg   61320
atcaccccgg cgttggccag caccggctcc acgatgaccg ccgcgatccg gtcgccgtcc   61380
cgggcgaaca gctcccgcag cgcgtccggg tcgttccagc cgagctgcac ggtgtgggcg   61440
agcgcctccg ggatcatccc cagcgcgccg ggacgacgt  cggtgggccg ggtgccctcc   61500
atgtgcagcg cggtcttgcc ggcccgcagg accgtttcgc tccagccgtg gtagtggccc   61560
tcgaaggtga cgaccagggt gcggccggtg gtggcgcggg ccagccgcag cgcggacgcc   61620
acggcctcgg taccggagtt ggcgaacctg acctgctcca cacccggcac cagctcggcg   61680
atgagcgcgc cggcccgggc gtccagctcg tgcggcagtc cggtcatgtg gcccttggcg   61740
aactggtcgg ccaccgcgtc gaggacctcc cggtcggcgt agccgaacag atggggcccg   61800
taccccatgt tgaggtcgat gatctcgccg tcctccacgt cgcggagcag gcaaccgccg   61860
gcgctccgta cgaccagcgg caatggaacc gccgcgcgc  gcatgctgct gctcactccg   61920
ccggcgatga cgcttttat  gccgtcaagg gactcggcat tcgtcgggcg gtcggcatcg   61980
ttggcaccca ctgagaacct ccggcttcga cggcatattc ccggaccaca gattgccgca   62040
gggcgttgct gtccgatagt gaccgttggc ggattggctg gatcgcgggg gtgggcggcc   62100
cgcacccgat ggcatgatcg gacgggccgc agcggcggac cgaagagggc gaatgccgag   62160
gagcgccacc gaaaaggaca gcgccacagc gaaagtgcac atcgcggacg ggggagtccc   62220
accgagaggg gatgtcatgt cgtctcgccg agccgtcgcc gtggtcaccg gggcgggtc   62280 gggactgggc gccgccgtcg cgctgcggct ggccgccacc catgacctgg tactgaccca   62340
tctgaccgag gacgacgcgc tcgccgagac cgccggggcgg gccgcggcgg ccggcgcccg   62400
ggtgctggcc accgtccccg gtgacctcac cgaccggcgg accgtggacc ggctcgaagc   62460
gcggatggcc gaaacgccg  aacacctcga cgtcctggtg tgcaacgcgg gcgcctaccg   62520
ttacgtgccc tggccggaaa cctcctggga ggacatccgg gcggccgtgg aagtcaatct   62580
gctggcgcat atcgcgtgca tacacgccgc aaccccgcat ttggtggcac gcggaatggg   62640
ccgcatcgtc gcgatttcca cggttctcac ccaactcgga cgggtggaac tcgcgccgta   62700
cattgccgcg aagggtggac tggagtcact cgttcgtgcg ctggctcgcg aactcgggcc   62760
```

```
gcacggcatt acagtgaatg ccgttcgacc agggtcgatc gagctgagtg tggaacaaag    62820
gcgccacccg gattatccca cctggcggca gcgcgagttc gcgcggcagt gcatcaaacg    62880
ccacgggcgc ccggaagatg tcgcggcggc ggtggccttt ctggtttccc cggaggccgg    62940
attcatcacg ggccagagtc tgaccgtgga cggcgggtgg gatctcaact gacctgcgtg    63000
cggctgcccg caggccgagc ccaaggacca tgacgctgat ggcgtacgga gaacaacccc    63060
tcacgcgcgt gctgctggtg cggcacgccc agtcccacgc cagtgtccgg aaggtcgtgg    63120
ccggcgccgc gacctgcgag ggcctcacgg aacacggccg tgaacaggcc ggacgcctgg    63180
ccgcccggct ggccgccgaa cggctgcgcc cggacgccct gctgaccagc ccggtccgcc    63240
gggcccggga gaccgccacc gtcctcgcgg ccggcctcgg cctgccggaa ccggtggtcg    63300
agcccgaggt gcgggaactg gacttcgcgc cggcggacgg cctgtcgatc gacgagtacg    63360
gccgccgcca cggcaccttc gacatgaccg ccgagcccga ccggcccttc gcccccggcg    63420
gcgagagctg gtccgggttc gcgcggccgg gccggccggg tgatgggcga gctggccgac    63480
ggtacccggg cggcaccgtc ctggtggtct gccacgccgg cctcatcgtc gccgccacct    63540
ccgggctgct ggacgtcgcc ccgccggtcc tcttcaccga cgcctcccg gccgccacgt    63600
ccgtcaacga gttcgtccgc tccgacaccg gctggagcct gctccggttc gacgacgccg    63660
cgcacctgga aggagccgcc gggccgctgc cgggcgaacc ggtgcgctga gtcaccgagg    63720
cgctgagccg atgcgcggtg ggccggtgcg gtgggtcggc tcggtgggcc ggtgcgatgg    63780
ccgatgcccg ccgggccagg ccggccggcg acggggcggg tgccggtgga ccggtcgcgg    63840
gggtcgcgat gcgccggggc gggtaccggc gggccggacg caagggtcgc gatgcgccgg    63900
ggcgggtacc ggcgggccgg actggtcgcg tccgcgccgc ggcggcgtac gggaacgcac    63960
accggcgtgg ggaccgccgt ggccgccggg tccgggcacg gcacatcccc gcccggcccc    64020
ggccccgtcg ccggctcggc cctcagcccc ggccccgtcg ccggcccggc cccagcccc    64080
ggcctcaggc ccggccggtc ccggcccccc agacccaggc ccggcccgg cacccgcgcc    64140
aggagccggg agggtgcgcg gccggccggg cgcgcgccgg gcactccgt tcgccgtacc    64200
gcccggcgga atgcatgtcc gcccgcgcg ggaatcgcgc cgtccgccgc gaacgccacc    64260
gcgcgcgccc ggaattccgt cgcccgcccc gcccggcccc ggcccggcgc cgagcgggcg    64320
gccggccgta ccggagaacc gcgagatccg gtcggatatg cggtggagcc ggtacggacg    64380
gcgggtggaa tccctgtcgc gccccgcttg agcccgccgt ctcgccgagg ccgcggagaa    64440
gcgggccgga cccggccgcg gccggtgatt tccggcgggg gggcgaacaa ctggccgaat    64500
gggtgatcgt atgcgtccgc tgagtgatgt attcgggtct tctggcgcag gactgagtga    64560
agaggccgtg tcgggacggc ttcctcgaaa cagtgcacgc ggcgcgtgtc ggcaccgcta    64620
cggtaagtcg cggggtgtcg cttcggggggc gcggcgagtc gattggccgg gaggagagag    64680
acatggtgca cgaacagtcc ggcggtacgc ccgccgagca cctcgacggg ctgctggccc    64740
gcgcccagaa cgggttcgag atcgacgata cggtcatcat ccggctgcgg gacgctctga    64800
tgcaccagac cgagctgcgt tcctgccgcc agtgcaacga ccgccggct ccccggggtt    64860
acaccacctt ccggcacatc ttcctgctcc cggacggcag cagcgtggtg ctgtgggagc    64920
tccagcacag cgccggcccg ggggacggcc tccagcacga gctgtacgcc gacgaggagg    64980
cgctgctgcg ggcggagcgg cgcgcgcacc tgcggaccgg cggcaccagc tgggcggagg    65040
tcaccctgga gggcctccgt cccgaggagg tgctgcgtac cccgctgccg gtggagacgg    65100
tacgggcgta cgtggcggac aactccgccg accacgcgcg gcgggtgctg cgccgggcgg    65160
```

```
agaacgagga ccggccgggc aaggacgtcg agcggctgct ggagacggcg ttcgcgcacg   65220
acatcgccct cgcccccaag ccccggcggc ggtcgggcgg cgaggacacc acctggtgcc   65280
gcttctacga gcacgcgttc ctgctggccg gcggggacga gatcaccctc tgggagctgg   65340
agcacaacct gaccagcgac ggacggctgg tctgcgaggt ctacctcgac gaggggggcgg  65400 ccgagatggc ggcggaccgg cgcgcccggg cccgcggcgt cgagctctga cgccgggccc   65460
ggccggggac ccactcggcc gcgcgcccgc ctgccccaca tggcggacac cggctcgccc   65520
gcgccgtggg cagccgccag cctgagggga tggaggccgg cgcgggtccg taccgtcgtg   65580
ggcgcccgga acggcgtccc tcgtgccggg cccggtggtg cacgcccccg ggccggacgt   65640
ccgcctgccc ccaccggccg gccggtgtcg ccgatcgggt gacgccggca acggcccggc   65700
gcgggatccc gtatccctcg gcactcctgc cccgggcgcc gctcccgtcc ggcccctgc    65760 tcccgctccc gcccctgctc ccgccccgg ggccgcggcc cgtggtgtcc cggcctgcgg    65820
tgacgcgccc gccggcgccc tcgctgccgc cgctccgccg tccggtggcg cgccgtccgc   65880
gagcacgggg ggcggcgccc cgccgaccgg caacgcgacg gccgtcccgc cggccggtga   65940
cgccctggcc ggtgacgccc tggccggtgg cgccccggcc gggggtgtcc cgtccggtgg   66000
aggtgccccg cccggtggca cggcggtccg gcgtgccggg tccggcccgc cgcaccgccg   66060
ccgagcgcgc ggcacggacc gccggtgagc acctgagccg gaccgctgcc gactgcccgg   66120
gggcgcgggc cgcccggggt cgcggggtgc ggcggggccg ggccggcgga gagcgggagt   66180
agccggtgcg gacaccggac ggcggggggcg gtggggggcgg cggcggtgac cggccgcggg   66240
gccggggcgc ccgccgggc ggcggtgcca acggccggga ggcggaccgg gagcggcggc     66300
ggaaccgcag gttcgccggc tggctctcgg ccgcccctgat cgcgggcggg gtggtcttcg  66360
acctgctgac cccgcggaac gtgtcggcgg caccgttctt cgcggccgcg ccgctgatcg   66420
cggccccctt cgccaccttc gccgtcaccg cgttcaccgc ggcggcgtcg gtcggcaccg   66480
ccctggtcct gatgctctgc cacgggttcg acggcccgca cgaccgcacc gagtcgctgt   66540
tcgagttcgt caccgtcctc accgtcgcgc tgctggccct cgccaccaac cgggtggtcc   66600
gccgcggcgg ccggaagctc gcctcggcac gcggcatcgc ggcggcggtg cagcgggcgg   66660
tgctcccggt gcccccgcgc gtggtcggcg ggctggggggt cgcggcgcgt tacgaggcgg   66720
cgcaggccga tgcgggcatc ggcggcgacc tgtacgcggt gcaggagacg ccgcacgggg   66780
tgcgcgccgt ggtgggggac gtacggggca aggggctggg cgcggtggag gccgtcacgg   66840
tggtcctcgg cgccttccgc gaggcggccg aggaggagcc cgacctggag gggctcgcgg   66900
gccggctgga acgggccctg accgggagg ggcggcgccg ggccaacctc gaccaggtgg    66960
agggcttcac caccgcggtg ctcgcggaga tcccgccggg cgcctccacc gtccggctgc   67020
tcaaccgcgg gcacccgcca ccgctgctgt cctcccccgg tgggggcgtc cggaccaccg   67080
agccggccgt tccggcgatg ccgctgggga tgcgcgagtc gggtgagtgg ccggaccgcg   67140
cggacgagct ggcgttcccg ccgggggcca cgctgctgct cttcaccgac ggggtgaccg   67200
aggcccggga cgcgcacggc gtcttctacg accggccgg ccggctgggg gaccggacct    67260
ggccggaccc ggacaccctg ctggacgcgc tggtcaccga tgtcgtccgg cacaccgggg   67320
gagcggcggc ggacgacatg gcgctgctcg ccgtccaccg cccgggggag tccggggagc   67380
cggcggcaga accggcccg gtggaacgga accggaccgg ccccgggaac ggtcccggga    67440
acggtcccgc cccgagccgg gacggttccg gcccggcctg atcccacacg ggcaggaggg   67500
```

```
accggacggg agagacccgg acgggaggga ccccggcccc ggcgcccgaa gtccccccgg    67560
ccgccccgtc ccaccagccg ggcacggccg ccgggtccgg tccggcccgc gcggcgaccg    67620
gcgcccggca cggagagtga tcacccatga ccgttccgga taacgattgg cgcacgatca    67680
cgcgcgcccc cgtttcacgc tcgccttcaa ccctcaggga attgcccggt tctgaccttg    67740
aacaccccaa agattcccgg ccacgaccaa cggattcggt gcagcggctt ggaatcgcgt    67800
cccggcttct attaacgttc gataacgcag cgcggtcgtc ccagccgcca gaaggtggca    67860
ccgtgcgccg tcgccgaatc ccgcacgcac cacggcagaa gacaagcagt gaccagcagt    67920
accagggaac cggggaacca ccatccttgg ggtgaatcgg gccgaagccg gcccgtagga    67980
gaccttcctg ctccgaaccc gtcagctaac ccggtaggcg agagggaagg aaaggagtgc    68040
gcctccgtgg cgtccaacag gtctgccctt gacgaggcac cgtacggctc cctcaccgga    68100
ccggccgacg gcgccgaccc cgcgaccgcc accctgaccg ccggcgaacc ggcgggcggc    68160
gagtggaacc ccactgccga gtcgctcgcc ccggtgcgcc gcaggcaccg ggtggtgaag    68220
cagcgcggca ccatggcacg gagcggcgcg gtcctcggcg tcggcgtgat cgccgcggtc    68280
ggcgcgggcg gcatggcgac cgccaaggac cgtcccaacc cgccgatctc gatgccggac    68340
ctcgcgcacc tcgccgacga cgtgacggat gcgctccccg ccgtgcagga cctgcccggc    68400
atcgggccgc tcctcgccgg ggaatccggc gaggagaccg ccggcgccgt gccggcccac    68460
ggctcccccc agcccttctc ccaggtcggg ctcaccgccc aggaccgcgc caacggcacc    68520
accgacgcgg gcgaggcact gcgggcccgg atcatgcgcc aggccgagca gcagcagacc    68580
gcggccgacg aggccgagcg cgaggcggcg gtgcgggcgg ccaccgaggc ggcgagcgag    68640
gccgcggcgg aacagaaggc gcaggaggag gccgagcgtg aggccgccgc gaaggaggcc    68700
gagcgcaagg cggcggccga ggccgaacgg aaggcggccg aggcgaagcg caaggcgcg    68760 gaggccgaac ggaaggcgga ggccgaccgg ctggccgaac tcgccggctc ctacgcgctg    68820
cccctgtcct cctacaccct cacctccacc ttcggtgagg ccggcgacat gtggtcggcg    68880
aaccacaccg gtcaggactt cgccgcgccc accggcaccc cggtgaaggc ggtgcacggc    68940
ggcaccatca ccgaagccgg ctgggcgggc gcctacgggt accgcatcgt gctcacgctc    69000
gacgacggaa ccgaggtctg gtactgccac ctctcctcga tggtccgcac ctcggggtcg    69060
gtgtccaccg gcgaggtgat cggcggggtc ggggccaccg gcaacgtcac cggcccgcac    69120
ctccacctgg aggtccgccc cggcggcggc gcgccgatca cccgctgtc ctggctgcgc    69180 cagttcggcc tcaaccccctg accgcgcccg ggcggcccg cacacccgcc ggcccggcgg    69240
acccgcccac cggcacaccg gcggcccggg tgctctcccc tcctgccacc ggcgccaccg    69300
gcgccgccgg acccgctccg gccgcgccgt cagggccgcc ggtcggccac ggcccaggag    69360
gccacggcca ccgcgccggc caccgcgaac accgacggcc caggccccga ccttcttcgc    69420
cagcgggtgt gacccggcga acgccgccac gtacaggccg ctcagcgccg cggcggtccc    69480
cgggccggcc ttctcccgcc agcccccgcgc ggccaccgca ccggcggcgg cgagcgccac    69540
cccgcccagc ggacgccgct tcgtccagcg cgccaccccg tatccgccga cgagtccgcc    69600
cgcggccacg acacctgccg gaatgccggc catggcacca acctcttcct cggttcgtag    69660
aacagttgcc gtgcccattc gaccgcatcc ggcacgggt ttccgcaccg gacggtcaca    69720
gcacgccgcc gttccggcaa caggacggc actcgccgcc gaacaggaag gacgcccgtg    69780
cccgcgcccc gcctcaccta ccgccccgcc accccgacg acgaggagca actgccgcc    69840 ctggacacct ccttcaccac ggacaccgtc caccgcgtga cggccggccc gaccggcttc    69900
```

```
accatccgcc ccgaaccggt gcacccgccc ctgaccaagc acttcccggc cgacgacgac   69960
gaggacgagg acgatgacga cgcaccgaag cacaccgtgg tggcgctcga cggtgaccgg   70020
gtgtgcggct tcgtcgcggt ggatcacgaa ccctggaacg cccggctcac catccgcgac   70080
atcgcggtcg cccccaccca ccgcggccac ggcatcgccg gcgaactcat gacccgggcc   70140
tacgcctacg gccggcagcg gggcgcccgc cacgtctggc tggaggtcac ccacctcaac   70200
gcccccgcca tccgcgcgta ccagcggatg ggcttcacct tctgtggcct cgacaccacc   70260
ctctacaccg gcaccccctc cgagggcgaa atcgccctct tcatgagccg ttcgctcccg   70320
accgctccgg acgcgccagg gcctacctcg cggccttgac ggagtaggtg tagacatcag   70380
ctggaagctc atagcgcaac ttccatacga tgcccatggg cttgcttccg gagtgggtgt   70440
cgtactcggc cgggccgagc agcatccagg gctgcgcccc gcctatgtcg gactttttat   70500
agcgacgcac gaaaagtaga acgtggctac caagtttttt atggttctgg tatcgctgcc   70560
cggttggtga ggcctccgac gtctgattct gggattccca gtggaaggag tcggaggtta   70620
tcgcatggtc cttgtagcgg gtctgcgggg agaagtcctt ctcatctttc tctagggtga   70680
tgaagagggc atctgttttg actccggggc accacttgac gccctccctg aagtgtcccg   70740
gcaagaaccc ggtgagattg gcttccccga gagcaggcag tatctcttcg cggctatagg   70800
aagcatggat ctgtagcggg gagtcggcgt agtcctcgtg tgttccatcg agtgggatgg   70860
ggtagtggtc ggcgtggtcg aggttgtagg cgagcaggtc gcgtagctcg cgacggaaag   70920
ctggatgctg tcggaggtac tcgaagccgg cggtgtagct cgtgaacccg ccacccagtg   70980
gccacagcga gaagaacaac atacgggcat aggcttgctg ttgggtgctg agtgactcat   71040
aggcggggcg gtcatcgctc accaacagac gatacgccgc aacgcgttga ggatcactga   71100
catgcaggaa ggaagagacg cgcttgagga gcttctcttc ccctgctggc gccgttcctg   71160
gaagaagtct tgcccttcga agcagatctg tccacgagcc atttccacga taaatctgct   71220
tgagttctct acggctttct cgcaggtagg cgccgagctg tgtctcgcca tactgggcaa   71280
cctccttggc gagttgttgg acgttgaccc tcagttgcga ctggatattt tccaggatgc   71340
gctgcttgga taccggatcc aagatgatgt gacaacccga aggcaattgg gggaaatctc   71400
gctctatgtg gtcggcgagc cgctgcctgg agaagttggt gagcgctcgg aactgttcct   71460
cgaagcgaaa ttccttgcgg tgctggccga tgaagtcgag aaccgtaagg acagccttgt   71520
gaggggtgcg ccgcaacccg cgtcccagct gctggaggaa gaccgtagcg cttgaggtgg   71580
gtcggagcag gagcagggtg tccacgtccg ggacgtccag cccctcgttg aacagatcga   71640
cggagaacag gatctgtacc ttgccgtccc gaagatcgtc gagggcctgg gctcgctctg   71700
ccctcggggt ggtgccgtcg agagccttgg cgttgatccc ttcctggcag aagacgtccg   71760
ccatgaacgt ggcatgggcg acggtgacac agaagcccag ggcccgcatg gtggcagggt   71820
ccgacacctt gtctcgcacc tgtctcacga tgagctgtgc acgctcctgg tcacctgcgt   71880
agaccttgcc cagctcaccc gtgtcatagc tgccgttgcg ccaggcgacc ccttgcaagt   71940
cggtttcgtc ggcgatcccg aagtagtgga aggggctgag gaggtcattc tccagtgctt   72000
cccatagacg catctcggcc gcaatgcgcc cgttgaagaa ctcgtcctgg acgttacggc   72060
catccatgcg ttcaggcgtc gcagtcaggc cgagcagttc gatgggcgg aagtgatcga   72120 tgactcgtcg gtaggtgggc gcgacaccgt ggtggaactc atcgatgacg accacgtcaa   72180
agtggtcggg ggcgagctgt tcgagggagc gggcgttgag ggactgaacg ctggcgaaga   72240
```

```
cgtgtcgcca gtgcttggga acgtctcccc ccaccagaag ctcgccgaag gtggggtcgc   72300
cgaggacgtt tcggtacgtc ctgagtgact gcgccaggat ctcctgccga tgtgcaacga   72360
agagcagccg gagtggcttc cctcggtgtt gttctctgag ggtccggtaa tccagggcag   72420
ccatgactgt tttgccggtt ccggtggcag caacgagcag gttccggtgg atcttgtgga   72480
tctctcgctc gatgcggagc cgttcgagca tgtcctcctg atgcgggtag ggacgcacct   72540
cccgccggga cagtgtcaga gccgcgggcc cgggtagccc ttggctgctg gcatgggcca   72600
gggcctcggc cagccgtgcg ccatccttgt cggggtcgta cggttcaaag gcggcatccg   72660
accagtaggt gtcgaaggtg gcctcgaact tctccaagac agcgggggtg gccaccgatg   72720
acagtcgaac gttccactcc aagccatcga ggagcgcggc cttggagagg ttggagctgc   72780
ctatgtaggc cgtgtcgtaa ccgctgtttc tccggaagag ccaagccttc gcgtggagcc   72840
gtgtggaccg cagttcgtag ttgaccttga cctgtgctcc gaactcggtc accaaacgat   72900
ccagcgcccg ctgctctgtt gcccccagat aggtggtcgt gatgaggcgc agcggaacgt   72960
tccgctcgcg ggccgatcgc agcgcctctt ccagaacacg cagaccatgc cacttcacga   73020
aggcgcagag caggtctacc tggtcggcgg ttgccagttc cgcccgtagc tcagaccccca  73080 ggttggggtc ttccggagca ttggtgatga gtgccgcctc cgagagtggg gtggcgggac   73140
ggatgctgta cacgccggga gcttcctcct cagcgacggc ggtgagttgg cgcggtccgt   73200
ctgccacgag gtcgatccac tggtgcgcgc cgtcagcgt gcctatcgat tcgagtatct   73260
ggttcgccgc gccgacctgc tgctccgcag gaagctgagt aagaacccgg tggacggtct   73320
cggcaatgtg acgcgcgagc acctgaggcg tagagccggc gcccacgtgc tgctcgatag   73380
ctcgccaggt gcccgcatcc agctgctgga gccgcccttc gagccggtgt gtgatgaggc   73440
gttcgtacag gcccggccgt gctgtgaact ccatgccgtc gtcggtcatg tcctgccccc   73500
ctggcgtctc gcatgtgggg gctgttctac cagccgcgag cgtcctcaga cgtgggtggt   73560
ggccggtcgg tggaagaagt tgatgacaga acgtgaccgt ttgctgatgg tgtcagaccc   73620
ttcatgcata gtttctggcc atggggatac gcaacctgct tctggatgtg ccaacacgt   73680 acgacaagag catgggtgtg aagcgcgggg tgttcgctca ggatcgcctc cgccaggtgg   73740
cagaggagtg ggcgccggcg ctgccttttg gatgtgaagc ggaaggttac ggcggtaagg   73800
gcgagggcag cgctacccccg tggattgggg tgtacgaccc ggatgtcacg cgggacccga   73860
aggaagggct ctacctggcc tacatctatg ccgcggacct gagcacggtc acgctgacgt   73920
tgcaacaggg tgtgacctcg ttggagccca cgttgggcac gggtaagcgc cggcaagcgt   73980
atctgtgggg cagagcgcgc gccatcgctg ccgggcttcc ccctgcagcc ctcaatgact   74040
gggctgatgt cccggacttc aagtgtgacc tcccccgccc cctgtcgtat gaggccggga   74100
gtgtcgcagc tcggtgttac cagaccgcgt ccctgcctga cgaagaccag ctgaggtcgg   74160
acctgagggc catggtggag ctgcttcagc gagctgcgct cgttgccgag cggctcaagc   74220
ctggggaaga cggggacggt tgggacgtac ctgccgatgt gcgcgagtac cgcggtttgg   74280
atgggtttcg ccccaagaac gacagtgact acatcacgca ttttcccgct cgcaccgtga   74340
ggaagaaacg aatccacgag cggctgatca gtgagtttgc cccgttcgtt gagaagcgtg   74400
gttttgttcc tattactcgg gacgtccatc ccaaggatct ggtgattcgc aagggaggcg   74460
tcgagtggct ggtggaagcg aaggtggtga agcgggcaaa tcccacgttg gcggtgcgcc   74520
aagcggtggg tcagctgttg gaataccagc acttcctta ccgccgggcg gagagggta   74580 cgccgcatct gcttgggctg tttacagaag atatcggtag gtatgccgat tacctggaag   74640
```

```
agctgggtat ggggtccgtt tggcggatcc cggaggggtg ggcggggtcg ccctccgccg   74700
ttgcctgggg gctggtgcag taggccgggg cccgggttac ggcggcgggg cagaggttcc   74760
gggggcggtc ggcggagttc cggtatccgg tggggcgacg gggtcggggc cgggcgtgcc   74820
gggcggggtg aggggccgg gggccgggtg ggggcgggg ccgtaggtgc cgggtgggta    74880
cggagcgggg ccgtatgcgc cggccgggta ggggtgcgtg agggtgggcg gggtgccggg   74940
gtgggcggcg tacaggccgg ggtgggcatg ggcgtacggg cccggctggg cgtgggggta   75000
cgggcctgcg tgggcgtgag ggtgggcggc gtacgggccg gggtgggcgt acgggccgta   75060
gggccaggcc cccgggtacg gcggtcggac cgggtacggg cggcggcgtg gagccggcgg   75120
caacagcgcg gcgtgcgcca ggatcggccg ggccacgtcc ttgcgctgcc acaggtggtg   75180
caggagttcc tgttcccgcg cggtgaagtc cggcccggg gtgtcccggt aggcgcggct    75240
gcggaggaag gcgagcgagg tggcgaaggc ggtgtactcg gccacggtgc gggccgccgc   75300
cggtccgtgg acgcgtcggg cgacgtcccg ggcgatgccg cgggcccgga aggaggacag   75360
cgccaccggt tcggggcgg tgagccagcc ggccgcctgg tagaccggca ggtacgcccg    75420
tatcgtccgc agctcgtggt tccgcgacca gacggccagc acaccagca ggccgaaggc    75480 ggggaccatg aagaggaggt agacggccat gaagccggcc ccgctgccga ggatcgccga   75540
accgttccac agcccgtgca ggaccatcgc ggcgagcagc ccggcgatcg gcagcaggac   75600
gcgccggacg cgctgccggt gggtggcggc cgccgccagg ccgaagccta tgccggtcat   75660
ggcggtgaag agcgggtgcg cgaacggcga catgatgacc cgcacgaaga aggtcgccgc   75720
ggtggtggac cgcagcccgg agtggccgaa ctcctgatcg ctgacgaagg cggagcccag   75780
gtagaggatg ttctcggtga aggcgaagcc ggtcgcggcg atgccggcta tcaccaggcc   75840
gtcgaggatg ccgttgaagt cccgccgccg gaacaggaag aggaacagca gggccccggc   75900
cttggcgctc tcctccacca cgggtgccac cagcgtggca ccccaggcat cggcgtcggc   75960
ggattcctcg gcggccgagg attcggcgat gttggtcacc agccattcgg tggcgaaccc   76020
gttggcgatc agtgcgacga gcgtcgcggc acaggcgccc caggcgaagg cgaagacgag   76080
gttccgccag ggtttgggct ccacccggtc cagccagcgg aacgccgcga ccagcagcgg   76140
caccggcagg acggacaggc ccagccccac caggaagccc tcggtgccgg tctgcttccg   76200
caccagcgcg aggatgatca ggccgcacag cgagaggacc agcaccagcg cggtggcccg   76260
cagcgcccgg ctctcccaca cggcgcgccg gggtcggtag cgccagcccg ccggttccgg   76320
caccgcgtcg aaacgcggct gcggactgta ggccgggacg ggtggtcccg ccggctggtc   76380
ggccacgccc acggcggcgc cgggcgggcc cgggacggtg gtggggtcgg tgggaccggt   76440
gggcgtgagg tctgtggtgg gggtgtcccg tccggtgccg aggtcagggg ccgggccggg   76500
gaccgggtgg ggagtggtcg cggtgccggg gccggtggcc gccccggagg ctcggaccgg   76560
ggagtcggcg gtgccgggag cgccgtgccc cgcgtcggcg ggccgggcgt ccggaccgg   76620 ggcggcggtg gacgggatgt ccgcgggccg ggcgtccggg gtcccggtgc ctgccggcgg   76680 cgctgccggcg ggcccggcgt cggttggccg cgcctcggcg gcctgggcct cggtggcccg   76740
ggggtcggcg gtccgggcat cggcggtccg gggagcgtcg ggcccggacc gaccggtggt   76800
ggcgtggccg ggccgctcgg ggccgggatc gtgcgggac gaggactggt gcacccgaag    76860
accctaacca aggggggagcg cgcacggggtt ggagatcatc tacctggtcc cggtacgccc   76920
gtcggggtgc cgcgcatcga ggccgcagcg gccgtcatca ccccggccgg tcgtgccggc   76980
```

```
gccggccagg gggcgggtgg aggaggccgg ggacggtccc gctgggtcag ggagacggcc    77040
tggggtgcgg gggcgggcca tcgtcggggg cggcggaccg gcccgctggc ctgcggcggc    77100
cgaccccggt gacgcgtccg ggaccccfac ggcgtgcccg gggccggtgg ggcgtcccgg    77160 aaccccfacg gcacgccccg ggtcggtggg gcgtccgggc acgtccgcc cggtgggggtg    77220 ctcgcgggcg gggcgggcga ccggggcgtc ccggcggggt gtccggggggc acgttccggt    77280 ggagccccgg cggcggctcg ctccgcgcg cccggtccg tgcgcctcag tccgtacggc    77340
ggcggaagag caggtcgtgc accacgtgcc ccttgtccag gccctggccc tcgaacttgg    77400
tcagcgggcg gaagtcgggg cgcggcgcat agccgccgtc cggctgcgtg ttctcgaagt    77460
cgggggaggc ggacagcacc tccagcatct gctccgcgta cggctcccag tcggtggcgc    77520
agtgcagcag tgcccccggc ctcaaccggg tggcggccag cgccgacgaac tcgggctgga    77580 tcagccggcg cttgtggtgc cgcttcttgg gccaggggtc ggggaagtag acgcgcagcc    77640
cggcgaggga ggagggagcg agcatctccc gcagcaggat gatcgcgtca ccgttcgcca    77700
cccggatgtt ggtcagcccg ttccgctccg cgagggcgag caggtttccc tgaccggggg    77760
tgtggacgtc ggcggcgaga atcccggtgc cggggtcggc cgccgccatc tgcgccgtgg    77820
cctcacccat gccgaagccg atctccagga cgacgggcat ctccgggtcc ccgaagagcc    77880
ggccgagatc gatgcggtgc agaccgtcga tgtccaggcc ccactgcggc cacaggcggc    77940
gcagtgcctg ctcctggccc ggtgtgaccc gtccgcggcg gggccggaag gaccggatgc    78000
ggcgttcgtg gtgcgagccg gccgggtcgg cggagggggcc cccggggaac aggcgagcgc    78060
cgcggtcgcg gtgatcgtgt gcttccgcgg agcggggtgc ggtggagttc tcggacatgt    78120
acgtcgattc tacggtcggg ggcgcggatg cccttccggc cgcggccccg ccgcggtgac    78180
gcgcgggccg tggcggctgg gcaccggtcc gcgcgcccgg tcccgccgg ccccttttccc    78240 ggtgacgcgc cccccttccgg ccgggcctcc gcggtgacgc gtgtctcccg gccggacctc    78300
ggcggtgacg cgtgtcgtgc gggtgcgccc tgcccggtga cggccactct tccgccgcct    78360
gccttctccg gtgaggcagg tccccccggc tgtgtgccgg ccgcaccgcg cccgtgcggc    78420
tgcgcgtgtc cgtgcggacc gtgcgtcctg ccggtgccg tgtccccttcc ggagtcaccc    78480 gggggcgaccc cgggccccgc tccgtacacc cggccccgct ccgtaccca accgtgtcct    78540 ttcggctacg ccccggaccg tacgcctcgg gtcccggtgg ggcgccgcga caccgtcgg    78600 aggcggatgc gccgggcacc ggccgcccgg gaccgcccga ggaccggcgc ctggacgacc    78660
gggcgagcgg ccgtccaggg ggcgcgggcg ggcggccggg cgcggggcgg gtggggtacg    78720
gggccgcggt gggcgtcggg cggtggccgg ccccggggggc cggggttcag ccgtcgaggg    78780
ccgccagcgc ccgccgggcc acctcccggc cgatcggcag ggaagccgtg gcggccgggg    78840
acggcgcgtt gagcacatgc accgcacggg ccgactcggc gaagaggaag tcgtccacca    78900
gggtgccgtc gggcagcacc gcctgggccc gtacccggc cggggcgcgt accaggtcgt    78960
ccgtccgcac caccggcaac agccggcgga cggcgtcggt gaaggccgc ttggaggccg    79020 agcgccgcag ctcacccgcg ccgtagcgcc agtgccgacg cgctatccgc caggctccgg    79080
ggtacgccag ggtggcggcg aactcgtccg gccgcaccgt gtgccaggtg tagccctccc    79140
gggcgagggc gggcaccgcg ttgggcccga tgtgcacccg gccgtcgatg ccgcgggtca    79200
ggtgcacccc gaggaacggg aacgccggat ccggtacggg gtacaccagc ccgcgcacca    79260
ggggcgcccg ggacgggacc agtcgtagt actccccgcg gaacggcacg atccgcatgc    79320
ccgggtcgtc ccccgccagc tgggcgatcc ggtcgcagtg cagccccgcg cagttcacca    79380
```

```
gcgccccggc ccggaccacc gaaccgctcg ccgtgcgcac cgccaccgcc gaggcacggc    79440
ggccgatggc ccggacctcc tcgccgtacc gcaccgaggt gccggcgtcg gtggccagtc    79500
cggccagccg gttcgccacc gcgccgtagt cgcaggtgcc ggtggtgccg acgtggatgg    79560
cggccagacc gcgcacatgg ggctcgtact ccatgatctg cgccgggccc agctcccgca    79620
ccggtatgcc gttctcccgg ccgcgctgca ccagggcgtg cagccggggc agctcggcgc    79680
ggtccgtggc cacgatcagc ttgccggtgg tctcgtgcgg gatgtcgtac tcggcgcaga    79740
acttcaccag ctcagcggcg ccctccacgg cgaagcgcgc cttcagcgac cccggcgggt    79800
agtagatgcc gctgtggatc acgccgctgt tgccggccgt ctgatggcgc gccggaccgg    79860
cttccttctc cagcacgatc acccgggtac cgggtgccgc ccgcgtgatc gcgtacgcgg    79920
tcgacaggcc gacgatccca ccaccgatca ccagcacatc gcagtcccac gccgtcacga    79980
cacctcactt ccccgcagct gccgacgctc aaccgcaccc acaccgatca ctatcatgac    80040
gcccgccact gacaacgggc cgggaacgtg ggggcggcgc cgctgtggcc ggcggatgtc    80100
ggccgccggt ccggcccggg acaccccgtc gcgcccggtc ccggtgcgcc cgtcccggtt    80160
ccgataggcc tgtcgctgct cctgggcccc ctgcccggtc ccggtgtgct ggccccggcc    80220
gccggtcgcc cgtcccggtc ccggtgcgcc cgtccgggcc gccggaccgt ctgcccggcg    80280
cctggccttc tgcctgcctt cccggacgtc ctgcacggcc gccacccccgg tccggctcct    80340 cggggccctc gccccaccgg acgcaccgcc ccaccggatg caccgggaca ccggacgcac    80400
cgggacgtac cgggacaccg cacggggcgg ggacgtgcag gcaccgggag ggccggggcg    80460
ccgggcgtgc gcccgcgcgc ccgtaccgct cacaccgggg cgaccagcag gggacgcgcc    80520
cgctcccgca gctccgcgac gcgcggctcg ttgccgtacg gctccaggcg gtgcagcagg    80580
tcgcgtacgt actccgtggt gcgggccgag gagatccggc cggccacctc caccgcccgg    80640
gcgccctggg cgcacgccgc gtccaggttg cccgactcca gctcggcgac cgccgacacc    80700
accagccgca gcccgtgcga gcgcacgaac tcctcggtgg gccgggccag ggcctgctcg    80760
gtgaaccgcc gcacctgccg gggcagccgc aggtcgcggt agcactcggc ggcgtccgcg    80820
gcgaaccgct cgtgggtgta gaagtccagc caggacgggc cggggtcgcc cgctcgggac    80880
cgctccagcc agccctcggc ggccttcagc gccgcgccgc aggccggccc gtcgcccgcc    80940
ttggcctgcg cccgggcctc gaccaggcgg aagaagctca tggtgcgcgc ggtggccaga    81000
ccgcggttgc gctccagcgc ggcctgcgcc aggtccacgc cctcgtcggc gaagccgcgg    81060
taggtcgcct gcagcgacat cgacgccagg acgtagccgc cgagcggtac gtcggccgcg    81120
gcacgggcca ggcgcagcgc ctggatgtag tagcgctggg cggcctcctg ctgaccggtg    81180
tcgaaggcca tccagccggc cagcgggtg  agttcggcgg tggccccgaa cagcgcccgg    81240
cccacctcgt cgctgtagga cccagcagc agcggcgccg cgtcgacccg caggcactcc    81300
ggcaccatcg acgaacgcca gtcgcccccg ccgtacttgg agtcccagcg gcgtgcgtcc    81360
tcggccgcct cgcgcagctt gttgacgtcg ctgtggccca cccgctgcgg taacccgtcg    81420
gtccccggcc cgtccgtctt gggctcccgg gccaccgagc tgtcggccgg ggatatcagc    81480
cagcgggacg cggggggtggc gtaggcgctc accgcgaagg acccggccag gctctgccag    81540
atgccgctgc ccccgcgccg ccccgccagg tccaggcggt acagctcggt ggcgctgcgc    81600 accgctgcc cgatgtcgcg cgggaaggcc agcccgacct cggggcgggg gtcggcgtcg    81660
gcgaggccga tctcgtgcag cgggaccggc cggcccagct tggagccgat ggcggcggcg    81720
```

```
atcagatggg gcgcggcacc ctgcgggacc atgcccttgg agacccagcg cgccaccgac   81780
gtcttgtcgt agcgcagcgt cagaccgcgc tgtgcgccga ggtcgttgac tctgcgcgcg   81840
agcccggcgt tgctgattcc cgcgagggcg agaacggcgc cgagcttctc gttcggcccg   81900
cgtggctccc tggacatgcg caccectcga acaacgccga cggccgcccc ggcataggca   81960
cggggcattc gtaaacccag cgtagttcgc cgcatcccga ccgttaagag gtctcatccc   82020
ggatggcggg attcttgtac gaacgcgggt gcgggagcgg gcgtgtgctc ccggtgcgtg   82080
tggccgtgcg cctgtgtgtg cgctctgtct gggccggtcc ggcggggctt ccatggaccg   82140
tgcgtgggtc ggccccatgg cacaaagcca gtgggctggg ggacaccgcc gcctcattcc   82200
ccgcgggcgg cggaacggtc cgggaggtgc acaccacctc ccggactgtg gtgttcgccc   82260
cccgagcgcg gtgccaggtc accgcgggcc cgcgccaggg tgcgtcggga atttggctga   82320
atgtcactcc tggcggccgg gctgccgcgc cgggccgggg aggggaggc ccgagcggcg   82380 gcccggcatc gaccctgtgc ggcccgcctg ttccgccgcg ttcgccacc ggtccgccac   82440 cggtccgcca ccggtccgca ggtgtccgtg gacgccgcg tgcccaccgc tggcggtgcc   82500
ccgcgcgggc cggtgaggcc ttccggcacc ggacaccggt atgccggact cgcgccgttc   82560
cgcggtgagt tgtgcggtgg aagcggtggt ggccgccgg cgtcccggcc gggcccgggg   82620
cgtgcgccgc ccgcgcgccg cgccgccgac cggttccggc cgtggcagca tgggcccggc   82680
cgagcggtgg cccgtcccgg ctcccggcca acggccgtac cggtcgggcg cggtccggca   82740
cccgtcgatg gcgacgctcg gtgaacgcgt cgcacacggc gtgatgttgt cgcaaaaccg   82800
gagtgacgag gtgggcccgg cgttgcccgg gtggctcccg gaaccggcga tcagccgtgc   82860
atgatggcgc gtgcgtactg gtggccacgg tcggtggagg cggcgatgcg gtggttggtg   82920
gggtggagca gagccaccgc gggacccgcc acggccggcg ccgacgccct ccagccggtc   82980
ggcgcccagc tgctgtggga cggcccggac ccgctgtggg cggtcggtga ctggcggccc   83040
gacgaggtgc gcgtggtgca gaccgatccc ctcaccccgg ctcgccgtcat cggctgctgc   83100 ggggccagcg acgaggagct gaggctgggg ctgttcgccg cccgcggagg cgcgctgcgc   83160
cacctcaccg catggcccgg gagctacacc gcggtggccc gcgccggccg ccggatcacc   83220
gtggtcggcg acctcgccgg agcccggccg gtgttccaca cccgctgggc cggcggcacc   83280
gcgtacgcca ccgccgccct gccgctcgcc gacctcgtcg aggcccagct cgacgtcagc   83340
cacctcgccg cactgctcgc ctgccccgac accccgagg cggtcggcga cggcacccce   83400 tacgccgggg tgcggcggac ggcgcccggc cacgcgctgg tcctccggga gggcgccccg   83460
gacctcgtcg gctacgaacc caccgcctcg ctcgcctccg ccgcaccccc gatggacccc   83520
gaggcggcgg tggccggggt gcgggacgcc ctcctgacg cggtacgggc ccggctcgcc   83580
gcaccccgtc acgcccgggg taccggcggc cggctcgacc ccggaccggt gcccggcatg   83640
ggaccggccg accggcgggc ggccggggc gcgccggccc ccggcctcgg tgccgacctg   83700
tccgccggca gcgcctccgg caccctggcg ctgctcgcgg cgggcctgcc cgggatcccg   83760
ggcaccccgg ccggccacgg tgcggaggcc ggcgaacggc tccaggccgt caccttcaac   83820 gacctggcg tggggcgcgg ccgggcccgc gaggccgaac tggagcgcgc ccgcgcgatg   83880
gcggagaacc cccggctgca ccacgtcgtg gtcgccggcg gcaccgaggc gctgccgtac   83940
gcggcgctgg acggcggccc gctgaccgac gagccggcct cctgcctggt gctcgccgaa   84000
cgccaccggc gccgcctcgt cgcgggcagc gccgaccact tcgtgggca cggcgcccgc   84060 caggtgctcg acgcgcaccc ggcccgcctc gccgacctgc tgctcgaccg gcgccgccgc   84120
```

```
cacctgctgc ggccggccac cgcgctggcc cgggcggacg ggccgtccgc gcactccttc    84180
ttcgtcccgt tcaccgtgta ccgggccgcc cgccggctgg cccgcacccc gtaccgggac    84240
ggactggagc aggtcgcgca ccacctgctg gagggccggt tcaccccga gccgggtccc     84300 ggccgccccg cgccgtctc ggcctcgctc gcggcgctga cctggtgccg gcccggcccg     84360
gccgcccgct ggctcaccgg cgaggcgctc gctgaagtat cggttcgcct ggaggccgcc    84420
gccgcccgcc cggcactcct gcggcgcccc ggcgagcgcc gtgccgacgc cgcgctgaac    84480
cggttcgccg ccgaccaccg catcttcgaa caggcggtgg aggtccgcgg ccagcggctg    84540
cacgcgccgt acctcgacaa ccaggtggta cgcgcctgcc gtgcgctgcc cgaggcgctg    84600
cgcgtccagc ccggggcgcg ggccgcggtg ctccgcgcgg tgctggcggg ggccggcgtc    84660
cgggacctgc cgcccggctg gggggccacc tcgcagggg  cgcacgtcac cgcggtgcgc    84720
gccggactcc gcacccatgc cggggagctg atcgacctct ccacgcccc  gctgctggcg    84780 gacgccggcc tggtcgaggc acgggtggta cggaaagcgc tgcgcgcggc ggccggcggg    84840
gaacggctgc cgctggacgg gctggccgaa ctcgtcgcca ccgaggtctg gctccgccgg    84900
ctgctggccc gccgcggcac ctgctggacc ggcaccgagg gcccgcgccg ccgcgcggtg    84960
gcgggcgggg tggtgccgcg gcaggggtg  tgagggagcc ggggccgggg ccgggtcggg    85020
gctagtcccc tgtccaggta ggccggggtc gggtcggggg cgctggtcag gacgggtcgg    85080
ggtcgtcggg cggctcgtcg tcggtctccg gacggtcggg gtccggctgg gaccccgggc    85140
gggtggggcc aaagtggtcg ggtccgggcc cgggcgggtg agggccgggg tggtccggtc    85200
cgggttccgg ccctccgtcc ggcccagggc tcgcccccgg cggcgccgtt catccgccgc    85260
cgccccgccg atcagcgagg acaatgaatc cgtgcggtat ctgatactcg gcgccaccga    85320
ggcgcgtgac agccatggac agccgctgcc gctcggcgcc ggtgcccggc tccgcgcgct    85380
gctgaccgcc ctcgccctgc gcgcgcgcg  agccctgccg gtgccggtgg acgtactcat    85440
cggtgaggtg tgggcggacg acccgccgca ggacccgccg gccgccctgc aggcactggt    85500
cggccggctc cgccgggtgg tcggcagggc cgcggtggac tccggccccg gcggttaccg    85560
actggtcacc ccggccgacg aggtcgatct gttccgcttc gagcggctgg tgggcgaggg    85620
cagccgggcg ctcgacagcg gtgacgcgga ccgccgcc   ggtacgctcc gggccgcgct    85680
cgccctgtgg cgcggccccg cgttcgccga cctgccggac cgcgagtccg ccgccgcccg    85740
ccccgaggcc ctccggacca ccgccctgta ccggcgcatc gaggccgacc tggcgctggg    85800
ccgggcggtg gaggtggtcc cggagcttcg cgaactcgtc gccggcgacc cgctgcacga    85860
gccgttccag gctcagctga tccgcgcgtt gagcgccgcg ggacggccgg ccgacgccct    85920 cacgcgtac  gaggacgcgc gccgggccat cgccgaccgg ctgggcagcc ggcccggcac    85980
cgaactcgcc gggctgcacg cccgtttgct gcgcggtgac cggccggccg acgcccggcg    86040
gggcgccgcc gacgggcgga acggaccgg  cacgccgtac gggccgccgt ggggtgccct    86100
cgacgttccg cccgcacccg gtcccgcacc cggtcccgca tccggcgtga cggcggacgg    86160
cggctcgccg acccgggagc tccgcgcacc cgggatcccg gcggtgggtg accggccgcc    86220
gcacgacgcc ccgaacgccg gcagcgcacc ggtgtccgcc ccggcgccgg gggccggcac    86280
accggcgccc gacggacgac cgcggagcgc accggcggac ggcgggccgg accacggtgc    86340
cgggtccggg                                                          86350
```

<210> SEQ ID NO 55

```
<211> LENGTH: 18
<212> TYPE: DNA
<213> ORGANISM: Artificial Sequence
<220> FEATURE:
<223> OTHER INFORMATION: synthetic oligonucleotide primer

<400> SEQUENCE: 55
gagcccgtcg cgatcgtc                                                18

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 56
cgcttcttcg aggatcatgt                                              20

<210> SEQ ID NO 57
<211> LENGTH: 32
<212> TYPE: DNA
<213> ORGANISM: Artificial Sequence
<220> FEATURE:
<223> OTHER INFORMATION: synthetic oligonucleotide primer

<400> SEQUENCE: 57
gaagatctgc atatgagcgg ccctggttac ct                                32

<210> SEQ ID NO 58
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 58
ggaattctca tttcctcgca accacttcg                                    29
```

PACTAMYCIN ANALOGS AND METHODS OF MAKING THEREOF

CROSS REFERENCE TO RELATED APPLICATION

This application is a continuation of U.S. patent application Ser. No. 12/596,429, filed Oct. 16, 2009, which is the U.S. National Stage of International Application No. PCT/US2008/060876, filed Apr. 18, 2008, which was published in English under PCT Article 21(2), which in turn claims the benefit of the earlier filing date of U.S. Provisional Application No. 60/912,824, filed Apr. 19, 2007, all of which are incorporated herein by reference in their entirety.

FIELD

This disclosure relates to antibiotic biosynthesis, in particular, to a pactamycin gene cluster, methods of its use, proteins encoded thereby and methods for using the gene cluster and parts thereof to synthesize pactamycin and analogs thereof.

BACKGROUND

The global emergence of multidrug-resistant bacterial infections has resulted in enormous healthcare costs and has become a major threat to public health. In the U.S. alone, the total cost linked to antibiotic-resistant infections has been estimated at $5 billion annually (Zinner, *Expert Rev. Anti. Infect. Ther.*, 3: 907-913, 2005). About 70 percent of the bacteria that cause infections in hospitals are now resistant to at least one of the drugs most commonly used for treatment. For example, some organisms are resistant to all approved antibiotics and can only be treated with experimental and potentially toxic drugs. Therefore, to stay ahead of the development of antibacterial drug resistance, there is a pressing necessity to identify new antibiotics, especially those with novel mechanisms of action, and methods for producing such antibiotics.

SUMMARY

This disclosure describes the molecular cloning of the pactamycin biosynthetic gene cluster from *Streptomyces pactum* (ATCC 27456), the characterization of the individual genes in the gene cluster and the proteins encoded thereby, and new chemical structures developed through genetic manipulation and utilization of the pactamycin gene cluster. The pactamycin gene cluster within SEQ ID NO: 54 (nucleotide residues 1-86350) includes fifty-three genes referred to as orf1 to orf53, respectively. Sequence analysis reveals peroxidase/hydrolase genes, oxidoreductase/mutase/dehydrogenase/hydroxylase genes, aminotransferase genes, carbamoyl-/nucleotidyl-/glycosyl-/phosphopantetheinyl-transferase genes, methyltransferase genes, kinase genes, polyketide synthtase (PKS) genes and regulatory genes, as described more fully herein.

The present disclosure also relates to the use of the pactamycin biosynthetic genes located within the identified gene cluster for drug design and development purposes, including the development of pactamycin analogs that are more efficacious and less toxic. Also provided are drugs and antibiotics so produced, as well as methods of their use.

The foregoing and other features and advantages of the disclosure will become more apparent from the following detailed description, which proceeds with reference to the accompanying figures.

BRIEF DESCRIPTION OF THE DRAWINGS

FIG. 8 also shows the chemical structures of compounds generated by these strains.

SEQUENCE LISTING

Figure 1A:
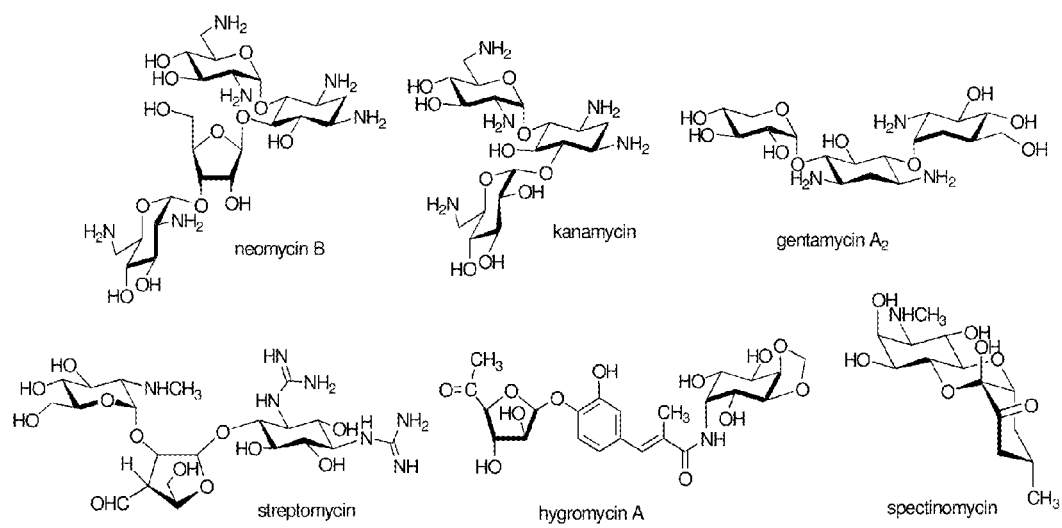
FIG. 1A illustrates the chemical structures of representative aminocyclitol antibiotics.

The nucleic and amino acid sequences listed in the accompanying sequence listing are shown using standard letter abbreviations for nucleotide bases, and three letter code for amino acids, as defined in 37 C.F.R. 1.822. Only one strand of the nucleic acid sequence is shown, but the complementary strand is understood as included by any reference to the displayed strand. In the accompanying sequence listing:

SEQ ID NO: 1 is the amino acid sequence for Orf1 encoded by orf1, corresponding to nucleotides 38 to 1489 of SEQ ID NO: 54. Orf1 is homologous to phosphoribosyl-formylglycinamidine synthase II.

SEQ ID NO: 2 is the amino acid sequence for Orf2 encoded by orf2, corresponding to nucleotides 1756 to 2630 of SEQ ID NO: 54. Orf2 is homologous to hypothetical protein SAV4137

SEQ ID NO: 3 is the amino acid sequence for Orf3 encoded by orf3, corresponding to the reverse complement of nucleotides 2803 to 4377 of SEQ ID NO: 54. Orf3 is homologous to N-acetylgalactosamine-6-sulfate sulfatase.

SEQ ID NO: 4 is the amino acid sequence for Orf4 encoded by orf4, corresponding to nucleotides 5443 to 7026 of SEQ ID NO: 54. Orf4 is homologous to amidophosphoribosyltransferase.

SEQ ID NO: 5 is the amino acid sequence for Orf5 encoded by orf5, corresponding to nucleotides 7060 to 8160 of SEQ ID NO: 54. Orf5 is homologous to phosphoribosylaminoimidazole synthetase.

SEQ ID NO: 6 is the amino acid sequence for Orf6 encoded by orf6, corresponding to the reverse complement of nucleotides 9066 to 10160 of SEQ ID NO: 54. Orf6 is homologous to a dehydrogenase.

SEQ ID NO: 7 is the amino acid sequence for Orf7 encoded by orf7, corresponding to nucleotides 10461 to 11279 of SEQ ID NO: 54. Orf7 is homologous to hypothetical protein SAV413.

SEQ ID NO: 8 is the amino acid sequence for Orf8 encoded by orf8, corresponding to the reverse complement of nucleotides 12500 to 13135 of SEQ ID NO: 54. Orf8 is homologous to hypothetical protein blr0521.

SEQ ID NO: 9 is the amino acid sequence for Orf9 encoded by orf9, corresponding to the reverse complement of nucleotides 14199 to 18185 of SEQ ID NO: 54. Orf9 is homologous to an ATP-dependent helicase.

SEQ ID NO: 10 is the amino acid sequence for Orf10 encoded by orf10, corresponding to nucleotides 18815 to 19801 of SEQ ID NO: 54. Orf10 is homologous to an integral membrane protein.

SEQ ID NO: 11 is the amino acid sequence for Orf11 encoded by orf11, corresponding to nucleotides 19889 to 21616 of SEQ ID NO: 54. Orf11 is homologous to a putative ECF-family RNA polymerase sigma factor.

SEQ ID NO: 12 is the amino acid sequence for Orf12 encoded by orf12, corresponding to nucleotides 21753 to 22910 of SEQ ID NO: 54. Orf12 is homologous to FAD-dependent pyridine nucleotide-disulphide oxidoreductase.

SEQ ID NO: 13 is the amino acid sequence for Orf13 encoded by orf13, corresponding to nucleotides 23582 to 24052 of SEQ ID NO: 54. Orf13 is homologous to hypothetical protein SC04094.

SEQ ID NO: 14 is the amino acid sequence for Orf14 encoded by orf14, corresponding to nucleotides 24165 to 24932 of SEQ ID NO: 54. Orf14 is homologous to translation initiation factor IF-2.

SEQ ID NO: 15 is the amino acid sequence for Orf15 encoded by orf15, corresponding to nucleotides 25050 to 25502 of SEQ ID NO: 54. Orf15 is homologous to translation initiation factor IF-2.

SEQ ID NO: 16 is the amino acid sequence for Orf16 encoded by orf16, corresponding to nucleotides 25602 to 27968 of SEQ ID NO: 54. Orf16 is homologous to ATP-dependent RNA helicase.

SEQ ID NO: 17 is the amino acids sequence for PtmY encoded by orf28 or ptmY, corresponding to the reverse complement of nucleotides 29893 to 31086 of SEQ ID NO: 54. PtmY is homologous to cytochrome P450 monooxygenase.

SEQ ID NO: 18 is the amino acids sequence for PtmZ encoded by orf29 or ptmZ, corresponding to the reverse complement of nucleotides 31140 to 31628 of SEQ ID NO: 54. PtmZ is homologous to glutathione peroxidase.

SEQ ID NO: 19 is the amino acids sequence for PtmA encoded by orf30 or ptmA, corresponding to the reverse complement of nucleotides 31845 to 33020 of SEQ ID NO: 54. PtmA is homologous to aminotransferase.

SEQ ID NO: 20 is the amino acid sequence for PtmB encoded by orf31 or ptmB, corresponding to the reverse complement of nucleotides 33035 to 34747 of SEQ ID NO: 54. PtmB is homologous to carbamoyltransferase.

SEQ ID NO: 21 is the amino acid sequence for PtmC encoded by orf32 or ptmC, corresponding to nucleotides 35020 to 36123 of SEQ ID NO: 54. PtmC is homologous to radical SAM oxidoreductase.

SEQ ID NO: 22 is the amino acid sequence for PtmD encoded by orf33 or ptmD, corresponding to nucleotides 36189 to 37265 of SEQ ID NO: 54. PtmD is homologous to methyltransferase.

SEQ ID NO: 23 is the amino acid sequence for PtmE encoded by orf34 or ptmE, corresponding to the reverse complement of nucleotides 37258 to 37794 of SEQ ID NO: 54. PtmE is homologous to glucokinase.

SEQ ID NO: 24 is the amino acid sequence for PtmF encoded by orf35 or ptmF, corresponding to the reverse complement of nucleotides 37794 to 38444 of SEQ ID NO: 54. PtmF contains a DNA-binding winged-HTH domain.

SEQ ID NO: 25 is the amino acid sequence for PtmG encoded by orf36 or ptmG, corresponding the reverse complement of nucleotides 38620 to 39756 of SEQ ID NO: 54. PtmG is homologous to nucleotydyltransferase and deacetylase.

SEQ ID NO: 26 is the amino acid sequence for PtmH encoded by orf37 or ptmH, corresponding to nucleotides 40175 to 42160 of SEQ ID NO: 54. PtmH is believed is homologous to methyltransferase.

SEQ ID NO: 27 is the amino acid sequence for PtmI encoded by orf38 or ptmI, corresponding to nucleotides 42192 to 42476 of SEQ ID NO: 54. PtmI is homologous to an acyl carrier protein.

SEQ ID NO: 28 is the amino acid sequence for PtmJ encoded by orf39 or ptmJ, corresponding to nucleotides 42482 to 43438 of SEQ ID NO: 54. PtmJ is homologous to glycosyltransferase.

SEQ ID NO: 29 is the amino acid sequence for PtmK encoded by orf40 or ptmK, corresponding to nucleotides 43435 to 45123 of SEQ ID NO: 54. PtmK is homologous to 3-oxoacyl-(ACP) synthase.

SEQ ID NO: 30 is the amino acid sequence for PtmL encoded by orf41 or ptmL, corresponding to nucleotides 45116 to 46843 of SEQ ID NO: 54. PtmL is homologous to methyltransferase.

SEQ ID NO: 31 is the amino acid sequence for PtmM encoded by orf42 or ptmM, corresponding to nucleotides 46894 to 48630 of SEQ ID NO: 54. PtmM is homologous to methyltransferase.

SEQ ID NO: 32 is the amino acid sequence for PtmN encoded by orf43 or ptmN, corresponding to nucleotides 48634 to 49689 of SEQ ID NO: 54. PtmN is homologous to oxidoreductase or a dehydrogenase.

SEQ ID NO: 33 is the amino acid sequence for PtmO encoded by orf44 or ptmO, corresponding to the reverse complement of nucleotides 50000 to 50773 of SEQ ID NO: 54. PtmO is homologous to hydrolase and acyltransferase.

SEQ ID NO: 34 is the amino acid sequence for PtmP encoded by orf45 or ptmP, corresponding to nucleotides 50883 to 51518 of SEQ ID NO: 54. PtmP is homologous to phosphopantetheinyltransferase.

SEQ ID NO: 35 is the amino acid sequence for PtmQ encoded by orf46 or ptmQ, corresponding to the reverse complement of nucleotides 52474 to 58008 of SEQ ID NO:

54. PtmQ is believed to function as a polyketide synthase or 6-methylsalicylic acid synthase.

SEQ ID NO: 36 is the amino acid sequence for PtmR encoded by orf47 or ptmR, corresponding to the reverse complement of nucleotides 58056 to 59129 of SEQ ID NO: 54. PtmR is homologous to oxoacyl-[acyl-carrier-protein] synthase.

SEQ ID NO: 37 is the amino acid sequence for PtmS encoded by orf48 or ptmS, corresponding to the reverse complement of nucleotides 59143 to 60660 of SEQ ID NO: 54. PtmS is homologous to acyl-CoA synthetase.

SEQ ID NO: 38 is the amino acid sequence for PtmT encoded by orf49 or ptmT, corresponding to the reverse complement of nucleotides 60657 to 61991 of SEQ ID NO: 54. PtmT is believed to function as an aminotransferase, such as a glutamate-1-semialdehyde aminotransferase.

SEQ ID NO: 39 is the amino acid sequence for PtmU encoded by orf50 or ptmU, corresponding to nucleotides 62153 to 62992 of SEQ ID NO: 54. PtmU is homologous to oxidoreductase.

SEQ ID NO: 40 is the amino acid sequence for PtmV encoded by orf51 or ptmV, corresponding to nucleotides 63030 to 63710 of SEQ ID NO: 54. PtmV is homologous to phosphoglycerate mutase/phosphatase.

SEQ ID NO: 41 is the amino acid sequence encoded by orf52 or ptm W, corresponding to nucleotides 64635 to 65450 of SEQ ID NO: 54. PtmW is homologous to a hypothetical protein SAV_3686.

SEQ ID NO: 42 is the amino acid sequence encoded by orf53 or ptmX, corresponding to nucleotides 66186 to 67481 of SEQ ID NO: 54. PtmX is homologous to integral membrane protein.

SEQ ID NO: 43 is the amino acid sequence for Orf17 encoded by orf17, corresponding to nucleotides 67855 to 69201 of SEQ ID NO: 54. Orf17 is homologous to peptidase.

SEQ ID NO: 44 is the amino acid sequence for Orf18 encoded by orf18, corresponding to nucleotides 69778 to 70359 of SEQ ID NO: 54. Orf18 is homologous to acetyltransferase.

SEQ ID NO: 45 is the amino acid sequence for Orf19 encoded by orf19, corresponding to the reverse complement of nucleotides 7034 to 7347 of SEQ ID NO: 54. Orf19 is homologous to ATP-dependent helicase.

SEQ ID NO: 46 is the amino acid sequence for Orf20 encoded by orf20, corresponding to nucleotides 73641 to 74723 of SEQ ID NO: 54. Orf20 is homologous to hypothetical protein LEUM_1013.

SEQ ID NO: 47 is the amino acid sequence for Orf21 encoded by orf21, corresponding to the reverse complement of nucleotides 74737 to 76386 of SEQ ID NO: 54. Orf21 is homologous to hypothetical protein SAV_4116.

SEQ ID NO: 48 is the amino acid sequence for Orf22 encoded by orf22, corresponding to nucleotides 76463 to 76867 of SEQ ID NO: 54. Orf22 is homologous to glycosyl transferase or hypothelical protein SCO5273.

SEQ ID NO: 49 is the amino acid sequence for Orf23 encoded by orf23, corresponding to the reverse complement of nucleotides 77327 to 78619 of SEQ ID NO: 54. Orf23 is homologous to methyltransferase.

SEQ ID NO: 50 is the amino acid sequence for Orf24 encoded by orf24, corresponding to the reverse complement of nucleotides 78767 to 79951 of SEQ ID NO: 54. Orf24 is homologous to dehydrogenase and hypothetical protein SCO4113.

SEQ ID NO: 51 is the amino acid sequence for Orf25 encoded by orf25, corresponding to the reverse complement of nucleotides 80490 to 81968 of SEQ ID NO: 54. Orf25 is homologous to sporulation associated protein.

SEQ ID NO: 52 is the amino acid sequence for Orf26 encoded by orf26, corresponding to nucleotides 82831 to 84993 of SEQ ID NO: 54. Orf26 is homologous to a secreted protein or asparagine synthetase.

SEQ ID NO: 53 is the partial amino acid sequence for Orf27 encoded by orf27, corresponding to nucleotides 85154 to 86350 of SEQ ID NO: 54.

SEQ ID NO: 54 is the nucleic acid sequence of an 86.35 kb genetic locus including a pactamycin gene cluster.

SEQ ID NOs: 55 and 56 are oligonucleotide sequences employed to amplify the ketosynthase domain in the rifB gene.

SEQ ID NOs: 57 and 58 are oligonucleotide sequences employed to amplify the aminotransferase gene cetM from the cetoniacytone A biosynthetic gene cluster.

DETAILED DESCRIPTION

I. Introduction

Aminocyclitol antibiotics have long been known for their significant biological activities. Many of them, e.g., gentamicin, kanamycin, neomycin, and streptomycin, have been used clinically for decades as potent antimicrobial agents (FIG. 1A; Begg and Barclay, *Br. J. Clin. Pharmacol.* 39: 597-603, 1995). Other analogs, e.g., hygromycin A and spectinomycin, are used frequently as animal medicines in veterinary and agricultural applications, and as selection markers in molecular genetic studies (Biehl, *Vet. Clin. North. Am. Food Anim. Pract.*, 2: 481-487, 1986; Nakagawa et al., *J. Antibiot.* (Tokyo) 40: 1627-1635, 1987; and Schwarz et al., *J. Antimicrob. Chemother.* 53: 379-382, 2004).

Figure 1B:
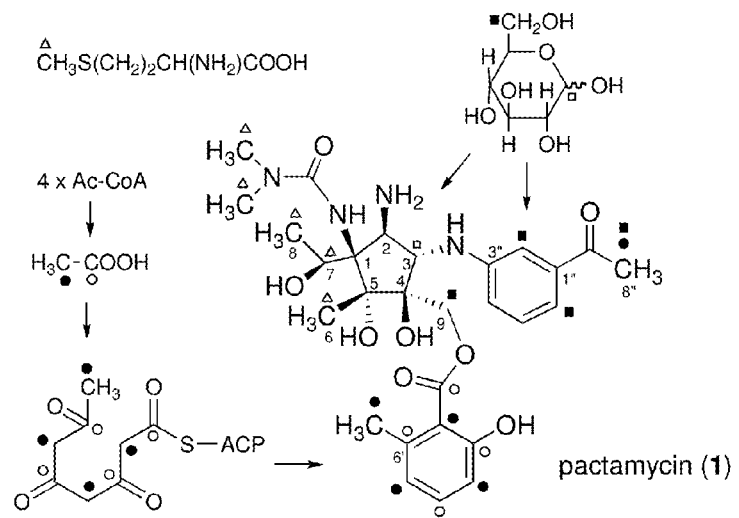
FIG. 1B illustrates the structure of pactamycin as well as the site of incorporation of certain carbons from precursors in the biosynthesis of pactamycin.

Pactamycin, a structurally unique aminocyclitol antibiotic isolated from *Streptomyces pactum*, consists of a 5-member ring aminocyclitol (cyclopentitol) unit, two aromatic rings (6-methyl salicylic acid and 1-(3-amino-phenyl)-ethanone) and a 1,1-dimethylurea (Wiley et al., *J. Org. Chem.*, 35: 1420-1425, 1970; and Rinehart et al., *J. Nat. Prod.* 43: 1-20, 1979; FIG. 1B). Cyclopentitol-derived aminocyclitols are relatively rare in nature. However, their biological activities and their unique structures have been attractive objects of investigation. Besides pactamycin, interesting cyclopentitol-derived natural products include allosamidin, a chitinase inhibitor isolated from *Streptomyces* sp. no. 1713 (Sakuda et al., *J. Antibiot.* (Tokyo) 40: 296-300, 1987) and trehazolin, a potent trehalase inhibitor produced by *Micromonospora coriacea* (SANK 62192; Ando et al., *J. Antibiot.* (Tokyo) 44: 1165-1168, 1991). Cyclopentitol moieties are also found in carbocyclic nucleosides and related compounds, e.g., neplanocin A (Hayashi et al., *J. Antibiot.* (Tokyo), 34: 675-680, 1981), aristeromycin (Kusaka et al., *J. Antibiot.* (Tokyo), 21: 255-263, 1968), adecypenol (Omura et al., *J. Antibiot.* (Tokyo) 39: 309-310, 1986), queuosine and its analog epoxyqueuosine (Nishimura, *Prog. Nucleic Acid Res. Mol. Biol.* 28: 49-73, 1986).

To date, biosynthetic studies of pactamycin have only been performed by conventional feeding experiments with isotopically labeled precursors. It has been suggested that the five-member ring aminocyclitol moiety of pactamycin is derived from glucose, whereas the 6-methyl salicylic acid is derived from acetic acid. The 1-(3-aminophenyl)-ethanone) or 3-aminoacetophenone moiety is derived from an unknown branch of the amino-shikimate pathway. The four-methyl groups and the hydroxymethine carbon in the molecule are derived from methionine as shown in FIG. 1B (Weller and Rinehart, *J. Am. Chem. Soc.*, 100: 6757-6760, 1978).

Pactamycin has potent antibacterial activities against Gram-positive and Gram-negative bacteria (Bhuyan, *Appl. Microbiol.*, 10: 302-304, 1962). It also shows a strong anti-tumor activity. However, clinical application of pactamycin was finally abandoned due to its high toxicity. To improve its efficacy and reduce its toxicity, further structural modification of the compound is desirable. Such an objective is difficult to achieve by chemical synthesis due to the complexity of the molecule, and therefore, requires alternative approaches, e.g., biosynthetic or genetic modification methods.

The application of contemporary molecular genetic approaches to study the biosynthesis of antibiotics has revolutionized the way drug discovery is conducted. Using genetically engineered microorganisms, dozens of structurally altered antibiotics have recently been generated (Staunton and Weissman, *Nat. Prod. Rep.*, 18: 380-416, 2001), ranging from analogs of the antibiotic erythromycin (Marsden et al., *Science,* 279: 199-202, 1998; and McDaniel et al., *Proc. Natl. Acad. Sci. U.S.A.* 96: 1846-1851, 1999) to the anthelmintic avermectins (Stutzman-Engwall et al., *Biotechnol. Bioeng.* 82: 359-369, 2003) and the anti-tumor agents, the epothilones (Arslanian et al., *J. Nat. Prod.* 65: 1061-1064, 2002). Similar approaches can be used for generating analogs of pactamycin. In addition, genetic methods can be used to generate analogs that are difficult to make using traditional synthetic methodologies. For example, the chemical cleavage of the two aromatic rings (6-methylsalicylic acid and 1-(3-amino-phenyl)-ethanone) may be difficult to accomplish without affecting other parts of the molecule.

However, inactivation of the genes that are responsible for the attachments of these side chains may results in mutant strains of bacteria that produce intermediates, which may have distinct pharmacological properties as compared to the parent compound. Structural variability at those positions can also be further developed using combinatorial synthetic approaches, mutasynthesis, or enzymatic methodologies to generate libraries of pactamycin analogs.

As the biosynthetic gene cluster for pactamycin was not available, it was necessary to identify and characterize the genes responsible for the production of this important antibiotic in *S. pactum*. Knowledge of the genetic information is a prerequisite for the success of the molecular genetic approaches described above.

This disclosure describes the molecular cloning of the pactamycin biosynthetic gene cluster from *S. pactum* ATCC 27456, characterization of the individual genes in the gene cluster and the proteins encoded thereby and their uses (such as for drug discovery and development purposes). The pactamycin gene cluster was isolated by constructing a genomic library using the Copy Control Fosmid system (EPICENTRE).

Figure 2:
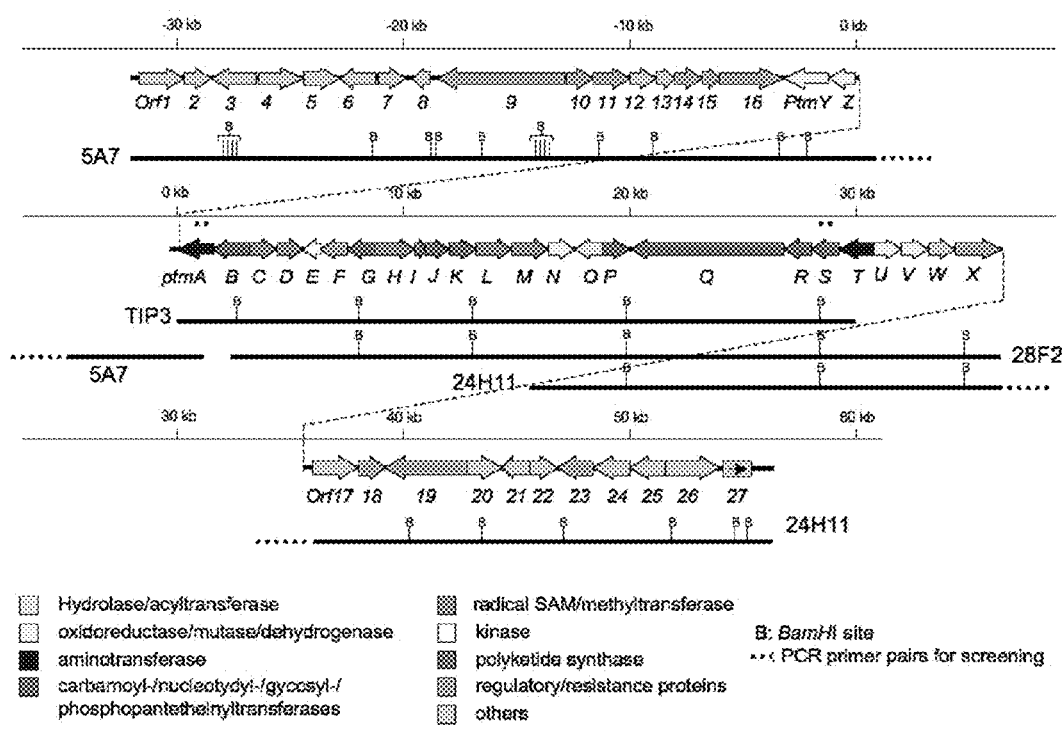
FIG. 2 is a schematic drawing showing the genetic organization of the pactamycin biosynthetic gene cluster from *S. pactum* ATCC 27456.

The library was screened using a number of heterologous probes including the PKS module of the rifamycin gene cluster (rifB) (August et al., *Chem. Biol.* 5: 69-79, 1998), the aminotransferase gene from the cetoniacytone A biosynthetic gene cluster (cetM) and the C-methyltransferase gene from the clorobiocin biosynthetic gene cluster (cloU) (Freitag et al., *Microbiology* 152: 2433-2442, 2006). The isolated genetic loci containing the pactamycin biosynthetic gene cluster is 86.35 kb (SEQ ID NO: 54) and includes 53 oils. Sequence analysis reveals peroxidase/hydrolase genes, oxidoreductase/mutase/dehydrogenase/hydroxylase genes, aminotransferase genes, carbamoyl-/nucleotidyl-/glycosyl-/phosphopantetheinyltransferase genes, methyltransferase genes, kinase genes, polyketide synthetase (PKS) genes and regulatory genes (FIG. 2).

II. Abbreviations and Terms a. Abbreviations aa amino acid
LCMS liquid chromatography mass spectrometry
NRPS non-ribosomal peptide synthetase
ORF open reading frame
PKS polyketide synthetase
Ptm or ptm pactamycin
SNP single nucleotide polymorphism b. Terms

Unless otherwise noted, technical terms are used according to conventional usage. Definitions of common terms in molecular biology may be found in Benjamin Lewin *Genes V* published by Oxford University Press, 1994 (ISBN 0-19-854287-9); Kendrew et al. (eds.) *The Encyclopedia of Molecular Biology*, published by Blackwell Science Ltd., 1994 (ISBN 0-632-02182-9); and Robert A. Meyers (ed.) *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Acyl: A group of the formula RC(O)— wherein R is an organic group.

Aliphatic: Moieties including alkyl, alkenyl, alkynyl, halogenated alkyl and cycloalkyl groups as described below. A "lower aliphatic" group is a branched or unbranched aliphatic group having from 1 to 10 carbon atoms.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. The terms "halogenated alkyl" or "haloalkyl group" refer to an alkyl group as defined above with one or more hydrogen atoms present on these groups substituted with a halogen (F, Cl, Br, I). The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous. Optionally substituted groups, such as "substituted alkyl," describes groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

Alkenyl: A hydrocarbon group of 2 to 24 carbon atoms and structural formula containing at least one carbon-carbon double bond.

Alkynyl: A hydrocarbon group of 2 to 24 carbon atoms and a structural formula containing at least one carbon-carbon triple bond.

Allelic variant: A naturally occurring alternate form of a polypeptide that is characterized as having a substitution, deletion, or addition of one or more amino acids as compared to the wildtype form of the sequence. In one example, the variant does not alter the biological function of the polypeptide. In other examples, the variant includes a mutation that alters the biological function of the polypeptide.

Amino acid: Amino acid refers to both natural and unnatural amino acids, including their D and L stereoisomers for chiral amino acids. Natural and unnatural amino acids are well known to those of ordinary skill in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Uncommon and unnatural amino acids include, without limitation, allyl glycine (AllylGly), biphenylalanine (Bip), citrulline (Cit), 4-guanidinophenylalanine (Phe(Gu)), homoarginine (hArg), homolysine (hLys), 2-napthylalanine (2-Nal), ornithine (Orn) and pentafluorophenylalanine (F5Phe).

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Additional amino acids that are classified in each of the above groups are known to those of ordinary skill in the art. Exemplary pactamycin analogs disclosed herein are functionalized, chemically or biosynthetically, with one or more amino acid residues. Amplification: When used in reference to nucleic acids, amplification refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Antibiotic: A substance, for example pactamycin, penicillin or streptomycin, often produced by or derived from certain fungi, bacteria, and other organisms, that can destroy or inhibit the growth of other microorganisms.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T, and ribose is substituted for deoxyribose). Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one of ordinary skill in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

Biological function: The function(s) of a polypeptide in the cells in which it naturally occurs. A polypeptide can have more than one biological function.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Conservative substitution: Amino acid substitutions that do not substantially alter the activity (specificity or binding affinity) of the molecule. Typically conservative amino acid substitutions involve substitutions of one amino acid for another amino acid with similar chemical properties (e.g., charge or hydrophobicity).

The following table shows exemplar conservative amino acid substitutions:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

DNA (deoxyribonucleic acid): A long chain polymer which comprises the genetic material of most living organisms (some viruses have genes comprising ribonucleic acid (RNA). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Domain: A portion of a molecule such as proteins or nucleic acids that is structurally and/or functionally distinct from another portion of the molecule.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential function(s) of a protein. See Stryer *Biochemistry* 3rd Ed., (c) 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *J. Immunol.* 159(5): 2502-12, 1997). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. Many methods for labeling polypeptides and labels useful for such purposes are well known in the art, and include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, 200, or even more amino acid residues.

Gene Cluster: A set of genetic elements the protein products of which form a biosynthetic pathway. For example, the pactamycin biosynthetic pathway from *Streptomyces pactum* can be formed by the gene cluster including ORFs 1 to 53.

Heterologous: As it relates to nucleic acid sequences such as coding sequences and control sequences, "heterologous" denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different than the native gene). Similarly, a host cell transformed with a construct which is not normally present in the host cell would be considered heterologous for purposes of this disclosure.

Homologous amino acid sequence: Any polypeptide which is encoded, in whole or in part, by a nucleic acid sequence that hybridizes to any portion of the coding region nucleic acid sequences. A homologous amino acid sequence is one that differs from an amino acid sequence shown in the sequence listing by one or more conservative amino acid substitutions. Such a sequence also encompasses allelic variants (defined above) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any one of the amino acid sequences.

Homologous amino acid sequences include sequences that are identical or substantially identical to the amino acid sequences of the sequence listing. By "substantially identical to the amino acid sequence" it is meant a sequence that is at least 90%, preferably 95%, more preferably 97%, and most preferably 99% identical to an amino acid sequence of reference. In an example, the sequence is at least 90% and differs from the sequence of reference by conservative amino acid substitutions. Polypeptides having a sequence homologous to any one of the amino acid sequences of the sequence listing include naturally-occurring allelic variants, as well as mutants or any other non-naturally occurring variants that retain the inherent characteristics (e.g., biosynthetic activity) of any polypeptide of the sequence listing. Homology can be measured using sequence analysis software such as Sequence Analysis Software Package of the Genetics Computer Group, University of Wisconsin Biotechnology Center, 1710 University Avenue, Madison, Wis. 53705 Amino acid sequences can be aligned to maximize identity. Gaps can also be artificially introduced into the sequence to attain optimal alignment. Once the optimal alignment has been set up, the degree of homology is established by recording all of the positions in which the amino acids of both sequences are identical, relative to the total number of positions. Homologous polynucleotide sequences are defined in a similar way. Preferably, a homologous sequence is one that is at least 45%, 50%, 60%, 70%, 75%, 80%, 85%, 86%, 87%, 88%, 89%, 90%, 91%, 92%, 93%, 94%, 95%, 96%, 97%, 98%, 99% or identical to any one of the coding sequences.

Hybridization: Oligonucleotides and other nucleic acids hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between two distinct nucleic acid sequences or two distinct regions of the same nucleic acid sequence.

For example, specifically hybridizable and specifically complementary are terms that indicate a sufficient degree of complementarity such that stable and specific binding occurs between a first nucleic acid (such as, an oligonucleotide) and a DNA or RNA target. The first nucleic acid (such as, an oligonucleotide) need not be 100% complementary to its target sequence to be specifically hybridizable. A first nucleic acid (such as, an oligonucleotide) is specifically hybridizable when there is a sufficient degree of complementarity to avoid non-specific binding of the first nucleic acid (such as, an oligonucleotide) to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though wash times also influence stringency. Calculations regarding hybridization conditions required for attaining particular degrees of stringency are discussed by Sambrook et al. (ed.) *Molecular Cloning: A Laboratory Manual,* 2nd ed., vol. 1-3, Cold Spring Harbor Laboratory Press, Cold Spring Harbor, N.Y., 1989, chapters 9 and 11.

The following are exemplary sets of hybridization conditions and are not meant to be limiting.

Very High Stringency (Detects Sequences that Share 90% Sequence Identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Detects Sequences that Share 80% Sequence Identity or Greater)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Detects Sequences that Share Greater than 50% Sequence Identity)
  Hybridization: 6×SSC at RT to 55° C. for 16-20 hours
  Wash at least twice: 2×-3×SSC at RT to 55° C. for 20-30 minutes each.

In-frame disruption: An alteration of a target nucleotide sequence (e.g., insertion, deletion, or other alteration of the sequence) that is made in frame and thereby does not lead to a frameshift, e g, maintains the translational reading frame of the target sequence and any downstream sequences. In certain instances, an in-frame disruption may alter the entire sequence of a gene product, so that the determination as to whether the alteration was made in-frame is made by reference to downstream nucleotide sequences and gene products encoded thereby. By way of contrast, an alteration to a target nucleotide sequence that is not in-frame, and therefore does not give rise to an in-frame disruption, would not maintain the translational reading frame of the target sequence or a sequence located downstream of the target sequence.

Isolated: An isolated biological component (such as a nucleic acid molecule or protein) is one that has been substantially separated or purified away from other biological components in the cell of the organism in which the component naturally occurs, such as other chromosomal and extra-chromosomal DNA and RNA, proteins and organelles. With respect to nucleic acids and/or polypeptides, the term can refer to nucleic acids or polypeptides that are no longer flanked by the sequences typically flanking them in nature. Nucleic acids and proteins that have been isolated include nucleic acids and proteins purified by standard purification methods. The term also embraces nucleic acids and proteins prepared by recombinant expression in a host cell as well as chemically synthesized nucleic acids.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (*Molecular Cloning: A Laboratory Manual*, Cold Spring Harbor, New York, 1989) and Ausubel et al. (*In Current Protocols in Molecular Biology*, John Wiley & Sons, New York, 1998).

Nucleic Acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Nucleotide: This term includes, but is not limited to, a monomer that includes a base linked to a sugar, such as a pyrimidine, purine or synthetic analogs thereof, or a base linked to an amino acid, as in a peptide nucleic acid. A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, or 20 bases.

Open reading frame (ORF): A series of nucleotide triplets (codons) coding for amino acids without any internal termination codons. These sequences are usually translatable into a peptide. For example, ORF, open reading frame, and pactamycin ORF refer to an open reading frame in the pactamycin biosynthetic gene cluster as isolated from *Streptomyces pactum*. The term also embraces the same ORFs as present in other pactamycin-synthesizing organisms. The term encompasses allelic variants and single nucleotide polymorphisms (SNPs). In certain instances the term pactamycin ORF is used synonymously with the polypeptide encoded by the pactamycin ORF and may include conservative substitutions in that polypeptide. The particular usage will be clear from context.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ortholog: Two nucleic acid or amino acid sequences are orthologs of each other if they share a common ancestral sequence and diverged when a species carrying that ancestral sequence split into two species. Orthologous sequences are also homologous sequences.

Pactamycin: A structurally unique aminocyclitol antibiotic isolated from *Streptomyces pactum*, consists of a 5-member ring aminocyclitol (cyclopentitol) unit, two aromatic rings (6-methyl salicylic acid 3-aminoacetophenone) and a 1,1-dimethylurea (Wiley et al., *J. Org. Chem.*, 35: 1420-1425, 1970; and Rinehart et al., *J. Nat. Prod.* 43: 1-20, 1979) as illustrated in FIG. 1B. It has been suggested that the five-member ring aminocyclitol moiety of pactamycin is derived from glucose, whereas the 6-methyl salicylic acid is derived from acetic acid. The 3-aminoacetophenone moiety is derived from an unknown branch of the amino-shikimate pathway. The four-methyl groups and the hydroxymethine carbon in the molecule are derived from methionine as shown in FIG. 1B (Weller and Rinehart, *J. Am. Chem. Soc.*, 100: 6757-6760, 1978). Pactamycin has potent antibacterial activities against Gram-positive and Gram-negative bacteria (Bhuyan, *Appl. Microbiol.*, 10: 302-304, 1962). It also shows a strong anti-tumor activity.

Polypeptide: A polymer in which the monomers are amino acid residues which are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase functional fragment of a polypeptide refers to all fragments of a polypeptide that retain an activity (such as a biological activity), or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell.

The term substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides, 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 17, 20, 23, 25, 30, 35, 40, 45, 50 or more consecutive nucleotides of desired nucleotide sequence. In particular examples, probes or primers can be at least 100, 250, 500, 600 or 1000 consecutive nucleic acids of a desired nucleotide sequence.

Protein: A biological molecule expressed by a gene and comprised of amino acids.

Purified: The term purified does not require absolute purity; rather, it is intended as a relative term. Thus, for example, a purified protein preparation is one in which the protein referred to is more pure than the protein in its natural environment within a cell.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins (or nucleic acids) with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

An alternative indication that two nucleic acid molecules are closely related is that the two molecules hybridize to each other (see "Hybridization" above).

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

*Streptomyces*: A genus of Actinobacteria, a group of Gram-positive and generally high GC-content bacteria.

Streptomycetes are found predominantly in soil and in decaying vegetation, and most produce spores. They are characterized by a complex secondary metabolism and produce a large number of antibiotics that are in clinical use (such as, neomycin and chloramphenicol).

Transfected: A process by which a nucleic acid molecule is introduced into cell, for instance by molecular biology techniques, resulting in a transfected (or transformed) cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

Suitable methods and materials for the practice of the disclosed embodiments are described below. In addition, any appropriate method or technique well known to the ordinarily skilled artisan can be used in the performance of the disclosed embodiments. Some conventional methods and techniques applicable to the present disclosure are described, for example, in Sambrook et al., *Molecular Cloning: A Laboratory Manual*, 2$^{nd}$ ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Pactamycin Gene Cluster, ORFs, and Proteins Encoded Thereby

This disclosure provides the nucleic acid sequence of a pactamycin gene cluster located within an 86.35 kb genetic locus (SEQ ID NO: 54), the ORFs contained therein, and the proteins encoded thereby. This information enables, for example, the isolation of related nucleic acid molecules encoding homologs of the pactamycin gene cluster and the corresponding ORFs, such as in other *Streptomyces* sp. This disclosure further enables the production of variants of the enzymes (such as, methyltransferases and peroxidases) or proteins (such as a regulatory protein) encoded by a pactamycin gene cluster or subsequence therein, nucleic acid molecules encoding such variants, and the production of in vitro systems for drug manufacture.

The pactamycin gene cluster (SEQ ID NO: 54, nucleotides 1-86350) includes 53 ORFs referred to as ORF 1 to 53, from which 26 ORFs are considered to be the core cluster directly involved in the biosynthesis of pactamycin (orf28-orf53 corresponding to ptmA-ptmZ). Exemplary functions of the proteins encoded by genes forming the core cluster (ptmA-ptmZ) and numerous additional genes upstream and downstream of the core cluster (orf1 to orf27) which may be involved in the transcriptional regulation of the pathway and/or in resistance, are provided in Table 1; these functions are assigned by homology.

TABLE 1

Function of proteins encoded by genes in the pactamycin gene cluster.

| Protein | SEQ ID NO. | aa | Exemplary function (homologous protein and/or source organism) | Identity (%) | Sim. (%) |
|---|---|---|---|---|---|
| PtmA | 19 | 391 | Glutamine-scyllo-inositol transaminase *Roseiflexus castenholzii*) L-alanine: N-amidino-3-keto-scyllo inosamine aminotransferase (StsC, *Strep. griceus*) | 43 37 | 54 50 |
| PtmB | 20 | 570 | Carbamoyltransferase (MmcS, *Strep. lavendulae*) | 47 | 59 |
| PtmC | 21 | 367 | Fe-S Radical SAM oxidoreductase (MitD, *Strep. lavendulae*) | 32 | 50 |
| PtmD | 22 | 358 | HemK family methyltransferase (*Strep. ambofaciens*) | 35 | 49 |
| PtmE | 23 | 178 | Hypothetical protein SACE-5647 (*Saccharopolyspora erythraea*) | 38 | 59 |
| PtmF | 24 | 216 | UDP-N-acetylglucosamine 1-carboxyvinyltransferase (*Streptococcus gordonii* str. Challis substr. CH1) or DNA binding winged-HTH domain (*Silicibacter* sp.) | 26 38 | 41 52 |
| PtmG | 25 | 378 | Putative deacetylase (MitC, *Strep. lavendulae*) | 38 | 46 |
| PtmH | 26 | 661 | Radical SAM + B12 domain protein (*Salinispora arenicola*) | 53 | 69 |
| PtmI | 27 | 94 | Putative acyl carrier protein (*Clostridium perfringens*) | 33 | 61 |
| PtmJ | 28 | 318 | Glycosyltransferase (MiB, *Strep. lavendulae*) | 34 | 43 |
| PtmK | 29 | 562 | 3-oxoacyl-(ACP) synthase (*Saccharopolyspora erythreae*) | 44 | 55 |
| PtmL | 30 | 575 | Radical SAM + B12 binding domain (*Rhodospeudomonas palustris*) | 32 | 47 |
| PtmM | 31 | 578 | Radical SAM + B12 binding domain (*Rhodospeudomonas palustris*) | 31 | 46 |
| PtmN | 32 | 351 | Oxidoreductase (YcjS, *Escherichia coli*) | 33 | 50 |
| PtmO | 33 | 257 | Hydrolase or acyltransferase (*Rhodococcus* sp.) | 40 | 52 |
| PtmP | 34 | 211 | Phosphopantetheinyltransferase (PptA, *Silicibacter pomeroyi*) | 43 | 55 |

TABLE 1-continued

Function of proteins encoded by genes in the pactamycin gene cluster.

| Protein | SEQ ID NO. | aa | Exemplary function (homologous protein and/or source organism) | Identity (%) | Sim. (%) |
|---|---|---|---|---|---|
| PtmQ | 35 | 1844 | PKS (6-methylsalicylic acid synthase) (ChlB1, S. antibioticus) | 53 | 63 |
| PtmR | 36 | 357 | 3-oxoacyl-(ACP) synthase (CalO4, Micromonospora echinospora) | 41 | 59 |
| PtmS | 37 | 505 | Acyl-CoA synthetase (HbmAI, Strep. hygroscopicus) | 29 | 37 |
| PtmT | 38 | 444 | Glutamate-1-semialdehyde aminotransferase (Staphylococcus aureus) | 37 | 56 |
| PtmU | 39 | 279 | NAD$^+$-dependent oxidoreductase (SimJ1, Strep. antibioticus) | 40 | 53 |
| PtmV | 40 | 226 | Phosphoglycerate mutase (Nocardia farcinica) | 37 | 53 |
| PtmW | 41 | 271 | Hypothetical protein SAV3686 (Strep. avermitilis) | 46 | 55 |
| PtmX | 42 | 431 | Integral membrane protein (Strep. coelicolor) | 58 | 68 |
| PtmY | 17 | 397 | Cytochrome P450 monooxygenase (Strep. tubercidicus) | 59 | 71 |
| PtmZ | 18 | 162 | Glutathione peroxidase (Mycobacterium vanbaaleni) | 60 | 72 |
| Orf1 | 1 | 483 | Phosphoribosylformylglycinamidine synthase II (Strep. coelicolor) | 86 | 92 |
| Orf2 | 2 | 295 | Hypothetical protein SAV4137 (Strep. avermitilis) | 59 | 68 |
| Orf3 | 3 | 524 | N-acetylgalactosamine-6-sulfate sulfatase (Therm. fusca) | 53 | 65 |
| Orf4 | 4 | 527 | Amidophosphoribosyltransferase (Strep. coelicolor) | 89 | 96 |
| Orf5 | 5 | 366 | Phosphoribosylaminoimidazole synthetase (Strep. coelicolor) | 84 | 90 |
| Orf6 | 6 | 364 | Valine dehydrogenase (NADP+) (Strep. avermitilis) | 85 | 93 |
| Orf7 | 7 | 272 | Hypothetical protein SAV4131 (Strep. avermitilis) | 71 | 82 |
| Orf8 | 8 | 211 | Hypothetical protein blr0521 (Brady. japonicum) | 37 | 44 |
| Orf9 | 9 | 1328 | ATP-dependent helicase (Strep. avermitilis) | 79 | 88 |
| Orf10 | 10 | 328 | Integral memberane protein (Strep. coelicolor) | 76 | 84 |
| Orf11 | 11 | 575 | ECF-family RNA polymerase signma factor (Sacch. erythraea) | 48 | 62 |
| Orf12 | 12 | 385 | FAD-dependent pyridine nucleotide-disulphide oxidoreductase (Sacch. erythraea) | 49 | 60 |
| Orf13 | 13 | 156 | Hypothetical protein SCO4094 (Strep. coelicolor) | 93 | 96 |
| Orf14 | 14 | 255 | Translation initiation factor IF-2 (Frankia alni) | 32 | 35 |
| Orf15 | 15 | 150 | Translation initiation factor IF-2 (Strep. avermitilis) | 40 | 40 |
| Orf16 | 16 | 788 | ATP-dependent RNA helicase (Strep. avermitilis) | 69 | 76 |
| Orf17 | 43 | 488 | Peptidase (Strep. avermitilis) | 56 | 66 |
| Orf18 | 44 | 193 | Nourseothricin acetyltransferase (Strep. noursei) | 57 | 67 |
| Orf19 | 45 | 1043 | ATP-dependent helicase (Strep. avermitilis) | 67 | 80 |
| Orf20 | 46 | 360 | Hypothetical protein LEUM_1013 | 28 | 45 |
| Orf21 | 47 | 549 | Hypothetical protein SAV_4116 (Strep. avermitilis) or integral membrane protein (Strep. coelicolor) | 61 / 60 | 72 / 70 |
| Orf22 | 48 | 134 | Glycosyl transferase family 51 (Salin. Arenicola) or hypothetical protein SCO5273 | 38 / 37 | 44 / 45 |
| Orf23 | 49 | 430 | tRNA methyltransferase (Strep. avermitilis) | 79 | 85 |
| Orf24 | 50 | 394 | Hypothetical protein SCO4113 (Strep. coelicolor) (predicted dehydrogenase) | 80 | 84 |
| Orf25 | 51 | 492 | Sporulation associated protein (Strep. coelicolor) | 90 | 93 |
| Orf26 | 52 | 720 | Secreted protein (Strep. coelicolor) or asparagine synthetase (Strep. avermitilis) | 69 / 26 | 77 / 36 |
| Orf27 | 53 | 398 | Partial amino acid sequence | | |

A number of in vitro enzyme assays have previously been developed within homologous systems that can be used to assess the activity of recombinant proteins from the pactamycin pathway. These include assays that assess the activity of the aminotransferases (Huang et al., Org. Biomol. Chem., 3: 1410-1418, 2005), the carbamoyltransferases (Meyers et al., Biochemistry, 43: 15022-15036, 2004), the nucleotidyltransferases (Kudo et al., J. Am. Chem. Soc., 127: 1711-1718, 2005), the acyltransferases (Xiong et al., Chembiochem 6: 834-837, 2005), the phosphopantetheinyltransferases (Sanchez et al., Chem. Biol. 8: 725-738, 2001), the oxidoreductases (Shen et al., J. Biol. Chem. 269: 30726-30733, 1994), and the cytochrome P450 monooxygenases (Walczak et al., J. Bacteriol. 181: 298-304, 1999). Similar work has been done on the recombinant expression of PKS modules, similar to those required for the biosynthesis of the 6-methylsalicylic acid moiety of pactamycin (Reviewed in: Finking et al., Annu Rev. Microbiol., 58: 453-488, 2004; Hill, Nat. Prod. Rep., 23: 256-320, 2006).

In addition to the in vitro characterization of enzymes from the ptm pathway, genetic modification of the host and/or heterologous expression of the entire or partial gene cluster encoding patamycin biosynthesis may be utilized as a tool to study enzyme function and generate derivative compounds. The methodology used to generate deletion mutants in Actinomycetes is widely available and many well developed vector constructs exist for episomal replication as well as chromosomal integration (Keiser et al. Practical Streptomyces Genetics. John Innes Foundation, Norwich 2000). These tools may be utilized to generate S. pactum deletion mutants that specifically alter expression levels or other characteristics of specific gene loci within the ptm cluster.

In certain examples, the entire or partial gene cluster may be heterologously expressed in host strains, such as Streptomyces lividans and Pseudomonas putida. S. lividans and P. putida have been extensively used in the expression of complex biosynthetic gene clusters resulting in the production of secondary metabolites (Keiser et al., Practical Streptomyces Genetics. John Innes Foundation, Norwich 2000; Gross et al., Chem. Biol., 13: 1253-1264, 2006b; Wenzel et al., Chem. Biol., 12: 349-356, 2005).

With the provision herein of the sequences of the disclosed gene locus (SEQ ID NO: 54) and the ORFs contained therein (ORFS 1 to 53), in vitro nucleic acid amplification (such as PCR) may be utilized as a simple method for producing nucleic acid sequences encoding one or more of the pactamycin biosynthetic proteins listed in Table 1. The following provides representative techniques for preparing a protein-encoding nucleic acid molecule in this manner.

RNA or DNA is extracted from cells by any one of a variety of methods well known to those of ordinary skill in the art. Sambrook et al. (In Molecular Cloning: A Laboratory Manual, Cold Spring Harbor Laboratory Press, New York, 1989) and Ausubel et al. (In Current Protocols in

*Molecular Biology*, Greene Publ. Assoc. and Wiley-Intersciences, 1992) provide representative descriptions of methods for RNA or DNA isolation. The pactamycin biosynthetic enzymes are expressed, at least, in *Streptomyces pactum*. Thus, in some examples, RNA or DNA may be extracted from *Streptomyces pactum* cells. Extracted RNA is used, for example, as a template for performing reverse transcription (RT)-PCR amplification to produce cDNA. Representative methods and conditions for RT-PCR are described by Kawasaki et al. (In *PCR Protocols, A Guide to Methods and Applications*, Innis et al. (eds.) 21-27 Academic Press, Inc., San Diego, Calif., 1990).

The selection of amplification primers will be made according to the portion(s) of the DNA that is to be amplified. In one embodiment, primers may be chosen to amplify a segment of a DNA molecule (e.g., a specific ORF or set of adjacent ORFs, with or without regulatory sequences, or regulatory sequences alone) or, in another embodiment, the entire DNA molecule. Variations in amplification conditions may be required to accommodate primers and amplicons of differing lengths and composition; such considerations are well known in the art and are discussed for instance in Innis et al. (*PCR Protocols, A Guide to Methods and Applications*, Academic Press, Inc., San Diego, Calif., 1990). By way of example, the nucleic acid molecules encoding selected pactamycin biosynthetic enzymes (such as, methyltransferases) may be amplified using primers directed towards the 5'- and 3'-ends of the prototypical *S. pactum* ptm C, D, H, L, and M sequences which encode proteins with SEQ ID NOs: 21, 22, 26, 30, and 31. It will be appreciated that many different primers may be derived from the provided nucleic acid sequences. Re-sequencing of amplification products obtained by any amplification procedure is recommended to facilitate confirmation of the amplified sequence and to provide information on natural variation between a pactamycin and amplified sequence. Oligonucleotides derived from any of the pactamycin sequences may be used in sequencing, for instance, the corresponding pactamycin (or pactamycin-related) amplicon.

In addition, both conventional hybridization and PCR amplification procedures may be utilized to clone sequences encoding orthologs of the pactamycin gene cluster, or pactamycin ORFs (for example, one or more of the nucleic acids encoding SEQ ID NOs: 1-53). Common to both of these techniques is the hybridization of probes or primers that are derived from the pactamycin gene cluster, with or without the upstream and downstream flanking regions, or pactamycin ORFs nucleic acid sequences. Furthermore, the hybridization may occur in the context of Northern blots, Southern blots, or PCR.

Direct PCR amplification may be performed on DNA libraries prepared from the bacterial species in question, or RT-PCR may be performed using RNA extracted from the bacterial cells using standard methods. PCR primers will comprise at least 10 consecutive nucleotides of the pactamycin gene cluster with or without the upstream and downstream flanking regions or pactamycin ORFs nucleic acid sequences. One of skill in the art will appreciate that sequence differences between the pactamycin gene cluster or pactamycin ORFs nucleic acid sequences and the target nucleic acid to be amplified may result in lower amplification efficiencies. To compensate for this, longer PCR primers or lower annealing temperatures may be used during the amplification cycle. Whenever lower annealing temperatures are used, sequential rounds of amplification using nested primer pairs may be useful to enhance amplification specificity.

Orthologs of the disclosed pactamycin biosynthetic proteins are likely present in a number of other members of the *Streptomyces* genus, in other strains of the *Streptomyces pactum* species, and in other organisms producing pactamycin-like antibiotics. For example, *Streptomyces* sp. SIPI-A3-121 produces pactamycin analogs such as 8"-hydroxy-pactamycin and 7-deoxypactamycin (Dobashi et al., *J. Antibiot.* 39(12), 1779-1783, 1986). With the provision of the nucleic acid sequence of the disclosed pactamycin gene cluster and its ORFs 1-53, the cloning by standard methods of protein-encoding DNA (such as, ORFs) and gene clusters that encode pactamycin biosynthetic enzyme orthologs in these other organisms is now enabled. Orthologs of the disclosed pactamycin biosynthetic enzymes and proteins have a biological activity or function as disclosed herein, including for example peroxidase/hydrolase activity, oxidoreductase/mutase/dehydrogenase/hydroxylase activity, aminotransferase activity, methyltransferase activity, kinase activity, polyketide synthase activity or a regulatory protein function.

Orthologs will generally share sequence identity with the nucleic acid sequences encoding the disclosed pactamycin biosynthetic proteins (for example, one or more of SEQ ID NOs: 1-53) so that the primary functions of the proteins, such as the functions provided in Table 1, are maintained. In specific embodiments, orthologous pactamycin gene clusters or pactamycin ORFs may share at least 35%, at least 40%, at least 50%, at least 60%, at least 70%, at least 75%, at least 80% at least 85%, at least 90%, at least 91%, at least 93%, at least 95%, at least 96%, at least 97%, or at least 98% sequence identity (or more) with one of the disclosed *Streptomyces pactum* nucleotide or amino acid sequences.

For conventional hybridization techniques, the hybridization probe is preferably conjugated with a detectable label such as a radioactive label, and the probe is preferably at least 10 nucleotides in length. As is well known in the art, increasing the length of hybridization probes tends to give enhanced specificity. A labeled probe derived from a pactamycin gene cluster or pactamycin ORF nucleic acid sequence may be hybridized to a bacterial DNA library and the hybridization signal detected using methods known in the art. The hybridizing colony or plaque (depending on the type of library used) is purified and the cloned sequence contained in that colony or plaque isolated and characterized.

In specific examples, genomic library construction can be accomplished rapidly using a variety of cosmid or fosmid systems that are commercially available (e.g., Stratagene or EPICENTRE®). Advantageously, these systems minimize instability of the cloned DNA. In such examples, genomic library screening is followed by cosmid or fosmid isolation, grouping into families of overlapping clones and analysis to establish cluster identity. Cosmid end sequencing can be used to obtain preliminary information regarding the relevance of a particular clone based on expected pathway characteristics predicted from the natural product structure and its presumed biosynthetic origin.

Orthologs of a pactamycin gene cluster or pactamycin ORF nucleic acid sequences alternatively may be obtained by immunoscreening of an expression library. With the provision herein of the disclosed 86.35 kb gene locus (SEQ ID NO: 54) and the identification of the ORFs therein, the corresponding proteins can be expressed and purified in a heterologous expression system (e.g., *E. coli* or *Streptomyces*) and used to raise antibodies (monoclonal or polyclonal) specific for the pactamycin biosynthetic enzymes or proteins, such as peroxidase, hydrolase, oxidoreductase, mutase, dehydrogenase, hydroxylase, aminotransferase, methyltransferase, kinase, or polyketide synthase. Antibodies also may be raised against synthetic peptides derived from the pactamycin amino acid sequences presented herein (SEQ ID NOs: 1-53). Methods of raising antibodies are well known in the art and are described generally in Harlow and Lane, *Antibodies, A Laboratory Manual*, Cold Springs Harbor, 1988. Such antibodies can be used to screen an expression library produced from bacteria. For example, this screening will identify the pactamycin orthologs. The selected DNAs can be confirmed by sequencing and enzyme activity assays.

Oligonucleotides derived from a pactamycin gene cluster or nucleic acid sequences (e.g., SEQ ID NO: 54), or fragments of these nucleic acid sequences, are encompassed within the scope of the present disclosure. In one embodiment, oligonucleotides may comprise a sequence of at least 10 consecutive nucleotides of a pactamycin gene cluster or a pactamycin ORF nucleic acid sequence. If these oligonucleotides are used with an in vitro amplification procedure (such as PCR), lengthening the oligonucleotides may enhance amplification specificity. Thus, in other embodiments, oligonucleotide primers comprising at least 15, 20, 25, 30, 35, 40, 45, 50, or more consecutive nucleotides of these sequences may be used. In another example, a primer comprising 30 consecutive nucleotides of a nucleic acid molecule encoding a pactamycin peroxidase/hydrolase (such as nucleotides encoding proteins with amino acid sequences set forth in SEQ ID NOs: 18 or 33), methyltransferase (such as nucleotides encoding proteins with amino acid sequences set forth in SEQ ID NOs: 21, 22, 26, 30, and 31) or a regulatory protein (such as, nucleotides encoding proteins with amino acid sequences set forth in SEQ ID NOs: 9, 10 11, 14, 15, 16, 18, 19, 24, or 42) will anneal to a target sequence, such as a pactamycin gene cluster or a pactamycin homolog present in a DNA library from another *Streptomyces* species (or other organisms producing pactamycin-like antibiotics), with a higher specificity than a corresponding primer of only 15 nucleotides. In order to obtain greater specificity, probes and primers can be selected that comprise at least 15, 20, 23, 25, 30, 35, 40, 45, 50 or more consecutive nucleotides of pactamycin gene cluster or a pactamycin nucleotide sequences. In particular examples, probes or primers can be at least 100, 250, 500, 600 or 1000, such as up to 2000 consecutive nucleic acids of a disclosed pactamycin gene cluster or a pactamycin nucleotide sequence encoding proteins with amino acid sequences set forth in SEQ ID NOs: 1 to 53. Oligonucleotides (such as, primers or probes) may be obtained from any region of a disclosed pactamycin gene cluster or a pactamycin ORF nucleic acid sequence. By way of example, an pactamycin gene cluster or a pactamycin ORF sequence may be apportioned into about halves, thirds, quarters or other desirable lengths based on sequence profiling, and the isolated nucleic acid molecules (e.g., oligonucleotides) may be derived from the first or second halves of the molecules, from any of the three thirds, from any of the four quarters or from any other desirable lengths of the molecule deduced by those of skill in the art. The nucleic acid sequence of interest also could be divided into smaller regions, e.g., about eighths, sixteenths, twentieths, fiftieths and so forth, with similar effect. Alternatively, it may be divided into regions that encode for conserved domains. For example, PtmC, which is believed to catalyze the cyclization of sugar precursor to the cyclopentitol unit, can be used as probe to identify other gene clusters of cyclopentitol-containing antibiotics. Also, swapping of conserved domains in PtmO (the acyltransferase) with those of other acyltransferases would alter the substrate specificity of the resulting enzymes, which in turn may produce different analogs of pactamycin.

IV. Pactamycin Biosynthetic Enzyme and Protein Variants

With the provision herein of pactamycin biosynthetic proteins and corresponding nucleic acid sequences, the creation of variants of these sequences is now enabled. In an example, variant pactamycin biosynthetic enzymes include proteins that differ in amino acid sequence from the disclosed prototype enzymes and still retain a measurable amount of the biological activity/function of the prototype proteins as listed in Table 1. In an alternative example, variant pactamycin biosynthetic enzymes include proteins that differ in amino acid sequence from the disclosed prototype enzymes and produce a protein with properties that are distinct (e.g., less toxic, different biological activity or function, etc.) from the prototype proteins as listed in Table 1.

In one embodiment, variant pactamycin biosynthetic proteins include proteins that differ in amino acid sequence from the disclosed pactamycin biosynthetic protein sequences (e.g., SEQ ID NOs: 1-53) but that share at least 65% amino acid sequence identity with such enzyme sequences. In other embodiments, other variants will share at least 70%, at least 75%, at least 80%, at least 85%, at least 90%, at least 95%, or at least 98% amino acid sequence identity. Manipulation of the disclosed pactamycin gene cluster (+/− upstream and downstream flanking regions) and pactamycin ORF nucleotide sequences using standard procedures (e.g., site-directed mutagenesis, gene disruption techniques or PCR), can be used to produce such variants. The simplest modifications involve the substitution of one or more amino acids for amino acids having similar biochemical properties. These so-called conservative substitutions are likely to have minimal impact on the activity of the resultant protein.

In some embodiments, the function of a pactamycin biosynthetic protein variant can be maintained if amino acid substitutions are introduced in regions outside of the conserved domains of the protein, where amino acid substitutions are less likely to affect protein function. By way of example, conserved domains can be determined by comparing the sequence of a protein as provided herein with the sequence of other proteins and noting those regions of the protein that are less likely to vary, that have been preserved through evolution, or that are required for function.

In another embodiment, more substantial changes in pactamycin biosynthetic enzyme function or other protein features may be obtained by selecting amino acid substitutions that are less conservative than conservative substitutions. In one specific, non-limiting, embodiment, such changes include changing residues that differ more significantly in their effect on maintaining polypeptide backbone structure (e.g., sheet or helical conformation) near the substitution, charge or hydrophobicity of the molecule at the target site, or bulk of a specific side chain. The following specific, non-limiting, examples are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant pactamycin biosynthetic enzyme or protein encoding sequences may be produced by standard DNA mutagenesis techniques. In one specific, non-limiting, embodiment, M13 primer mutagenesis is performed. Details of these techniques are provided in Sambrook et al. (In *Molecular Cloning: A Laboratory Manual*, Cold Spring Harbor Laboratory Press, New York, 1989), Ch. 15. By the use of such techniques, variants may be created that differ from the disclosed pactamycin enzyme or protein sequences. DNA molecules and nucleotide sequences that are derivatives of those specifically disclosed herein, and which differ from those disclosed by the deletion, addition, or substitution of nucleotides while still encoding a protein having the biological activity of the prototype enzyme.

In one embodiment, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed pactamycin enzymes and amino acid sequences (e.g., SEQ ID NOs:1-53). For example, because of the degeneracy of the genetic code, four nucleotide codon triplets—GCT, GCG, GCC and GCA—code for alanine. The coding sequence of any specific alanine residue within a pactamycin synthetic enzyme, therefore, could be changed to any of these alternative codons without affecting the amino acid composition or characteristics of the encoded protein. Based upon the degeneracy of the genetic code, variant DNA molecules may be derived from the nucleic acid sequences disclosed herein using standard DNA mutagenesis techniques, as described above, or by synthesis of DNA sequences. Thus, this disclosure also encompasses nucleic acid sequences that encode a synthetic pactamycin enzyme (such as, peroxidase, hydrolase, polyketide synthase, kinase, methyltransferase, aminotransferase, oxidoreductase, mutase, dehydrogenase, or hydroxylase) or protein (such as, regulatory protein), but which vary from the disclosed nucleic acid sequences by virtue of the degeneracy of the genetic code.

In one embodiment, variants of a pactamycin biosynthetic enzyme or protein may also be defined in terms of its sequence identity with the prototype pactamycin biosynthetic enzymes or variants. Nucleic acid sequences that encode such proteins/fragments readily may be determined simply by applying the genetic code to the amino acid sequence of a pactamycin biosynthetic enzyme, protein or fragment thereof, and such nucleic acid molecules may readily be produced by assembling oligonucleotides corresponding to portions of the sequence.

Nucleic acid molecules that are derived from a pactamycin gene cluster and pactamycin ORF nucleic acid sequences include molecules that hybridize under low stringency, high stringency, or very high stringency conditions to the disclosed prototypical pactamycin gene cluster, pactamycin ORFs and fragments thereof.

Nucleic acid molecules encoding one or more pactamycin biosynthetic enzyme or protein (including the amino acid sequences set forth in SEQ ID NOs: 1-53, and nucleic acids encoding these sequences), and orthologs and homologs of these sequences, may be incorporated into transformation or expression vectors.

V. Biosynthetic Production of Pactamycin and Intermediates

Biosynthetic methods for synthesizing pactamycin disclosed herein are useful for efficient production of the antibiotic. In certain embodiments the biosynthetic methods employ variant enzymes that alter the biosynthesis, for example to improve efficiency or produce analog compounds. In analogous fashion others have employed polyketide synthase cassettes to prepare natural products and their analogs. For example, Kosan Biosciences, Inc. has used biosynthetic methods to produce erthyromycin antibiotics and the epothilone antitumor agents. In another example, Walsh and Marahiel laboratories have successfully attached synthetic polypeptides as well as hybrid polyketides-polypeptides to PEGA resin beads to effect macrocyclization reactions from cloned and soluble thioesterases (TEs), such as that from the tyrocidine A pathway (Kohli et al., *Proc. Natl. Acad. Sci USA,* 99: 1247-1252, 2002; and Kohli et al., *Nature,* 418:658-661, 2002). Thus, cloning and expression of the pactamycin biosynthetic gene cluster or ORFs in a heterologous host, such as *E. coli* or *Streptomyces*, can be used to increase production of pactamycin, a pactamycin precursor, a pactamycin intermediate, or an enzyme or protein included within the gene cluster. In addition, genetic recombination and domain-exchange constructs permit the creation of pactamycin structures that would be difficult to make using traditional synthetic methodologies. Pactamycin is a very complex compound with a densely functionalized structure, which makes it very difficult to be synthesized chemically. Thus alternative methods of structure modification e.g., via genetic or biosynthetic approaches are needed.

In an embodiment, a recombinant expression system is selected from prokaryotic hosts. Bacterial cells are available from numerous sources, including commercial sources known to those skilled in the art, such as the American Type Culture Collection (ATCC; Manassas, Va.). Commercial sources of cells used for recombinant protein expression also provide instructions for usage of such cells. One representative heterologous host system for expression of a pactamycin gene cluster is *Streptomyces* sp. In specific examples, *Streptomyces* has been used as an artificial host to express NRPS-encoding gene clusters of very large sizes (see, e.g., Stutzman-Engwall and Hutchinson *Proc. Natl. Acad. Sci. USA* 86: 3135-3139, 1989; Motamedi and Hutchinson Proc. *Natl. Acad. Sci. USA* 84: 4445-4449, 1987; Grim et al. *Gene* 151: 1-10 1994; Kao et al. *Science* 265: 509-512, 1994: and Hopwood et al. *Meth. Enzymol.,* 153: 116-166, 1987). *Streptomyces* sp. are useful heterologous host systems because they are easily grown, plasmids and cosmids for the expression and/or integration of biosynthetic gene clusters are well characterized, and they house many of the modifying and auxiliary enzymes required to produce functional pathways (Donadio et al., *J. Biotechnol.,* 99:187-198, 2002).

Another representative heterologous host system for expression of a pactamycin gene cluster (or one or more of its ORFs) is *E. coli. E. coli* has successfully been used for the functional production of NRPS and PKS enzyme systems (Kealey et al., *Proc. Natl. Acad. Sci. USA,* 95(2):505-509, 1998; Pfeifer, *App. Environ. Microbiol.,* 69(11): 6698-6702, 2003). *E. coli* is an attractive artificial expression system because it is fast growing and easy to genetically manipulate. Recent advances in *E. coli*-based expression systems have greatly aided efforts to simultaneously express multiple genes in a single host organism. Multiple ORFs from a complex biosynthetic system can now be expressed simultaneously in E. coli. To ensure adequate and coordinate production of multiple biosynthetic enzymes from a single pathway, each ORF is optionally placed under control of a single type of promoter, such as the inducible T7 promoter. Novagen (San Diego, Calif.) has introduced the Duet™ vectors, which are designed with compatible replicons and drug resistance genes for effective propagation and maintenance of four plasmids in a single cell. This allows for the coexpression of up to eight different proteins. The activity of particular enzymes may require the correct post-translational modification of the corresponding peptidyl carrier protein. Typically this is accomplished by the co-expression of an appropriate phosphopantetheinyl transferase (PPtase) gene, for example sfp from *Bacillus subtilus* (Quadri et al., *Biochem.*, 37(6):1585-1595, 1998).

The choice of the expression system will be influenced by the features desired for the expressed polypeptides. Any transducible cloning vector can be used as a cloning vector for the nucleic acid constructs presently disclosed. If large clusters are to be expressed, it is preferable that phagemids, cosmids, P1s, YACs, BACs, PACs, HACs, MACs, or similar cloning vectors are used for cloning the nucleotide sequences into the host cell and subsequent expression. These vectors are advantageous due to their ability to insert and stably propagate larger fragments of DNA, compared to M13 phage and lambda phage.

In an embodiment, one or more of the disclosed ORFs and/or variants thereof can be inserted into one or more expression vectors, using methods known to those of skill in the art. Vectors are used to introduce pactamycin biosynthesis genes or a gene cluster into host cells either integrated or episomal. Prokaryotic host cells or other host cells with rigid cell walls may be transformed using any method known in the art, including, for example, calcium phosphate precipitation, or electroporation. Representative prokaryote transformation techniques are described in Dower (*Genetic Engineering, Principles and Methods,* 12: 275-296, Plenum Publishing Corp., 1990) and Hanahan et al. (*Methods Enzymol.*, 204: 63, 1991). Vectors include one or more expression control sequences operably linked to the desired ORF(s). However, the choice of an expression cassette may depend upon the host system selected and features desired for the expressed polypeptide or natural product. Typically, the expression cassette includes a promoter that is functional in the selected host system and can be constitutive or inducible. In an embodiment, the expression cassette includes for each ORF a promoter, ribosome binding site, a start codon (ATG) if necessary, and optionally a region encoding a leader peptide in addition to the desired DNA molecule and stop codon. In addition, a 3' terminal region (translation and/or transcription terminator) can be included within the cassette. The ORF constituted in the DNA molecule may be solely controlled by the promoter so that transcription and translation occur in the host cell. Promoter encoding regions are well known and available to those of skill in the art. Examples of promoters include control sequences derived from pactamycin and/or NRPS gene clusters, bacterial promoters (such as those derived from sugar metabolizing enzymes, such as galactose, lactose and maltose), promoter sequences derived from biosynthetic enzymes such as tryptophan, the beta-lactamase promoter system, bacteriophase lambda PL and TF and viral promoters.

The presence of additional regulatory sequences within the expression cassette may be desirable to allow for regulation of expression of the one or more ORFs relative to the growth of the host cell. These regulatory sequences are well known in the art. Examples of regulatory sequences include sequences that turn gene expression on or off in response to chemical or physical stimulus as well as enhancer sequences. In addition, to the regulatory sequences, selectable markers can be included to assist in selection of transformed cells. For example, genes that confer antibiotic resistance or sensitivity to the plasmid may be used as selectable markers.

It is contemplated that various pactamycin ORFs and/or gene cluster or proteins of interest can be cloned into one or more recombinant vectors as individual cassettes, with separate control elements, or under the control of a single control element (e.g., a promoter). In an embodiment, the cassettes include two or more restriction sites to allow for the easy deletion and insertion of other open reading frames so that hybrid synthetic pathways can be generated. The design and use of such restriction sites is well known in the art and can be carried out by using techniques described above such as PCR or site-directed mutagenesis. Proteins expressed by the transformed cells can be recovered according to standard methods well known to those of skill in the art. For example, proteins can be expressed with a convenient tag to facilitate isolation. Further, the resulting polypeptide can be purified by affinity chromatography by using a ligand (such as a compound related to pactamycin) that binds to the polypeptide.

After production, the novel secondary metabolites can be purified and/or analyzed by methods well known to one of skill in the art including a multitude of chromatographic and spectroscopic techniques, including HPLC, LC-MS, GC-MS, and NMR analysis.

In certain embodiments, the metabolites produced as described herein will be isolated from mutant *S. pactum* strains or other host organisms and will provide pactamycin analogs for biochemical evaluation or further semisynthetic modification. For example, a compound produced using a variant pactamycin gene cluster can be isolated and semi-synthetically modified by one or more chemical reactions to produce novel pactamycin analogs.

VI. Pharmaceutical Compositions

This disclosure includes pharmaceutical compositions comprising at least one pactamycin-like antibiotic formulation for use in human or veterinary medicine. Embodiments of pharmaceutical compositions include a pharmaceutically acceptable carrier and at least one active ingredient. Useful pharmaceutically acceptable carriers and excipients are known in the art. Active ingredients may comprise, for example, at least one pactamycin compound such as pactamycin as described herein. In addition, other medicinal or pharmaceutical agents, for example, with similar, related or complementary effects on the affliction being treated, may be included as active ingredients in pharmaceutical compositions.

The pharmaceutical compositions comprising pactamycin-like antibiotics may be formulated in a variety of ways depending, for example, on the mode of administration and/or on the location and type of disease to be treated. For example, such pharmaceutical compositions may be formulated as pharmaceutically acceptable salts. As another example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The dosage form of the pharmaceutical composition will be determined by the mode of administration chosen. For example, in addition to injectable fluids, topical and oral formulations may be employed. Topical preparations may include eye drops, ointments, sprays and the like. Oral formulations may be liquid (e.g., syrups, solutions or suspensions), or solid (e.g., powders, pills, tablets, or capsules). For solid compositions, conventional non-toxic solid carriers may include pharmaceutical grades of mannitol, lactose, starch, or magnesium stearate. Actual methods of preparing such dosage forms are known, or will be apparent, to those skilled in the art.

Certain embodiments of the pharmaceutical compositions comprising pactamycin-like antibiotics as described herein may be formulated in unit dosage form suitable for individual administration of precise dosages. The amount of a therapeutic compound administered will depend on the subject being treated, the severity of the affliction, and the manner of administration, and is known to those skilled in the art. Within these bounds, the formulation to be administered will contain a quantity of the pactamycin analogs disclosed herein in an amount effective to achieve the desired effect in the subject being treated (e.g., eliminating Gram-positive pathogens, Gram-negative pathogens or anti-tumor activity).

VII. Therapeutic Uses

The present disclosure contemplates treatments for infection of a subject by a Gram-positive bacteria and/or Gram-negative bacteria. Such treatments include administering a pactamycin derivative, or a combination of the derivative and one or more other pharmaceutical agents (also referred to herein as "drug" or "drugs"), to the subject in a pharmaceutically acceptable carrier and in an amount effective to treat a Gram-positive and/or Gram-negative bacteria. Subjects can be selected using more specific criteria, such as a definitive diagnosis of a condition based on, for example, a biological specimen that has been provided to be tested for a bacterial infection.

In other examples, the present disclosure contemplates treatments for tumors, such as cancer. Such treatments include administering a pactamycin derivative, or a combination of the derivative and one or more other pharmaceutical agents (also referred to herein as "drug" or "drugs"), to the subject in a pharmaceutically acceptable carrier and in an amount effective to reduce or eliminate the tumor, such as inhibiting tumor growth. Subjects can be selected using more specific criteria, such as a definitive diagnosis of a condition based on, for example, a biological specimen that has been provided to be tested for tumor cells.

The vehicle in which the drug is delivered may include, for example, the pharmaceutical compositions described above. Routes of administration include but are not limited to oral and parenteral routes, such as intravenous (iv), intraperitoneal (ip), rectal, topical, ophthalmic, nasal, and transdermal.

Therapeutically effective doses of a pactamycin derivative can be determined by one of skill in the art. An example of a dosage range is 0.1 to 200 mg/kg body weight orally in single or divided doses. Another example of a dosage range is 1.0 to 100 mg/kg body weight orally in single or divided doses. For oral administration, the compositions are, for example, provided in the form of a tablet containing 0.1 or 1.0 to 1000 mg of the active ingredient, particularly 1, 5, 10, 15, 20, 25, 50, 100, 200, 400, 500, 600, and 1000 mg of the active ingredient for the symptomatic adjustment of the dosage to the subject being treated.

The specific dose level and frequency of dosage for any particular subject may be varied and will depend upon a variety of factors, including the activity of the specific pactamycin compound, the metabolic stability and length of action of that compound, the age, body weight, general health, sex and diet of the subject, mode and time of administration, rate of excretion, drug combination, and severity of the condition of the subject undergoing therapy.

The following examples are provided to illustrate certain particular features and/or embodiments. These examples should not be construed to limit the invention to the particular features or embodiments specifically described.

EXAMPLES

Example 1

Isolation and Characterization of a Pactamycin Gene Cluster

This Example describes the cloning and characterization of a pactamycin biosynthesis gene cluster.

Materials and Methods

Preparation of the Fosmid Library of Pactamycin Gene Cluster from *S. pactum* ATCC 27456.

In order to obtain the biosynthetic gene cluster of pactamycin in *S. pactum* ATCC 27456 (purchased from American Type Culture Collection, Manassas, Va.), a genomic library was prepared using the Copy Control™ Fosmid system (EPICENTRE®). This strain was cultured in YMG medium at 30° C. overnight. The broth was centrifuged at 5,000 rpm for 5 min. The supernatant was discarded, and the pellet was washed with 10.3% sucrose solution. The suspension was further washed with 2×TE buffer. Six mL of lysis buffer (10 mg/mL lysozyme, 0.1 M EDTA, 10 mM Tris-HCl pH 8, 15% sucrose) was added, and then mixed gently. Furthermore, 100 µL proteinase K (20 mg/mL) and 3.6 mL SDS (10%) were added to the suspension, and the mixture was incubated at 37° C. for 1.5 hr. CTAB (1.6 mL) was added to the solution and incubated at 65° C. for 10 min. Following incubation, an equal volume of Phenol/CHCl$_3$ (1:1) was added to the CTAB/supernatant solution and mixed until milky. The aqueous layer was removed, placed into a new tube and then, extracted with CHCl$_3$. Following extraction with CHCl$_3$, the aqueous layer was transferred into a new tube. A one-tenth volume of 3M NaOAc (pH 5.2) and 2 volumes of 100% EtOH was added to the supernatant, incubated at room temperature, and centrifuged at 13,000 rpm for 20 min. The EtOH solution was discarded and the pellet washed with 70% EtOH twice. The precipitated chromosomal DNA was spooled using a Sheppard's hook and the pellet was redissolved in water. Analysis of the genomic DNA by gel electrophoresis indicated that DNA fragments were ~40 Kb.

Fosmid library preparation of the genomic DNA of *S. pactum* ATCC 27456 was carried out according to the protocols of the CopyControl™ Fosmid Library Production Kit (EPICENTRE®). To repair the ends of insert DNA, genomic DNA was treated with End-repair Enzyme at room temperature for 45 min and then the reaction was quenched by incubation at 70° C. for 20 min. The gel containing ~40 Kb DNA was cut and the expected DNA (30-40 Kb) was isolated by DNA Extraction KIT (FERMENTAS; Glen Burnie, Md.).

The chromosomal DNA was ligated together with Fast-link ligase and the pCC1 FOS vector. Then, the ligation reaction was added into the packaging extract and incubated at 30° C. for 90 min. Phage Dilution buffer and a small amount of $CHCl_3$ was added to the mixture. The suspension was centrifuged for 1 min.

The competent cells, EPI300-TI, for titering were cultured in LB/0.2% maltose/10 mM $MgSO_4$ medium at 37° C. until Mom of 0.8. The cells were pelleted, resuspended in half of their original volume with 10 mM $MgSO_4$, and further diluted to an Mom of 0.5 with 10 mM $MgSO_4$. Ten microliters of packaging reaction and 100 μL of the bacterial cells were mixed and incubated at 37° C. for 30 min. The supernatant was spread on LB agar with 12.4 μg/mL chloramphenicol, and incubated at 37° C. overnight. Once the tittering was complete and optimized, the remainder of the packaging extract was used to infect the EPI300 cells. In total, 3,000 Fosmid colonies were obtained on the agar plates.

DNA Probe and Southern Hybridization Screening.

A heterologous PKS probe was initially used to screen the library. Since, 6-methylsalicylic acid is a precursor involved in pactamycin biosynthesis, homologous genes encoding 6-methylsalicylate synthase were initially identified through a detailed literature search, including the 6-methylsalicylate synthase cloned from the fungus *Glarea lozoyensis* (Lu et al., *Mol. Genet. Genomics,* 273: 207-216, 2005). The homology of this gene sequence was searched by BLAST and the results suggested that the sequence is homologous with a RifB, a PKS gene involved in rifamycin biosynthesis. Thus, the ketosynthase domain in the rifB gene was amplified by PCR with the primers KS_F (GAG CCC GTC GCG ATC GTC, SEQ ID NO: 55) and RifB_KS_R (CGC TTC TTC GAG GAT CAT GT, SEQ ID NO: 56), Taq DNA polymerase and *Amycolatopsis mediterranei* (a rifamycin producer that contains rifB) genomic DNA as template. For library screening, library colonies were transferred onto Hybond-$N^+$ nylon membrane. Hybridization was performed with rifB KS domain probe by DIG-labeling (DIG Easy hyb protocol) to give 44 positive fosmid clones.

In addition, pactamycin has two amino groups, which are predicted to be introduced by aminotransferase enzymes. Therefore, the aminotransferase gene (cetM) was prepared from the cetoniacytone A biosynthetic gene cluster as a heterologous probe, which was amplified by PCR using primers: CetM-F (GAA GAT CTG CAT ATG AGC GGC CCT GGT TAC CT, SEQ ID NO: 57) and CetM_R (GGA ATT CTCAT TTC CTC GCA ACC ACT TCG, SEQ ID NO: 58), Taq DNA polymerase, and cetoniacytone producer (*Actinomyces* sp.) genomic DNA as a template. Fosmid DNA from the 44 positive fosmids isolated in the PKS screening was digested with ApaI. The fragmented DNA was separated on an electrophoresis gel and then transferred onto a nylon membrane. Hybridization was further carried out with the aminotransferase probe to obtain 10 fosmid clones that contained genes homologous to both PKS and aminotransferases.

Finally, the pactamycin compound has a number of methyl and ethyl groups derived from methionine. The attachment of these groups may be catalyzed by methyltransferase related to cloU (C-methyltransferase) from the clorobiocin biosynthetic gene cluster. C/o U was generously provided by L. Heide and used to screen the 44 PKS-positive fosmids by Southern hybridization. Notably, only fosmid TIP3 was positive for all three heterologous probes and was further analyzed for its involvement in pactamycin biosynthesis. Further screening using PCR approaches resulted in the identification of three additional fosmid clones that housed DNA fragments overlapping with sequences found in fosmid TIP3.

In order to confirm the sequence of TIP3, a 2.5 kb ApaI fragment of TIP3 was cloned into pBluescript ($SK^-$). The plasmid was transferred into *E. coli* DH-10B. The sequence of the 2.5 kb fragment of TIP3 revealed a putative carbamoyltranferase and radical SAM enzyme. As the chemical structure of pactamycin contains a carbamoyl group as well as several methyl- and other groups that are derived from SAM, it is suggested that carbamoyltranferase and radical SAM enzymes may be involved in the biosynthesis of pactamycin) Additional primers were designed on the basis of these genes to get more sequence for the gene cluster. The sequence of the complete gene cluster was obtained by gene walking with the primers and by pyrosequencing technology carried out by Macrogen Inc.

Results i. Isolation of Gene Cluster

The biosynthetic gene cluster of pactamycin in *S. pactum* ATCC 27456 was isolated as described above in the Material and Methods Section. In brief, the library was screened using a number of heterologous probes including the PKS module of the rifamycin gene cluster (rifB) (August et al., *Chem. Biol.,* 5: 69-79, 1998), the aminotransferase gene from the cetoniacytone A biosynthetic gene cluster (cetM), and the C-methyltransferase gene from the clorobiocin biosynthetic gene cluster (cloU) (Freitag et al., *Microbiology,* 152: 2433-2442, 2006). Screening using the PKS probe (rifB) resulted in 44 positive clones, whereas screening using cetM and cloU resulted in 10 and 6 positive clones, respectively. Among them, only one clone (TIP3) was positive with all three different probes.

A total of 86.35 kb of DNA sequence of TIP3 and the flanking regions was obtained using a combination of pyrosequencing, shotgun sequencing, and primer walking methodologies. Analysis of the sequence using BLAST Search indicated the presence of 53 ORFs (FIG. 2). These represent a combination of structural and regulatory genes involved in pactamycin biosynthesis. For example, PtmA (391 aa, SEQ ID NO: 19) shows homology to DegT/DnrJ/EryC1/StsC aminotransferase family (37% identity, 50% similarity). The members of this family have been characterized as pyridoxal-phosphate-dependent aminotransferase enzymes with a variety of molecular functions. The aminotransferase activity was demonstrated for purified StsC protein as the L-alanine:N-amidino-3-keto-scyllo-inosose aminotransferase, which catalyses the first amino transfer in the biosynthesis of the streptidine subunit of the antibiotic streptomycin (Ahlert et al., *Arch. Microbiol.* 168: 102-113, 1997).

PtmB (570 aa, SEQ ID NO: 20) is homologous with the carbamoyltransferase MmcS from *Streptomyces lavendulae* (47% identity, 59% similarity), which is involved in mitomycin biosynthesis (Mao et al., *Chem. Biol.* 6: 251-263, 1999). This enzyme is predicted to catalyze N-carbamoylation of cyclopentitol core unit.

PtmC (367 aa, SEQ ID NO: 21) is similar to MitD (32% identity/50% similarity; Mao et al., *Chem. Biol.* 6: 251-263, 1999), and thought to catalyze one of several different types of reactions including either methylation, oxidation, isomerization, sulfur insertion or protein radical formation. Within the pactamycin cluster, this enzyme is predicted to act as a methyltransferase or a cyclase.

PtmD (358 aa, SEQ ID NO: 22) indicates homology to the HemK family methyltransferase (35% identity, 49% similarity) from *S. ambofaciens* (Ikeda et al., *Nat. Biotechnol.* 21: 526-531, 2003; Omura et al., *Proc. Natl. Acad. Sci. U.S.A.* 98: 12215-12220, 2001). PtmD is predicted to convert the carbamoyl group generated by PtmB into the N-dimethyl functionality seen in the final product.

PtmE (178 aa, SEQ ID NO: 23) is homologous to a glucokinase from *Xanthomonas campestris* (Thieme et al., *J. Bacteria* 187: 7254-7266, 2005). The enzyme may be involved in the phosphorylation of the C-1 of the cyclopentitol unit, the product of which may be then converted to a nucleotidyldiphosphate derivative.

PtmF (216 aa; SEQ ID NO: 24) demonstrates weak homology to DNA binding response regulators or two-component transcription regulators (i.e., DNA winged). The protein is predicted to be involved in the transcriptional regulation of the pathway.

PtmC (SEQ ID NO: 21), PtmH (SEQ ID NO: 26), PtmL (SEQ ID NO: 30), and PtmM (SEQ ID NO: 31) have all been identified by BLAST analysis as Radical SAM enzymes. Radical SAM enzymes include a large superfamily of enzymes involved in several different types of reactions, including: methylation, oxidation, isomerization, sulfur insertion, and protein radical formation. Homology between family members is often low, but a conserved $CX_3CX_2C$ motif is present in all family members, including PtmC, -H, -L, and -M, and has been shown to coordinate the [4Fe-4S] cluster. Of the four Radical SAM homologs, PtmL and PtmM share high sequence homology (79% identity) with one another, whereas they share only modest homology with PtmH (14% identity with PtmM) and PtmC (7% identity with PtmM). BLAST analysis of PtmL and PtmM revealed that in addition to the iron-sulfur binding motif, they also contain a B12-like binding domain. Several members of this subfamily of Radical SAM enzymes have been shown to act as methyltransferases. Thus, PtmL and PtmM are predicted to mediate C-methyltransferase activity during pactamycin biosynthesis. Although PtmH shares low sequence homology with PtmL or PtmM, it also retains a conserved B12-like binding domain and is predicted to act as a C-methyltransferase as well. Analysis of PtmC has revealed that this enzyme lacks a B12-like binding motif and more closely resembles the subfamily of Radical SAM enzymes involved in redox chemistry. PtmC, PtmJ (SEQ ID NO: 28; putative glycosyltransferase), and PtmG (SEQ ID NO: 25; putative deacetylase) are predicted to be involved in the formation of cyclopentitol 6 (FIG. 3), and that this process may be similar to the formation of the mitosane core structure during mitomycin biosynthesis.

Figure 3:
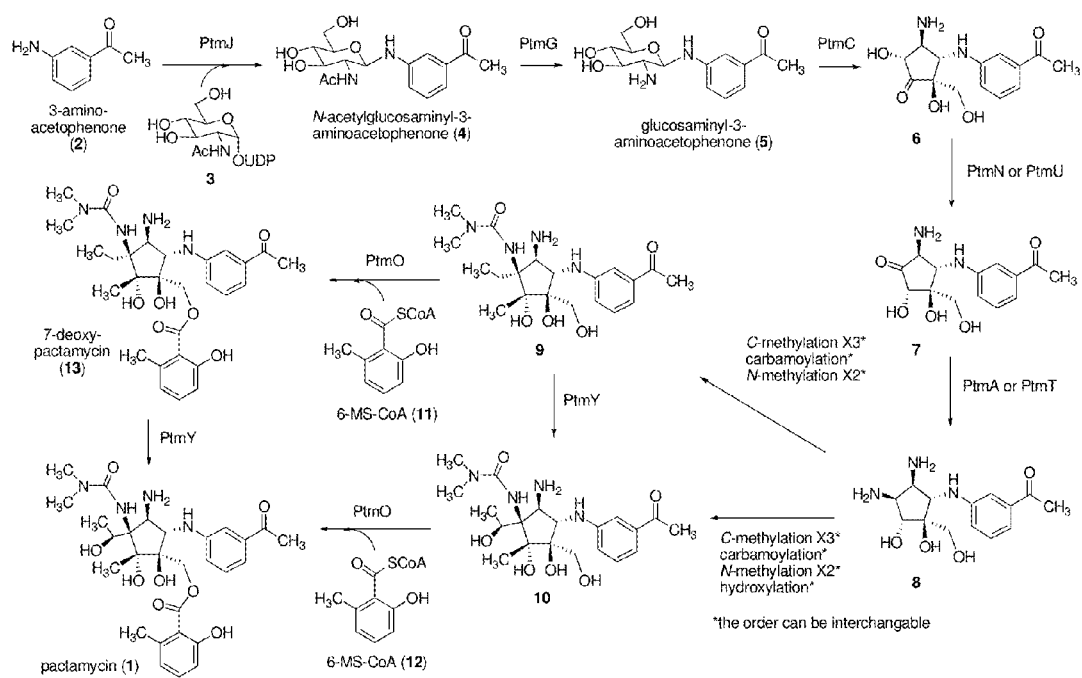
FIG. 3 is a proposed biosynthetic pathway for the formation of pactamycin.

The Radical SAM enzyme MitD, the glycosyltransferase MitB, and the putative N-deacetylase MitC from the mitomycin biosynthetic gene cluster are close homologs of PtmC, PtmJ, and PtmG, respectively. During mitomycin biosynthesis, D-glucosamine is assembled into the mitosane core structure via condensation with an AHBA subunit. The MitB homolog (PtmJ) is capable of coupling UDP-N-acetyl-α-D-glucosamine and 3-aminoacetophenone. Intermediate 4 is predicted to undergo deacetylation, possibly by the N-deacetylase homolog PtmG followed by radical-mediated rearrangement by PtmC to form the cyclopentitol ring structure. Alternatively, cyclopentitol formation could also be mediated through an $NAD^+$-dependent oxidoreductase reaction mechanism involving PtmN or PtmU. One of the latter enzymes is also proposed to mediate a conversion of intermediate 6 to compound 7 (FIG. 3).

Figure 4:
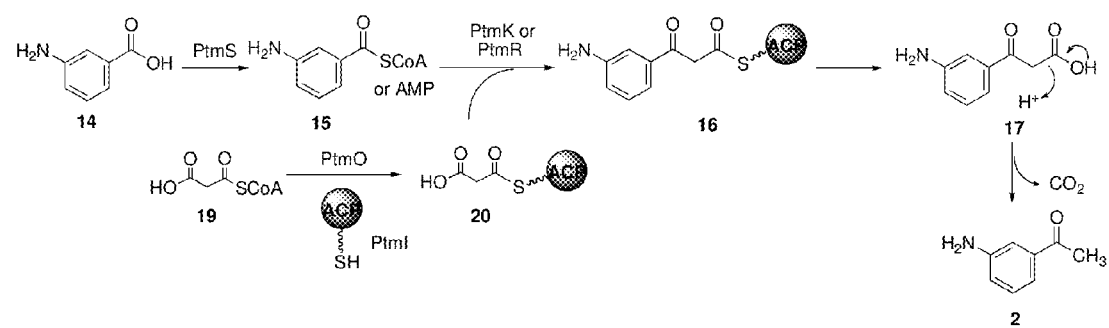
FIG. 4 is a proposed biosynthesis pathway to the formation of the 3-aminoacetophenone unit.

The 3-aminoacetophenone unit (2) is derived from the shikimate pathway, possibly diverging at the dehydroquinate (DHQ) or dehydroshikimate (DHS) intermediate steps. The putative PtmA (SEQ ID NO: 19) or PtmT (SEQ ID NO: 38) aminotransferase enzymes may be involved with the transamination of DHS to 3-aminobenzoic acid (14). Further processing of this molecule by PtmI (SEQ ID NO: 27), PtmK (SEQ ID NO: 29), PtmR (SEQ ID NO: 36), and PtmS (SEQ ID NO: 37) are predicted to complete the biosynthesis of the aminoacetophenone precursor (FIG. 4). PtmK is similar to α-ketoacyl-ACP synthase (KAS) I and II, whereas PtmR is similar to KAS III, which are responsible for the elongation steps in fatty acid biosynthesis. PtmK or PtmR are predicted to be involved in this extension as depicted in FIG. 4. In this scenario, the putative acyl-CoA synthetase (PtmS; SEQ ID NO: 37) is proposed to activate 3-aminobenzoic acid (14) to 3-aminobenzoyl-CoA (15). Alternatively, PtmS is predicted to function as an adenylation domain, as it contains an AMP binding domain similar to the loading domain of RifA from the rifamycin biosynthetic gene cluster. Thus, PtmS may convert 14 to its AMP derivative. If PtmK (a KAS I/II homolog) is involved in the chain extension, it may require two ACP-bound substrates, whereas if PtmR (KAS III) is involved, it may require a CoA-ester starter unit and an ACP-bound extender unit. Given that only one discrete acyl carrier protein (ACP) gene (ptmI) is present in the cluster, it is predicted that PtmR is the enzyme that catalyzes the condensation reaction. The extender unit malonyl-CoA (19) may be loaded onto the discrete ACP (PtmI) by the putative hydrolase/acyltransferase PtmO (FIG. 4). PtmO (SEQ ID NO: 33) may also be involved in the release of the product from the ACP-bound intermediate, although it is not clear if the same enzyme can catalyze both reactions. Finally, decarboxylation of the product is predicted to yield the aminoacetophenone precursor (2). This decarboxylation may occur spontaneously or is catalyzed by a yet to be identified dedicated enzyme. Further investigations are being made to reveal the mode of formation of 3-aminoacetophenone in *S. pactum*.

PtmO (257 aa, SEQ ID NO: 33) shows homology to putative hydrolase/acyltransferase from *Nocardia farcinica* (Ishikawa et al., *Proc. Natl. Acad. Sci. U.S.A.* 101: 14925-14930, 2004), which normally catalyzes esterification reactions. This enzyme may be involved in the attachment of 6-methyl salicylic acid to the 5-member core cyclitol unit. Therefore, PtmO may be important in drug discovery and development efforts as inactivation of this enzyme may result in the production of pactamycin analogs lacking the 6-methylsalicylic acid side chain. The resulting intermediate can be used as a scaffold for generating libraries of pactamycin analogs, as the free primary hydroxyl group can be modified by attaching various side chains using mutasynthetic, chemical synthetic, or enzymatic approaches. The intermediate or the products thereof may also be linked to cancer specific monoclonal antibodies. The products could potentially be used as 'smart bullets' that selectively target cancer cells, and leave normal cells unaffected.

PtmP (211 aa, SEQ ID NO: 34) is similar with phosphopantetheinyltransferases, including PptA from *Silicibacter pomeroyi* (Moran et al., *Nature* 432: 910-913, 2004). This enzyme is predicted to be responsible for the activation of ACP domains of PtmI and PtmQ.

PtmQ (SEQ ID NO: 35) shares high similarity with the iterative type I PKS, ChlB1, that is involved in the biosynthesis of 6-methylsalicylic acid (6-MSA) in *S. antibioticus*.

The activity of PtmQ in the biosynthesis of the 6-MSA subunit of pactamycin has been confirmed through heterologous expression and gene inactivation, and is required for pactamycin biosynthesis as described herein. 6-MSA may be converted to 6-MSA-CoA and subsequently ligated with the pactamycin core structure(s) (i.e. compounds 9 and/or 10) as proposed in FIG. 3.

PtmS (505 aa, SEQ ID NO: 37) shows homology with acyl CoA synthetases that contain AMP binding domains (29% identity/37% similarity). Similar enzymes have been found to activate the starter unit 3-amino-5-hydroxy-benzoic acid (AHBA) in the biosynthesis of ansamycin antibiotics rifamycin (August et al., Chem. Biol. 5: 69-79, 1998; Schupp et al., FEMS Microbiol. Lett. 159: 201-207, 1998; Admiraal et al., Biochemistry 40: 6116-6123, 2001; Admiraal et al., Biochemistry 41: 5313-5324, 2002), geldanamycin and herbimycin (Rascher et al., Appl. Environ. Microbiol. 71: 4862-4871, 2005). In pactamycin biosynthesis, PtmS is proposed to catalyze the conversion of 3-aminobenzoic acid to 3-aminobenzoyl-CoA (FIG. 4). For example, ptmS encodes the protein PtmS corresponding to SEQ ID NO: 37.

The deduced product of ptmQ has the characteristic of PKS domains, including ketosynthase (KS), acyltransferase (AT) and PP binding domains. This enzyme shows high homology with the iterative type I PKS, ChlB1, that is involved in the biosynthesis of 6-methylsalicylic acid (6-MSA) in S. antibioticus (Jia et al., Chem. Biol. 13, 575-585, 2006).

Figure 5:
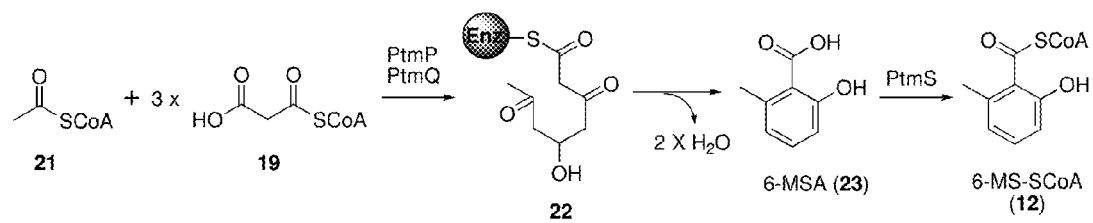
FIG. 5 is a proposed biosynthetic pathway to 6-MSA-CoA.

As there is only one acyl-CoA synthetase gene (ptmS) present in the pactamycin cluster, PtmS (SEQ ID NO: 37) may catalyze the activation of 3-aminobenzoic acid or 6-MSA or both (FIGS. 4 and 5). Similarly, the putative acyltransferase, PtmO (SEQ ID NO: 33), which was proposed to be involved in the loading of malonyl-CoA to the ACP (PtmI) in the formation of 3-aminoacetophenone, may instead catalyze the attachment of 6-MSA to the core cyclopentitol moiety.

PtmT (444 aa, SEQ ID NO: 38) is similar to glutamate-1-semialdehyde aminotransferase (37% identity, 56% similarity) from Staphylococcus aureus (Holden et al., Proc. Natl. Acad. Sci. U.S.A. 101: 9786-9791, 2004), which may be involved in the biosynthesis of 3-aminobenzoic acid.

PtmU (279 aa, SEQ ID NO: 39) is similar to NAD$^+$-dependent oxidoreductase (40% identity; 53% similarity) from S. antibioticus (Galm et al., Arch. Microbiol. 178 (2): 102-114, 2002).

PtmV (226 aa, SEQ ID NO: 40) is similar to phosphoglycerate mutase (37% identity; 53% similarity) from Nocardia farcinica (Ishikawa et al., Proc. Natl. Acad. Sci. U.S.A. 101: 14925-14930, 2004). PtmV may play a role in the oxidative metabolism of intermediates during pactamycin biosynthesis, similar to PtmN or PtmU.

PtmW (271 aa, SEQ ID NO: 41) is similar to hypothetical protein SAV3686 (46% identity; 55% similarity) from S. avermitilis (Ikeda et al., Nat. Biotechnol. 21 (5): 526-531, 2003; Omura et al., Proc. Natl. Acad. Sci. U.S.A. 98 (21): 12215-12220, 2001).

PtmX (SEQ ID NO: 42) is similar to an integral membrane protein (58% identity; 68% similarity) from S. colicolor (Bentley et al. Nature 417: 141-147, 2002). This protein is predicted to have a role in the transport of pactamycin across the cell membrane.

PtmY (SEQ ID NO: 17) shares high homology with cytochrome P450-dependent monooxygenases (CYP) sharing 59% identity and 71% similarity with CYP107L3 from Streptomyces tubercidicus, and is predicted to mediate hydroxylation of C-7 of pactamycin.

PtmZ (SEQ ID NO: 18) is highly conserved with glutathione peroxidases with 60% identity and 72% similarity with the putative glutathione peroxidase from Mycobacterium vanbaalenii.

Orf11 (SEQ ID NO: 11) shares high homology with the extracytoplasmic function (ECF) subfamily of RNA polymerase sigma factors (48% identity and 62 similarity). Sigma factors can enhance the transcriptional initiation processes of RNA polymerase by increasing specific binding of the polymerase to gene promoters. ECF sigma factors are present in complex prokaryotic genomes and are divergent from most other sigma factors. Many of the characterized ECF sigma factors are co-transcribed with one or more negative regulators. These can include transmembrane proteins that bind with the sigma factor and inhibit its activity until the appropriate stimulus activates the transmembrane protein and releases the sigma factor so that it can bind to and activate RNA polymerase at the appropriate gene targets. In the ptm cluster, the neighboring open reading frame, Orf10 (SEQ ID NO: 10), shares high homology with integral membrane proteins, and thus, may serve as the negative regulator for the Orf11 sigma factor. The positioning of Orf11 near the biosynthetic enzymes in the pactamycin gene cluster suggests that this factor may be involved with the regulation of pactamycin gene expression.

Orf14 (SEQ ID NO: 14) and Orf15 (SEQ ID NO: 15) are hypothetical proteins that have low identity to translation initiation factor IF-2 from Frankia alni ACN4a and Streptomyces avermitilis MA-4680, respectively. These proteins are predicted to be involved in regulating the biosynthetic enzyme production.

Orf9 (SEQ ID NO 9), Orf16 (SEQ ID NO: 16), and Orf19 (SEQ ID NO: 19) are highly related to the family of ATP-dependent (DEAD-box) RNA helicases. RNA helicases can facilitate the unwinding of secondary structures in mRNA and promote ribosome assembly. Orf16 and/or Orf19 are predicted to play a role in the regulation of pactamycin biosynthesis.

Orf18 (SEQ ID NO: 44) shares high homology with nourseothricin acetyltransferase from Streptomyces noursei. Nourseothricin is a nucleoside peptide that has potent antifungal and antibacterial activity due to its ability to inhibit translation and ultimately, protein synthesis. In the producing strain, S. noursei, the nourseothricin acetyltransferase gene confers resistance to the compound by mediating N-acetylation at the C-16 position. Similarly, pactamycin resembles a nucleoside moiety, which alters tRNA binding at the P-site of the ribosome and inhibits the translocation of translated products. Orf18 is predicted to mediate host resistance, such as via the acetylation of pactamycin or an intermediate structure during pactamycin biosynthesis. Orf18 is distantly similar to ribosomal-protein-alanine acetyltransferase, which may be important in self-defense strategy to the producing strain by modifying its own ribosome.

Orf23 (SEQ ID NO: 49) is homologous with the tRNA methyltransferase from S. avermitilis. Orf23 is predicted to be involved in the methylation/modification of the cellular tRNA binding site of pactamycin, inhibiting or reducing the toxicity of pactamycin in the producing strain, S. pactum.

ii. Characterization of Gene Cluster

In order to confirm the authenticity of the cluster and develop a heterologous expression system, the putative polyketide synthase gene (ptmQ) was subcloned into pJTU780, which was derived from pRSET-B (Invitrogen).

Figure 6:
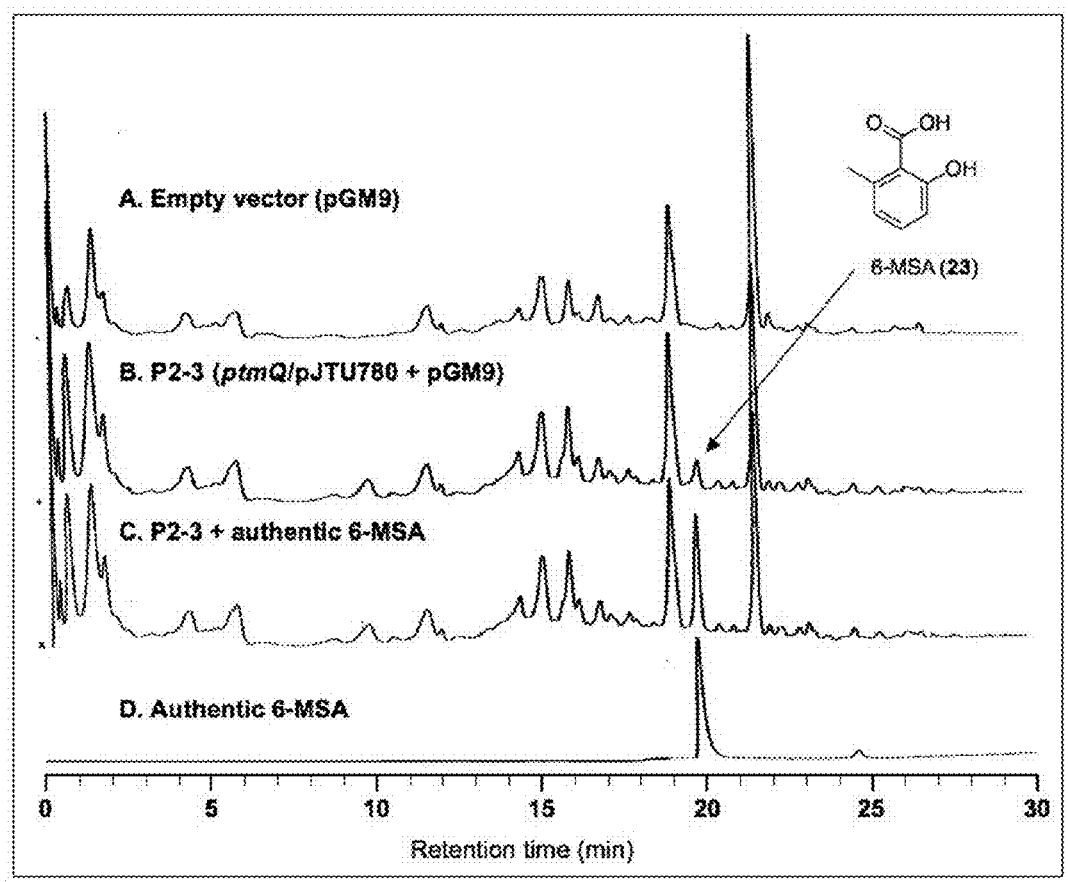
FIG. 6 is a series of HPLC profiles illustrating 6-MSA-CoA production in *S. lividans* T7.

The resulting plasmid was then linearized by HindIII digestion and ligated with pGM9 vector. Plasmid pGM9 can replicate in *S. lividans*, but not in *E. coli*. The fusion of the entire pJTU780 into pGM9 resulted in a shuttle plasmid that can replicate in both *E. coli* and *S. lividans*. The product was amplified in *E. coli* DH10B and introduced into *S. lividans* T7 by a standard protoplast transformation method (Kieser et al., "Practical *Streptomyces* Genetics", The John Innes Foundation, 2000, Norwich, England). The transformants were grown in R2YE medium, supplemented with 50 μg/mL kanamycin and 7.5 μg/mL thiostrepton (inducer), at 30° C. for 5 days, and the culture supernatants were analyzed by LC-MS. A new peak corresponding to 6-MSA (23) (m/z 141 $[M-H]^-$) was detected in a sample prepared from the culture of transformant P2-3, which harbors the ptmQ gene, compared with the sample prepared from the culture of *S. lividans* harboring the empty vector, pGM9 (FIG. 6). In order to confirm this peak as 23, the samples were co-injected with an authentic 6-MSA (23) standard, which was synthesized from 2-amino-6-methylbenzoic acid. The co-elution of the mutant product with the synthetic compound supports the identity of the new peak as 6-MSA (23). Further confirmation was achieved by GC-MS analyses after TMS derivatization of the samples.

Example 2

Genetic System for Gene Inactivation Experiments

This Example provides a genetic system for gene inactivation experiments with *S. pactum* ATCC 27456.

Figure 7A:
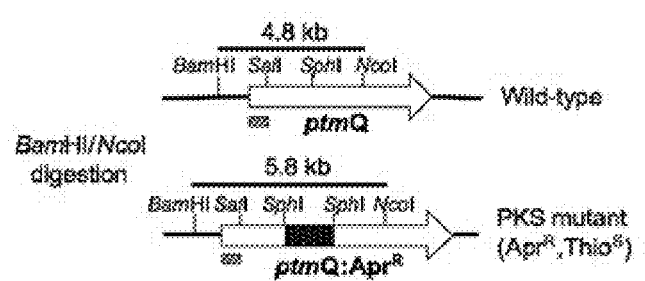
FIG. 7A is an illustration of the expected fragments from digesting ptmQ with BamHI/NcoI.
Figure 7B:
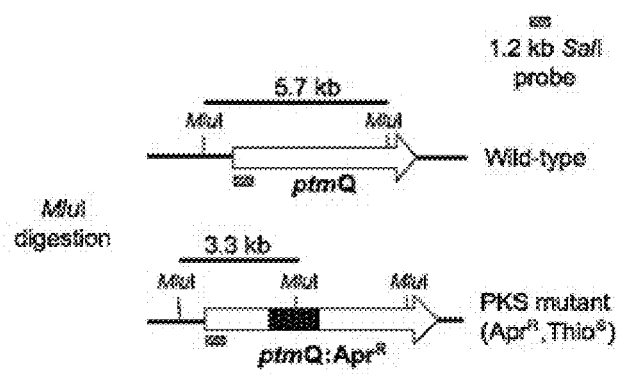
FIG. 7B is an illustration of the expected fragments from digesting ptmQ with MluI.
Figure 7C:
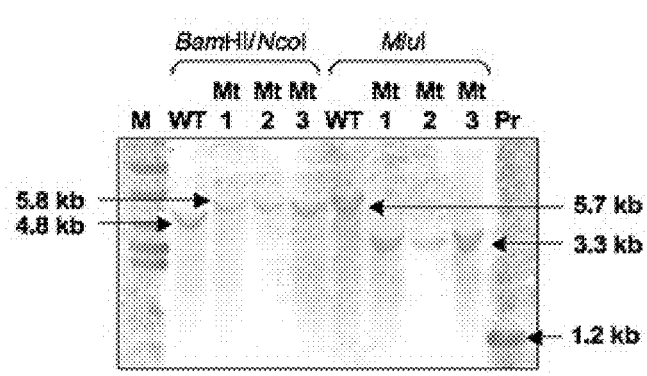
FIG. 7C is a digital image of a Southern blot illustrating a successful gene disruption of ptmQ in *S. pactum*.

In order to genetically engineer the pactamycin producer a workable genetic system was developed for gene inactivation studies. The polyketide synthase gene (ptmQ) was targeted for gene disruption because it has been confirmed by heterologous expression to be the 6-MSA synthase responsible for the biosynthesis of the side-chain moiety of pactamycin. The gene was cloned by PCR and incorporated into pJTU780 to give pTAK1. A 1 kb DNA fragment of the apramycin resistance ($Apr^R$) gene (aac(3)IV) was amplified from pOJ446, and introduced into the SphI site of the ptmQ gene on pTAK1. The product, pTAK1/$Apr^R$, was then double digested with SalI and NcoI to give a DNA fragment containing the $Apr^R$ gene flanked on either side by 1.2 kb each of ptmQ fragments. The digested 3.4 kb SalI/NcoI fragment was Klenow filled and subsequently subcloned into the pHZ1358 vector to give pTML1. This vector contains a thiostrepton resistance ($Thio^R$) gene and the OriT transfer elements required for conjugation. pTML1 was introduced into *S. pactum* by conjugation and $Apr^R$/$Thio^R$ colonies were obtained. These colonies presumably contained pTML1 either replicating autonomously or integrated into *S. pactum* genome by single crossover homologous recombination. To eliminate colonies that contain self-replicating vectors and to induce double crossover recombination, the mutant colony PKSM1 was selected, streaked on MS agar containing apramycin, and screened by replica plating for thiostrepton sensitivity. Three colonies showing $Apr^R$ and $Thio^S$ were isolated (PKSM1/3, PKSM1/8, PKSM1/19) and double cross over recombinants containing the in frame integration of Apr gene into ptmQ were confirmed by step-up PCR (with two different annealing temperatures) and Southern hybridization. FIG. 7A illustrates the expected fragments from BamHI/NcoI digestion. FIG. 7B provides the expected fragment from MluI digestion. FIG. 7C illustrates the Southern hybridization results confirming the successful mutation (M, DNA marker; WT, wild-type; Mt, mutant; Pr, the 1.2 kb probe). The biological consequence of the mutation is described in Example 3.

Example 3

Metabolic Analyses of the ptmQ Mutants

This Example illustrates the effect of ptmQ inactivation on pactamycin biosynthesis.

Figure 8:
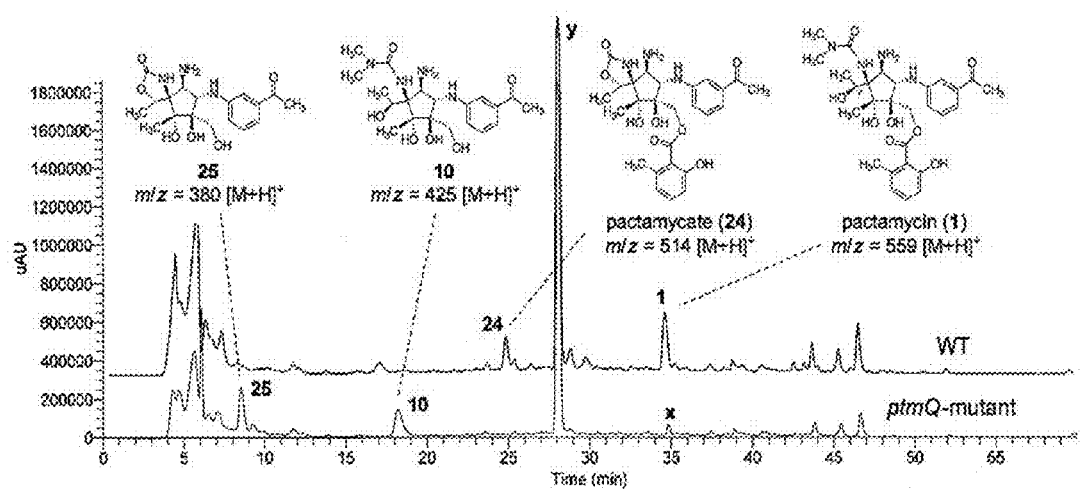
FIG. 8 is a series of tracing generated by liquid chromatography-mass spectrometry (LCMS) analysis of wild-type and ptmQ mutant strains of *S. pactum*.

Wild-type and ptmQ mutant strains of *S. pactum* were cultivated in modified Bennet medium at 30° C. for 5 days. The metabolites were analyzed by Liquid chromatography-mass spectrometry (LCMS). As shown in FIG. 8, the ptmQ mutants were not able to produce pactamycin (1) and/or pactamycate (24), but instead produced two new metabolites, 10 and 25. Peaks x and y are unknown metabolites. The molecular mass of compounds 10 (MW=424) and 25 (MW=379) are consistent with those expected for de-6-MSA-pactamycin and de-6-MSA-pactamycate, respectively. There were also a number of minor metabolites, e.g., 8"-hydroxypactamycin and 8"-hydroxypactamycate, in the culture broths of the wild-type strain but were also missing in those of the ptmQ mutants.

The production of compounds 10 and 25 suggests that the attachment of 6-MSA takes place last in the pathway, after the hydroxylation of C-7, which contradicts the earlier notion that 7-deoxypactamycin (13) is the direct precursor of pactamycin (1). Consequently, it is now possible to suggest that the acyltransferase enzyme that is involved in the condensation of 6-MSA with the cyclopentitol moiety is rather flexible in terms of its substrate specificity, as both compounds 9 and 10 (FIG. 3) can be used as substrates. More importantly, the generation of the ptmQ mutant strains and the production of compounds 10 and 25 provide invaluable tools to explore the possibility of generating a library of pactamycin analogs that would represent pharmaceutical leads from an untapped chemical class.

Example 4

Synthesis of Pactamycin Analogs

This Example describes representative methods for producing novel pactamycin analogs.

Figure 9:
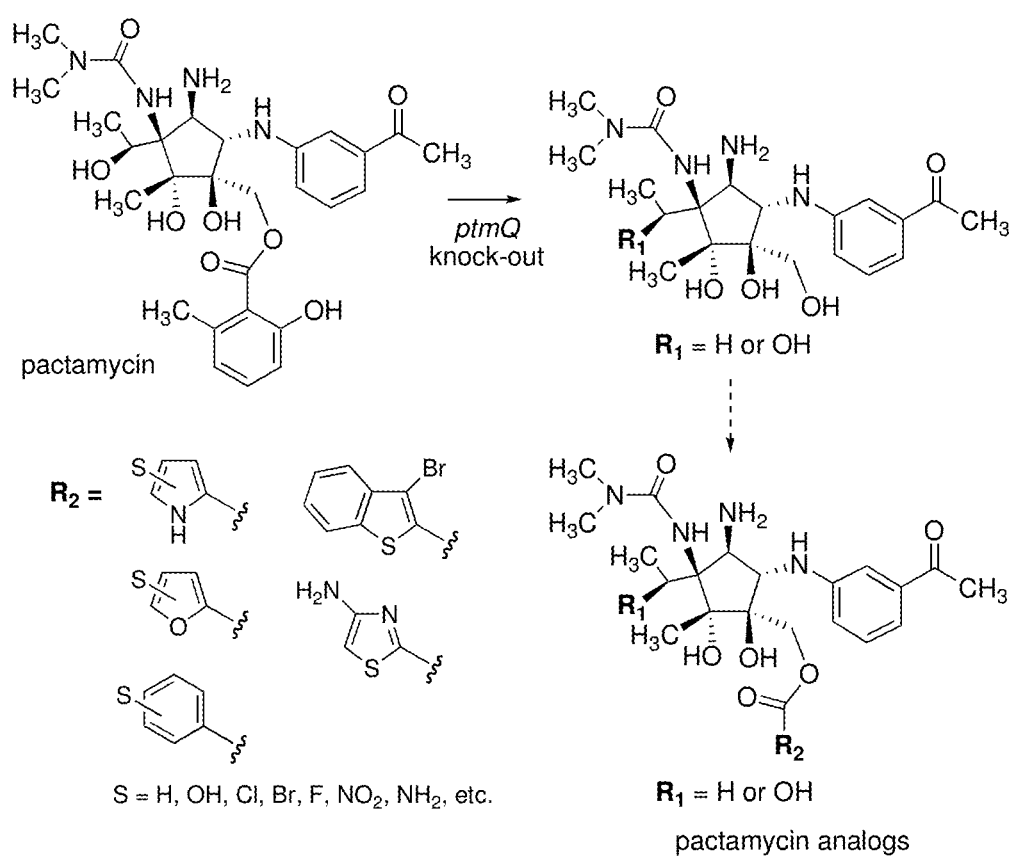
FIG. 9 is a proposed biosynthetic pathway for the mutasynthesis of pactamycin analogs.
Figure 10:
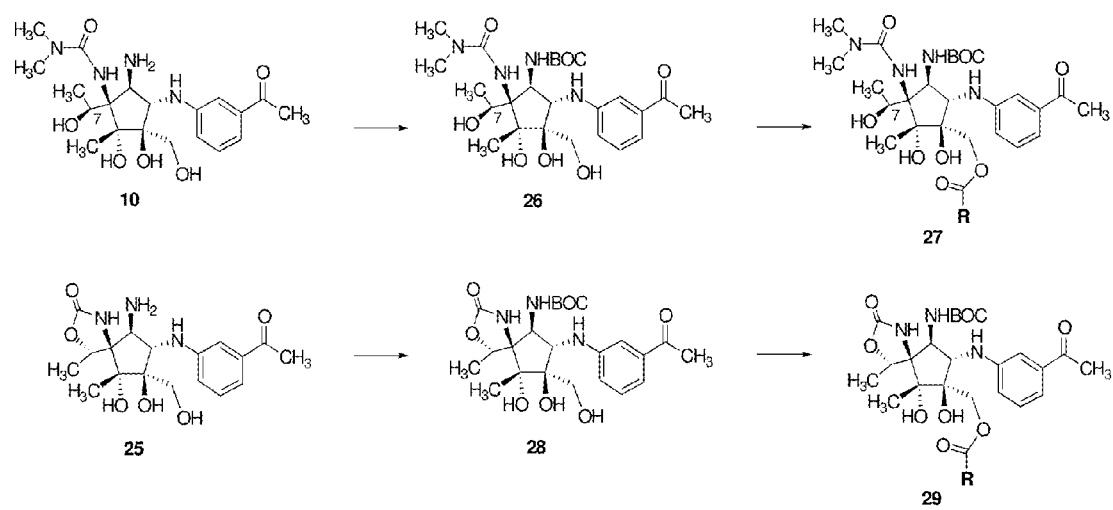
FIG. 10 is a proposed biosynthetic pathway for the semi-synthesis of pactamycin analogs.
Figure 11:
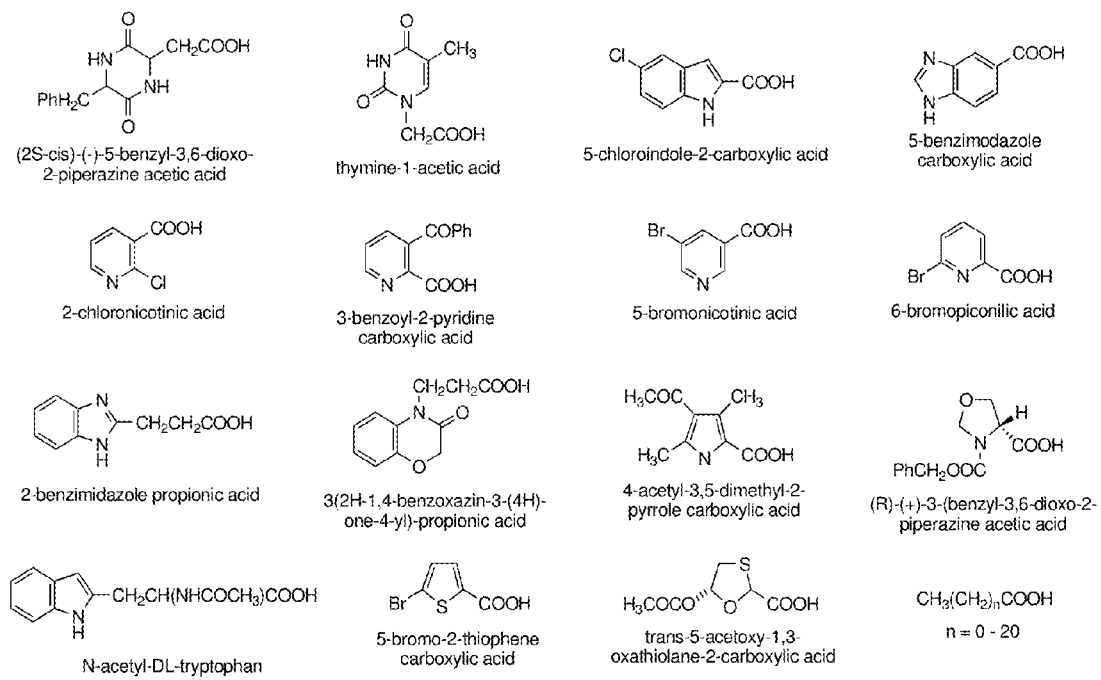
FIG. 11 shows the chemical structures of exemplary carboxylic acids to be used as side chain in the synthesis of pactamycin analogs.

The inactivation of the polyketide synthase (PtmQ) resulted in the abolishment of pactamycin biosynthesis (see, for example, Examples 2 and 3). Without being limited to any particular theory, this abolishment is believed to be due to the loss of 6-MSA production. Consistent with the teachings herein, pactamycin analogs can be generated by supplying alternative building block molecules to cultures of the mutant strains. In particular, carboxylic acids have been demonstrated to be taken up by *Streptomyces*, thus pactamycin analogs having the formula wherein $R^2$ is derived from a carboxylic acid building block, which is introduced via activation as the corresponding CoA ester, and esterification of the pactamycin core molecule with the activated CoA ester. Any carboxylic acid (or their N-acetylcysteamine derivatives) can be used to introduce the $R^2$ group, particularly aromatic carboxylic acids, including without limitation the commercially available carboxylic acids, such as substituted or unsubstituted pyrrole-2-carboxylic acids, furoic acids, benzoic acids, benzothiophene-2-carboxylic acids and thiazole-carboxylic acids. Administration of such compounds to the ptmQ mutant strain of *S. pactum* in the absence of the natural substrate 6-MSA results in the corresponding ester analog as illustrated in FIG. 9.

Figure 12:
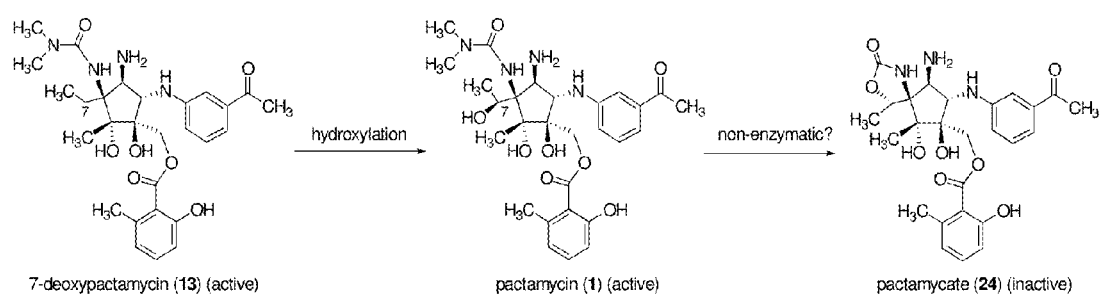
FIG. 12 is a proposed biosynthetic pathway for the conversion of 7-deoxypactamycin to pactamycin and subsequently to pactamycate.

Alternatively, such pactamycin analogs can be prepared semisynthetically, for example by isolating from the ptmQ mutant compounds lacking the 6-methylsalicylic acid (6-MSA) moiety and selectively functionalizing the free primary hydroxyl. Such de-6-MSA compounds can be used as scaffolds to generate a library of compounds. Such compounds, including de-6-MSA-pactamycin and de-6-MSA-pactamycate, contain a free amino group, which can be selectively protected as is known to those of skill in the art of organic synthesis. Examples of suitable amine-protecting groups commonly used in the art can be found in Greene and Wuts, Protective Groups in Organic Synthesis, third edition, John Wiley & Sons, New York, 1999, the disclosure of which is hereby incorporated by reference. Suitable protecting groups include but are not limited to, allyloxycarbonyl (Aloc), benzyloxycarbonyl (Cbz), ethoxycarbonyl, 9-fluorenylmethoxycarbonyl (Fmoc), and tert-butoxycarbonyl (Boc). The Boc is a preferred protecting group for selectively blocking the amine. De-6-MSA-pactamycin has four free hydroxyl groups: one primary, one secondary, and two tertiary hydroxyl groups. De-6-MSA-pactamycate has three hydroxyl groups: one primary and two tertiary hydroxyl groups. Because the primary hydroxyl group is more reactive in acylation reactions than secondary or tertiary hydroxyl groups, attachment of an acyl moiety at this position can be performed without further protection. Condensation of carboxylic acids with the selected de-6MSA pactamycin analog in the presence of a carbodiimide, such as EDCI, and catalytic DMAP yields (after deprotection of the amino group) acyl ester products (FIG. 10) of the formulas:

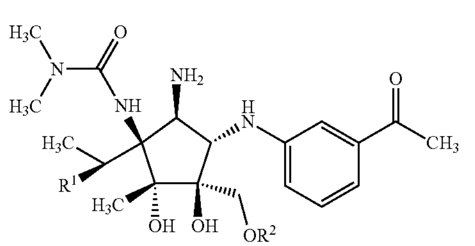

wherein $R^1$ is H or —OH and $R^2$ is an acyl group. In principle any carboxylic acid moiety can be incorporated as the $R^2$ group. In particular examples carboxylic acids having cyclic groups, such as heterocyclic groups, including aromatic groups, are incorporated. In other examples, the carboxylic acid employed is an aliphatic carboxylic acid, such as a fatty acid derivative. Examples of suitable carboxylic acids include, without limitation, those illustrated in FIG. 11.

As stated above, the primary amine moiety of the pactamycin analogs can be selectively functionalized. Thus, other pactamycin analogs prepared semisynthetically described herein include those of the formulas:

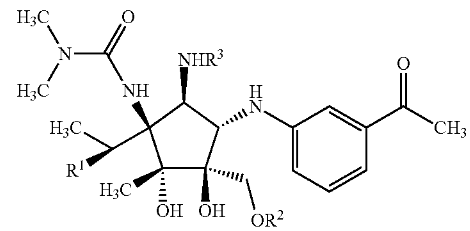

wherein $R^3$ represents —C(O)$R^5$—C(O)O$R^6$; —C(O)N$R^7R^8$ and $R^5$, $R^6$, $R^7$ and $R^8$ independently are H, lower aliphatic, aryl or aralkyl.

With reference to the formulas above, in one embodiment, $R^2$ represents the group —C(O)$R^4$ wherein $R^4$ is an aromatic group, such as an optionally substituted mono- or polycyclic aromatic group. By way of example, such $R^4$ groups include, without limitation:

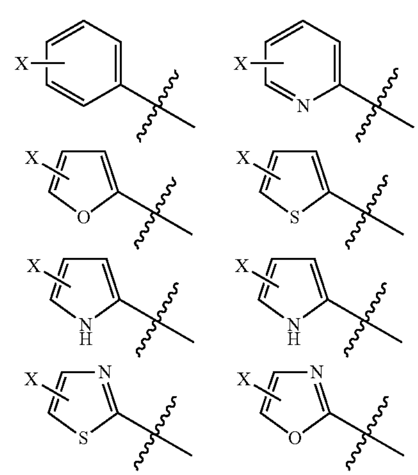

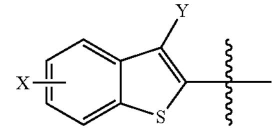

and

;

wherein X is selected from H, lower alkyl, —O$R^9$, halogen, —$NO_2$, —N$R^{10}R^{11}$; Y is H, halogen or lower alkyl; and $R^9$, $R^{10}$ and $R^{11}$ independently are selected from H, lower alkyl and acyl.

One class of important pactamycin analogs produced herein is the 7-deoxy compounds, for example 7-deoxypactamycin (13) (FIG. 12). During pactamycin biosynthesis, the CYP-mediated oxidation reaction by PtmY is predicted to take place late in the pathway, as a 7-deoxy analog of pactamycin also accumulates in *S. pactum* cultures. 7-Deoxypactamycin (13) is equally active against a number of Gram-positive and Gram-negative bacteria, which suggests that the C-7 hydroxyl group in pactamycin is less relevant to its bioactivity. On the other hand, the presence of a hydroxyl group at C-7 is less favorable, because this nucleophile may attack the carbamoyl carbonyl to form an inactive cyclic derivative (FIG. 12). In fact, such a derivative, namely pactamycate (24), was found in *S. pactum* cultures. Therefore, inactivation of the hydroxylation enzyme prevents the formation of pactamycate (24), and increases the production of 7-deoxypactamycin (13).

Example 5

Inactivation of the ptm Genes in *S. pactum*

This Example provides methods of inactivating ptm genes to identify the function of the individual genes within the ptm cluster.

Inactivation studies can be performed according to the general method developed for ptmQ as described herein (see, for example, Example 3). In particular examples, genes encoding the aminotransferases (PtmA and PtmT), the α-carbamoyltransferase (PtmB), the radical SAM enzymes (PtmC, PtmH, PtmL, and PtmM), the putative N-methyltransferase (PtmD), the glycosyltransferase (PtmJ), the oxidoreductases (PtmN and PtmU), the hydrolase/acyltransferase (PtmO), and/or the cytochrome P450 monooxygenase (PtmY) can be inactivated. In some examples, the proposed function of a gene can be explored with gene disruption studies, such as for the glutathione peroxidase homolog, PtmZ. These genes can be individually inactivated and the resulting phenotypes (metabolites) can be analyzed using routine methods known to those of skill in the art including TLC, LC-MS, and NMR. When new metabolites are identified, further efforts to isolate the compounds can be attempted by liquid chromatography (using silica gel, ion-exchange and gel filtration resins) and HPLC. The chemical structures of the metabolites can be determined using standard NMR methodologies, mass spectrometry, ultraviolet spectroscopy, and/or infrared spectroscopy.

Example 6

Heterologous Expression of the ptm Genes in *S. lividans*

This Example provides methods of expressing portions of the pactamycin gene cluster in heterologous hosts to generate mutant strains of *S. lividans*. The generated *S. lividans* mutant strains can be used to produce novel biosynthetic intermediates, which can then be used as scaffolds for the synthesis of novel bioactive chemical entities. It is contemplated that the intermediate or the products thereof may also be linked to cancer specific monoclonal antibodies. The products could potentially be used as 'smart bullets' that selectively target cancer cells, and leave normal cells unaffected.

As described herein, the iterative type I PKS (6-MSA synthase) gene (ptmQ) has been successfully expressed in *S. lividans*. To express parts of the cluster in fast-growing hosts, e.g., *E. coli* (to produce intermediate compounds, which can be used as scaffolds for the synthesis of novel bioactive chemical entities), target genes can be individually cloned into the expression vector pJTU780, a pRSET-B derivative containing a MfeI site, which is compatible with EcoPI, upstream of the T7 promoter region. The genes can be sequentially stitched together by ligating the MfeI/EcoRI DNA fragment from the donor plasmid with the EcoRI-digested acceptor plasmid. The product can be digested with EcoPI and ligated with another MfeI/EcoRI fragment harboring the next required gene. This can be done sequentially until all candidate genes have been inserted into the acceptor plasmid. No MfeI or EcoPI sites are present in any of these genes. The orientation of the inserted genes can be determined based on their restriction patterns. An advantage of this cloning technique is that each gene has its own T7 promoter, which can be induced by IPTG.

A cassette of five genes (ptmA, ptmI, ptmO, ptmR, and ptmS) can first be cloned and tested for the production of 3-aminoacetophenone. The putative substrate of ptmA is dehydroshikimic acid, which is a primary metabolite involved in the biosynthesis of aromatic amino acids. Therefore, no external genes for the biosynthesis of dehydroshikimic acid are required. However, if necessary, dehydroshikimic acid will be added into the cultures to increase the production of 3-aminoacetophenone.

Figure 13:
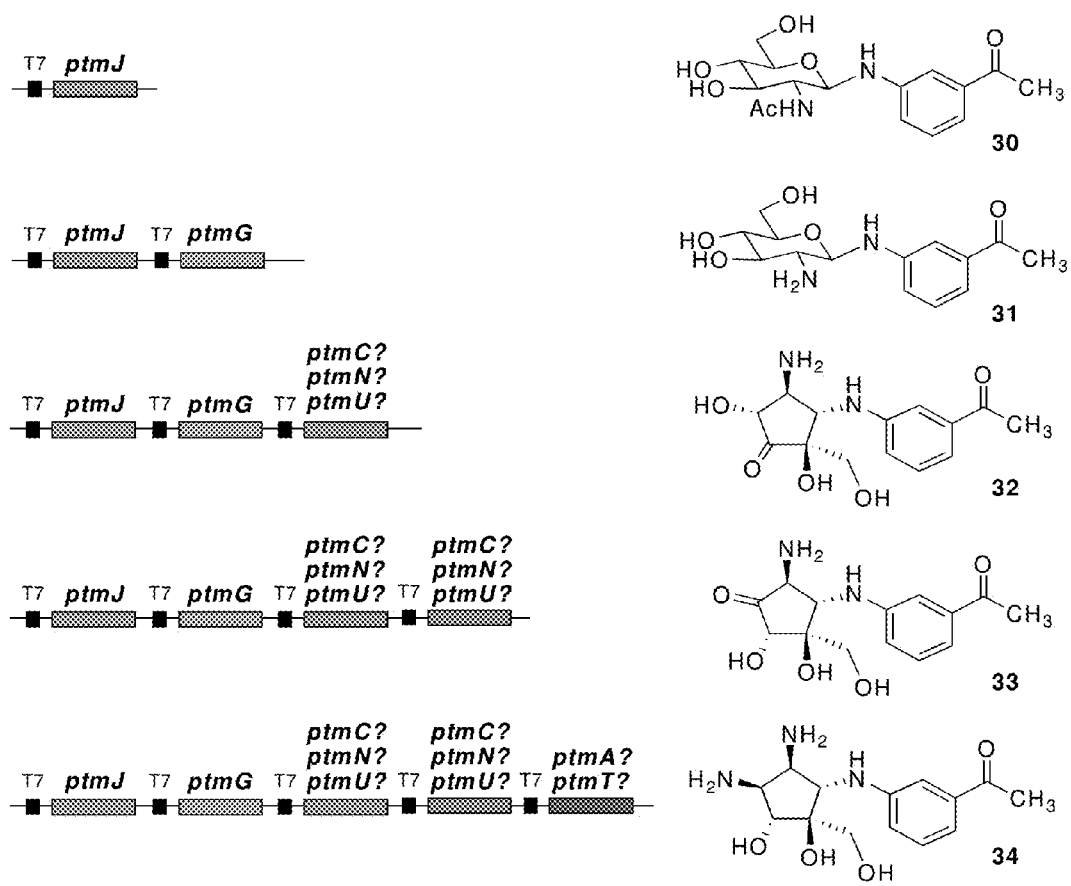
FIG. 13 is an illustration of the combinatorial expressions of ptm genes and the proposed chemical structures of their expected products.

Additional genes from the cluster can be added onto the plasmid. For example, an addition of the glycosyltransferase gene (ptmJ) into the plasmid is predicted to result in the production of N-acetylglucosaminyl-3-aminoacetophenone. In this fashion, a number of plasmids can be constructed containing various additional components of the pathway; e.g., ptmJ only; ptmJ and ptmG (the putative deacetylase); ptmJ, ptmG, and either ptmC (radical SAM), ptmN (oxidoreductase), or ptmU (oxidoreductase); etc. and are predicted to yield novel intermediates in the biosynthetic pathway (FIG. 13). The products can be individually transferred into *E. coli* and gene expression, with or without IPTG induction, and can be monitored by RT-PCR. The production of the expected secondary metabolites can be analyzed using TLC, HPLC, LC-MS, and NMR.

If *E. coli* harboring the initial gene cassette for 3-aminoacetophenone biosynthesis does not produce the compound, individual clones can be generated including constructs containing ptmJ only; ptmJ and ptmG; ptmJ, ptmG, and either ptmC, ptmN, or ptmU. The genes can be expressed in *E. coli*, which is cultivated in cultures containing 3-aminoacetophenone.

An advantage of the above constructs is the portability of the cassette, as the whole set of genes can be easily retrieved by cleaving the plasmid with MfeI and EcoPI and transferred to another expression vector applicable for a different host system. Therefore, the MfeI/EcoRI fragment harboring the complete gene cassette can be transferred into a replicative vector for a different host (e.g., *S. lividans* T7 or *S. coelicolor*) and the strain can be transformed by either conjugation or protoplast transformation. Whenever necessary, the genes can be integrated into the host genome using an appropriate integration vector, e.g., pSET152, which can be used in many *Streptomyces* spp. Transformation can be carried out using well-established conjugation methodologies. Resulting transformants can be analyzed for compound production.

Example 7

Inactivation and Identification of Regulatory Genes in *S. pactum* ATCC 27456

This Example provides methods of inactivating and identifying regulatory genes in *S. pactum* to generate strains with higher production capability.

As the production yield of pactamycin from *S. pactum* ATCC 27456 is relatively low (about 3 mg/L), it is desirable to generate strains with higher production capability. Strains producing high levels of the antibiotic are critical to ensure supply and to lower production costs. Industrial strains of antibiotic producers have been commonly generated by random mutagenesis using chemicals or UV irradiation. These methods involve a tedious screening system and have yet to define an easy way to identify the mutated genes. Therefore, an alternative mutagenesis procedure is desirable to systematically identify the regulatory genes involved in the production of the antibiotic. It is widely accepted that regulatory proteins, which up-regulate or down-regulate the production based on certain conditions, dictate the biosynthesis of the antibiotics. Therefore, the production yield of pactamycin in *S. pactum* can be improved by inactivation of these regulatory genes. Although the biochemical events involved in the process are presumably more complex, inactivation of the negative-regulatory genes is predicted to improve production of the antibiotic. The genes may be located in the vicinity of the biosynthetic gene cluster but may also reside at distant locations on the chromosome.

In the pactamycin gene cluster, there are a number of genes that are involved in the regulation of pactamycin biosynthesis. Those genes can include ptmF, ptmX, orf 9, orf10, orf11, orf14, orf15, orf16, orf18, and orf19. To inactivate and identify the regulatory genes of pactamycin biosynthesis, in frame deletion of these putative regulatory genes from the chromosome of *S. pactum* can be carried out using a double crossover gene replacement strategy as described herein. The mutants can be analyzed for their production yield of pactamycin by LC-MS. If more than one negative-regulatory genes can be identified (e.g., the knockout mutants show an increase in pactamycin biosynthesis), mutants that contain multiple gene deletions in these regulatory elements can be generated to further improve the production yield of pactamycin. As the strategy used for the double crossover inactivation does not introduce any antibiotic resistance marker into the genome, construction of multiple gene deletions using the same vector backbone should be possible, making sequential inactivation experiments easy and efficient. Alternatively, if pactamycin biosynthesis decreases as a result of gene disruption, this would suggest that a positive regulator of pactamycin biosynthesis has been located. In this case, overexpression constructs can be designed in the integrating pSET152 vector downstream of the constitutive promoter PermE*. The resulting construct can be transferred into *S. pactum* via conjugation and the mutant strains analyzed for their ability to produce more pactamycin.

Example 8

Synthesis of Pactamycin Analogs via Knockout Variants

This Example describes the production of pactamycin analogs via knockout mutants. Knockout mutants can be produced as described herein and as is known to those of skill in the art by, for example, transforming a host cell with one or more expression vectors including one or more of the nucleic acid sequences that encode an amino acid sequence set forth in SEQ ID NOs:1-53, including an in-frame disruption.

For example, inactivation of the carbamoyltransferase gene (ptmB) may give mutant strains that produce compound:

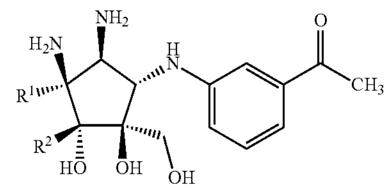

wherein $R^1$ is H or lower alkyl, such as methyl or ethyl or hydroxyalkyl and $R^2$ is H or lower alkyl, such as methyl.

Inactivation of the N-methyltransferase gene (ptmD) may give mutant strains that produce compounds of the formula 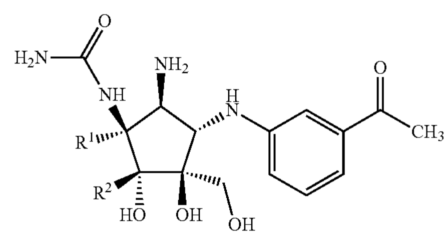 wherein $R^1$ is H or lower alkyl, such as methyl or ethyl or hydroxyalkyl and $R^2$ is H or lower alkyl, such as methyl.

Inactivation of the oxidoreductase gene (ptmN or ptmU) may give mutant strains that produce compounds of the formula:

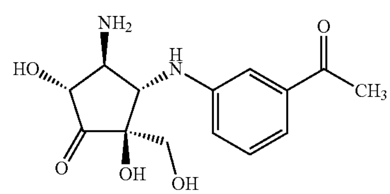 [SMILES: CC(=O)c1cccc(N[C@H]2[C@H](N)[C@@H](O)C(=O)[C@@]2(O)CO)c1]

Inactivation of the aminotransferase gene (ptmA or ptmT) may give mutant strains that produce compound:

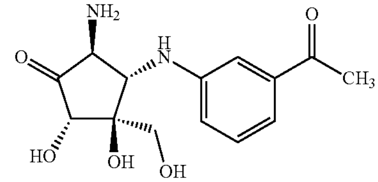 [SMILES: CC(=O)c1cccc(N[C@H]2[C@H](N)C(=O)[C@@H](O)[C@@]2(O)CO)c1]

Inactivation of the radical SAM genes (ptmH, ptmL, or ptmM) may give mutant strains that produce compounds of the formula:

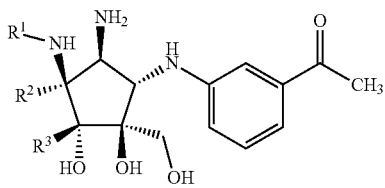

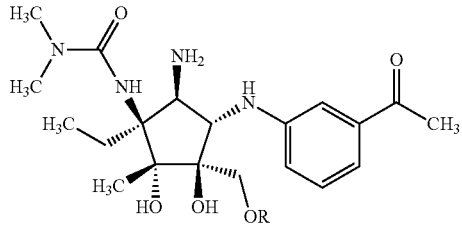

wherein $R^1$ is H or carbamoyl (—C(O)NR$^4$R$^5$), such as dimethylcarbamoyl ($R^4$ and $R^5$ are methyl)

$R^2$ is H or lower alkyl, such as methyl or ethyl or hydroxyalkyl $R^3$ is H or lower alkyl, such as methyl; and $R^4$ and $R^5$ independently are H or lower alkyl.

Inactivation of the cytochrome P450 monooxygenase gene (ptmY) may give mutant strains that produce compounds of the formula:

wherein R is H or acyl, such as a 6-MSA residue.

Moreover, the above knockout variants can be used in combination with semisynthetic techniques to produce additional pactamycin analogs. For example, 6-MSA synthase mutant strains can be supplied with N-acetylcysteamine (NAC)-derivatives of unnatural precursors. As is set forth in the scheme below, novel analogs of pactamycin can be generated by supplying alternative side chain molecules, as their NAC-derivatives, to cultures of the ptmQ mutant strain.

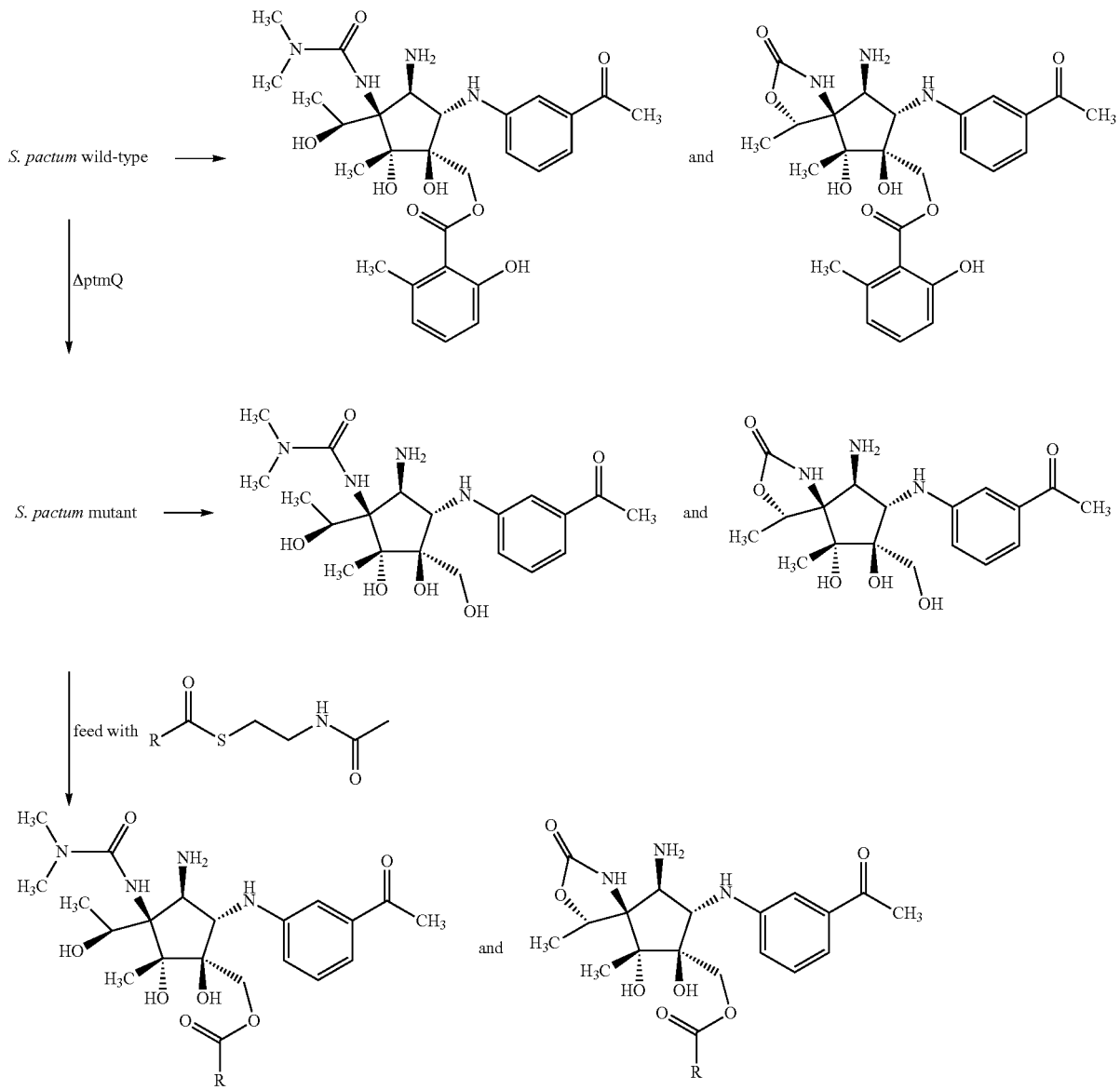

wherein R is an aliphatic or aromatic moiety, such as a lower alkyl group, an optionally substituted phenyl ring or an amino acid residue.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound according to the formula

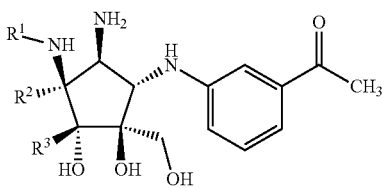

wherein $R^1$ is H or $C(O)NR^4R^5$;
$R^2$ is H or lower alkyl, or hydroxyalkyl;
$R^3$ is H or lower alkyl; and
$R^4$ and $R^5$ independently are H or lower alkyl.

2. The compound of claim 1, wherein $R^1$ is $C(O)NR^4R^5$.

3. The compound of claim 2, wherein $R^4$ and $R^5$ are methyl.

4. The compound of claim 1, wherein $R^2$ is lower alkyl or hydroxyalkyl.

5. The compound of claim 4, wherein the lower alkyl is methyl or ethyl.

6. The compound of claim 5, wherein the lower alkyl is methyl.

7. The compound of claim 1, wherein $R^3$ is lower alkyl.

8. The compound of claim 7, wherein the lower alkyl is methyl.

9. The compound of claim 1, wherein $R^1$ is $C(O)NR^4R^5$, and $R^2$, $R^3$, $R^4$, and $R^5$ are methyl.

10. A method of making the compound of claim 1, comprising:
transforming a host cell with one or more expression vectors comprising an isolated nucleic acid molecule encoding a protein consisting of SEQ ID Nos.: 1 to 53; and
culturing the host cell in a culture medium to produce the compound of claim 1.

11. The method of claim 10, wherein $R^1$ is $C(O)NR^4R^5$.

12. The method of claim 11, wherein $R^4$ and $R^5$ are methyl.

13. The method of claim 10, wherein $R^2$ is lower alkyl or hydroxyalkyl.

14. The method of claim 13, wherein the lower alkyl is methyl or ethyl.

15. The method of claim 14, wherein the lower alkyl is methyl.

16. The method of claim 10, wherein $R^3$ is lower alkyl.

17. The method of claim 16, wherein the lower alkyl is methyl.

18. The method of claim 10, wherein $R^1$ is $C(O)NR^4R^5$, and $R^2$, $R^3$, $R^4$, and $R^5$ are methyl.

* * * * *